OTHER PUBLICATIONS

US006001981A
United States Patent [19]
DeAmicis et al.
[11] Patent Number: 6,001,981
[45] Date of Patent: Dec. 14, 1999
[54] SYNTHETIC MODIFICATION OF SPINOSYN COMPOUNDS
[75] Inventors: Carl Vincent DeAmicis, Indianapol

Pickett, J.A., (1988), Chemistry in Brittain, 137–142.
Kirst et al., Tetrahedron Letters (1991) 32(37):4839–4842.
Whaley et al., Tetrahedron Letters (1980) 21:3659–3662.
Kreuzman et al., J. Biological Chemistry (1988), 263 (30): 15626–15633.
Snyder et al., J. Am. Chem. Soc. (1984) 106:787–789.
Mertz et al., "Int. J. Syst. Bact." (1990) 40(1):34–39.
Celmer et al., J. Chem. Soc., (1980) 102(12):4203–4209.
Aizawa et al. (1979) The Journal of Antibiotics, 32(3):193–196.
Ikeda et al. (1985) J. Antibiotic, 38(3):436–438.
Jomon et al. (1972) The Journal of Antibiotics, 25(5):271–280.
Dybas and Babu (1988) Brighton Crop Protection Conference, 57–64.
Borchardt et al. (1979) Biochem. & Biophys. Res. Comm., 89(3):919–924.
Vedel et al. (1978) Biochem. & Biophys. Res. Comm., 85(1):371–376.
Omura, (1984) Macrolide Antibiotics, Chapter 13.
Fuller (1978) Biochemical Pharmacology, 27:1981–1983.
Jackson et al. (1988) Abstracts of the 1988 ICAAC, 26026.
Umezawa (1980) Supplement to Index of Antibiotics from Actinomycetes, Journal of Antibiotics, 33(3):15–26.
Umezawa, Institute of Microbial Chemistry, Tokyo, Index of Antibiotics from Actinomycetes, vol. II (1967).
Omura and Tannaka (1984) Macrolide Antibiotics, Chapter 1.
Schulman and Ruby (1987) Antimicrobial Agents and Chemotherapy, 31(6):964–965.
Schulman et al., Journal of Antibiotics (1985) 38(11):1494–98.
Ito and Hirata (1972) Tetrahedron Letters, 12:1185–1188.
Catalogue of Bacteria and phages, ATCC, 7th Ed., 1989.
Derwent Abstract 84–278337/45, SSSE 16.03.88.
Derwent Abstract 84–252941/41, SSSE 16.02.83.
Derwent Abstract 92:144960k.
Derwent Abstract 1167c/07, KAKE 31.05.78; JP55000310, Jan. 1980.
Derwent Abstract 92:211459u.
Derwent Abstract 88–095030/14, SSSE 00.00.86; JP63045280, Feb. 1988.
Derwent Abstract 85–245719/40, SSSE 01.02.84; JP60160888, Aug. 1985.
Derwent Abstract 54333S–BCD,Fuji, 17.02.69.
Derwent Abstract JP59151896, Aug. 1984.
Derwent Abstract JP62226925, Oct. 1987.
Derwent Abstract JP73039922.
Derwent Abstract JP63045280, Feb. 1988.
Derwent Abstract JP71028833, Aug. 1971.
Derwent Abstract JP59170092, Sep. 1984.
Tatsuta et al., J. Amer. Chem. Soc., Aug. 17, 1977, 99917):5826.
Nakabayashi et al., Carbohydrate Research (1986) 150:C7–C10.
Greene, *Protecting Groups in Organic Syntheses* (1991) 17–18, Wiley & Sons.
Fischer et al., Chem. Ber. (1920) 53:2363.
Flynn et al., J. Amer. Chem. Soc., Jun. 20, 1954, 76:3121–3131.

SYNTHETIC MODIFICATION OF SPINOSYN COMPOUNDS

CROSS-REFERENCE TO RELATED APPLICATION

This is a continuation of application Ser. No. 08/662,549 filed Jun. 13, 1996, now abandoned.

FIELD OF THE INVENTION

This invention relates to compounds produced by chemical modifications of Spinosyn compounds produced by *Saccharopolyspora spinosa*. The compounds have insecticidal activity.

BACKGROUND OF THE INVENTION

The fermentation product identified in U.S. Pat. No. 5,362,634, which is incorporated herein by reference, as A83543 is a family of related compounds produced by *Saccharopolyspora spinosa*. These compounds have been referred to as factors or components A, B, C, D, E, F, G, H J, K, L, M, N, O, P, Q, R, S, T, U, V, W, Y and the like (also see PCT WO 93/09126 and PCT WO 94/20518) and are hereinafter referred to as Spinosyn A, B, and the like. The Spinosyn compounds are useful for the control of arachnids, nematodes and insects, in particular Lepidoptera and Diptera species. The naturally produced Spinosyn compounds consist of a 5,6,5-tricylic ring system, fused to a 12-membered macrocyclic lactone, a neutral sugar (rhamnose) and an amino sugar (forosamine) (see Kirst et al. (1991), *Tetrahedron Letters*, 32:4839). If the amino sugar is not present the compounds have been referred to as the pseudoaglycone of A, D, etc. and if the neutral sugar is not present then the compounds have been referred to as the reverse pseudoaglycone of A, D, etc. A more preferred nomenclature is to refer to the pseudoaglycones as Spinosyn A 17-Psa, Spinosyn D 17-Psa, and the like. A more preferred nomenclature is to refer to the reverse pseudoaglycones as Spinosyn A 9-Psa, Spinosyn D 9-Psa, and the like. The Spinosyn compounds typically have had the following structures:

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|

(I)

[Structure of Spinosyn core with positions 1–21 labeled, showing $R^{1'}$, $R^{2'}$, $R^{3'}O$, $R^{4'}$, $R^{5'}O$, $OR^{6'}$, $OR^{7'}$ substituents and $CH_3$ group]

| | | | | | | | |
|---|---|---|---|---|---|---|---|
| Spinosyn A | H | $CH_3$ | $(CH_3)_2N$—[sugar]—$CH_3$—O | $C_2H_5$ | $CH_3$ | $CH_3$ | $CH_3$ |
| Spinosyn B | H | $CH_3$ | $(CH_3)NH$—[sugar]—$CH_3$—O | $C_2H_5$ | $CH_3$ | $CH_3$ | $CH_3$ |
| Spinosyn C | H | $CH_3$ | $H_2N$—[sugar]—$CH_3$—O | $C_2H_5$ | $CH_3$ | $CH_3$ | $CH_3$ |
| Spinosyn D | $CH_3$ | $CH_3$ | $(CH_3)_2N$—[sugar]—$CH_3$—O | $C_2H_5$ | $CH_3$ | $CH_3$ | $CH_3$ |
| Spinosyn E | H | $CH_3$ | $(CH_3)_2N$—[sugar]—$CH_3$—O | $CH_3$ | $CH_3$ | $CH_3$ | $CH_3$ |

-continued

| Factor | R1' | R2' | R3' | R4' | R5' | R6' | R7' |
|---|---|---|---|---|---|---|---|
| Spinosyn F | H | H | 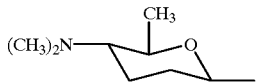 | C₂H₅ | CH₃ | CH₃ | CH₃ |
| Spinosyn G | H | CH₃ | 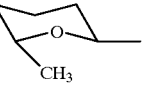 | C₂H₅ | CH₃ | CH₃ | CH₃ |
| Spinosyn H | H | CH₃ | 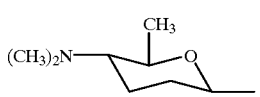 | C₂H₅ | H | CH₃ | CH₃ |
| Spinosyn J | H | CH₃ | 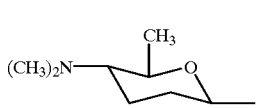 | C₂H₅ | CH₃ | H | CH₃ |
| Spinosyn K | H | CH₃ | 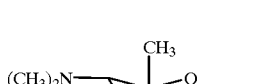 | C₂H₅ | CH₃ | CH₃ | H |
| Spinosyn L | CH₃ | CH₃ | 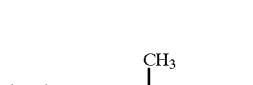 | C₂H₅ | CH₃ | H | CH₃ |
| Spinosyn M | H | CH₃ | 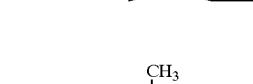 | C₂H₅ | CH₃ | H | CH₃ |
| Spinosyn N | CH₃ | CH₃ | 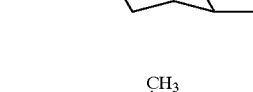 | C₂H₅ | CH₃ | H | CH₃ |
| Spinosyn O | CH₃ | CH₃ | 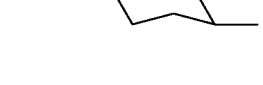 | C₂H₅ | CH₃ | CH₃ | H |
| Spinosyn P | H | CH₃ |  | C₂H₅ | CH₃ | H | H |
| Spinosyn Q | CH₃ | CH₃ | 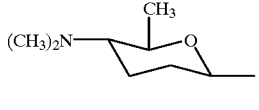 | C₂H₅ | H | CH₃ | CH₃ |
| Spinosyn R | H | CH₃ | 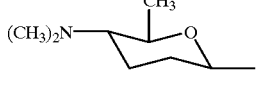 | C₂H₅ | H | CH₃ | CH₃ |

-continued

| Factor | R1' | R2' | R3' | R4' | R5' | R6' | R7' |
|---|---|---|---|---|---|---|---|
| Spinosyn S | H | $CH_3$ | (CH$_3$)$_2$N—[sugar, CH$_3$] | $CH_3$ | H | $CH_3$ | $CH_3$ |
| Spinosyn T | H | $CH_3$ | (CH$_3$)$_2$N—[sugar, CH$_3$] | $C_2H_5$ | H | H | $CH_3$ |
| Spinosyn U | H | $CH_3$ | (CH$_3$)$_2$N—[sugar, CH$_3$] | $C_2H_5$ | H | $CH_3$ | H |
| Spinosyn V | $CH_3$ | $CH_3$ | (CH$_3$)$_2$N—[sugar, CH$_3$] | $C_2H_5$ | H | $CH_3$ | H |
| Spinosyn W | $CH_3$ | $CH_3$ | (CH$_3$)$_2$N—[sugar, CH$_3$] | $C_2H_5$ | $CH_3$ | H | H |
| Spinosyn Y | H | $CH_3$ | (CH$_3$)$_2$N—[sugar, CH$_3$] | $CH_3$ | $CH_3$ | $CH_3$ | H |
| Spinosyn A 17-Psa | H | $CH_3$ | H | $C_2H_5$ | $CH_3$ | $CH_3$ | $CH_3$ |
| Spinosyn D 17-Psa | $CH_3$ | $CH_3$ | H | $C_2H_5$ | $CH_3$ | $CH_3$ | $CH_3$ |
| Spinosyn E 17-Psa | H | $CH_3$ | H | $CH_3$ | $CH_3$ | $CH_3$ | $CH_3$ |
| Spinosyn F 17-Psa | H | H | H | $C_2H_5$ | $CH_3$ | $CH_3$ | $CH_3$ |
| Spinosyn H 17-Psa | H | $CH_3$ | H | $C_2H_5$ | H | $CH_3$ | $CH_3$ |
| Spinosyn J 17-Psa | H | $CH_3$ | H | $C_2H_5$ | $CH_3$ | H | $CH_3$ |
| Spinosyn L 17-Psa | $CH_3$ | $CH_3$ | H | $C_2H_5$ | $CH_3$ | H | $CH_3$ | and

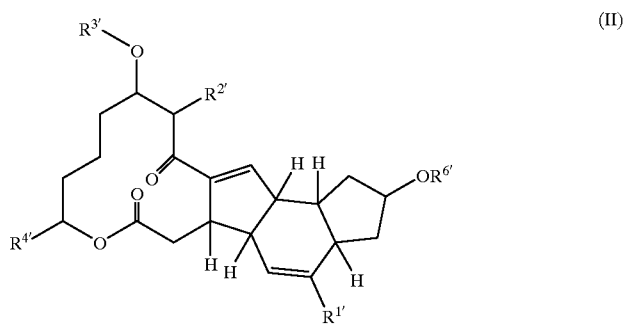

(II)

| | R1' | R2' | R3' | R4' | R6' |
|---|---|---|---|---|---|
| Spinosyn A 9-Psa | H | $CH_3$ | (CH$_3$)$_2$N—[sugar, CH$_3$] | $C_2H_5$ | H |

-continued

| Factor | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| Spinosyn D 9-Psa | CH₃ | CH₃ | 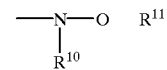 | C₂H₅ | H | | |
| Spinosyn A Aglycone | H | CH₃ | H | C₂H₅ | H | | |
| Spinosyn D Aglycone | CH₃ | CH₃ | H | C₂H₅ | H | | |

The naturally produced Spinosyn compounds may be produced via fermentation from cultures NRRL 18719, 18537, 18538, 18539, 18743, 18395 and 18823. These cultures have been deposited and made part of the stock culture collection of the Midwest Area Northern Regional Research Center, Agricultural Research Service, United States Department of Agriculture, 1815 North University Street, Peoria, Ill. 61604.

As previously stated, the Spinosyn compounds are particularly effective against Lepidoptera and Diptera species. The Spinosyn compounds are quite environmentally friendly and have an appealing toxicological profile. However, in some applications it would be most desirable to have a longer residual effect than provided by spinosyns disclosed in previous patents and publications. A Spinosyn analog that has a longer residual effect could be used to control mites on fruits and nuts or to control codling moth, which effects pome fruit.

SUMMARY OF THE INVENTION

The invention disclosed herein is to the synthetic modification of products produced by *Saccharopolyspora spinosa* to thereby produce intermediates and/or insecticidal products for use in the agricultural and animal health markets. The numerous synthetic modifications were made to the rhamnose sugar, forosamine sugar, to the molecule via hydrogenation, epoxidation, reduction, halogenation, oxidation, adding alkyl groups, adding nitrogen groups, and the addition and elimination of substituents on the macrocyclic lactone.

DETAILED DESCRIPTION OF THE INVENTION

The compounds of the present invention are prepared directly or indirectly by modifying the compounds that are naturally produced from *Saccharopolyspora spinosa*, see U.S. Pat. No. 5,362,634 to DowElanco which is fully incorporated herein by reference. The compounds of the invention have been shown to have activity against insects, arachnids and nematodes. Therefore, the compounds may be used to make other compounds or the compounds themselves may be used for inhibiting or inactivating an insect or mite. An inhibitory or inactivating amount of the compound comes into contact with the locus of an insect or mite. The "locus" of the insect refers to the environment in which the insect or mite lives or where its eggs are present, including the air surrounding it, the food it eats, or objects which it contacts. Typically these compounds are applied to the foliage of a plant which an insect or mite might feed on. Unless otherwise specified herein, the phrases and terms have the following meaning: By the term "haloalkyl" it is meant an alkyl having 1 to 4 carbon atoms, where there is at least one halogen bound to a carbon atom. By the term "halogen" it is meant Cl, F, Br, or I. By the term "alkanoyl" it is meant an alkyl having 1 to 4 carbon atoms, where at least one carbonyl group is attached to an alkyl group. By the term "alkylhydroxyl amino" it is meant a substitutent having the formula $$-\underset{R^{10}}{N}-O\quad R^{11}$$

wherein $R^{10}$ and $R^{11}$ are independently an alkyl having 1 to 4 carbon atoms or an alkanoyl having 1 to 5 carbon atoms. By the term "protected hydroxyl" it is meant substituted methyl ethers, such as but not limited to methoxy methyl, tetrahydropyran, substituted ethyl ethers such as but not limited to 1-ethoxy ethyl, substituted benzylethers such as but not limited to p-methoxybenzyl, silylethers such as but not limited to silylethers having 1 to 2 carbon atoms, typically trimethylsilyl, esters, typically esters having 1 to 2 carbon atoms, more specifically formate or acetate, carbonates typically carbonates having 1 to 2 carbon atoms, more specifically methyl carbonate, and sulfonates, typically having 1 to 2 sulfurs, more specifically methyl sulfonates. These protecting groups are described in more detail in Greene, T. W., Wuts, P. G. M. *Protecting Groups in Organic Syntheses*, John Wiley and Sons, New York, 1991, p. 17–18, which is incorporated in full by reference. By the term "protected amino" it is meant carbamates having 1 to 2 carbon atoms, amides having 1 to 4 carbon atoms, typically n-formyl and n-acetyl, and imines such as n-benzyliene. These protecting groups are further described in Greene *Protecting Groups in Organic Syntheses*. By the term "inhibiting an insect or mite" it is meant that there is a decrease in the number of living insects or mites or a decrease in the number of eggs. By "inactivating amount" it is meant that an amount of compound is used to cause measurable reduction in the treated insect or mite population. Typically from about 1 to about 1,000 ppm (or 0.01 to 1 Kg/acre) of compound is used.

These compounds are typically active against *Macrosteles fascifrons* (aster leafhopper), *Spodoptera exiqua* (beet armyworm), *Meloidogyne arenaria* (peanut root knot nematode), *Aphis gossypii* (cotton aphids), *Tetranychus urticae* (two spotted spider mite), *Diabrotica undecimpunctata howardi* (Southern corn rootworm), *Heliothis zea* (cotton bollworm), *Peregrinus maidis* (corn planthopper), *Heliothis virescens* (Tobbacco budworm), *Blattella germanicus* (German cockroach), *Ostrinia nubilalis* (European cornborer), *Nephotettix cinciticeps* (green rice leafhopper), *Nilaparvata lugens* (brown planthopper), and *Chilo suppressalis* (rice stem borer)and the like.

The synthetic compounds are typically prepared by modifying the rhamnose sugar, modifying the forosamine sugar, or starting with 9- or 17- pseuodoaglycone and then substituting a nonsugar or different sugar with rhamnose or forosamine sugar. Synthetic compounds were also prepared by modifying the 5,6,5-tricyclic and/or 12-membered macrocyclic lactone part of the compounds naturally produced or of the pseudoaglycone of the natural compounds as described in the Examples herein. The compounds claimed herein include all isomers and any acid addition salts of the compounds and their isomers.

The compounds claimed herein exist in several diastereomeric isomers. Because there are multiple stereogenic centers, it is anticipated that the diastereomeric isomers will have utility as insecticides. Although some diastereomeric isomers may be more effecacious than others, all the diastereomeric isomers are equivalent to the claimed invention.

In Example 17 Part A, the rhamnose sugar at R5', R6' and R7' of Formula I is modified by adding long chain alkyl groups, aromatic groups and/or the addition of long chain alkyl groups, aromatic groups with halogen substitutents. Esters were also made at the R5', R6' and R7' position. Additional sugars were also placed at these positions. Another type of modification was to add hetero substituents containing atoms such as nitrogen, sulfur, phosphorus and silicon. In addition to the modifications on the rhamnose sugar, the double bond between the C5 and C6 position in Formula I was modified by epoxidation or hydrogenation.

In Example 17 Part B, the forosamine sugar is replaced with a nonsugar substitutent through an ester linkage. The esters typically have nitrogen heterocyclic groups, halogen, or amino groups. In Example 17, Part C, the forosamine sugar was modified by changing the substitution on the nitrogen from H or methyl to a long chain alkyl group, acyl group, quaternary ammonium salt or N-oxide. In Example 17, Part D, the molecule was modified at the double bond at the C13 and C14 positions by hydrogenation, epoxidation, reduction and adding alkyl groups and nitrogen groups such as hydroxyl amines and cyanide. In Example 17, Part E, the C17 substituent of the macrocyclic lactone is eliminated to give a double bond and/or the C5 and C6 positions of the molecule is modified with halogens, epoxides and alkoxides. In Example 17, Part F, at the C5 and C6 position, the molecule is modified by hydrogenation, epoxidation, halogenation, oxidation and the adding of hetero atoms substituents and esters.

In Example 17, Part G, the forosamine is replaced with another sugar, such as a rhamnose derivative. In Example 17, Part H, the Spinosyn starting material is alkylated or N-demethylated. The resulting materials are preferably used as starting materials for making other compounds. In Example 17, Part I deoxygenated rhamnose analogs are prepared and further modified with ester and heteroatom substitutions. In Example 17, Part J, the rhamnose sugar is replaced with other sugars and nonsugars such as esters and ethers. In Example 17, Part K, the C9 position of the 5,6-5-tricyclic portion of the molecule is modified by oxidation of the hydroxyl group to a ketone and then adding alkyl groups to the C-O double bond. Also, the hydroxyl group at C9 was deoxygenated or replaced with nitrogen containing groups.

Not only are the compounds disclosed herein useful in producing agricultural product, acid addition salts of these compounds are also desirous products. Acid addition salts may be prepared from the compounds disclosed in Formulas I, II, IV, VI, VIII, and XV. The salts of the compounds are prepared using standard technology for preparing salts which are well known to those skilled in the art. Salts can be neutralized to form an acid addition salt. Acid addition salts that are particularly useful include, but are not limited to, salts formed by standard reactions with both organic and inorganic acids such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

Compositions are prepared according to the procedures and formulas which are conventional in the agricultural or pest control art. The compositions may be concentrated and dispersed in water or may be used in the form of a dust, bait or granular formulation. The dispersions are typically aqueous suspensions or emulsions prepared from concentrated formulations of the compounds. The water-soluble or water-suspension or emulsifiable formulations are either solids, wettable powders, or liquids, known as emulsifiable concentrates or aqueous suspensions. Wettable powders may be agglomerated or compacted to form water dispersible granules. These granules comprise mixtures of compound, inert carriers and surfactants. The concentration of the compound is typically between about 0.1% to about 90% by weight. The inert carrier is typically attapulgite clays, montmorillonite clays and the diatomaceous earths or purified silicates.

Surfactants comprise typically about 0.5% to about 10% of the wettable powder, where the surfactants are typically sulfonated lignins, condensed napthalene-sulfonates, the napthalene-sulfonates, alkyl-benenesulfonates, alkysulfonates or nonionic surfactants such as ethylene oxide adducts of alkylphenols or mixtures thereof. Emulsifiable concentrates of the claimed compounds typically range from about 50 to about 500 grams of compound per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents -rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble compounds, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants as discussed herein. Inert ingredients such as inorganic salts and synthetic or natural gums may also be employed to increase the density and/or viscosity of the aqueous vehicle as is desired.

Precipitated flowables may be prepared by dissolving the active molecule in a water-miscible solvent and surfactants or surface active polymers. When these formulations are mixed with water, the active compound precipitates with the surfactant controlling the size of the resulting microcrystaline precipitate. The size of the crystal can be controlled through the selection of specific polymer and surfactant mixtures.

The compounds may also be applied as a granular composition that is applied to the soil. The granular composition typically contains from about 0.5% to about 10% by weight of the compound. The compound is dispersed in an inert carrier which is typically clay or an equivalent substance. Generally, granular compositions are prepared by dissolving the compound in a suitable solvent and applying it to a granular carrier which has been preformed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The compounds may also be combined with an appropriate organic solvent. The organic solvent is typically a bland petroleum oil that is widely used in the agricultural industry. These combinations are typically used as a spray. More typically, the compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The amount of compound applied to the loci of insects and mites is not critical and can easily be determined by those skilled in the art. Generally the concentrations of from about 10 ppm to about 5,000 ppm provide the desired control. For crops such as soybeans and cotton, the rate of application is about 0.01 to about 1 kg/ha, where the compound is applied in a 5 to 50 gal/A spray formulation. The compounds may be applied to any locus inhabited by an insect or mite. Such locus typically is cotton, soybean and vegetable crops, fruit and nut trees, grape vines, houses and ornamental plants. The compounds of the present invention are also useful for the treatment of animals to control arthropods, i.e., insects and arachnids, which are pests on animals. These arthropod pests typically attack their hosts on the external ("ecto") surface; agents which control such pests are referred to as "ectoparasiticides".

All animals are subject to attack by such pests, though the problems are most severe among vertebrate hosts. Human beings are potential hosts for many parasites, and in tropical areas and in areas with minimal sanitation, parasitic infections are a regular problem in medical practice. Also highly subject to attack by parasites are the numerous livestock animals, such as cattle, sheep, pigs, goats, buffalo, water buffalo, deer, rabbits, chickens, turkeys, ducks, geese, ostriches, and the like. Horses and other pleasure animals are subject to parasitic attack, as are mink and other animals grown for their fur, and rats, mice and other animals used in laboratory and research settings. Companion animals such as dogs and cats are highly subject to attack by parasites, and because of their close relationship with humans, such parasitism poses problems for the humans with whom they are associated. Fish, crustacea, and other aquatic species are also subject to parasitic attack. In short, parasitism involves as hosts essentially the whole range of animals.

The economic toll from ectoparasitic infestations is large. In the livestock realm, animals suffer reduced feed efficiency and growth rates. Milk and wool production suffer, and there is damage to fleece, hides, and pelts. Animals are rendered susceptible to secondary microbiological infections and to further parasite attack. Ectoparasites also cause considerable discomfort even when they are not severely detrimental to health and production.

Although a number of parasiticides are in use, they suffer from a variety of problems, including a limited spectrum of activity, environmental toxicity, the need for repeated treatment, and, in many instances, resistance by ectoparasites. Therefore, there is a continuing need for new ectoparasiticides.

The present compounds provide a new tool in the armamentarium for controlling ectoparasites. In this embodiment, the present invention is directed to a method for inhibiting or killing an arthropod pest on a host animal, which comprises contacting the pest with an effective amount of a compound of the present invention.

The present compounds can be used to control a wide variety of arthropod pests. Representative pests which can be controlled by the present compounds are the following:

Arachnids, *Amblyomma americanum* (Lone-star tick), *Amblyomma maculatum* (Gulf Coast tick), *Argas persicus* (fowl tick), *Boophilus microplus* (cattle tick), Chorioptes spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), *Sarcoptes scabiei* (mange mite), Insects- Aedes(mosquitoes), Anopheles (mosquitoes), Culex (mosquitoes), Culiseta, *Bovicola bovis* (cattle biting louse), *Callitroga homnivorax* (blowfly), Chrysops spp. (deer fly), *Cimex lectularius* (bed bug), Cochliomyia spp. (screwworm), *Ctenocephalides canis* (dog flea), *Ctenocephalides felis* (cat flea), Culicoides spp. (midges, sandflies, punkies, or no-see-ums), *Damalinia ovis* (sheep biting louse), Dermatobia spp. (warble fly), *Gasterophilus haemorrhoidalis* (nose bot fly), *Gasterophilus intestinalis* (common horse bot fly), *Gasterophilus nasalis* (chin fly), Glossina spp. (tsetse fly), *Haematobia irritans* (horn fly, buffalo fly), *Haematopinus asini* (horse sucking louse), *Haematopinus eurysternus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), Lucilia spp. (maggot fly), *Melophagus ovinus* (sheep ked), Musca spp. (house fly, face fly), *Oestrus ovis* (nose bot fly), Pediculus spp. (lice), Phlebotomus spp. (sandfly), *Phormia regina* (blowfly), Psorophora spp. (mosquito), Pthirus spp. (lice), Reduvius spp. (assassin bug), Simulium spp. (black fly), *Solenopotes capillatus* (little blue cattle louse), *Stomoxys calcitrans* (stable fly), Tabanus spp. (horse fly), Tenebrio spp. (mealworms), Triatoma spp. (kissing bugs).

The present compounds' ectoparasiticidal activity is achieved when the compounds contact the pests. The contact can be of the egg, larvae, adult, or other life stage. "Contact" includes ingestion of the compound by the pest.

Techniques for delivering ectoparasiticides are well known to those skilled in the art. In general, a present compound is applied to the exterior surface of an animal, whereby it contacts pests already present on the host as well as those which arrive on the host's body within the efficacy period of the compound. Typically, the compound is formulated in a liquid formulation which is sprayed onto the animal's surface or poured onto the animal's surface. Another conventional treatment is a "dip", whereby cattle are treated by being substantially immersed in a dilute solution of an ectoparasiticide. For some hosts and pests, the formulation can be a dust, which is sprinkled onto the host, or a shampoo or cream which is employed in bathing the animal. Collars on cats and dogs are also employed as a way of delivering an ectoparasiticide directly to the animal's surface.

In another technique, an ectoparasiticide is applied to locations frequented by animals, so that pests are thereby contacted by the compound even as in direct application to the host. Application to pet bedding is well known, as is application to carpeting. For cattle, dusting bags are well known. These are positioned in a doorway where the cattle inevitably rub against the bag and pests are contacted by the present compound.

In yet another embodiment, the present compounds can be used to control insects and arachnids which are pests in the feces of cattle and other animals. In this embodiment, the compounds are administered orally and the compounds travel through the intestinal tract and emerge in the feces. Control of pests in the feces indirectly protects the animals from the pests.

The compounds are formulated for use as ectoparasiticides in manners known to those skilled in the art. In general, a formulation will include a compound of the present invention and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

In another embodiment, the present compounds are usefully combined with other ectoparasiticides or with anthelmentics, the latter also known as endoparasiticides ("endo"=internal, controlling internal parasites which are typically platyhelminthes and nemathelminthes). Representative such endoparasiticides include the following:

Abamectin, Albendazole, Avermectin, Bunamidine, Coumaphos, Dichlorvos, Doramectin, Epsiprantel, Febantel, Fenbendazole, Flubendazole, Ivermectin, Levamisole, Mebendazole, Milbemycin, Morantel, Moxidectin, Netobimin, Niclosamide, Nitroscanate, Oxfendazole, Oxibendazole, Piperazine, Praziquantel, Pyrantel, Ricombendazole, Tetramisole, Thiabendazole, Clorsulon, Closantel, Diamphenethide, Nitroxynil, Oxyclozanide, Rafoxanide, Triclabendazole.

Representative other ectoparasiticides include the following:

Abamectin, Alphamethrin, Amitraz, Avermectin, Coumaphos, Cycloprothrin, Cyfluthrin, Cyhalothrin, Cypermethrin, Cyromazine, Deltamethrin, Diazinon, Diflubenzuron, Dioxathion, Doramectin, Famphur, Fenthion, Fenvalerate, Flucythrinate, Flumethrin, Hexaflumuron, Ivermectin, Lindane, Lufenuron, Malathion, Methoprene, Metriphonate, Moxidectin, Permethrin, Phosme, Pirimiphos, Propetamphos, Propoxur, Rotenone, Temephos, Tetrachlorvinphos, Trichlorfon, Zetacypermethrin, B.t. Biotoxins and Boric Acid.

EXAMPLES

General Experimental Section

All reagents and solvents were used directly as purchased from commercial suppliers and all reactions were conducted with constant magnetic stirring at ambient temperature (20–22° C.), unless otherwise noted. All reactions involving organometallic, moisture sensitive, or metal hydride reagents were conducted in commercially available dry solvents under a dry nitrogen atmosphere. Partitions, extractions, or washes with NaCl, NaHCO$_3$, NH$_4$Cl, and other salts refer to saturated aqueous solutions of these salts. Reactions are typically "worked-up" by extraction of an organic solution of the products with one of the above salt solutions; the organic layer was dried with K$_2$CO$_3$, Na$_2$SO$_4$, or MgSO$_4$, filtered and evaporated in vacuo. Reversed-phase thin layer chromatography (RPTLC) was done on glass-backed octadecylsilane-bonded plates, 0.2 mm thickness from Whatman. Chromatography refers to flash chromatography and was performed on E. Merck silica gel 60 (230–400 mesh). Reversed-phase high performance liquid chromatography (RPHPLC) was performed on C18 bonded silica gel (Rainin Dynamax 60 A, 8 μm). All melting points were determined in open capillaries and are uncorrected. $^1$H NMR and $^{13}$C NMR spectra were determined at 300 or 400 MHz and 75 or 101 MHz, respectively, in CDCl$_3$. Mass spectral data were measured via electrospray ionization (ESI). Elemental analyses were provided by analytical laboratory of DowElanco or Midwest Microlabs.

Example 1

Synthesis of Spinosyn A aglycone

A sample of Spinosyn A (8.50 g, 11.61 mmol) was dissolved in EtOH (100 mL). Water (100 mL) was added, and upon stirring, to this solution was added 4N $H_2SO_4$ (aq) solution (200 mL). The reaction mixture was heated to reflux, under a nitrogen atmosphere, for 4.5 hr. It was cooled to room temperature, diluted with toluene (250 mL) and ethyl acetate (300 mL), and brine (300 mL) was added. After extraction, the phases were separated. The water layer was extracted once more with ethyl acetate (100 mL). The combined organic layers were washed successively with diluted brine (3×) and 5% aqueous $NaHCO_3$ (2×) and then dried over anhyd $MgSO_4$ and concentrated in vacuo. The residue was purified on a flash $SiO_2$ column (250 g; Ethyl acetate). After concentration to dryness of the chromatographically pure fractions, Spinosyn A aglycone was obtained as a glassey solid (4.08 g, 87%), $[a]_{589}$=−145.6° (MeOH), $[a]_{589}$=−131.7° ($CHCl_3$).

Example 2

Synthesis of Spinosyn A 17-Psa

Spinosyn A (20.0 gms, 27.4 mmol) was dissolved in 300 ml of 1N $H_2SO_4$ and heated to 80° C., with mechanical stirring for 2 hr. The reaction was then cooled to room temperature. The precipitate was filtered with suction, and washed with fresh 1N $H_2SO_4$. The solid product was then dissolved in dichloromethane, washed with brine, dried over $K_2CO_3$, and evaporated under reduced pressure. The crude product was purified by silica gel chromatography with 70% EtOAc in Hexane to give Spinosyn A 17-Psa (14.46 gms; 89%) as a colorless glass.

Example 3

Spinosyn A 9-Psa

A suspension of N-chlorosuccinimide (1.20 gm, 9.00 mmol) in dichloromethane (45 ml) was cooled to −78° C. under nitrogen. Diethyl sulfide (1.07 ml, 9.90 mmol) was added neat to this suspension over 5 min. and the mixture was stirred at −78° C. for 0.5 hr. Spinosyn J (2.15 gm, 3.00 mmol) in 8 mL dichloromethane was added slowly to this mixture over 15 min keeping the reaction temperature below −60° C. When the addition had been completed, the solution was stirred at −78° C. for 6 hrs. Triethylamine (1.25 mL, 9.00 mmol) was then added dropwise and the solution was allowed to warmed to room temperature. The reaction was diluted with 40 mL dichloromethane and poured into 20 mL 1N sodium bisulfate and 30 mL water. The layers were separated and the organic layer extracted with 30 mL saturated sodium bicarbonate and dried over sodium sulfate. The solvent was evaporated under reduced pressure, and the residue was dissolved in MeOH (100 ml). Anhydrous $K_2CO_3$ (4.15 gm, 30.00 mmol) was added and the suspension was stirred at room temperature. After stirring for 2 hr., the mixture was cooled to 0° C. and solvent evaporated to ⅕th its volume on a rotary evaporator. Dichloromethane (100 mL) and water (100 mL) were added and the layers separated. The aqueous layer was extracted with 3×50 mL dichloromethane and the organic extracts combined and washed with first with water then brine solution. The solution was dried over sodium sulfate, filtered and concentrated on a rotary evaporator to give 2.49 g tacky yellow oil. This product was purified by flash chromatography (250 gm silica gel, 5% MeOH in dichloromethane with 0.5% conc $NH_4OH$, to give Spinosyn A 9-Psa as a white foam (1.52 gm ; 93%) $^1HNMR$ ($CDCl_3$) δ 78 (br s, 1, H-13), 4.63 (m, 1, H-21), 4.43 (m, 2, H-1", H-9), 2.23 (s, 6, $N(CH_3)_2$.

Example 4
Preparation of Spinosyn with Culture *Saccharopolyspora spinosa* NRRL 18395

Part A. Shake-flask Fermentation

The culture *Saccharopolyspora spinosa* NRRL 18395, either as a lyophilized pellet or as a suspension maintained in liquid nitrogen, was used to inoculate a vegetative medium having composition A or B (medium B is preferred for large scale production), where vegetative medium A was comprised of (amount in %) trypticase soy broth* 3.0, yeast extract 0.3, $MgSO_4 \cdot 7H_2O$ 0.2, glucose 0.5, maltose 0.4, deionized water q.s. 1 liter, without a pH adjustment (*purchased from Baltimore Biological Laboratories) and vegetative medium B was comprised of enzyme-hydrolyzed casein 3.0, yeast extract 0.3, $MgSO_4 \cdot 7H_2O$ 0.2, glucose 1.0, deionized water q.s.1 liter, with a pH of 6.2 which was adjusted to 6.5 with sodium hydroxide, (purchased from NZ Amine A, Sheffield Products, P.O. Box 638, Norwich, N.Y. 13815). Slants or plates were prepared by adding 2.5% agar to vegetative seed medium A or B. The inoculated slant were incubated at 30° C. for from about 10 to 14 days. The mature slant culture was scraped with a sterile tool to loosen the spores and remove and macerate the mycelial mat. About one-fourth of the loosened spores and culture growth thus obtained was used to inoculate 50 mL of a first-stage vegetative seed medium. Alternatively, the first-stage medium may be inoculated from a liquid nitrogen ampoule. When the culture is maintained in liquid nitrogen, ampoules are prepared using equal volumes of vegetative culture (48–72 hr. incubation, 30° C.) and suspending medium. The suspending medium contains lactose (100 g), glycerol (200 mL) and deionized water (q.s. to 1 L). A liquid nitrogen ampoule is used to inoculate 100 mL of vegetative medium in 500-mL Erlenmeyer flasks (or 50 mL medium in 250-mL flasks). The cultures are incubated at 30° C. for 48 hours on a shaker orbiting in a two-inch (5.08 cm) circle at 250. The incubated culture (5% v/v inoculum) is used to inoculate 100 mL of a production medium having the following composition: (amount in %) glucose 4.0, vegetable protein, partially hydrolyzed enzymatically* 1.5–3.0, cottonseed flour** 1.0, $CaCO_3$ (reagent or technical grade) 0.3, soybean oil 1.0,tap water q.s. 1 liter (presterilization pH adjusted to 7.0 with NaOH) *Sheftone H, Sheffield Products, **Proflo, Traders Protein, P.O. Box 8407, Memphis, Tenn. 38108. The inoculated production medium was incubated in 500-mL Erlenmeyer flasks at 28–30° C. for 6 to 8 days on a shaker orbiting in a two-inch circle at 250 rpm.

B. Stirred Bioreactor Fermentation

In order to provide a larger volume of inoculum, 10 mL of incubated first-stage medium, prepared as described in Section A, was used to inoculate 400 mL of a second-stage vegetative medium having the same composition as that of the first-stage vegetative medium. This second-stage medium was incubated in a 2-L wide-mouth Erlenmeyer flask for about 48 hours at 30° C. on a shaker orbiting in a two-inch circle at 250 rpm. Incubated second-stage vegetative medium (2 L) thus prepared was used to inoculate 80 to 115 liters of sterile production medium, prepared as described in Section A. Additional soybean oil is added to control foaming, if needed.

The inoculated production medium was allowed to ferment in a 165-L stirred bioreactor for 5 to 8 days at a temperature of 28° C. The airflow and agitator speed in the stirred vessel were computer controlled to maintain a dissolved oxygen level at or above 50% of air saturation.

Example 5
Isolation of Spinosyn A, B, C and D

Fermentation broth (225 liters), prepared as described in Example 4, was filtered using a filter aid (1% Hyflo), and the separated biomass was washed with water (~50 L). The biomass was then agitated with methanol (~100 L) for about one hour and filtered. The methanol filtrate was concentrated to a volume of about 1 liter. The concentrate was extracted three times with diethyl ether (1 L each). The combined ether extracts were concentrated to a volume of about 200 mL. A portion of the concentrate (8 mL) was chromatographed on a silica gel column (RP-8 Lobar, size B, E.M. Science, a Division of E.M. Industries, 30 Inc.). This procedure was repeated for a total of 12 runs (cycles). The instrumental set-up and execution procedure to perform the preparative chromatography in an "Autoprep" mode is described as follows:

A complete "Autoprep" HPLX system was comprised of three Rainin Rabbit HPX pumps, one pressure module, one Gilson Model 20 lB HPLC fraction collector, one Isco-v4 absorbance detector and one Apple Macintosh Plus computer. The complete system is arranged according to instructions given in the Dynamax HPLC Method Manager manual from Rainin Instrument Company, Inc. The "Autoprep" HPLC configuration takes advantage of system automation to permit preparative separations to be run repetitively under virtually identical conditions with virtually identical results. Collecting and pooling corresponding fractions from multiple runs provides chromatographic capacity without the need for a large column. Two solvent mixtures (A) and (B) were used in the isocratic mode at a flow rate of 8.0 mL/min. Solvent system A was comprises of 95 mL $CH_3OH$, 95 mL $CH_3CN$, 10 mL $H_2O$, and solvent system B was 100 mL $CH_3OH$, 100 mL $CH_3CN$, 0 mL $H_2O$. The isocratic mixture used contains 60% of solvent B.

The runtime for each cycle was 28.0 minutes. The eluates from the first 16 minutes of each run were discarded. The following eluates were collected in 6 time-factions, 2 minutes (16 mL) each. The automatically combined fractions from each of the 12 cycles resulted in 6 final fractions (chromatographic cuts). The presence of the active Spinosyn compounds was determined by analyzing each final fraction for mosquito larvae activity and also by analytical HPLC. The active fractions were then combined according to their activity and HPLC profiles and were further purified, using the same "Autoprep" HPLC and solvent system, but with a high resolution, 21.4-mm×25-cm preparative column (Rainin Dynamax), prepacked with 8µ C-18 reversed phase silica gel, to give Spinosyn A, B, C and D. Spinosyns A and D crystallize from $CH_3OH/H_2O$.

Example 6

Purification of Spinosyn A and D

Fermentation broth (10 L) was prepared as described in Example 4 Sect. A, except that 1) 200 mL of production medium was used in 1-L flasks; 2) soybean oil was omitted from the production medium; and 3) incubation was at 30° for 4–6 days. The broth was filtered. The filtrate, containing 4 mcg of Spinosyn A/mL and no detectable quantities of Spinosyn B, C, or D/mL, was discarded. The biomass was washed with water and extracted for one hour with methanol. The extract (7 L) contained 72 mcg of Spinosyn A/mL and 7 mcg of Spinosyn D/mL. The methanol extract was concentrated to a volume of 5 L, and added to HP-20 resin (150 mL, Mitsubishi Chemical Industries, Ltd., Japan) in water (2 L). This mixture was stirred for one hour. The HP-20 resin mixture was then placed in a glass column. The initial effluent and the eluate using methanol:water (1:1, 1 L) were not active. The second eluate using methanol:water (7:3, 1 L) contained trace quantities of Spinosyn A. The following eluate using methanol (1 L) contained the Spinosyn A and Spinosyn D activity. The methanol eluate was concentrated and combined with 2 similar fractions from other work-ups and concentrated to dryness. The residue was dissolved in 75 mL of methanol:THF (4:1) and precipitated by addition into 10 volumes of acetonitrile. The mixture was filtered, and the filtrate was concentrated to dryness. The residue was dissolved in methanol (25 mL) and applied to a 5.5×90-cm column of LH-20 Sephadex (Pharmacia LKB Biotechnology Inc., U.S.A.), prepared in methanol, collecting and analyzing 125 25-mL fractions, using the HPLC procedure described in Example 1.

Fractions containing the desired compounds were combined and concentrated. The residue was dissolved in methanol (10 mL) and applied to a 41.1-mm×25-cm preparative column prepacked with 8µ C-18 reversed phase silica gel (Rainin Dynamax). The column was conditioned in methanol:acetonitrile:water (37.5:37.5:25). After sample application, the column was developed using a 180-min linear gradient of the following solvents: solvent system A 37.5 mL $CH_3OH$, 37.5 mL $CH_3CN$, 25 mL $H_2O$, and solvent system B was 45 mL $CH_3OH$, 45 mL $CH_3CN$, 10 mL $H_2O$. Fractions containing Spinosyn A were pooled, to dryness, dissolved in t-BuOH (5 mL) and lyophilized to give 778 mg of pure Spinosyn A. Fractions containing Spinosyn D were combined with D-containing fractions from 6 similar separations and were concentrated and chromatographed as described herein, using the same column but different solvents. The column was conditioned in methanol:acetonitrile:water (40:40:20). The solvent systems used to develop the column in a 180-min linear gradient operation were: solvent system A was comprises of 40 mL $CH_3OH$, 40 mL $CH_3CN$, 20 mL $H_2O$, and solvent system B was 95 mL $CH_3OH$, 95 mL $CH_3CN$, 10 mL $H_2O$. Fractions containing Spinosyn D were combined and concentrated. The residue was dissolved in t-BuOH (5 mL) and lyophilized to give 212 mg of Spinosyn D.

Example 7

Isolation of Components Spinosyn E, F, G, H and J and the Spinosyn A 17-Psa

Fermentation broth (8 L), prepared using procedures similar to those described in Example 4, was treated as described in Example 4.

Fractions from the LH-20 Sephadex column containing the desired compounds were combined with corresponding fractions from similar fermentations. Since components E, F, G, H, J and the pseudoaglycone of A were produced in very small quantities, numerous fermentations were required to provide sufficient quantities for further purification.

A pool of minor factors, prepared in this manner and containing approximately 1.6 grams of solid 15 material, was applied to an HPLC column (Rainin Dynamax) prepacked with 8 micron C-18 reversed phase silica gel (ODS), as described in Example 4. The column was conditioned in $CH_3OH:CH_3CN:H_2O$ (75:75:50), and the gradient was run from 100% of solvent (A) to 50% (B) with the following solvent systems: Solvent system A 75% $CH_3OH$, 75% $CH_3CN$, 50% $H_2O$ and solvent system B 95% $CH_3OH$, 95% $CH_3CN$, 10% $H_2O$ were collected in 25-mL fractions. The following fractions 30 were pooled:

| Pool | Fractions |
| --- | --- |
| 1 | 31–44 |
| 2 | 45–63 |
| 3 | 64–69 |
| 4 | 70–80 |
| 5 | 81–130 |
| 6 | 131–160 |

A portion of pool 5 (100 mL) was concentrated to a residue, dissolved in methanol (1 mL) and applied to a 21.4-mm×250-mm HPLC column (Rainin Dynamax), as described in Example 5. The column was conditioned using solvent system (A) of the following solvent systems: solvent system A 30:30:40 $CH_3OH/CH_3CN/H_2O$(1N $NH_4OAc$,pH 5), and solvent system B 95:95:10 $CH_3OH/CH_3CN/H_2O$ (1N $NH_4OAc$,pH 5) were developed using a 120-minute linear gradient from 100% solvent (A) to 50% of solvent (B), collecting 15-mL fractions at 7.5 mL/min. Elution was continued at 50% (B) for an additional 60 minutes. The following fractions were pooled:

| Pool | Fraction | Component |
| --- | --- | --- |
| 1 | 37 | F |
| 2 | 38–48 | E |
| 3 | 52–63 | B,G |
| 4 | 65–70 | H,J |

These pools were combined with pools from other chromatographic runs using similar starting materials. The combined pools were further purified using column chromatography, as described herein; desalted on HP-20 resins, using standard techniques; and concentrated and lyophilized to give the following components:

| Pool | Fraction | Component |
| --- | --- | --- |
| E | 249 | 717 |
| F | 4 | 717 |
| G | 104 | 731 |
| H, J | 87 | 717 |
| Pseudo A | 288 | 590 |

*by mass spectrometry

Example 8

Preparation of Spinosyn K, Spinosyn O and Spinosyn Y with Culture NRRL 18743

A. Shake-flask Fermentation

The culture *Saccharopolyspora spinosa* NRRL 18743, either as a lyophiiized pellet or as a suspension maintained in liquid nitrogen, was used to inoculate a vegetative medium having the following composition:

Vegetative Medium

| Ingredient | Amount (g) |
| --- | --- |
| Trypticase soy broth* | 30 |
| Yeast extract | 3 |
| $MgSO_4$—$H_2O°$ | 2 |
| Glucose | 5 |
| Maltose | 4 |
| Deionized water | q.s. 1-L |
| autoclave 30 min at 120° C. | |

*Baltimore Biological Laboratories, Cockeysville, MD

Slants or plates can be prepared by adding 2.5% agar to the vegetative medium. The inoculated slant was incubated at 30° C. for about 10 to about 14 days. The mature slant culture was scraped with a sterile tool to loosen the spores and remove and macerate the mycelial mat. About one-fourth of the loosened spores and culture growth thus obtained was used to inoculate 50 ml of a first-stage vegetative medium. Alternatively, the first-stage medium may be inoculated from a liquid nitrogen ampoule.

Liquid-nitrogen-stock inoculum was prepared by homogenizing a vegetative culture, diluting 1:1 (volume:volume) with a sterile suspending agent of glycerol:lactose:water (2:1:7), and dispensing into sterile tubes (1.5 ml/tube). The diluted inoculum was then stored over liquid nitrogen in appropriate storage containers and used as a working stock inoculum for the cultivation of shake-flask cultures and fermenter seed inoculum.

Liquid nitrogen ampoule was quick thawed and 0.5 ml was used to inoculate 50 ml of vegetative medium in 250-ml wide-mouth Erlenmeyer flasks. The cultures are incubated at 32° C. for 48 hours on a shaker orbiting in a two-inch (5.08 cm) circle at 250 rpm.

The incubated cultures (5% v/v inocutum) was used to inoculate 25 ml of a production medium having the following composition:

Production Medium

| Ingredient | Amount (g) |
| --- | --- |
| Glucose | 80 |
| Peptonized milk* | 20 |
| Cottonseed flour** | 30 |
| Corn steep liquor | 10 |
| $CaCO_3$ (tech. grade) | 5 |
| Methyl oleate | 30 |
| Tap water | q.s. to 1-L |

*Peptonized Milk Nutrient, Sheffield Products, Norwich, NY
**Proflo, graders Protein, Memphis TN The inoculated production medium is incubated in 250-ml wide-mouth Erlenmeyer flasks at 30° C. for 7 days on a shaker orbiting in a two-inch circle at 250 rpm.

B. Stirred Reactor Fermentation

In order to provide a larger volume of inoculum, 10 ml of incubated first stage medium, prepared as described above, is used to inoculate 400 ml of a second-stage vegetative medium having the same composition as that of the first-stage medium. This second-stage vegetative medium is >98% pure. Spinosyn K containing pools from the first preparative HPLC separation and the repurification of Spinosyn O were combined, concentrated to 200 ml. and desalted in the same manner as Spinosyn O. Fractions containing >98% pure component K were pooled, concentrated to dryness, and lyophilized from t-BuOH to give Spinosyn K (11.1 g; >99% pure).

Example 9

Isolation of Spinosyn K, Spinosyn O and Spinosyn Y from Strain NRRL 18743

Fermentation broth (260-L) was prepared as substantially described in the Example above part B. Acetone (260-L) was added to the whole broth after adjusting the pH to 3.0 with 5N HCL. The resulting mixture was filtered through a ceramic filter to give filtrate (480-L) which was held over the weekend under refrigeration. The broth/acetone filtrate was adjusted to pH 12 with 25% NaOH and refiltered twice through the ceramic filter prior to loading onto a steel column (10-L, 10 cm×122 cm) containing HP-20ss resin (Mitsubishi Chemical Industries, Ltd., Japan) at a flow rate of 0.5-L/minute. The column was washed with $CH_3CN$—$CH_3OH$—0.1% aq.$NH_4OAc$ (adjusted to pH 8.1 with $NH_4OH$) (25:25:50; 20-L). Spinosyn K, O and Y were eluted with $CH_3CN$—$CH_3OH$—0.1% aq. $NH_4OAc$ (adjusted to pH 8.1 with $NH_4OH$) (95:95:10; 30-L) at a flow rate of 1-L/minute. The equate (30-L) was concentrated, redissolved in $CH_3OH$, reconcentrated to dryness, redissolved in $CH_3OH$ (100 ml), then precipitated into $CH_3CS$ (2-L). The resulting precipitate was removed by filtration, washed with $CH_3CN$, and discarded: the combined filtrate and wash (3-L) was concentrated to dryness. The resulting residue was redissolved in dichloromethane (50 ml) and applied to a column (7.5 cm×50 cm) of silica gel (EM grade 62. 60–200 mesh) equilibrated in acetonitrile. The column was eluted with $CH_3CN$ (10-L), then $CH_3CN$—$CH_3OH$ (9:1:20-L), followed by $CH_3CN$—$CH_3OH$ (8:2:10L), collecting 1-L fractions. Fractions 11–30 were pooled and concentrated to dryness. The resulting residue was dissolved in $CH_3OH$ (50 ml) and applied (in 10 runs) to a preparative reverse phase HPLC column (Rainin Dynamax-60 Å 8 μm C18, 41.4 mm ID×25 cm with 41.4 mm×5 cm guard module) equilibrated in $H_2O$—$CH_3OH$—$CH_3CN$; (50:175:175, containing 0.1% $NH_4OAc$). The column was eluted at a flow rate of 40 ml/minute with a 60 minute linear gradient from $H_2O$ $CH_3OH$—$CH_3CN$; (50:175:175, containing 0.1; $NH_4OAc$) to $H_2O$—$CH_3OH$ $CH_3CN$: (10:45:45, containing 0.1; $NH_4OAc$). Progress of the separation was monitored with a variable wavelength UV detector tuned to 250 nm. The first three peaks collected (10 runs pooled) corresponded to the elution of minor Spinosyn Y (pool 1, 1-L), Spinosyn K (pool 2, 8-L) and Spinosyn O (pool 3, 4-L). spinosyn K was concentrated to a small volume, then desalted by rechromatographing on the same column, eluting without buffer. The effluent corresponding to the UV absorption peak was concentrated to dryness, dissolved in t-BuOH, and lyophilized to give pure Spinosyn K (7.3 g). Spinosyn O was desalted and lyophilized in like manner to give pure Spinosyn O (1.4 g). Spinosyn Y was desalted by similar chromatography (Rainin Dynamax-60A 8 pm C18 column, 21.4 mm ID×25 cm with 21.4 mm×5 cm guard module) and lyophilized in like manner to give pure Spinosyn Y (46 mg).

Example 10

Preparation of Spinosyn J, Spinosyn L, Spinosyn M, and Spinosyn N with NRRL 18719

The culture Saccharopolyspora spinosa NRRL 18719 was used to obtain Spinosyn J, Spinosyn L, Spinosyn M, and Spinosyn N.

A. Shake-flask Fermentation

The culture Saccharopolyspora spinosa NRRL 18719, either as a lyophilized pellet or as a suspension maintained in liquid nitrogen, was used to inoculate a vegetative medium having the following composition:

| Vegetative Medium | |
|---|---|
| Ingredient | Amount(g) |
| Trypticase broth* | 30 |
| Yeast extract | 3 |
| $MgSO_4.7H_2O$ | 2 |
| Glucose | 5 |
| Maltose | 4 |
| Deionized water | q.s. 1 L |
| Autoclave 30 min at 120° C. | |

*Baltimore Biological Laboratories, Cockeysville, MD

Slants or plates were prepared by adding 2.5% agar to the vegetative medium. The inoculated slant was incubated at 30° C. for about 10 to about 14 days. The mature slant culture was scraped with a sterile tool to loosen the spores and to remove and macerate the mycelial mat. About one-fourth of the loosened spores and culture growth thus obtained were used to inoculate 50 ml of a first-stage vegetative medium. Alternatively, the first-stage medium may be inoculated from a liquid nitrogen ampoule.

When the culture is maintained in liquid nitrogen, ampoules are prepared by homogenizing a vegetative culture (48–72 hours incubation, 30° C.), diluting 1:1 (volume:volume) with a sterile suspending agent, and dispensing into sterile tubes (1.5 ml/tube). The suspending agent contains lactose (100 g), glycerol (200 ml), and deionized water (q.s. to 1 L).

A liquid nitrogen ampoule was used to inoculate 100 ml of vegetative medium in 500-ml Erlenmeyer flasks (or 50 ml of medium in 250-ml flasks). The cultures were incubated at 30° C. for 48 hours on a shaker orbiting in a two-inch (5.08 cm) circle at 260 rpm.

The incubated culture (10% v/v inoculum) was used to inoculate 50 ml or 100 ml, dependent on the size of the Erlenmeyer flask, of a production medium having the following composition:

| Production Medium | |
|---|---|
| Ingredient | Amount (g) |
| Glucose | 80 |
| Peptonized milk* | 20 |
| Cottonseed flour** | 30 |
| Corn steep liquor | 10 |
| $CaCO_3$ (tech. grade) | 5 |
| Methyl oleate | 30*** |
| Tap water | q.s. to 1 L | pH adjusted to pH 7.0 with 1N NaOH, sterilized 40 min. at 120° C.
*Peptonized Milk Nutrient, Sheffield Products, Norwich, NY 13815
**Proflo, Traders Protein, Memphis TN 38108
***The amount of methyl oleate was 30 ml The inoculated production medium was incubated in 250-ml or 500-ml Erlenmeyer flasks at 30° C. for 7 to 10 days on a shaker orbiting in a two-inch circle at 260 rpm.

B. Stirred Reactor Fermentation

In order to provide a larger volume of inoculum, 10 ml of incubated first stage medium, prepared as described in Section A, was used to inoculate 400 ml of a second-stage vegetative medium having the same composition as that of the first-stage medium. This second-stage vegetative medium was incubated in a 2-L wide-mouth Erlenmeyer flask for about 48 hours at 30° C. on a shaker orbiting in a two-inch circle at 260 rpm. The incubated second-stage vegetative medium (2 L) was used to inoculate 80 to 115 liters of sterile production medium, prepared as described in Section A above.

The inoculated production medium was allowed to ferment in a 165-L stirred bioreactor for 7 days to 10 days at a temperature of 30° C. The air-flow and agitator speed in the stirred vessel were computer controlled to maintain a dissolved oxygen level at or above 60% to about 80% of air saturation.

The following tables illustrate the amount of Spinosyn J, Spinosyn L, Spinosyn M, and Spinosyn N that were produced by culture NRRL 18719

TABLE I

Amount of Spinosyn compounds produced by shake-flask fermentation with culture NRRL 18719

| Factor | Amount (mg/ml) |
|---|---|
| Spinosyn J | 661 |
| Spinosyn L | 133 |
| Spinosyn M | ND* |
| Spinosyn N | ND* |

*Not determined by HPLC assay

TABLE II

Amount of spinosyn compounds produced by stirred reactor fermentation with culture NRRL18719

| Factor | Amount (mg) |
|---|---|
| Spinosyn J | 5,282 |
| Spinosyn L | 2,487 |
| Spinosyn M | 136 |
| Spinosyn N | 71 |

Example 11

Spinosyn J, Spinosyn L, Spinosyn M, and Spinosyn N with culture NRRL 18719

Fermentation broth (105 L), prepared as described above, was adjusted to pH 10 (initially pH 6.8) by adding 5N NaOH. The resulting mixture was filtered through a ceramic filter. The filtrate was discarded, a mixture of acetone and water (1:1, 50 L) was added to the mycelial solids, and the resulting mixture was filtered. A second mixture of acetone and water (1:1, 50 L) was added to the mycelial solids, and the pH of the resulting mixture was adjusted to pH 3.0 with 25% sulfuric acid. The resulting mixture was filtered, and a third mixture of acetone and water (1:1 50 L) was added to the mycelial solid. The resulting mixture was filtered and the acidic filtrates were combined.

The combined filtrates were extracted with heptane (10 L). The phases were separated and the aqueous phase added to a second portion of heptane (10 L). The pH of the resulting mixture was adjusted to pH 10 with 5N NaOH. The resulting emulsion was diluted with 50 L of water. The phases were separated and the aqueous phase extracted with a third portion of heptane (10 L). The phases were separated and the second and third heptane extracts were combined and concentrated to a volume of about 4 liters. Upon standing, the concentrate separated into 3 phases: aqueous, emulsion, and organic. The organic phase was lyophilized to give 15.29 g of crude product.

The crude product was dissolved in methanol (500 mL), filtered, and concentrated to dryness in vacuo. The residue was dissolved in a second portion of methanol (20 ml) and applied to a column of LH-20 SEPHADEX (Pharmacia LKB Biotechnology, Inc., Piscataway, N.J., 7.5 cm×46 cm), eluting with methanol and collecting 25 ml fractions. Using the HPLC system, the fractions were analyzed to determine which fractions contained the spinosyn compounds. Fractions 18–50 were combined and concentrated to dryness.

The residue was dissolved in a mixture of methanol, acetonitrile, and water (5:5:1) and chromatographed in 1 ml portions on a preparative reverse-phase HPLC column (Rainin Dynamax-60A, C18, 41.4 mm×300 mm, 8 mm particles, 60 Å pore, Woburn, Mass.). The column was eluted with a mixture of methanol, acetonitrile and water (87.5:87.5:25) with ammonium acetate added to a final concentration of 0.1% (pH 7.6). The fractions were analyzed using an HPLC system, combining like fractions and concentrating to give three semi-pure concentrates A, B, and C.

Semi-pure concentrate C was rechromatographed on the system described in the preceding paragraph, loading 200 mL on each of 10 runs. The fractions from each of the runs were combined and concentrated to give preparations C1 and C2. Preparation C2 was chromatographed a third time; however, water was used in place of the 0.1% ammonium acetate (desalting step). Fractions containing Spinosyn L in at least 99.5% HPLC purity were combined and concentrated. The residue was crystallized from ethanol/water (1:1) to give 2.4 g of Spinosyn L.

Preparation C1 and semi-pure concentrate B were combined and desalted as described in the preceding paragraph (12×200 mL runs); however, the desired compound was eluted with a mixture of methanol, acetonitrile, and water (11:11:3). The fractions containing Spinosyn J in at least 99.5% HPLC purity were combined and concentrated. The residue was dissolved in hot t-butanol and lyophilized to give 4.3 g of Spinosyn J.

Semi-pure concentrate A was chromatographed as described above, except the desired compounds were eluted with a mixture of methanol, acetonitrile, and water (37.5:37.5:25), with ammonium acetate added to final concentration of 0.1%. The fractions from each of the runs (4) were combined and concentrated to give preparations A1, A2, and A3.

Preparation A1 was chromatographed using the column described above; however, the column was eluted with a mixture of methanol, acetonitrile, and water (2:2:1). Fractions containing Spinosyn M in at least 99.5% HPLC purity were combined and concentrated. The residue was dissolved in t-butanol and lyophilized to give 136 mg of Spinosyn M.

Preparation A2 was chromatographed and processed as described in the preceding paragraph to give 71 mg of Spinosyn N.

Example 12
Preparation of Spinosyn Q with Culture NRRL 18823
  A. Shake-flask Fermentation The culture *Saccharopolyspora spinosa* NRRL 18823, either as a lyophilized pellet or as a suspension maintained in liquid nitrogen, was used to inoculate a vegetative 5 medium having the following composition:

| Vegetative Medium 1 | |
| --- | --- |
| Ingredient | Amount (g) |
| Trypticase Broth* | 30 |
| O Yeast extract | 3 |
| MgSO4 7H$_2$O | 2 |
| Glucose | 5 |
| Deionized water | q.s. 1 L |
| Autoclave 30 min at 120° C. | |

*Baltimore Biological Laboratories, Cockeysville, MD

The first-stage medium may be inoculated from a liquid nitrogen ampoule. Such ampoules are prepared by homogenizing a vegetative culture (48–72 hours incubation, 30° C.) diluting 1:1 (volume:volume) with a sterile suspending agent, and dispensing into sterile tubes (1.5 ml/tube). The suspending agent contains lactose (100 9), glycerol (200) ml, and deionized water(q.s. to 1 L). A liquid nitrogen ampoule is used to inoculate 50 ml of vegetative medium in 250-ml wide-mouthed Erlenmeyer flasks. The cultures are incubated at 32° C. for 48 hours on a shaker orbiting in a two-inch (5.08 cm) circle at 250 rpm.

The incubated culture (58 v/v inoculum) was used to inoculate 50 ml Erlenmeyer flask, of a production medium having the following composition:

| Production Medium | |
| --- | --- |
| Ingredient | Amount (g) |
| Glucose | 80 |
| Peptonized milk* | 20 |
| Cottonseed flour** | 30 |
| Corn steep liquor | 10 |
| CaCO$_3$ (tech. grade) | 5 |
| Methyl oleate | 30*** |
| Tap water | q.s. to 1 L | pH adjusted to pH 7.0 with 1N NaOH, sterilized 40 min. at 120° C.
*Peptonized Milk Nutrient, Sheffield Products, Norwich, NY
**Proflo, Traders Protein, Memphis, TN
***The amount of methyl oleate was 30 ml The inoculated production medium is incubated in 250-ml Erlenmeyer flasks at 30° C. for 7 days on a shaker orbiting in a two-inch circle at 250 rpm.

B. Stirred Reactor Fermentation

In order to provide a larger volume of inoculum, 10 ml of incubated first stage medium prepared as described in Section A above, is used to inoculate 400 ml of a second-stage vegetative medium having the same composition as that of the first-stage medium. This second-stage vegetative medium is incubated in a 2 L wide-mouth Erlenmeyer flask for about 48 hours at 32° C. on a shaker orbiting in a two-inch circle at 260 rpm. Incubated second-stage vegetative medium (2 L) thus prepared is used to inoculate 115 liters of sterile production medium, prepared as described in Section A above.

The inoculated production medium is allowed to ferment in a 165 L stirred bioreactor for 7 days at a 5 temperature of 30° C. The air-flow and agitator speed in the stirred vessel are computer controlled to maintain a dissolved oxygen level at or above 60% to about 80% of air saturation.

Example 13
Isolation of Spinosyn Q, Spinosyn R, Spinosyn S and Spinosyn T from Culture NRRL 18823

Fermentation broth (100 L; harvest titer Spinosyn H, 303 pg/ml, Spinosyn Q, 50 pg/ml), prepared as described in the Example above, was refrigerated two days prior to processing. Acetone (100 L) was added to the whole broth after adjusting the pH to 3.0 with 5N HCl. The resulting mixture was filtered through a ceramic filter to give filtrate (170 L) which was held over the weekend under refrigeration. The broth/acetone filtrate was adjusted to pH 13 and refiltered through the ceramic filter prior to loading onto a steel column (10 L; 10 cm×122 cm) containing HP-20SS resin (Mitsubishi Chemical Industries, Ltd., Japan) at a flow rate of 1 L/minute The column was fluted at a flow rate of 1 L/minute with a gradient mixed from solvent "A" (0.1% aq. NH$_4$OAc, adjusted to pH 8.1 with NH$_4$OH) and solvent "B" (CH$_3$CN CH$_3$OH 1:1), collecting 4 L fractions. The pumping system was programmed to generate a gradient from 0 to 50% B in one minute, followed by a gradient from 50 to 100% B in 90 minutes, followed by isocratic delivery of 100% B for an additional 15 minutes. HPLC analysis indicated that fraction 17 (4 L), contained predominantly Spinosyn R with additional more polar materials and a small amount of Spinosyns T and H; fractions 18–22 contained predominantly Spinosyn H with lesser amounts of Spinosyns R and Q and small amounts of Spinosyn S and more polar materials; fractions 23–24 contained Spinosyns H and Q. HPLC analysis of the pools suggested the following total quantities: Spinosyn H. 23.0 g; Spinosyn Q. 3.4 g; Spinosyn R 2.0 g; Spinosyn S. 0.2 g; Spinosyn T. 0.2 g.

Example 14

Recovery of Spinosyn Q, Spinosyn R, Spinosyn S, and Spinosyn T from a Spinosyn Q-producing strain Fermentation broth (85 L; harvest titer Spinosyn H, 302 pg/ml, Spinosyn Q, 44 pg/ml), prepared as Q-producing strain, was refrigerated overnight prior to processing. Acetone (90 L) was added to the whole broth after adjusting the pH to 3.0 with 5N HCl. The resulting mixture was filtered through a ceramic filter to give filtrate (176 L) which was held over the weekend under refrigeration. The broth/acetone filtrate was adjusted to pH 13 with 50% NaOH and refiltered through the ceramic filter (140 L filtrate) prior to loading onto a steel column (10 L; 10 cm×122 cm) containing HP-20SS resin (Mitsubishi Chemical Industries, Ltd., Japan) at a flow rate of 1 L/minute. The column was eluted at a flow rate of 1 L/minute with a gradient mixed from solvent "A" (0.1% $NH_4OAc$, adjusted to pH 8.1 with $NH_4OH$) and solvent "B" ($CH_3CN$—$CH_3OH$ 1:1), collecting 4 L (approx.) fractions. The pumping system was programmed to generate a gradient from 0 to 50% B in one minute, followed by a gradient from 50 to 100% B in 90 minutes, followed by isocratic delivery of 100% B for an additional 10 minutes. HPLC analysis indicated that pool 1 (fractions 16–21; 24.5 L), contained Spinosyns H (12.32 g) and Q (0.34 g); pool 2 (fractions 22–25; 16L) contained Spinosyns H (4.66 g), Q (2.06 g), R, S and T.

A. Isolation of pure component Q

Pool 2 was concentrated to dryness, redissolved in dichloromethane (50 ml), and applied to a glass column (5.5 cm×30 cm) containing silica gel (EM grade 62, 60–200 mesh) and equilibrated in dichloromethane.

The column was washed with dichloromethane (3 L), then developed with dichloromethane—methanol (95.5), collecting 250 ml fractions. Fractions 3 through 15 were combined and concentrated to residue, then dissolved in ethanol/water (400 ml) and allowed to stand at room temperature over the weekend. The resulting crystals were washed with cold ethanol/water (1:1) and dried to give 6.1 g of dried crystals containing 68.7% Spinosyn H and 31.2% Spinosyn Q by HPLC analysis. The dried crystalline material was dissolved in tetrahydrofuran/methanol (1:1) and applied to a preparative reverse phase HPLC column (Rainin Dynamax 60A 8 pm C18, 41.4 mm ID×25 cm with 41.4 mm×5 cm guard module) in 12 runs. The column was fluted at a flow rate of 50 ml/minute with a gradient mixed from solvent "A" ($H_2O$—$CH_3CN$; 30:35:35 containing 0.1% $NH_4OAc$) and solvent "B" ($H_2O$—$CH_3CN$—$CH_3OH$; 10:45:45 containing 0.1% $NH_4OAc$). The pumping system was programmed to generate a gradient from 50 to 100% B in 60 minutes. Progress of the separation was monitored with a variable wavelength UV detector tuned to 250 nm.

Peak 1, containing Spinosyn H (99%; 6 L) eluted first, followed by Spinosyn Q. Combined peak 2 (containing Spinosyn H. 20%, component Q. 80%; 8 L) from all (12) runs was concentrated to 500 ml, reapplied to the same column, and eluted under the same mobile phase conditions in 5 runs. Pool 2 (2 L), containing 99% pure Spinosyn Q was desalted by applying it to the same column equilibrated in $H_2O$—$CH_3OH$—$CH_3CN$ (20:40:40). The column was eluted with $H_2O$—$CH_3OH$—$CH_3CN$ (10:45:45), collecting 10 three-minute fractions. Fractions 2 through 7 were combined, concentrated to residue, and dissolved in hot EtOH (80 ml). An equal volume of $H_2O$ was added and the solution was allowed to cool overnight. The resulting crystals were collected on a filter, washed with cold EtOH—$H_2O$ (1:1), and dried to give 1.5 g pure Spinosyn Q.

Example 15 Insecticidal Compositions
A. Aqueous Suspension

| | |
|---|---|
| Spinosyn Compound | 12.5% |
| TERGITOL TMN-6 (nonionic surfactant) | 1.0% |
| ZIOSYL 200 (silica) | 1.0% |
| AF-100 (silicon based antifoam agent) | 0.2% |
| Xanthan solution (2%) | 10.0% |
| MAKON 10 (10 moles ethyleneoxide nonylphenol surfactant) | 9.0% |
| Tap Water | 66.3% |

B. Emulsifiable Concentrate

| | |
|---|---|
| Spinosyn Compound | 12.4% |
| EXXON 200 (naphthalene solvent) | 83.6% |
| TOXIMUL H (nonionic/anionic surfactant blend) | 2.0% |
| TOXIMUL D (nonionic/anionic surfactant (blend) | 2.0% |

Example 16 Formulations of the Invention
A. Feed Premix

| | |
|---|---|
| Spinosyn Compound | 10% |
| Rice hulls | 85 |
| Light mineral oil | 5 |

B. Feed Premix

| | |
|---|---|
| Spinosyn Compound | 25% |
| Alfalfa meal | 60 |
| Powdered clay | 5 |
| Molasses | 10 |

C. Suspension

| | |
|---|---|
| Spinosyn Compound | 30% |
| Naphthalenesulfonate salt | 5 |
| Nonionic surfactant | 5 |
| Fumed silica | 1 |
| Water | 59 |

D. Drip-On Solution

| | |
|---|---|
| Spinosyn Compound | 20% |
| Nonionic surfactant | 0.8 |
| Propylene glycol | 15 |
| Water | 64.2 |

E. Drip-On Suspension

| | |
|---|---|
| Spinosyn Compound | 10 |
| Nonionic surfactant | 1 |
| Light mineral oil | 89 |

F. Injectable Solution

| | |
|---|---|
| Spinosyn Compound | 15% |
| Propylene glycol | 85 |

G. Injectable Suspension

| | |
|---|---|
| Spinosyn Compound | 25% |
| Propylene glycol | 15 |
| Water | 60 |

H. Injectable Suspension

| | |
|---|---|
| Spinosyn Compound | 30% |
| Polyvinylpyrrolidone | 2 |
| Water | 68 |

Example 17
Synthetic Modifications
 Part A Rhamnose-Modified Derivatives
  Example A1
(5,6-Dihydro Derivative of Compound 9-O-(2,3,4-Tri-O-ethyl-α-L-rhamnosyl) Spinosyn A 9-Psa Compound 9-O-(2,3,4-Tri-O-ethyl-α-L-rhamnosyl) Spinosyn A 9-Psa (106 mg, 0.137 mmol) was dissolved in 5 mL toluene. To this solution was added tris-triphenylphoshine Rhodium(I)chloride (11.9 mg, 0.0128 mmol). Evacuated the flask head space and introduced nitrogen three times. Evacuated and introduced hydrogen three times. Maintained flask under hydrogen with balloon and heated reaction to 110–120° C. After 3.5 hr. cooled flask to RT and evacuated hydrogen and replaced with nitrogen. Evaporated off tolune solvent and replaced with 20 mL ether. Extracted ether solution with 3×10 mL 1N HCl. Combined acid extracts and neutralized with 10 ml 4N NaOH. Extracted neutralized suspension with 3×10 mL ether, combined ether extracts, washed with 20 mL brine, dried over $K_2CO_3$, and evaporated in vacuo. Gave compound 5,6-dihydro derivative of compound 9-O-(2,3,4-tri-O-ethyl-α-L-rhamnosyl) Spinosyn A 9-Psa, 39.4 mg, 36.8% partial $^1$H-NMR δ 6.84 (1H, bs), 1.01 (1H, m), 0.68 (1H, m).

Example A2
2'-O-Dichloroacetyl Spinosyn Q

Compound Spinosyn Q (302 mg, 0.412 mmol) was dissolved in dry $CH_2Cl_2$ (8 ml). The solution was stirred at RT under nitrogen and DMAP (269 mg, 2.20 mmol) was added. Dichloroacetic anhydride (492 mg, 315 μl, 2.05 mmol) was then introduced. After 45 min. pyridine (1.5 ml) was added, followed by EtOAc (50 ml) and toluene (50 ml). The solution was extracted with 5% aq. $NaHCO_3$ (3×). The organic phase was dried over anh. $Na_2SO_4$ and concentrated in vacuo. The residue was purified over a flash $SiO_2$ column (30 g/EtOAc then 5% EtOH in EtOAc). Pure fractions gave compound 2'-O-dichloroacetyl Spinosyn Q; 310 mg, 89% CI MS m/z 844 (M+3), 842 (M+1); IR ν 1772 cm$^{-1}$; $^1$H-NMR ($CDCl_3$) δ 6.70 (1H, bs), 6.00 (1H, s), 5.43 (1H, bs), 5.19 (1H, dd: 3.1, 1.8 Hz), 1.67 (3H, $CH_3$, bs) ppm.

Example A3
2'-O-Trifluoroacetyl Sponosyn Q

Compound Spinosyn Q(330 mg, 0.451 mmol) was dissolved in dry $CH_2Cl_2$ (10 ml). The solution was stirred at RT under nitrogen and DMAP (306 mg, 2.50 mmol) was added. Trifluororoacetic anhydride (473 mg, 320 μl, 2.25 mmol) was then introduced. After 14 hrs. pyridine (1.5 ml) was added, followed by EtOAc (50 ml) and toluene (50 ml). The solution was extracted with 5% aq. $NaHCO_3$ (3×). The organic phase was dried over anh. $Na_2SO_4$ and concentrated in vacuo. The residue was purified over a flash $SiO_2$ column (100 g/EtOAc then 5% EtOH in EtOAc). Pure fractions gave compound 2'-O-trifluoroacetyl Spinosyn Q; 199 mg, 54% $^1$H-NMR ($CDCl_3$) δ 6.69 (1H, bs), 5.43 (1H, bs), 5.26 (1H, dd: 2.9, 1.6 Hz), 1.66 (3H, $CH_3$, bs); $^{13}$C-NMR ($CDCl_3$) δ 156.7 (d: 32.5 Hz), 114.0 (q: 286 Hz) ppm.

Example A4
2'-O-(p-Trifluoromethyl)benzoyl Spinosyn Q

Compound Spinosyn Q(430 mg, 0.587 mmol) was dissolved in dry $CH_2Cl_2$ (10 ml). DMAP (367 mg, 3.0 mmol) was added, followed by p-trifluoromethylbenzoyl chloride (613 mg, 440 ml, 2.94 mmol). After 2 hrs. of stirring at RT, the reaction mixture was diluted with EtOAc (100 μl) and toluene (30 ml). the solution was washed successively with brine and 5% aq. $NaHCO_3$ (3×). The organic layer was dried over anh. $Na_2SO_4$ and concentrated in vacuo. The residue was separated on a flash $SiO_2$ column (70 g/EtOAc) to give compound 2'-O-(p-trifluoromethyl)benzoyl Spinosyn Q; 473 mg, 89% $^1$H-NMR ($CDCl_3$) δ 8.13, (1H, bd: 8.1 Hz), 7.68 (1H, bd: 8.2 Hz), 6.73 (1H, bs), 5.45 (1H, bs), 5.42 (1H, dd: 3.3, 1.8 Hz), 1.69 (3H, $CH_3$, bs); Elemental Analysis: for $C_{49}H_{68}NO_{11}F_3$ calc.: C 65.10, H 7.58, N 1.55; found: C 64.89, H 7.55, N 1.56.

Example A5
(5S,6R)-Epoxy-2'-O-(p-trifluoromethyl)benzoyl Spinosyn Q

Compound (5S,6R)-epoxy-Spinosyn Q (406 mg, 0.543 mmol) was dissolved in dry $CH_2Cl_2$ (10 ml). DMAP (369 mg, 3.0 mmol) was added, followed by (p-trifluoromethyl) benzoyl chloride (623 mg, 445 μl, 2.98 mmol). After stirring for 14 hrs. at RT, triethylamine (2 ml) was added and stirring was continued for 30 min. The solution was diluted with EtOAc (100 ml) and toluene (30 ml), then washed successively with brine, 5% aq. $NaHCO_3$ (2×) and water (1×) and dried over $K_2CO_3$. The organic layer was concentrated in vacuo. The residue was purified over a flash $SiO_2$ column (80 g/EtOAc) to furnish compound (5S,6R)-Epoxy-2'-O-(p-trifluoromethyl)benzoyl Spinosyn Q; 391 mg, 78% IR ν 1728, 1664, 1324, 1272 cm$^{-1}$; $^1$H-NMR ($CDCl_3$) δ 8.12 (1H, bd: 8.2 Hz), 7.67 (1H, bd: 8.2 Hz), 6.54 (1H, bs)5.42 (1H, dd: 3.2, 1.8 Hz)1.31 (3H, $CH_3$, bs).

Example A6
2'-O-Dichloroacetyl Spinosyn H

Compound Spinosyn H (170 mg, 0.237 mmol) was dissolved in dry pyridine (3 ml). DMAP (30 mg, 0.246 mmol) was added. The solution was stirred at RT and dichloroacetic anhydride (0.077 ml, 120 mg, 0.50 mmol) was added. After 30 min. toluene (50 ml) and EtOAc (50 ml) were added. The solution was washed with brine, then with 5% aq. $NaHCO_3$ (3×). The organic layer was dried over $Na_2SO_4$ and concentrated in vacuo. The residue was purified over a flash $SiO_2$ column (15 g/EtOAc) to furnish compound 2'-O-dichloroacetyl Spinosyn H; 155 mg, 79% CI MS m/z 830 (M+3), 828 (M+1); $^1$H-NMR ($CDCl_3$) δ 6.70 (1H, bs), 5.99 (1H,s), 5.18 (1H, dd: 3.0, 2.0 Hz).

Example A7
(2'R)-(diethyl)phosphite of Spinosyn H

Compound Spinosyn H (351 mg, 0.489 mmol) was dissolved in dry pyridine (5 ml). DMAP (62 mg, 0.51 mmol) was added and stirring at RT under nitrogen was continued for 5 min. Diethyl chlorophosphite (157 mg, 0.145 ml, 1.0 mmol) was added. After 30 min. toluene (50 ml) and EtOAc (50 ml) were added. The solution was washed successively with brine (2×) and 5% aq. $NaHCO_3$. The organic layer was dried over $Na_2SO_4$ and concentrated. The residue was separated over a flash $SiO_2$ column (100 g/EtOAc) to give compound 2'R)-(diethyl)phosphite of Spinosyn H; 306 mg, 75% CI MS m/z 838 (M+1); $^1$H-NMR ($CDCl_3$) δ 6.69 (1H, bs), 4.40 (1H, m), 3.83 (4H, 2× $CH_2$, m), 1.18 (6H, 2× $CH_3$, m); Elemental Analysis: for $C_{44}H_{72}NO_{12}P$ calc. C 63.06, H 8.66, N 1.67 found: C 62.94, H 8.88, N 1.71.

Example A8
(2'R)-(diethyl)thiophosphate of Spinosyn H

Compound Spinosyn H (261 mg, 0.364 mmol) was dissolved in dry pyridine (3 ml). DMAP (60 mg) was added, followed by diethyl chlorothiophosphate (152 mg, 125 μl, 0.80 mmol). The reaction mixture was stirred at RT under nitrogen. After 12 hrs. toluene (50 ml) and EtOAc (50 ml) were added. The solution was extracted with brine, then with 5% aq. $NaHCO_3$. The organic layer was dried over and $Na_2SO_4$ and concentrated in vacuo. The residue was purified over a flash $SiO_2$ column (30 g/EtOAc) to give compound 2'R)-(diethyl)thiophosphate of Spinosyn H; 84 mg, 27%) CI MS m/z 870 (M+1); $^1$H-NMR ($CDCl_3$) δ 6.74 (1H, bs), 4.80 (1H, m), 4.22 (4H, 2× $CH_2$, m), 1.30 (6H, 2× $CH_3$, m).

Example A9
2'-O-(Ethyl)oxalyl Spinosyn H

Compound Spinosyn H (720 mg, 1.003 mmol) was dissolved in dry dichloroethane (15 ml). DMAP (80 mg) was added, followed by dry triethylamine (2 ml). The mixture was stirred at RT under nitrogen. Ethyl oxalyl chloride (1 ml) was added. After stirring for 1 hr., the reaction mixture was diluted with toluene (50 ml) and EtOAc (100 ml). The solution was washed successively with brine, 5% aq. $NaHCO_3$ (3×), and water (1×). The organic phase was dried over $K_2CO_3$ and concentrated in vacuo. The residue was purified on a flash $SiO_2$ column (110 g/EtOAc) to give compound 2'-O-(ethyl)oxalyl Spinosyn H; 668 mg, 81% CI MS 818 (M+1); $^1$H-NMR (CDCl$_3$) δ 6.69 (1H, bs), 5.22 (1H, dd: 3.0, 1.8 Hz), 4.27 (2H, q:7.2 Hz), 1.29 (3H, t: 7.2 Hz); Elemental Analysis: for $C_{44}H_{67}NO_{13}$ calc. C 64.60, H 8.26, N 1.71; found C 64.43, H 8.41, N 1.80.

Example A10

2'-O-Trichloroacetyl Spinosyn H

Compound Spinosyn H (295 mg, 0.411 mmol) was dissolved in dry pyridine (5 ml). Trichloroacetyl chloride (1 ml, an excess) was added and the reaction mixture was stirred at RT under nitrogen for 14 hrs. Toluene (50 ml) and EtOAc (50 ml) were added. The solution was extracted with 5% aq. $NaHCO_3$. The organic layer was dried over $Na_2SO_4$ and concentrated in vacuo. The residue was purified over flash $SiO_2$ column (60 g/EtOAc) to give compound 2'-O-trichloroacetyl Spinosyn H; 249 mg, 70% CI MS m/z 866 (M+5), 862 (M+1); $^1$H-NMR (CDCl$_3$) δ 6.70 (1H, bs), 5.18 (1H, dd: 2.2, 1.8 Hz), 2.16 (6H, 2× $CH_3$, s).

Example A11

2'-O-Chloroacetyl Spinosyn H

Compound Spinosyn H (306 mg, 0.43 mmol) was dissolved in dry pyridine (5 ml). Chloroacetic chloride (0.50 ml) was added dropwise. The reaction mixture was stirred at RT under nitrogen. After 3 hrs. toluene (50 ml) and EtOAc (50 ml) were added. The solution was washed successively with brine, 5% $NaHCO_3$ (2×) and water. The organic phase was dried over anh. $Na_2SO_4$ and concentrated in vacuo. The residue was separated on a flash $SiO_2$ column (80 g/EtOAc) to furnish compound 2'-O-chloroacetyl Spinosyn H; 71 mg, 21% $^1$H-NMR (CDCl$_3$) δ 6.72 (1H, bs), 5.16 (1H, dd: 2.2, 1.8 Hz), 3.69 (2H, bs); $^{13}$C-NMR (CDCl$_3$) d 169.9 (C=O), 41.4 (—$CH_2Cl$) ppm.

Example A12

(3'R)-2'-Keto-3'-methoxy-3'-(thiomethyl)methyl Spinosyn H

Compound Spinosyn H (3.10 g, 4.32 mmol) was dissolved in dry DMSO (8 ml). To this mixture, stirred at RT under nitrogen was added triethylamine (3 g, 7 equiv.) followed by Py-$SO_3$ complex (2.06 g, 12.9 mmol). The reaction mixture was stirred for 14 hrs. at RT. Toluene (100 ml) and EtOAc (100 ml) were added. The solution was successively extracted with brine, diluted brine, water, 5% aq. $K_2CO_3$ and water. The organic layer was dried over $K_2CO_3$ and concentrated in vacuo. The residue was purified by flash column chromatography ($SiO_2$/EtOAc) and then separated by HPLC on a reversed phase C-18 column with 10% water in methanol as the mobile phase. Pure fractions obtained afforded upon evaporation compound (3'R)-2'-keto-3'-methoxy-3'-(thiomethyl)methyl Spinosyn H; 697 mg, 39% IR ν 1738, 1721, 1661, 1161, 1038 cm$^{-1}$; EI MS m/z 776 (M+); $^1$H-NMR (CDCl$_3$) δ 6.71 (1H, bs), 3.99 (1H, m: $W_{H/2}$=18 Hz), 3.53 (3H, $CH_3$, s), 3.36 (3H, $CH_3$, s), 2.19 (6H, 2× $CH_3$, bs), 2.08 (3H, $CH_3$, s).

Example A13

2'-O-Acetyl-2'-epi Spinosyn H and 2'-epi Spinosyn H

Compound 2'-keto Spinosyn H (2.95 g, 4.12 mmol) was dissolved in dry $Et_2O$ (60 ml). The solution was cooled to 0° C. under nitrogen and Li(t-BuO)$_3$AlH (97%, 1.62 g, 6.18 mmol, 1.5 equiv.) was added. Stirring was continued at 0° C. for 20 min. The reaction mixture was quenched carefully with brine. Diethyl ether (50 ml) was added and phases were separated. The organic layer was washed with 5% aq. $NaHCO_3$ (4×), dried over anh. $K_2CO_3$ and concentrated in vacuo. The residue was purified over a flash $SiO_2$/EtOAc column. The 2'-epimeric alcohols thus obtained did not separate either on silica or by HPLC on C-18/acetonitrile-MeOH-water (60-30-10). The mixture of 2'-alcohols (1.84 g, 2.56 mmol) was dissolved in dry $CH_2Cl_2$ (10 ml). Pyridine (5 ml) and DMAP (80 mg) were added, followed by $Ac_2O$ (3 ml, an excess). Stirring at RT under nitrogen was continued for 8 hrs. The reaction mixture was diluted with EtOAc (50 ml) and benzene (50 ml). The solution was rinsed successively with brine (2×) and 5% aq. $NaHCO_3$ (2×). The organic layer was dried over $Na_2SO_4$ and concentrated in vacuo. The residue was separated by flash $SiO_2$ column chromatography (230–400 m, 120 g/EtoAc) to give pure compound a) 2'-O-acetyl-2'-epi Spinosyn H; 1.176 g, 60% $^1$H-NMR (CDCl$_3$) δ 6.67 (1H, bs), 4.83 (1H, d: 3.8 Hz), 4.52 (1H, dd: 10.0, 3.8 Hz), 3.47 (6H, 2× $CH_3$, s), 2.14 (6H, 2× $CH_3$, s), 2.01 (3H, $CH_3$, s) ppm. Compound 2'-O-acetyl-2'-epi-Spinosyn H (280 mg, 0.368 mmol) was dissolved in EtOH (5 ml). MeOH (5 ml) was added followed by 10% aq. $K_2CO_3$ solution (3 ml). The reaction mixture was stirred at RT under nitrogen for 15 min. Brine (10 ml) was then added, followed by EtOAc (50 ml) and PhH (50 ml). Phases were separated. The organic layer was washed with water (3×), dried over $K_2CO_3$ and concentrated in vacuo. The residue was purified over a flash $SiO_2$ column (80 g/EtOAc) to give compound b) 2'-epi-Spinosyn H; 228 mg, 86% $^1$H-NMR (CDCl$_3$) δ 6.67 (1H, bs), 4.68 (1H, d: 3.8 Hz), 3.55 (3H, $CH_3$, s), 3.46 (3H, $CH_3$, s), 2.14 (6H, $CH_3$, s) ppm; $^{13}$C-NMR (CDCl$_3$) δ 203.2, 172.9, 147.9, 144.7, 144.5, 129.7, 129.3, 103.9, 97.6, 86.1, 84.9, 81.1, 77.3, 77.1, 74.1, 73.0, 67.6, 65.4, 61.3, 61.1, 49.8, 48.2, 48.1, 46.5, 42.0, 41.7, 41.2 (2×C), 37.9, 37.0, 34.8, 34.6,, 31.4, 30.6, 28.9, 22.2, 19.5, 18.9, 18.2, 16.6, 9.9 ppm.

Example A14

2'-O-Trimethylsilyl Spinosyn H

Compound Spinosyn H (1.59 g, 2.21 mmol) was dissolved in $CH_2Cl_2$ (10 ml). DMAP (0.80 g) was added. The mixture was stirred at RT under nitrogen. TMS triflate (0.90 ml, an excess) was slowly introduced via a syringe and stirring was continued for 1 hr. EtOAc(50 ml) and PhH (50 ml) were added. The solution was washed with 5% aq. $NaHCO_3$ solution (3×). The organic layer was dried over $K_2CO_3$ and concentrated in vacuo. The residue was purified on a flash $SiO_2$ column (100 g/EtOAc) to give compound 2'-O-trimethylsilyl Spinosyn H; 1.615 g, 92% m.p.=163° C. (Et$_2$O); EI MS 791 (M+); $^1$H-NMR (CDCl$_3$) δ 6.69 (1H, bs), 3.81 (1H, dd:2.6, 2.0 Hz),3.46 (3H, $CH_3$, s), 3.38 (3H, $CH_3$, s), 2.16 (6H, 2× $CH_3$, s) ppm.

Example A15

2'-O-Ethyl Spinosyn H

Compound Spinosyn H (2.21 g; 3.08 mmol) was dissolved in $CH_2Cl_2$ (60 ml). Water (20 ml), 10% aq. NaOH (25 ml) and solid $K_2CO_3$ (5 g) were added, followed by diethyl sulfate (8 ml, an excess). The reaction mixture was stirred vigorously at RT under nitrogen for 48 hrs. $H_2O$ (50 ml) and $CH_2Cl_2$ (50 ml) were added, layers were separated, the organic layer was washed with $H_2O$ (2×), dried over $K_2CO_3$ and concentrated in vacuo. The residue was separated by a flash $SiO_2$ column chromatography (230–400 m, 250 g/EtOAc). Pure fractions furnished compound 2'-O-ethyl Spinosyn H; 635 mg, 28% CI MS m/z 746 (M+1); $^1$H-NMR (CDCl$_3$) δ 6.71 (1H, bs), 3.61 (2H, $CH_2$, m), 3.49 (3H, $CH_3$, s), 3.42 (3H, $CH_3$, s), 2.17 (6H, 2× $CH_3$, s), 1.18 (3H, $CH_3$, t: 7.0 Hz) ppm; $^{13}$C-NMR (CDCl$_3$) δ 67.0 (—$CH_2$—), 16.0

Example A16
(2'R)-(Ethyl)carbonate of Spinosyn H

Triphenylphosphine (6.5 g, 24.8 mmol) was dissolved in dry THF (30 ml). Diethyl azodicarboxylate (4.8 ml, 5.32 g, 30.5 mmol) was added and the mixture was stirred for 5 min. at RT. Absolute EtOH (1.43 ml, 1.14 g, 24.8 mmol) was added. After stirring for another 5 min. compound (1.20 g, 1.67 mmol) was introduced. Stirring at RT under nitrogen was continued for 24 hrs. Ethyl acetate (50 ml) and benzene (100 ml) were added. The solution was washed successively with brine, 5% aq. $NaHCO_3$ (2×) and water (1×). The organic layer was dried over $K_2CO_3$ and concentrated in vacuo. The residue was separated on a flash $SiO_2$ column (120 g/EtOAc) to give compound (2'R)-(ethyl)carbonate of Spinosyn H; 233 mg, 18% IR ν 1747, 1720, 1645, 1263 $cm^{-1}$; $^1$H-NMR ($CDCl_3$) δ 6.74 (1H, bs), 4.95(1H, dd: 3.3, 1.8 Hz), 4.19 (2H, q: 7.1 Hz) ppm; Elemental Analysis: for $C_{43}H_{67}NO_{12}$ calc. C 65.37, H 8.55, N 1.97; found C 65.44, H 8.49, N 2.05.

Example A17
2'-O-Trifluoromethanesulfonyl Spinosyn H

Compound Spinosyn H (2.12 g, 2.95 mmol) was dissolved in dry 1,2-dichloroethane (3 ml). Pyridine (3 ml) was added. The solution was cooled to 0° C. under nitrogen. Trifluoromethanesulfonic anhydride (1.20 ml, 7.0 mmol) was added. After 1 hr. of stirring PhH (50 ml) and EtOAc (100 ml) were added. The solution was washed with 5% aq. $NaHCO_3$ (3×). The organic layer was dried over $K_2CO_3$ and concentrated in vacuo. The residue was purified over a flash $SiO_2$ column (160 g/EtOAc) to give compound 2'-O-trifluoromethanesulfonyl Spinosyn H; 1.77 g, 71% IR ν 1415, 1212, 1068 and 918 $cm^{-1}$; $^1$H-NMR ($CDCl_3$) δ 6.72 (1H, bs), 4.93 (1H, dd: 2.8, 1.9 Hz) ppm.

Example A18
2'-O-n-Propyl Spinosyn H

Compound Spinosyn H (1.22 g, 1.70 mmol) was dissolved in $CH_2Cl_2$ (20 ml). Water (10 ml) and 25% aqueous NaOH (15 ml) were added, followed by $K_2CO_3$ (2 g), tetrabutylammonium chloride (1.2 g) and benzyltriethylammonium chloride (1.5 g). 1-Iodopropane (10 ml) was added and the reaction mixture was vigorously stirred at RT under $N_2$ for 48 hrs. $CH_2Cl_2$ (20 ml) was added and the phases were separated. The organic layer was washed with water (2×), dried over $K_2CO_3$ and concentrated in vacuo. The residue was purified over a flash $SiO_2$ column (120 g/EtOAc). Concentration of pure fractions furnished compound 2'-O-n-propyl Spinosyn H; 535 mg, 41%) $^1$H-NMR ($CDCl_3$) δ 6.67 (1H, bs), 2.13 (6H, 2× $CH_3$, s), 0.81 (3H, $CH_3$, t: 7.4 Hz) ppm; Elemental Analysis: for $C_{43}H_{69}NO_{10}$ calc. C 67.95, H 9.15, N 1.84; found C 67.74, H 9.37, N 1.84.

Example A19
2'-O-n-Pentyl Spinosyn H

Compound Spinosyn H (1.02 g, 1.42 mmol) was dissolved in $CH_2Cl_2$ (20 ml). Water (10 ml) and 25% aqueous NaOH (20 ml) were added, followed by $K_2CO_3$ (3.5 g), tetrabutylammonium chloride (0.8 g) and benzyltriethylammonium chloride (1.3 g). 1-Iodopentane (15 ml) was added and the reaction mixture was vigorously stirred at RT under N2 for 72 hrs. $CH_2Cl_2$ (20 ml) was added and the phases were separated. The organic layer was washed with water (3×), dried over $K_2CO_3$ and concentrated in vacuo. The residue was purified over a flash $SiO_2$ column (200 g/EtOAc). Concentration of pure fractions furnished compound 2'-O-n-pentyl Spinosyn H; 559 mg, 50% $^1$H-NMR (—$CH_3$) ppm; Elemental Analysis: for $C_{42}H_{67}NO_{10}$ calc. C 67.61, H 9.07, N 1.88; found C 67.80, H 1.87, N 9.20.

($CDCl_3$) δ 6.69 (1H, bs), 2.16 (6H, 2× $CH_3$, s), 0.82 (3H, $CH_3$, t: 7.4 Hz) ppm; Elemental Analysis: for $C_{45}H_{73}NO_{10}$ calc. C 68.58, H 9.34, N 1.78; found C 68.29, H 9.32, N 1.80.

Example A20
2'-O-Benzyl Spinosyn H

Compound Spinosyn H (1.48 g, 2.06 mmol) was dissolved in $CH_2Cl_2$ (20 ml). Water (10 ml) and 25% aqueous NaOH (20 ml) were added, followed by $K_2CO_3$ (3 g), tetrabutylammonium chloride (0.85 g) and benzyltriethylammonium chloride (1.2 g). Benzyl chloride (10 ml) was added and the reaction mixture was vigorously stirred at RT under $N_2$ for 72 hrs. $CH_2Cl_2$ (20 ml) was added and the phases were separated. The organic layer was washed with water (3×), dried over $K_2CO_3$ and concentrated in vacuo. The residue was purified over a flash $SiO_2$ column (200 g/EtOAc). Concentration of pure fractions furnished compound 2'-O-benzyl Spinosyn H; 806 mg, 48% $^1$H-NMR ($CDCl_3$) δ 7.24 (5H, m), 6.67 (1H, bs), 4.62 (2H, m), 3.60 (1H, dd: 2.5, 1.6 Hz), 2.14 (6H, 2× $CH_3$, s) ppm; Elemental Analysis: for $C_{47}H_{69}NO_{10}$ calc. C 69.86, H 8.61, N 1.73; found C 69.78, H 8.93, N 1.81.

Example A21
2'-O-Acetyl Spinosyn Q

Compound Spinosyn Q (11.0 mg, 0.015 mmol) was dissolved in dry $CH_2Cl_2$ (3 ml). Triethylamine (5 ml) was added. The solution was stirred at RT under nitrogen and $Ac_2O$ (0.70 ml, an excess) was added. After 20 hrs EtOAc (50 ml) and PhH (20 ml) were added. The solution was extracted successively with brine, 5% aq. $NaHCO_3$ (4×) and $H_2O$ (1×). The organic phase was dried over $K_2CO_3$ and concentrated in vacuo. The residue was purified over a flash $SiO_2$ column (5 g/EtOAc) to give compound 2'-O-acetyl Spinosyn Q; 11.0 mg, 95% $^1$H-NMR ($CDCl_3$) δ 6.74 (1H, bs), 5.46 (1H, bs), 5.18 (1H, dd: 2.4, 1.8 Hz), 2.02 (3H, $CH_3$, s), 1.70 (3H, $CH_3$, bs) ppm.

Example A22
3'-O-n-Propyl Spinosyn J

Compound Spinosyn J (311 mg, 0.433 mmol) was dissolved in $CH_2Cl_2$ (10 ml). 15% Aqueous NaOH (5 ml) was added, followed by $K_2CO_3$ (0.70 g), tetrabutylammonium chloride (0.3 g) and benzyltriethylammonium chloride (0.83 g). 1-Iodopropane (4.0 ml) was added and the reaction mixture was vigorously stirred at RT under $N_2$ for 48 hrs. $CH_2Cl_2$ (50 ml) and water (50 ml) were added and the phases were separated. The organic layer was washed with water (2×), dried over $K_2CO_3$ and concentrated in vacuo. The residue was purified over a flash $SiO_2$ column (80 g/EtoAc). Concentration of pure fractions furnished compound Spinosyn J(140 mg) and compound 3'-O-n-propyl Spinosyn J; 156 mg, 86%) $^1$H-NMR ($CDCl_3$) δ 6.65 (1H, bs), 2.11 (6H, 2× $CH_3$, s), 0.84 (3H, $CH_3$, t: 7.3 Hz) ppm; $^{13}$C-NMR ($CDCl_3$) δ 72.4 (O—$CH_2$—), 23.8 (—$CH_2$—), 11.2 ($CH_3$) ppm.

Example A23
3'-O-Ethyl Spinosyn J

Compound Spinosyn J (747 mg, 1.04 mmol) was dissolved in $CH_2Cl_2$ (20 ml). 15% Aqueous NaOH (10 ml) was added, followed by $K_2CO_3$ (1.10 g) and benzyltriethylammonium chloride (1.2 g). 1-Iodoethane (5.5 ml) was added and the reaction mixture was vigorously stirred at RT under $N_2$ for 48 hrs. $CH_2Cl_2$ (50 ml) and water (50 ml) were added. The phases were separated. The organic layer was washed with water (2×), dried over $K_2CO_3$ and concentrated in vacuo. The residue was purified over a flash $SiO_2$ column (100 g/EtOAc). Concentration of pure fractions furnished a) compound Spinosyn J (192 mg) and b) compound 3'-O-ethyl Spinosyn J; 401 mg, 70% $^1$H-NMR (CDCl$_3$) δ 6.65 (1H, bs), 3.58 (2H, q: 7.2 Hz), 2.12 (6H, 2× CH$_3$, s), 1.14 (3H, CH$_3$, t:7.2 Hz) ppm; $^{13}$C-NMR (CDCl$_3$) δ 66.1 (O—CH$_2$—), 16.3 (CH$_3$) ppm; Elemental Analysis: for C$_{42}$H$_{67}$N$_{O10}$ calc. C 67.62, H 9.05, N 1.88; found C 67.91, H 9.33, N 2.00.

Example A24
3'-O-Ethyl Spinosyn K

Compound Spinosyn K (30.6 mg, 0.043 mmol) was dissolved in CH$_2$Cl$_2$ (5 ml). 15% Aqueous NaOH (5 ml) was added, followed by K$_2$CO$_3$ (0.30 g) and benzyltriethylammonium chloride (0.41 g). 1-Iodoethane (2.0 ml) was added and the reaction mixture was vigorously stirred at RT under N$_2$ for 72 hrs. CH$_2$Cl$_2$ (50 ml) and water (50 ml) were added. The phases were separated. The organic layer was washed with water (2×), dried over K$_2$CO$_3$ and concentrated in vacuo. The residue was purified over a flash SiO$_2$ column (10 g/EtOAc). Concentration of pure fractions furnished a) compound (15.1 mg) and b) compound 3'-O-ethyl Spinosyn K; 5.5 mg, 34%) $^1$H-NMR (CDCl$_3$) δ 6.72 (1H, bs), 3.82 (1H, m), 3.57 (2H, m), 2.18 (6H, 2× CH$_3$, s), 1.17 (3H, CH$_3$, t: 7.3 Hz) ppm.

Example A25
3'-O-Ethyl Spinosyn L

Compound Spinosyn L (330 mg, 0.451 mmol) was dissolved in CH$_2$Cl$_2$ (15 ml). 20% Aqueous NaOH (10 ml) was added, followed by K$_2$CO$_3$ (1.30 g) and benzyltriethylammonium chloride (1.1 g). 1-Iodoethane (5.0 ml) was added and the reaction mixture was vigorously stirred at RT under N$_2$ for 96 hrs. CH$_2$Cl$_2$ (50 ml) and water (50 ml) were added. The phases were separated. The organic layer was washed with water (2×), dried over K$_2$CO$_3$ and concentrated in vacuo. The residue was purified over a flash SiO$_2$ column (85 g/EtOAc). Concentration of pure fractions furnished compound 3'-O-ethyl Spinosyn L; 127 mg, 37% $^1$H-NMR (CDCl$_3$) δ 6.64 (1H, bs), 5.37 (1H, bs), 3.60 (1H, m), 2.12 (6H, 2× CH$_3$, s), 1.17 (3H, CH$_3$, t: 7.4 Hz) ppm; $^{13}$C-NMR (CDCl$_3$) δ 66.1 (O—CH$_2$—), 16.3 (CH$_3$) ppm.

Example A26
3'-O-Allyl Spinosyn J

Compound Spinosyn J (370 mg, 0.515 mmol) was dissolved in CH$_2$Cl$_2$ (15 ml). 15% Aqueous NaOH (10 ml) was added, followed by K$_2$CO$_3$ (1.40 g) and benzyltriethylammonium chloride (0.98 g). Allyl bromide (3.0 ml) was added and the reaction mixture was vigorously stirred at RT under N$_2$ for 28 hrs. CH$_2$Cl$_2$ (50 ml) and water (50 ml) were added. The phases were separated. The organic layer was washed with water (2×), dried over K$_2$CO$_3$ and concentrated in vacuo. The residue was dissolved in toluene (10 ml) and heated to reflux for 10 min. The solution was cooled to RT and concentrated in vacuo. The residue was purified over a flash SiO$_2$ column (80 g/EtOAc). Concentration of pure fractions furnished compound 3'-O-allyl Spinosyn J; 121 mg, 31% $^1$H-NMR (CDCl$_3$) δ 6.67 (1H, bs), 5.77 (1H, m), 5.22 (1H, bd: 17.2 Hz), 5.08 (1H, bd: 10.3 Hz), 4.07 (2H, bd: 4.2 Hz), 2.13 (6H, 2× CH$_3$, s) ppm; Elemental Analysis: for C$_{43}$H$_{67}$NO$_{10}$ calc. C 68.14, H 8.91, N 1.85; found C 68.38, H 9.10, N 1.77.

Example A27
3'-O-Propargyl Spinosyn J

Compound Spinosyn J (392 mg, 0.546 mmol) was dissolved in CH$_2$Cl$_2$ (15 ml). 15% Aqueous NaOH (10 ml) was added, followed by K$_2$CO$_3$ (1.50 g) and benzyltriethylammonium chloride (1.10 g). Propargyl bromide (80% solution in toluene; 4.0 ml) was added and the reaction mixture was vigorously stirred at RT under N$_2$ for 40 hrs. CH$_2$Cl$_2$ (50 ml) and water (50 ml) were added. The phases were separated. The organic layer was washed with water (2×), dried over K$_2$CO$_3$ and concentrated in vacuo. The residue was dissolved in toluene (10 ml) and heated to reflux for 20 min. The solution was cooled to RT and concentrated in vacuo. The residue was purified over a flash SiO$_2$ column (80 g/EtOAc). Concentration of pure fractions furnished compound 3'-O-propargyl Spinosyn J; 138 mg, 33% $^1$H-NMR (CDCl$_3$) δ 6.66 (1H, bs), 4.22 (2H, m), 3.66 (1H, dd: 9.4, 3.3 Hz), 2.37 (1H, dd: 2.4, 2.4 Hz), 2.12 (6H, 2× CH$_3$, s) ppm; Elemental Analysis: for C$_{43}$H$_{65}$NO$_{10}$ calc. C 68.32, H 8.67, N 1.85; found C 68.39, H 8.62, N 1.75.

Example A28
3'-O-(Cyclopropyl)methyl Spinosyn J

Compound Spinosyn J (470 mg, 0.655 mmol) was dissolved in CH$_2$Cl$_2$ (10 ml). 15% Aqueous NaOH (15 ml) was added, followed by K$_2$CO$_3$ (1.50 g) and benzyltriethylammonium chloride (1.0 g). (Cyclopropyl)methyl bromide (3.9 ml) was added and the reaction mixture was vigorously stirred at RT under N$_2$ for 72 hrs. CH$_2$Cl$_2$ (50 ml) and water (50 ml) were added. The phases were separated. The organic layer was washed with water (2×), dried over K$_2$CO$_3$ and concentrated in vacuo. The residue was purified over a flash SiO$_2$ column (90 g/EtOAc). Concentration of pure fractions furnished a) compound Spinosyn J (216 mg) and b) compound 3'-O-(cyclopropyl)methyl Spinosyn J; 25.1 mg, 9% $^1$H-NMR (CDCl$_3$) δ 6.71 (1H, bs), 3.07 (1H, m), 2.17 (6H, 2× CH$_3$, s), 0.48 (1H, m), 0.18 (1H, m) ppm.

Example A29
3'-O-(Chloro)methyl Spinosyn J

Compound Spinosyn J (510 mg, 0.71 mmol) was dissolved in CH$_2$Cl$_2$ (5.0 ml). K$_2$CO$_3$ (1.10 g) was added. The reaction flask was immersed in a water bath (10° C.) and 15% aqueous NaOH (10 ml) was added with vigorous stirring, followed by benzyltriethylammonium chloride (1.20 g). Chloroiodomethane (5.0 ml) was added and the reaction mixture was vigorously stirred at RT under N$_2$ for 72 hrs. CH$_2$Cl$_2$ (100 ml) and water (50 ml) were added. The phases were separated. The organic layer was washed with water (2×), dried over K$_2$CO$_3$ and concentrated in vacuo. The residue was purified over a flash SiO$_2$ column (70 g/EtOAc). Concentration of pure fractions furnished a) compound (111 mg) and b) compound 3'-O-(chloro)methyl Spinosyn J; 120 mg, 28%) $^1$H-NMR (CDCl$_3$) δ 6.66 (1H, bs), 4.70 (2H, bs), 3.74 (1H, dd: 9.5, 3.4 Hz), 2.12 (6H, 2× CH$_3$, s) ppm; Elemental Analysis: for C$_{41}$H$_{64}$NO$_{10}$Cl calc. C 64.25, H 8.42, N 1.83; found C 64.49, H 8.37, N 1.74.

Example A30
3'-O-(Pentafluorophenyl)-thionocarbonate of Spinosyn L

Compound Spinosyn L (733 mg, 1.0 mmol) was dissolved in dry pyridine (5.0 ml). The solution was stirred at RT (water bath) under nitrogen. (Pentafluorophenyl) chlorothionoformate (1.5 ml, an excess) was added dropwise during 5 min. After 10 min. PhH (50 ml) and EtOAc (50 ml) were added. The solution was extracted with 5% aq. NaHCO$_3$ (3×). The organic phase was dried over anh. Na$_2$SO$_4$ and concentrated in vacuo. The residue was purified over a flash SiO$_2$ column (80 g/EtOAc) to give compound 3'-O-(pentafluorophenyl)-thionocarbonate of Spinosyn L; 712 mg, 74% $^1$H-NMR (CDCl$_3$) δ 6.69 (1H, bs), 5.46 (1H, dd: 9.5, 3.2 Hz), 5.40 (1H, bs), 3.77 (1H, dd: 3.1, 2.0 Hz), 2.23 (6H, CH$_3$, s), 1.64 (3H, CH$_3$, bs) ppm; $^{13}$C-NMR (CDCl$_3$) δ 191.5 (C=S), 87.0 (C$_3$—O) ppm.

Example A31
3'-Deoxy Spinosyn L

Compound 3'-O-(pentafluorophenyl)-thionocarbonate of Spinosyn L (690 mg, 0.72 mmol) was dissolved in dry toluene (10 ml). Tri-n-butyltin hydride (0.50 ml, 1.86 mmol) was added at RT under nitrogen. AIBN (20 mg) was then added. The reaction mixture was heated under reflux for 15 min. After cooling to RT, the solution was concentrated in vacuo. The residue was purified on a flash $SiO_2$ column (75 g/EtOAc) to give compound 3'-deoxy Spinosyn L; 236 mg, 46% $^1$H-NMR (CDCl$_3$) δ 6.68 (1H, bs), 5.39 (1H, bs), 3.53 (2H, m), 2.15 (6H, 2× CH$_3$, s), 1.63 (3H, CH$_3$, bs) ppm; Elemental Analysis: for $C_{41}H_{65}NO_9$ calc. C 68.78, H 9.15, N 1.96; found C 68.70, H 8.87, N 2.03.

Example A32
3'-O-(Isopropyl)carbonate of Spinosyn J

Compound Spinosyn J (330 mg, 0.46 mmol) was dissolved in dry HMPA (3.5 ml). Silver carbonate (0.66 g) was added. The mixture was stirred at RT under nitrogen for 5 min. 2-Iodopropane (1.5 ml) was introduced. The reaction mixture was stirred for 18 hrs. EtoAc (20 ml) and PhH (100 ml) were added. The solution was extracted with water (3×). The organic layer was dried over $K_2CO_3$ and concentrated in vacuo. The residue was separated on a flash $SiO_2$ column (20 g/EtOAc) to give a) compound (98 mg) and b) compound (3'-O-(isopropyl)carbonate of Spinosyn J; 87 mg; 34%) $^1$H-NMR (CDCl$_3$) δ 6.68 (1H, bs), 4.84 (2H, m), 3.54 (3H, m), 2.14 (6H, 2× CH$_3$, s), 1.23 (6H, 2× CH$_3$, 6: 6.2 Hz) ppm; Elemental Analysis: for $C_{44}H_{69}NO_{12}$ calc. C 65.73, H 8.65, N 1.74; found C 65.63, H 8.78, N 1.75.

Example A33
3'-O-Dichloroacetyl Spinosyn L

Compound Spinosyn L (244 mg, 0.33 mmol) was dissolved in dry pyridine (4 ml). Dichloroacetic acid anhydride (0.50 ml, an excess) was added and stirring at RT under nitrogen was continued for 16 hrs. EtOAc (50 ml) and PhH (100 ml) were added. The solution was washed with 5% aq. NaHCO$_3$ (3×). The organic layer was dried over anh. $K_2CO_3$ and concentrated in vacuo. The residue was purified over a flash $SiO_2$ column (80 g/EtOAc) to give compound 3'-O-dichloroacetyl Spinosyn L; 129 mg, 46% EI MS m/z 842 (M+); $^1$H-NMR (CDCl$_3$) δ 6.71 (1H, bs), 5.98 (1H, s), 5.43 (1H, bs), 5.14 (1H, dd: 9.6, 3.2 Hz), 3.57 (3H, m), 2.18 (6H, 2× CH$_3$, s), 1.66 (3H, CH$_3$, s) ppm.

Example A34
3'-O-Dichloroacetyl Spinosyn J

Compound Spinosyn J (302 mg, 0.42 mmol) was dissolved in dry pyridine (5 ml). Dichloroacetic acid anhydride (0.50 ml, an excess) was added and stirring at RT under nitrogen was continued for 16 hrs. EtOAc (50 ml) and PhH (100 ml) were added. The solution was washed with 5% aq. NaHCO$_3$ (3×). The organic layer was dried over anh. $K_2CO_3$ and concentrated in vacuo. The residue was purified over a flash $SiO_2$ column (80 g/EtOAc) to give compound 3'-O-dichloroacetyl Spinosyn J; 293 mg, 84% $^1$H-NMR (CDCl$_3$) δ 6.66 (1H, bs), 5.95 (1H, s), 5.07 (1H, dd: 8.7, 3.2 Hz), 3.52 (3H, m), 2.15 (6H, 2× CH$_3$, s) ppm; Elemental Analysis: for $C_{42}H_{63}NO_{11}Cl_2$ calc. C 60.86, H 7.66, N 1.70; found C 60.59, H 7.65, N 1.96.

Example A35
3'-O-n-Butyl Spinosyn J

Compound Spinosyn J (296 mg, 0.41 mmol) was dissolved in CH$_2$Cl$_2$ (5.0 ml). K$_2$CO$_3$ (1.10 g) was added. The reaction flask was immersed in a water bath (10° C.) and 15% aqueous NaOH (10 ml) was added with vigorous stirring, followed by benzyltriethylammonium chloride (0.88 g). 1-Iodobutane (3.0 ml) was added and the reaction mixture was vigorously stirred at RT under N$_2$ for 40 hrs. CH$_2$Cl$_2$ (100 ml) and water (50 ml) were added. The phases were separated. The organic layer was washed with water (2×), dried over K$_2$CO$_3$ and concentrated in vacuo. The residue was purified over a flash SiO$_2$ column (60 g/EtOAc). Concentration of pure fractions furnished a) compound (211 mg) and b) compound 3'-O-n-butyl Spinosyn J; 20.5 mg, 22% $^1$H-NMR (CDCl$_3$) δ 6.71 (1H, bs), 3.58 (2H, m), 2.18 (6H, 2× CH$_3$, s), 0.88 (3H, CH$_3$, t: 7.3 Hz) ppm; $^{13}$C-NMR (CDCl$_3$) δ 70.5 (O—CH$_2$), 32.8 (CH$_2$), 30.4 (CH$_2$), 14.5 (CH$_3$) ppm.

Example A36
3'-O-Isobutyryl Spinosyn J

Compound Spinosyn J (359 mg, 0.50 mmol) was dissolved in dry pyridine (4 ml). N,N-Dimethylaminopyridine (66 mg) was added. The solution was cooled under nitrogen to 10° C. (water bath). Isobutyric chloride (2.0 ml, an excess) was added and stirring at RT under nitrogen was continued for 70 hrs. EtOAc (50 ml) and PhH (100 ml) were added. The solution was washed with 5% aq. NaHCO$_3$ (3×). The organic layer was dried over anh. K$_2$CO$_3$ and concentrated in vacuo. The residue was purified over a flash SiO$_2$ column (80 g/EtOAc) to give compound 3'-O-isobutyryl Spinosyn J; 364 mg, 92% $^1$H-NMR (CDCl$_3$) δ 6.70 (1H, bs), 5.02 (1H, dd: 9.6, 3.2 Hz), 3.57 (2H, m), 3.49 (1H, dd: 3.2, 1.8 Hz), 2.16 (6H, 2× CH$_3$, s), 1.15 (6H, 2× CH$_3$, d: 7.0 Hz) ppm; Elemental Analysis: for $C_{44}H_{69}NO_{11}$ calc. C 67.06, H 8.82, N 1.78; found C 66.78, H 8.86, N 1.75.

Example A37
3'-O-Pivaloyl Spinosyn J

Compound Spinosyn J (426 mg, 0.59 mmol) was dissolved in dry pyridine (4 ml). N,N-Dimethylaminopyridine (116 mg) was added. The solution was cooled under nitrogen to 10° C. (water bath). Pivaloyl chloride (2.0 ml, an excess) was added and stirring at RT under nitrogen was continued for 70 hrs. EtOAc (50 ml) and PhH (100 ml) were added. The solution was washed with 5% aq. NaHCO$_3$ (3×). The organic layer was dried over anh. K$_2$CO$_3$ and concentrated in vacuo. The residue was purified over a flash SiO$_2$ column (80 g/EtoAc) to give compound 3'-O-pivaloyl Spinosyn J; 433 mg, 91% EI MS m/z 802 (M+); $^1$H-NMR (CDCl$_3$) δ 6.65 (1H, bs), 4.94 (1H, dd: 9.8, 3.2 Hz), 3.52 (2H, m), 3.45 (1H, dd: 3.2, 1.8 Hz), 2.14 (6H, 2× CH$_3$, s), 1.14 (9H, 3× CH$_3$, s) ppm.

Example A38
5,6-Dihydro-3'-O-ethyl Spinosyn J

Compound 5,6-dihydro-Spinosyn J (399 mg, 0.554 mmol) was dissolved in CH$_2$Cl$_2$ (5.0 ml). K$_2$CO$_3$ (1.10 g) was added. The reaction flask was immersed in a water bath (10° C.) and 15% aqueous NaOH (10 ml) was added with vigorous stirring, followed by tetrabutylammonium hydrogen sulfate (0.90 g). 1-Iodoethane (5.0 ml) was added and the reaction mixture was vigorously stirred at RT under N$_2$ for 72 hrs. CH$_2$Cl$_2$ (100 ml) and water (50 ml) were added. The phases were separated. The organic layer was washed with water (2×), dried over K$_2$CO$_3$ and concentrated in vacuo. The residue was purified over a flash SiO$_2$ column (100 g/EtOAc). Concentration of pure fractions furnished compound 5,6-dihydro-3'-O-ethyl Spinosyn J; 217 mg, 52% $^1$H-NMR (CDCl$_3$) δ 6.72 (1H, bs), 3.57 (1H, m), 3.49 (2H, m), 2.13 (6H, 2× CH$_3$, s), 1.14 (3H, CH$_3$, t: 7.3 Hz) ppm; Elemental Analysis: for $C_{42}H_{69}NO_{10}$ calc. C 67.44, H 9.30, N 1.87; found C 67.64, H 8.95, N 1.87.

Example A39
5,6-Dihydro-3'-O-n-propyl Spinosyn J

Compound 5,6-dihydro-Spinosyn J (86 mg, 0.119 mmol) was dissolved in CH$_2$Cl$_2$ (3.0 ml). K$_2$CO$_3$ (0.68 g) was added. The reaction flask was immersed in a water bath (10° C.) and 20% aqueous NaOH (6 ml) was added with vigorous stirring, followed by tetrabutylammonium hydrogen sulfate (0.81 g). 1-Iodopropane (1.20 ml) was added and the reaction mixture was vigorously stirred at RT under N$_2$ for 20 hrs. CH$_2$Cl$_2$ (100 ml) and water (50 ml) were added. The phases were separated. The organic layer was washed with water (2×), dried over $K_2CO_3$ and concentrated in vacuo. The residue was purified over a flash $SiO_2$ column (25 g/EtOAc). Concentration of pure fractions furnished compound 5,6-dihydro-3'-O-n-propyl Spinosyn J; 55.0 mg, 60% $^1$H-NMR (CDCl$_3$) δ 6.78 (1H, bs), 3.55 (3H, m), 2.16 (6H, 2× CH$_3$, s), 0.89 (3H, CH$_3$, t: 7.5 Hz) ppm; $^{13}$C-NMR (CDCl$_3$) δ 72.5 (O—CH$_2$—), 23.9 (CH$_2$) and 11.2 (CH$_3$) ppm.

Example A40
2'-Epi-2'-O-ethyl Spinosyn H

Compound 2'-O-acetyl-2'-epi Spinosyn H (502 mg, 0.664 mmol) was dissolved in CH$_2$Cl$_2$ (4.0 ml). K$_2$CO$_3$ (1.10 g) was added. The reaction flask was immersed in a water bath (10° C.) and 20% aqueous NaOH (10 ml) was added with vigorous stirring, followed by tetrabutylammonium hydrogen sulfate (0.82 g). 1-Iodoethane (4.0 ml) was added and the reaction mixture was vigorously stirred at RT under N$_2$ for 22 hrs. CH$_2$Cl$_2$ (100 ml) and water (50 ml) were added. The phases were separated. The organic layer was washed with water (2×), dried over K$_2$CO$_3$ and concentrated in vacuo. The residue was purified over a flash SiO$_2$ column (80 g/EtOAc). Concentration of pure fractions furnished compound 2'-epi-2'-O-ethyl Spinosyn H; 132 mg, 27% $^1$H-NMR (CDCl$_3$) δ 6.66 (1H, bs), 4.70 (1H, d: 3.7 Hz), 2.12 (6H, 2× CH$_3$, s), 1.14 (3H, CH$_3$, t: 7.5 Hz) ppm; $^{13}$C-NMR (CDCl$_3$) δ 66.8 (O—CH$_2$—) and 16.2 (CH$_3$) ppm.

Example A41
5,6-Dihydro-3'-O-n-butyl Spinosyn J

Compound 5,6-dihydro-Spinosyn J (93 mg, 0.129 mmol) was dissolved in CH$_2$Cl$_2$ (3.0 ml). K$_2$CO$_3$ (0.70 g) was added. The reaction flask was immersed in a water bath (10° C.) and 20% aqueous NaOH (10 ml) was added with vigorous stirring, followed by tetrabutylammonium hydrogen sulfate (0.66 g). 1-Iodobutane (2.0 ml) was added and the reaction mixture was vigorously stirred at RT under N$_2$ for 20 hrs. CH$_2$Cl$_2$ (100 ml) and water (50 ml) were added. The phases were separated. The organic layer was washed with water (2×), dried over K$_2$CO$_3$ and concentrated in vacuo. The residue was purified over a flash SiO$_2$ column (25 g/EtOAc). Concentration of pure fractions furnished compound (5,6-dihydro-3'-O-n-butyl Spinosyn J; 63 mg, 63% $^1$H-NMR (CDCl$_3$) δ 6.78 (1H, bs), 3.57 (3H, m), 2.16 (6H, 2× CH$_3$, s), 0.87 (3H, CH$_3$, t: 7.2 Hz) ppm; Elemental Analysis: for $C_{44}H_{73}NO_{10}$ calc. C 68.10, H 9.48, N 1.80; found C 68.23, H 9.65, N 1.83.

Example A42
2'-O-(S-Methyl-N-benzylcarbonimidothioyl) Spinosyn H

To a cold (0° C.), well stirred suspension of sodium hydride (50% dispersion in mineral oil, 12.0 mg, 0.26 mmol) in anhydrous THF (1.5 mL), a solution of Spinosyn H, 0.1 g, 0.14 mmol) in THF (1.5 mL) was added dropwise during 2–3 min. The mixture was stirred for 30 min at 0° C. then N-benzylisothiocyanate (25 μL, 0.18 mmol) was added in one portion by syringe. The cooling bath was removed and the mixture stirred for 4.5 h at ambient temperature. Methyl iodide (30 μL, 0.48 mmol) was then added in one portion and the mixture stirred for 30 min. The solvent was then removed in vacuo and the residue was dissolved in anhydrous ether (20 mL). Any insolubles were removed by filtration through Celite and washed with ether. Concentration of the combined filtrate and wash left 0.13 g of crude 2'-O-(S-methyl-N-benzylcarbonimidothioyl) Spinosyn H which was purified by flash column chromatography over silica (40 mL) using 3.5% methanol in dichloromethane as eluent to give 0.12 g (97%) of pure 2'-O-(S-Methyl-N-benzylcarbonimidothioyl) Spinosyn H as a colorless oil: $^1$HNMR (CDCl$_3$) δ 2.48 (s,1, SCH$_3$), 5.40 (m,1, H-2').

Example A43
2'-O-Trichloroacetimidoyl Spinosyn H X504447

To a cold (0° C.), well stirred suspension of sodium hydride (50% dispersion in mineral oil, 12 mg, 0.26 mmol) in anhydrous THF (2.0 mL), a solution of Spinosyn H (0.1 g, 0.14 mmol) in THF (2.0 mL) was added dropwise during 2–3 min. The mixture was stirred at 0° C. for 20 min., then trichloroacetonitrile (20 μL, 0.2 mmol) was added in one portion and the mixture stirred at 0° C. for 2 h. Glacial acetic acid (16 μL, 0.27 mmol) was then added in one portion and the reaction mixture stirred in the cold for 10 min. The solvent was then removed in vacuo and the residue of crude 2'-O-trichloroacetimidoyl Spinosyn H purified by flash chromatography over silica (40 mL) using 3% methanol in dichloromethane as eluent. Pure 2'-O-trichloroacetimidoyl Spinosyn H (95 mg, 79%) was obtained as a white foam: $^1$HNMR (CDCl$_3$) δ 5.30 (m,1, H-2'), 8.36 (s,1, =NH); mass spectrum (CI,CH$_4$), m/z (rel.intensity) 861 (MH$^+$,4), 142 (100).

Example A44
3'-O-Trifluoromethanesulfonyl Spinosyn J

To a cold (−10° C.), well stirred solution of Spinosyn J (0.2 g, 0.28 mmol) and dry pyridine (0.1 mL, 1.26 mmol) in dry CH$_2$Cl$_2$ (5 mL), triflic anhydride (60 μL, 0.35 mmol) was added in one portion by syringe. The resulting orange brown solution was stired at −10° C. for 1.5 h, then diluted with CH$_2$Cl$_2$ (20 mL) and washed successively with water (5 ml), sat. Na$_2$CO$_3$ (4 mL), water again (5 mL) and, finally, dried (MgSO$_4$). Concentration left 216 mg (91%) of 3'-O-trifluoromethanesulfonyl Spinosyn J which was pure enough to be used without further purification: $^1$HNMR (CDCl$_3$) δ 4.98 (dd, 1, H-3').

Example A45
3:1 Mixture of 9-O-(2,3,4-Tri-O-ethyl-α-L-rhamnosyl) Spinosyn A 9-Psa: 9-O-(2,3,4-Tri-O-ethyl-β-L-rhamnosyl) Spinosyn A 9-Psa To a cold (0° C.), well stirred solution of Spinosyn A 9-Psa (2.1 g, 3.86 mmol) and pyridinium p-toluenesulfonate (1.3 g, 5.17 mmol) in dry CH$_2$Cl$_2$ (200 mL) containing powdered 4A molecular sieves (2.6 g), a solution of O-(2, 3,4-tri-O-ethyl-α-L-rhamnopyranosyl) trichloroacetimidate (5.0 g, 12.75 mmol) in CH$_2$Cl$_2$ (20 mL) was added dropwise during 20 min. After 3 h at 0° C., more imidate (2.0 g) in CH$_2$Cl$_2$ (6 mL) was added in one portion. The cooling bath was then removed and the reaction mixture stirred at ambient temperature for 16 h. More imidate (0.8 g) was then added. After an additional 7 h, the reaction mixture was filtered through Celite, the Celite washed with CH$_2$Cl$_2$ (25 mL) and the combined filtrate and wash washed with sat. Na$_2$CO$_3$ (2×80 mL) and brine (50 mL) and dried (MgSO4). Concentration left 11.5 g of residue which was flash chromatographed over silica (700 mL) using 3% MeOH in CH$_2$Cl$_2$ to yield 2.0 g (67%) compound a) 9-O-(2,3,4-Tri-O-ethyl-α-L-rhamnosyl) Spinosyn A 9-Psa: 9-O-(2,3,4-Tri-O-ethyl-β-L-rhamnosyl) Spinosyn A 9-Psa as a 3:1 mixture. This mixture was separated by hplc in ten portions of ~200 mg over a 21.4 mm (i.d.)×25 cm (1) Rainin reverse phase C18 column using 4% H$_2$O (containing 0.01% NH$_4$OH) in MeOH as eluent. The β-anomer elutes first. Compound b) 9-O-(2,3,4-tri-O-ethyl-β-L-rhamnosyl) Spinosyn A 9-Psa: 0.35 g; colorless foam; 1HNMR (CDCl$_3$) d 4.36 (s, 1, H-1'), 4.45 (m,2, H-1", H-9). Compound c) 9-O-(2,3,4-tri-O-ethyl-α-L-rhamnosyl) Spinosyn A 9-Psa: 1.2 g; colorless foam; 1HNMR (CDCl$_3$) δ 4.43 (bd, 1,H-1"), 4.77 (s,1, H-1').

Example A46
3'-Keto Spinosyn J

A suspension of N-chlorosuccinimide (104.7 mg, 0.78 mmol) in dichloromethane (2.6 ml) was cooled to −78° C.

under nitrogen. Diisopropyl sulfide (125 μL, 0.86 mmol) was added to this suspension, and the mixture was stirred at −78° C. for 0.5 hr. Spinosyn J (184.6 mg, 0.26 mmol) in dichloromethane (1 mL) was then added slowly. When the addition had been completed the solution was stirred at −78° C. for 6.25 hr, and triethylamine (109 μL, 0.78 mmol) was then added, and the solution was warmed to room temperature, giving a red color. After warming, Et$_2$O (6 mL) was added and a precipitate formed. Dichloromethane was added to dissolve the precipitate and was then combined with the Et$_2$O solution and washed with 0.1 N HCl, then washed with brine, dried with MgSO$_4$ and evaporated at room temperature. The resulting colorless glass (215 mg) purified by flash chromatography with 5% MeOH in dichloromethane, giving 3'-keto Spinosyn J as a colorless semi-solid (151.2 mg, 82%). Partial $^1$H-NMR (CDCl$_3$) δ 6.78 (bs, 1H); 5.88 (d, 1H); 5.81 (dt, 1H); 5.03 (s, 1H); 4.70 (m, 1H); 4.44 (bd, 1H); 4.35 (bd, 1H); $^{13}$C-NMR (CDCl$_3$) δ 204, 203 ppm.

Example A47
(4'R)-4'-Desmethoxy-4'-amino Spinosyn A

To a solution of 4'-keto Spinosyn K (115.3 mg, 0.16 mmol) in methanol (2 ml), ammonium acetate (149.3 mg, 1.9 mmol) was added followed by sodium cyanoborohydride (10 mg, 0.16 mmol). The reaction mixture stirred at room temperature for 7 hours. The mixture was then diluted with 1 N HCl and washed with ether. The aqueous was brought to pH 11 with 5 N NaOH, and saturated with NaCl. It was then extracted with fresh ether. This ether was dried with MgSO$_4$, and evaporated at room temperature under reduced pressure. The crude product was seperated by chromatography on silica, eluting with 10% methanol in dichloromethane and then 50% methanol in dichloromethane in a single step. (4'R)-4'-Desmethoxy-4'-amino Spinosyn A (23.3 mg; 20% yield) was a colorless glass, isolated as the most polar material, FDMS, m/e (relative intensity) 717 (60), 716 (M$^+$, 100), 142 (35), 114 (30).

Example A48
2'-Oxo-3'-en-4'-desmethoxy Spinosyn H

The reaction was run as described in Example 3 for the preparation of Spinosyn A 9-Psa using a 35:65 mixture of Spinosyn H and Spinosyn J (5.02 gm, 7.0 mmol), N-chlorosuccinimide (2.68 gm, 20 mmol), dichloromethane (90 mL), dimethylsulfide (3.1 mL, 42.0 mmol), triethylamine 2.8 mL, 21.0 mmol) and potassium carbonate (12.8 gm, 92.2 mmol), respectively. This gave Spinosyn A 9-PSa (2.32 gm; 94% yield, base on Spinosyn J) and 2'-oxo-3'-en-4'-desmethoxy Spinosyn H (920 mg; 55% yield based on Spinosyn H), FDMS, m/e (relative intensity) 684 (M$^+$, 30), 683 (100) as white solids.

Example A49
2'-(a-L-2,3,4-Tri-O-methylrhamnosyl) Spinosyn H3'-(a-L-2,3,4-tri-O-methylrhamnosyl) Spinosyn J To a mixture of Spinosyn H and Spinosyn J (35:65, respectivly; 1.0 gm, 1.44 mmol) in anhydrous dichloromethane, 1-bromo-2,3,4-tri-O-acetylrhamnose[1] (1.26 g, 3.57 mmol) was added followed by diisopropylamine (301 ml, 1.73 mmol) and then silver triflate (456.8 mg, 1.73 mmol). The reaction mixture was stirred at room temperature in the dark for 2 days. The mixture was then diluted with dichloromethane and washed with water. The dichloromethane was filtered to remove insoluables, dried with MgSO$_4$, and evaporated at room temperature under reduced pressure. The crude product was seperated from unreacted starting materials by chromatography on silica, eluting with 5% ethanol in dichloromethane. The crude product mixture was purified by preparative HPLC on a C$_{18}$ column, eluting with acetonitrile:methanol:0.1% NH$_4$OAc (42.5:42.5:12.5 to 45:45:10 in a 90 minute linear gradient). This gave compound a) 2'-(α-L-2,3,4-tri-O-methylrhamnosyl) Spinosyn H (47 mg), FDMS, m/e (relative intensity) 990 (M$^+$, 100) and compound b) 3'-(α-L-2,3,4-tri-O-methylrhamnosyl) Spinosyn J (16 mg), FDMS, m/e (relative intensity) 990 (M$^+$, 25), 989 (70), 988 (100) as white solids.

[1] Fisher, E.; Bergmann, M.; Rabe, A. *Chem. Ber.* 1920, 53, 2363.

Example A50
2'-(N-Hydroxy)imino Spinosyn H

To a solution of crude 2'-keto Spinosyn H (238.3 mg, 0.33 mmol) and hydroxylamine hydrochloride (24.9 mg, 0.36 mmol) in absolute ethanol (10 ml), anhydrous sodium acetate (60.0 mg, 0.73 mmol) was added. The reaction mixture stirred at room temperature for 3 hours. The mixture was then diluted with dichloromethane, washed with water, brine, dried with Na$_2$SO$_4$ and evaporated at room temperature under reduced pressure. The product was purified by chromatography on silica, eluting with 5% methanol in dichloromethane. This gave 2'-(N-Hydroxy)imino Spinosyn H (73.9 mg) as a white solid, FDMS, m/e (relative intensity) 731 (M$^+$, 50), 730 (100).

Example A51
4'-Keto Spinosyn K

The reaction was run as described in Example A46 using Spinosyn K (1.49 gm, 2.07 mmol). This gave 4'-keto Spinosyn K (1.48 gm; ~100% yield) as a sticky white solid, FDMS, m/e (relative intensity) 715 (M$^+$, 100).

Example A52
2'-(N-Hydroxy)imino-4'-desmesthoxy-3',4'-dehydro Spinosyn H

The reaction was run as described in Example A50, starting with 2'-oxo-3'-en-4'-desmethoxy Spinosyn H (579.8 mg, 0.85 mmol). This gave 2'-(N-Hydroxy)imino-4'-desmesthoxy-3',4'-dehydro Spinosyn H (223 mg; 42% yield, based on recovered starting material) as an off white solid, FDMS, m/e (relative intensity) 699 (M$^+$, 70), 698 (100).

Example A53
9-O-(2,3,4-Tri-O-ethyl-α-L-rhamnosyl Spinosyn A 9-Psa Hemiglutarate salt Compound 9-O-(2,3,4-tri-O-ethyl-α-L-rhamnosyl) Spinosyn A 9-Psa (99.6 mg, 0.128 mmol) was dissolved in 2 mL acetone and a solution of glutaric acid (8.5 mg, 0.064 mmol) in 2 mL acetone was added. The solution was stirred for 3 hr then the solvent was removed in vacuo. This gave compound 9-O-(2,3,4-Tri-O-ethyl-α-L-rhamnosyl Spinosyn A 9-Psa Hemiglutarate salt, 105.7 mg. Anal. Calc. for C$_{44}$H$_{71}$N$_{10}$·½(C$_5$H$_8$O$_4$): C 66.48, H 8.99, N 1.67; Found C 66.30, H 8.58, N 1.71; mp. 76–82° C.

Example A54
3'-O-Ethyl Spinosyn J Hemiglutarate salt

Compound 3'-O-ethyl Spinosyn J(130.4 mg, 0.174 mmol) was dissolved in 3 mL acetone and a solution of glutaric acid (11.5 mg, 0.087 mmol) in 2 mL acetone was added. The solution was stirred solution over night. Evaporation of solvent gave compound 3'-O-ethyl Spinosyn J hemiglutarate salt, 131 mg. Anal calcd. for C$_{42}$H$_{67}$NO$_{10}$·½(C$_5$H$_8$O$_4$) C 65.82, H 8.81, N 1.72; Found C 65.65, H 8.46, N 1.72; mp. 75–82° C.

Example A55
3'-O-Pentadeuterioethyl Spinosyn J Hemiglutarate salt

Compound 3'-O-pentadeuterioethyl Spinosyn J (97.4 mg, 0.129 mmol) was dissolved in 3 mL acetone and a solution of glutaric acid (8.6 mg, 0.065 mmol) in 2 mL acetone was added. The solution was stirred at RT for 2 hr. Evaporation of the solvent under vacuum gave compound 3'-O-pentadeuterioethyl Spinosyn J hemiglutarate salt, 102 mg.

Anal. calcd. for $C_{42}H_{62}NO_{10}D_5 \cdot \frac{1}{2}(C_5H_8O_4)$ C 65.02, H 9.27, N 1.70; Found C 65.12, H 9.01, N 1.85; mp. 104–114° C.

Example A56
5,6-Dihydro-3'-O-n-propyl Spinosyn J Hemiglutarate salt

Compound 5'6-dihydro-3'-O-n-propyl Spinosyn J (88.3 mg, 0.115 mmol) was dissolved in 3 mL acetone and a solution of glutaric acid (7.5 mg, 0.056 mmol) in 2 mL acetone was added. Stirred solution at RT overnight. Evaporation of the solvent under vacuum gave compound 5,6-dihydro-3'-O-propyl-Spinosyn J hemiglutarate salt, 86.1 mg. Anal. calcd. for $C_{43}H_{71}NO_{10} \cdot \frac{1}{2}(C_5H_8O_4)$ C 65.99, H 9.12, N 1.69; Found C 65.30, H 10.00, N 1.77; mp. 74–84° C.

Example A57
3'-O-Ethyl Spinosyn L Hemiglutarate salt

Compound 3'-O-ethyl Spinosyn L(84.2 mg, 0.110 mmol) was dissolved in 3 mL acetone and a solution of glutaric acid (7.5 mg, 0.056 mmol) in 3 mL acetone was added. The solution was stirred at RT overnight. Evaporation of the solvent gave compound 3'-O-ethyl Spinosyn L hemiglutarate salt, 91.0 mg). Anal. calcd. for $C_{43}H_{69}NO_{10} \cdot \frac{1}{2}(C_5H_8O_4)$ C 66.16, H 8.90, N 1.69; Found C 65.43, H 9.16, N 1.69; mp. 77–82° C.

Example A58
(3'S)-4'-Nor-3'-deoxy-3'-[(R)-(α-methoxy,α-propionoxy) methyl] Spinosyn J and (3'S)-4'-nor-3'-deoxy-3'-[(S)-(α-methoxy,α-propionoxy)methyl] Spinosyn J Compound 3'-O-trifluoromethanesulfonyl Spinosyn J (496 mg, 0.583 mmol) was dissolved in dry DMF (14 ml). Cesium propionate compound with propionic acid (1.09 g, an excess) was added. The reaction mixture was cooled to RT while being sonicated at 600 W (55% amplitude) for 15 min. PhH (70 ml) and EtOAc (50 ml) were added. The solution was washed with 2% aq. $NaHCO_3$ solution (2×) and with saturated aq. $NaHCO_3$ solution (1×). The organic phase was dried over $K_2CO_3$ and concentrated in vacuo. The residue was purified by an $SiO_2$ flash column chromatography to give a mixture (275 mg). This sample was then separated by repeated RP C-18 HPLC (MeOH-$H_2O$: 90-10) to give compound a) (3'S)-4'-nor-3'-[R-(α-methoxy,α-propionoxy)-methyl Spinosyn J; 62 mg, 23%):$^1$H-NMR (CDCl$_3$) δ 5.96 (1H, d: 9.2 Hz) 4.99 (1H, s) ppm and compound b) (3'S)-4'-nor-3'-deoxy-3'-[(S)-(α-methoxy,α-propionoxy)methyl] Spinosyn J; 84 mg, 31%: $^1$H-NMR (CDCl$_3$) δ 5.89 (1H, dd: 9.4, 1.2 Hz), 4.99 (1H, bs). The stereochemistry at C(3') of compounds and was corroborated by NOEDS and by molecular modeling results.

Example A59
(3'S)-4'-Nor-3'-deoxy-3'-[(RS)-a-chloro,-a-methoxy) methyl] Spinosyn J Compound 3'-O-trifluoromethanesulfonyl Spinosyn J(488 mg, 0.574 mmol) was dissolved in dry DMF (20 ml). Lithium chloride (1.80 g, an excess) was added. The mixture was cooled to RT while being sonicated (600 W, 52% amplitude) for 7 min PhH (70 ml) and EtOAc (50 ml) were added. The solution was washed with diluted brine (2×) and with water (2×). The organic layer was dried over $K_2CO_3$, filtered and concentrated in vacuo. The residue was purified over a short $SiO_2$/EtOAc column and then repeatedly separated by RP C-18 HPLC (MeOH-$H_2O$: 92-8). This purification protocol yielded the mixture of epimers (3'S)-4'-nor-3'-[R/S-(α-chloro,α-methoxy)-methyl Spinosyn J; 45 mg, 11%: 5.02 (0.5 H, s), 5.00 (0.5 H, s), 4.57 (0.5 H, d: 9.5 Hz), 4.55 (0.5 H, d: 4.5 Hz), 2.16 (6H, 2× CH$_3$, s).

Example A60
(3'S)-4'-Nor-3'-deoxy-3'-[(R)-(α-fluoro,α-methoxy)methyl] Spinosyn J (3'R)-2'-nor-3'-deoxy-3'-[(R)-(α-fluoro,α-methoxy)methyl] Spinosyn J Compound Spinosyn J(697 mg, 0.97 mmol) was dissolved in dry toluene (10 ml). Pyridine (1 ml) was added upon stirring under $N_2$, diethylaminosulfur trifluoride. (DAST; 0.70 ml, 0.85 g, 5.2 mmol) was added. The reaction mixture was immediately brought up to the boiling point. After 10 min. the solution was cooled to room temperature. Benzene (50 ml) and EtOAc (75 ml) were added. The solution was washed with 5% aqueous $NaHCO_3$. The organic layer was dried over $K_2CO_3$ and concentrated in vacuo. The residue was separated over a flash $SiO_2$ column (80 g/EtOAc) to give a white solid (626 mg). A portion of this sample (400 mg) was further separated by RP C-18 HPLC (MeOH-$H_2O$: 90-10) to give compound a) (3'R)2'-nor-3'-[R-(α-fluoro,α-methoxy)-methyl] Spinosyn J; 82 mg, 21%: $^1$H-NMR (CDCl$_3$) δ 5.13 (dd: 66.3, 5.4 Hz) ppm and compound b) (3'S)4'-nor-3'-[R-(α-fluoro,α-methoxy)-methyl] Spinosyn J; 292 mg, 64%): $^1$H-NMR (CDCl$_3$) δ 5.26 (dd: 65.1, 8.6 Hz) ppm.

Example A61
(1'S,2'S)-[1'-(2'S)]abeo-2'-Deoxy-1'-fluoro Spinosyn H

Compound Spinosyn H (916 mg, 1.28 mmol) was dissolved in dry toluene (15 ml). Pyridine (1.8 ml) was added. The solution was heated to reflux under nitrogen. At the beginning of the heating process DAST (0.62 ml, 4.6 mmol) was added. After 10 min. of boiling, the reaction mixture was cooled to RT and cautiously quenched with 5% aq. $NaHCO_3$. Benzene (50 ml) and EtOAc (75 ml) were added. The solution was washed with 5% aq. $NaHCO_3$ (3×). The organic layer was dried over $K_2CO_3$ and concentrated in vacuo. The residue was purified on a flash $SiO_2$ column (100 g/EtOAc). Collected fractions gave compound (1'S,2'S)-[1'-(2'S)]abeo-2'-deoxy-1'-fluoro Spinosyn H; 662 mg, 72%): $^1$H-NMR (CDCl$_3$) δ 4.99 (dd: 52.8, 7.0 Hz) ppm.

Example A62
3'(E)-(N-n-butyl)imino Spinosyn J

Compound 3'-O-trifluoromethanesulfonyl Spinosyn J(591 mg, 0.695 mmol) was dissolved in dry DMF (20 ml). 15% TBAF/Al$_2$O$_3$ (2.7 g, an excess) was added. The reaction flask was placed in a water cooling bath and the reaction mixture was sonicated at 600 W (55% amplitude) for 10 min. EtOAc (50 ml) and PhH (70 ml) were added. The solution was filtered, extracted with water (3×) and dried over $K_2CO_3$. The organic phase was concentrated in vacuo. The residue was separated by a flash chromatographic column (SiO$_2$, 75 g/EtOAc) to furnish compound (3'(E)-(N-n-butyl)imino Spinosyn J; 144 mg, 23%): $^1$H-NMR (CDCl$_3$) δ 4.81 (1H, d: 2.0 Hz), 4.71 (1H, s),3.79 (1H, m), 0.81 (CH$_3$, t:7.4 Hz) ppm.

Example A63
3'-O-Pentadeuterioethyl Spinosyn J

Compound Spinosyn J(882 mg, 1.22 mmol) was dissolved in CH$_2$Cl$_2$ (5 ml). K$_2$CO$_3$ (1.42 g) was added. The reaction flask was placed in a water cooling bath (ca. 10° C.). Upon stirring, 15% aq. solution of NaOH (15 ml) was added, followed by TEBA-Cl (0.92 g) and NBu$_4$HSO$_4$ (0.30 g). C$_2$D$_5$I (5 g, 31 mmol) was then added and the reaction mixture was vigorously stirred at RT for 48 hrs. Methylene chloride (100 ml) and water (100 ml) were then added. Phases were separated after extraction. The organic layer was washed with water (2×) and concentrated in vacuo. The residue was purified on a flash SiO$_2$ column (120 g/EtOAc) to give compound 3'-O-pentadeuterioethyl Spinosyn J; 815 mg, 88%: $^1$H-NMR (CDCl$_3$) δ 6.64 (1H, bs), 4.69 (1H, d: 1.2 Hz), 3.43 (3H, CH$_3$, s), 3.36 (3H, CH$_3$, s), 2.10 (6H, 2× CH$_3$, s) ppm.

Example A64
3'-Deoxy-3'-azido Spinosyn J (1:1 3'R and 3'S mixture) and (3'S)-4'-nor-3'-deoxy-3'-[(RS)-(α-azido,α-methoxy)methyl] Spinosyn J Compound 3'-O-trifluoromethanesulfonyl 440 mg, 0.518 mmol) was dissolved in dry DMF (20 ml). Sodium azide (1.44 g, an excess) was added. The mixture was sonicated (600 W, 50% amplitude) for 10 min. at RT. EtOAc (50 ml) and PhH (100 ml) were added. The solution was washed with 5% aq. KHCO$_3$ solution (3x). The organic layer was dried over anh. K$_2$CO$_3$, filtered and concentrated in vacuo. The residue was purified by flash column chromatography over SiO$_2$ (50 g/EtOAc) and then by RP C-18 HPLC (MeCH—H$_2$O: 88—12) to give compound a) 3'-deoxy-3'-azido Spinosyn J (1:1 3'R and 3'S mixture); 40 mg, 10%: $^1$H-NMR (CDCl$_3$) δ 4.83 (0.5 H, d: 2.4 Hz), 4.64 (0.5 H, d:2.8 Hz), 3.95 (0.5 H, m), 3.85 (0.5 H, dd:2.8, 4.0 Hz), 3.81 (0.5 H, m), 2.17 (6H, 2x CH$_3$, s) ppm and compound b) (3'S)-4'-nor-3'-deoxy-3'-[(RS)-(α-azido,α-methoxy)methyl] Spinosyn J; 101 mg, 26%: $^1$H-NMR (CDCl$_3$) δ 5.00 (0.5 H, s), 4.98 (0.5 H, s), 4.52 (0.5 H, d: 9.9 Hz), 4.35 (0.5 H, d: 9.9 Hz), 2.14 (6H, 2x CH$_3$, s) ppm.

Example A65
(3'S)-4'-Nor-3'-deoxy-3'-[(RS)-α-chloro, α-methoxy) methyl] Spinosyn J Compound 3'-O-trifluoromethanesulfonyl spinosyn J (488 mg, 0.574 mmol) was dissolved in dry DMF (20 ml). Lithium chloride (1.80 g, an excess) was added. The mixture was cooled to RT while being sonicated (600 W, 52% amplitude) for 7 min. PhH (70 ml) and EtOAc (50 ml) were added. The solution was washed with diluted brine (2x) and with water (2x). The organic layer was dried over K$_2$CO$_3$, filtered and concentrated in vacuo. The residue was purified over a short SiO$_2$/EtOAc column and then repeatedly separated by RP C-18 HPLC (MeOH-H$_2$O: 92-8). This purification protocol yielded the mixture of epimers (3'S)-4'-nor-3'-[R/S-(α-chloro,α-methoxy)-methyl Spinosyn J;45 mg, 11%: $^1$H-NMR (CDCl$_3$) δ 5.02 (0.5 H, s), 5.00 (0.5 H, s), 4.57 (0.5 H, d: 9.5 Hz), 4.55 (0.5 H, d: 4.5 Hz), 2.16 (6H, 2x CH$_3$, s) ppm.

Example A66
5,6-Dihydro-2'-O-ethyl Spinosyn H

Compound 5,6-dihydro Spinosyn H (462 mg, 0.64 mmol) was dissolved in CH$_2$Cl$_2$ (6 ml). Potassium carbonate powder (1.0 g) was added. The reaction flask was placed in a water cooling bath (ca. 10° C.). With vigorous stirring, 10% aq. NaOH solution (15 ml) was added, followed by solid NBu$_4$HSO$_4$ (1.2 g). Ethyl iodide (4.0 ml) was then added. The reaction mixture was vigorously stirred at RT under nitrogen for 46 hrs. Methylene chloride (100 ml) and H$_2$O (100 ml) were added. After extraction phases were separated. The organic phase was dried over anh. K$_2$CO$_3$ and concentrated in vacuo. The residue was purified over a flash SiO$_2$ column (80 g/EtOAc) to give the pure compound (5,6-dihydro-2'-O-ethyl Spinosyn H; 336 mg, 70%: $^1$H-NMR (CDCl$_3$) δ 6.69 (1H, bs), 4.59 (1H, bs), 3.37 (3H, CH$_3$, s), 3.30 (3H, CH$_3$, s), 2.06 (6H, 2x CH$_3$, s) ppm.

Example A67
5,6-Dihydro-2'-O-n-propyl Spinosyn H

Compound 5,6-dihydro Spinosyn H (488 mg, 0.68 mmol) was dissolved in CH$_2$Cl$_2$ (8 ml). Potassium carbonate powder (1.1 g) was added. The reaction flask was placed in a water cooling bath (ca. 10° C.). With vigorous stirring, 10% aq. NaOH solution (20 ml) was added, followed by solid NBu$_4$HSO$_4$ (0.95 g). n-Propyl iodide (5.0 ml) was then added. The reaction mixture was vigorously stirred at RT under nitrogen for 48 hrs. Methylene chloride (100 ml) and H$_2$O (100 ml) were added. After extraction phases were separated. The organic phase was dried over anh. K$_2$CO$_3$ and concentrated in vacuo. The residue was purified over a flash SiO$_2$ column (80 g/EtOAc) to give pure compound (5,6-dihydro-2'-O-n-propyl Spinosyn H; 355 mg, 69%: $^1$H-NMR (CDCl$_3$) δ 6.72 (1H, bs), 4.63 (1H, d: 1.3 Hz), 3.41 (3H, CH$_3$, s), 3.34 (3h, CH$_3$, s), 2.10 (6H, 2x CH$_3$, s), 0.67 (3H, CH$_3$, t: 7.4 Hz) ppm.

Example A68
3'-Epi Spinosyn J

Compound 3'-keto-Spinosyn J (3.61 g, 5.04 mmol) was dissolved in dry Et$_2$O (100 ml). The solution was cooled to 0° C. under nitrogen. Lithium tri-t-butoxyaluminohydride (1.45 g; 97%, 5.53 mmol) was added in one portion. Stirring at 0° C. was continued for 15 min., then another portion of LTBAH (1.05 g, 4.00 mmol) was introduced. Stirring was continued for another 35 min. Benzene (60 ml) was added. The excess of hydride was slowly decomposed with saturated brine (20 ml) at 0° C. Phases were separated. The organic layer was successively washed with brine-H$_2$O (8:1), with 10% aq. NaOH solution, and with water. The organic phase was dried over anh. K$_2$CO$_3$, filtered and concentrated in vacuo. The product thus obtained (3.215 g, 89%) was further purified by flash column chromatography (160 g SiO$_2$/EtOAc) to give 95% pure compound 3'-epi Spinosyn J; 2.715 g, 75%: $^1$H-NMR (CDCl$_3$) δ 6.63 (1H, bs), 4.71 (1H, bs), 4.55 (1H, m), 4.28 (2H, m), 4.04 (1H, m), 3.78 (1H, m), 3.49 (1H, m), 3.33 (3H, CH$_3$, s), 3.31 (3H, CH$_3$, s), 2.11 (6H, 2x CH$_3$, s) ppm.

Example A69
3'-Epi-3'-O-trifluoromethanesulfonyl Spinosyn J

Compound 3'-epi Spinosyn J (1.53 g, 2.13 mmol) was dissolved in dry CH$_2$Cl$_2$ (20 ml). Pyridine (5.0 ml, dry) was added. The solution was cooled to 0° C. under nitrogen. Trifluoromethanesulphonic anhydride (1.0 ml, an excess) was slowly introduced via a syringe. Stirring at 0° C. was continued for 16 hrs. EtOAc (50 ml) and PhH (100 ml) were added. The solution was extracted with diluted brine (2x), and with 5% aq. KHCO$_3$ solution (2x). The organic phase was dried over anh. Na$_2$SO$_4$, filtered and concentrated in vacuo. The residue was purified over a flash SiO$_2$ column (100 g/EtoAc) to give compound (3'-epi-3'-O-trifluoromethanesulfonyl Spinosyn J; 1.36 g, 75%): $^1$H-NMR (CDCl$_3$) δ 6.69 (1H, bs), 5.03 (1H, dd: 3.2, 3.5 Hz), 4.68 (1H, bs), 3.90 (1H, dq: 8.9, 6.4 Hz), 3.39 (3H, CH$_3$, s), 3.35 (3H, CH$_3$, s), 2.13 (6H, 2x CH$_3$,s) ppm.

Example A70
3'-O-(α,α,β-trifluoro-γ-buten)-α-yl Spinosyn J

Compound Spinosyn J(790 mg, 1.10 mmol) was dissolved in CH$_2$Cl$_2$ (5 ml). Potassium carbonate (1.1 g) was added, followed by 15% aq. NaOH solution (15 ml), Bu$_4$NHSO$_4$ (0.80 g) and 4-bromo-1,1,2-trifluorobutene (3.0 g, an excess). DMSO (4.0 ml) was added. Stirring at RT under nitrogen was continued for 16 hrs. CH$_2$Cl$_2$ (100 ml) and water (100 ml) were added. After extraction, phases were separated. The organic phase was dried over K$_2$CO$_3$, filtered and concentrated in vacuo. The residue was separated over a flash SiO$_2$ column (100 g/EtOAc) to give (a) compound 3'-O-α,α,β-trifluoro-γ-buten-α-yl Spinosyn J; 194 mg, 21% $^1$H-NMR (CDCl$_3$) δ 6.66 (1H, bs), 6.28 (1H, m: W$_{H/2}$=65 Hz) 5.43 (1H, m: W$_{H/2}$=60 Hz), 5.28 (1H, d: 17.4 Hz), 5.02 (1H, dd: 11.4, 1.4 Hz), 2.13 (6H, 2x CH$_3$'s) ppm and (b) recovered compound Spinosyn J (520 mg, 75%).

Example A71
2'-Epi-3'-keto Spinosyn J

3'-keto Spinosyn J (755 mg, 1.05 mmol) was dissolved in dry THF (10 ml). Tetraethylsilane (1.0 ml) was added, followed by 15% Bu$_4$NF/Al$_2$O$_3$ (0.55 g, an excess). The reaction mixture was stirred at RT under nitrogen for 16 hrs. Benzene (70 ml) and EtOAc (30 ml) were added. The mixture was extracted with 5% aq. KHCO$_3$ solution (2×). The organic layer was dried over K$_2$CO$_3$, filtered and concentrated in vacuo. The residue was separated over a flash SiO$_2$ column (120 g/EtOAc) to give (a) 3'-keto Spinosyn J (290 mg, 38%) and (b) compound 2'-epi-3'-keto Spinosyn J; 375 mg, 50% $^1$H-NMR (CDCl$_3$) δ 6.60 (1H, bs), 5.06 (1H, d: 4.1 Hz), 3.39 (3H, CH$_3$,s), 3.36 (3H, CH$_3$, s), 2.08 (6H, 2× CH$_3$, s) ppm.

Example A72

2'-Epi-3'-epi Spinosyn J

Compound 2'-epi-3'-keto Spinosyn J (305 mg, 0.426 mmol) was dissolved in dry THF (10 mL) and dry Et$_2$O (10 ml) was added. To this solution, cooled to 0° C. and stirred under nitrogen was added in one portion Li(t-BuO)$_3$AlH (200 mg, 0.76 mmol). Stirring at this temperature was continued for 30 min. Afterwards the excess hydride was cautiously quenched with brine. The mixture was partitioned between Et$_2$O and brine containing 5% NaOH. The organic layer was successively washed with brine containing 5% NaOH and with 5% aq. KHCO$_3$ (2×), dried over K$_2$CO$_3$, filtered, concentrated and dried in vacuo to give a white solid foam containing exclusively compound 2'-epi-3'-epi Spinosyn J, 303 mg, 99% $^1$H-NMR (CDCl$_3$) δ 6.61 (1H, bs), 4.78 (1H, d: 3.3 Hz), 3.84 (1H, dq: 9.8, 6.3 Hz), 3.37 (3H, CH$_3$, s), 3.35 (3H, CH$_3$,s), 2.14 (6H, 2× CH$_3$,s) ppm.

Example A73

2'-Epi-3'-epi-3'-O-ethyl Spinosyn J

Compound 2'-epi-3'-epi Spinosyn J (250 mg, 0.348 mmol) was dissolved in CH$_2$Cl$_2$ (5 ml). Potassium carbonate (1.0 g) was added. The flask was placed in a cooling bath (10° C). 20% aq. NaOH (20 ml) was added, followed by Bu$_4$NHSO$_4$ (0.71 g), ethyl iodide (2.0 ml) and DMSO (5 ml). The reaction mixture was vigorously stirred under nitrogen for 60 hrs. Methylene chloride (100 ml) and water (100 ml) were added. After extraction, phases were separated. The organic phase was dried over K$_2$CO$_3$, filtered and concentrated in vacuo. The residue was separated over a flash SiO$_2$ column (30 g/EtoAc) to furnish compound 2'-epi-3'-epi-O-ethyl Spinosyn J, 43 mg, 17% $^1$H-NMR (CDCl$_3$) δ 6.72 (1H, bs), 4.81 (1H, d: 4.0 Hz), 4.01 (1H, m), 3.36 (3H, CH$_3$,s), 3.33 (3H, CH$_3$,s), 2.16 (6H, 2× CH$_3$, s) ppm.

Example A74

3'-Deoxy-3'-fluoro Spinosyn J (1:1 mixture of 3' isomers)

3'-Epi Spinosyn J (570 mg, 0.794 mmol) was dissolved in dry CH$_2$Cl$_2$ (10 ml). The solution was cooled to −25° C. under nitrogen. Diethylaminosulfur trifluoride (315 ml, 2.38 mmol) was introduced via a syringe. Stirring at −25° C. under nitrogen was continued for 3 hrs, then the temperature was raised to RT during 30 min. Pyridine (0.5 ml) was added and stirring at RT was continued for another 15 min. The mixture was partitioned between CH$_2$Cl$_2$ (100 ml) and 5% aq. KHCO$_3$ (150 ml). The organic phase was rinsed with 5% aq. KHCO$_3$, dried over K$_2$CO$_3$, filtered and concentrated in vacuo. The residue was purified over a flash SiO$_2$ column (100 g/EtOAc) and then by RP C-18 HPLC (10% water in MeOH) to give compound 3'-deoxy-3'-fluoro Spinosyn J, 1:1 mixture of 3'a-F:3'b-F, 168 mg, 29% $^1$H-NMR (CDCl$_3$) δ 6.68 (1H, bs), 4.60 (1H, nm), 4.36 (0.5 H, ddd: 44.6, 2.9, 2.5 Hz), 3.38 (1.5 H, CH$_3$, s), 3.36 (1.5 H, CH$_3$,s), 3.33 (1.5 H, CH$_3$, s), 3.32 (1.5 H, CH$_3$, s), 2.12 (6H, 2× CH$_3$,s) ppm.

Example A75

3'-O-Phenyl Spinosyn J

Compound 3'-epi Spinosyn J (148 mg, 0.206 mmol) was dissolved in dry toluene (3 ml). The solution was stirred at RT under nitrogen and triphenylphosphine (118 mg, 0.45 mmol) was added, followed by phenol (42.5 mg, 0.45 mmol). After stirring for 15 min., to the mixture was added diethyl azodicarboxylate (DEAD, 75 ml (95%), 0.45 mmol). The mixture was stirred for 16 hrs at RT, then it was diluted with PhH (70 ml) and EtOAc (50 ml), washed with 5% aq. KHCO$_3$ and dried over potassium carbonate. The residue was purified over a flash SiO$_2$ column and then separated over a RP C-18 HPLC column (12% water in MeOH) to give (a) recovered 3'-epi Spinosyn J (101 mg; 68%) and (b) compound 3'-O-phenyl Spinosyn J; 3.1 mg, 1.9% $^1$H-NMR (CDCl$_3$) δ 7.28 (2H, m), 6.99 (3H, m), 6.76 (1H,bs), 4.84 (1H, d: 1.6 Hz), 4.54 (1H, dd: 9.4, 3.1 Hz), 3.53 (3H, CH$_3$, s), 3.46 (3H, CH$_3$, s), 2.11 (6H, 2× CH$_3$, s) ppm.

Example A76

3'-O-(S-Phenyl)dithiocarbonate of Spinosyn J

Spinosyn J (1.20 g, 1.67 mmol) was dissolved in dry CH$_2$Cl$_2$ (10 ml). Pyridine (dry, 2 ml) was added, followed by DMAP (70 mg). The reaction mixture was stirred at RT under nitrogen, with cooling in a water bath. Phenyl chlorodithioformate (1.80 ml, an excess) was slowly added via a syringe. The mixture was then stirred at RT under nitrogen for 16 hrs. PhH (70 ml) and EtOAc (70 ml) were added. The organic phase was washed with 5% KHCO$_3$ (4×), dried over K$_2$CO$_3$ and concentrated in vacuo. The residue was separated over a flash SiO$_2$ column (120 g/EtOAc) to furnish compound 3'-O-(S-phenyl)dithiocarbonate of Spinosyn J; 780 mg, 54% $^1$H-NMR (CDCl$_3$) δ0.50 (2H, m), 7.33 (3H, m), 6.68 (1H, bs), 5.73 (3H, m), 4.69 (1H, bs), 3.32 (3H, CH$_3$, s), 3.12 (3H, CH$_3$, s), 2.15 (6H, 2× CH$_3$, s) ppm.

Example A77

3'-O-(Pentafluorophenyl)thionocarbonate of Spinosyn J

Spinosyn J (1.52 g, 2.12 mmol) was dissolved in dry acetonitrile (15 ml). DMAP (0.84 g, 6.88 mmol) was added and dissolved. The solution was cooled to 0° C. under nitrogen. Pentafluorophenyl chlorothionoformate (1.60 ml, 10.0 mmol) was slowly added dropwise. The reaction mixture was stirred for 16 hrs at RT. PhH (70 ml) and EtOAc (50 ml) were added. The solution was extracted with 5% KHCO$_3$ (3×) and dried over anh. K$_2$CO$_3$. The organic layer was concentrated in vacuo. The residue was purified over a flash SiO$_2$ column (120 g/EtOAc) to give compound 3'-O-(pentafluorophenyl)thionocarbonate of Spinosyn J; 1.77 g, 88% $^1$H-NMR (CDCl$_3$) δ 6.65 (1H, bs), 5.42 (1H, dd: 9.4, 3.2 Hz), 3.41 (3H, CH$_3$, s), 3.39 (3H, CH$_3$, s), 2.10 (6H, 2× CH$_3$,s) ppm.

Example A78

3'-O-[(3'R)-3'-Desoxy Spinosyn J]-3'-yl Spinosyn J, 1:1 mixture of (3'R) and (3'S) 3'-allyl-3'-deoxy Spinosyn J, and (3'S)-3'-allyl-3'-deoxy Spinosyn J Compound 3'-O-(pentafluorophenyl)thio-nocarbonate of Spinosyn J (1.65 g, 1.75 mmol) was dissolved in dry toluene (25 ml). Allyltributyltin (1.70 ml, 5.32 mmol) was added, followed by AIBN (180 mg). The mixture was heated to reflux under nitrogen for 20 hrs. It was then cooled, concentrated and submitted directly on a flash SiO$_2$ column (220 g/EtOAc). The purified fractions were further separated by RP C-18 HPLC (10% water in MeOH) to furnish compound a) 3'-O-[(3'R)-3'-desoxy Spinosyn J]-3'-yl Spinosyn J; 373 mg, 30% $^1$H-NMR (CDCl$_3$) δ 6.66 (1H, bs), 4.59 (1H, bs), 3.52 (2H, m), 3.28 (3H, CH$_3$,s), 3.24 (3H, CH$_3$,s), 2.12 (6H, 2× CH$_3$, s) ppm; Elemental Analysis: for C$_{80}$H$_{124}$N$_2$O$_{19}$ calc. C 67.77, H 8.82, N 1.98, found C 67.69, H 8.70, N 2.24, and compound b) (a 1:1 mixture of (3'R) and (3'S) 3'-allyl-3'-deoxy Spinosyn J; 144 mg, 11%. This mixture was further separated by repeated RP C-18 HPLC on a 5 micron Rainin column, to give compound c) ($^3$'S)-3'-allyl-3'-deoxy Spinosyn J; 18 mg, 1.4% $^1$H-NMR (CDCl$_3$) δ 6.73 (1H, bs), 5.73 (1H, m), 5.02 (2H, m), 4.63 (1H, d: 2.6 Hz), 3.82 (1H, m), 3.34 (3H, CH$_3$, s), 3.28 (3H, CH$_3$, s), 2.18 (6H, 2× CH$_3$), s) ppm.

Example A79
(14R)-13,14-Dihydro-3'(E)-(carbomethoxy)methylene-3'-deoxy Spinosyn J Compound 3'(E)-(carbomethoxy)methylene-3'-deoxy Spinosyn J (308 mg, 0.39 mmol) was dissolved in dry $Et_2O$ (10 ml). Glacial AcOH (5 ml) was added. The mixture was stirred at RT and $NaBH_3CN$ (180 mg, an excess) was added. Stirring at RT under nitrogen was continued for 16 hrs. PhH (100 ml) and EtOAc (50 ml) were added. The solution was extracted with dilute brine (2x), then with 5% aq. $NaHCO_3$ (2x). The organic layer was dried over anh. $K_2CO_3$, filtered and concentrated in vacuo. The residue was purified on a flash $SiO_2$ column (55 g, EtOAc) to give compound (13,14β-dihydro-3'-(E)-(carbomethoxy)methylene-3'-deoxy Spinosyn J; 222 mg, 72%) $^1$H-NMR ($CDCl_3$) δ 6.18 (1H, d: 1.6 Hz), 4.89 (1H, d: 4.1 Hz), 4.36 (1H, d: 6.3 Hz), 3.79 (1H, dd: 1.7, 6.3 Hz), 3.61 (3H, $CH_3$, s), 3.39 (3H, $CH_3$, s), 3.21 (3H, $CH_3$, s), 2.11 (6H, 2x $CH_3$, s) ppm.

Example A80
3'(E)-(Hydroxymethyl)methylene-3'-deoxy Spinosyn J (14S,21S)-1,21-deoxy-13,14-dihydro-1,21-dihydroxy-3'(E)-(hydroxymethyl)methylene-3'-deoxy-1,21-seco Spinosyn J and Compound 3'(E)-(carbomethoxy)methylene-3'-deoxy Spinosyn J (340 mg, 0.44 mmol) was dissolved in dry $CH_2Cl_2$ (5 ml). Dry THF (1.5 ml) was added. The solution was cooled to 0° C. under nitrogen and DIBALH (1.95 ml, 1.0 M solution in cyclohexane, 1.95 mmol) was added. Stirring was continued for 45 min. Saturated aq. solution of $NH_4OH$-$NH_4Cl$ (1:1) was added dropwise at 0° C. PhH (70 ml) and EtOAc (70 ml) were added and the mixture was extracted with saturated aq. solution of $NH_4OH$-$NH_4Cl$ (1:1), then with 2N aq. NaOH and finally with 5% aq. $KHCO_3$ solution (2x). The organic layer was dried over $K_2CO_3$, filtered and concentrated in vacuo. The residue was separated by a flash column chromatography on $SiO_2$ (30 g/EtoAc) to give compound a) 3'(E)-(hydroxymethyl)methylene-3'-deoxy Spinosyn J; 91 mg, 28% $^1$H-NMR ($CDCl_3$) δ 6.71 (1H, bs), 5.87 (1H, t: 6.2 Hz), 4.51 (1H, d: 3.9 Hz), 3.33 (3H, $CH_3$, s), 3.31 (3H, $CH_3$, s), 2.16 (6H, 2x $CH_3$, s) ppm, and compound b) 13,14α-dihydro-1,21S-dihydroxy-3'(E)-(hydroxymethyl)methylene-3'-deoxy-1,21-seco Spinosyn J; 104 mg, 31.5% $^1$H-NMR ($CDCl_3$) δ 5.82 (1H, t: 6.2 Hz), 4.47 (1H, d: 3.9 Hz), 3.29 (3H, $CH_3$, s), 3.26 (3H, $CH_3$, s), 2.78 (2H, m), 2.12 (6H, 2x $CH_3$, s) ppm.

Example A81
4'-O-n-propyl Spinosyn K

Spinosyn K (322 mg, 0.448 mmol) was dissolved in methylene chloride (4 ml). Potassium carbonate (1.1 g) was added. The flask was placed in a water bath (ca.+10° C.). 15% NaOH aq. solution (25 ml) was added, followed by $Bu_4NHSO_4$ (1.2 g), n-propyl iodide (3.0 ml) and DMSO (4 ml). After 16 hrs. additional $Bu_4NHSO_4$ (0.70 g) was introduced. Vigorous stirring at RT under nitrogen was continued for a total of 60 hrs. Water (100 ml) and $CH_2Cl_2$ (100 ml) were added. After extraction, phases were separated. The organic layer was dried over anh. $K_2CO_3$, filtered and concentrated in vacuo. The residue was separated over a flash $SiO_2$ column (100 g/EtOAc) to furnish compound 4'-O-n-propyl Spinosyn K; 225 mg, 66% $^1$H-NMR ($CDCl_3$) δ 6.66 (1H, bs), 4.75 (1H, bs), 3.67 (1H, m), 3.39 (6H, 2x $CH_3$, s), 2.13 (6H, 2x $CH_3$, s), 0.82 (3H, $CH_3$, t: 7.4 Hz), 0.71 (3H, $CH_3$, t: 7.4 Hz) ppm.

Example A82
Methyl-2,3,4-tri-O-ethyl-L-rhamnopyranoside

Methyl L-rhamnopyranoside (Fischer, E. *Chem.Ber.*, 1895, 28, 1158) as a mixture of α and β anomers (21.0 g, 0.118 mol) was added to a well-stirred mixture of 50% (w/w) aq. NaOH (200 ml), DMSO (100 mL) and tetrabutylammonium hydrogen sulfate (20.0 g, 0.059 mol). To this mixture was added ethyl iodide (75.0 mL). A slight exotherm was observed during the first 20–30 min of reaction (external cooling, ice bath, was used to maintain the reaction temperature near 25°). After a reaction period of 3 h, 75 mL more ethyl iodide was added. After 3 more h, more ethyl iodide (75 mL) and more 50% NaOH solution (200 mL) were added. After 3 more h, ethyl iodide (70 mL) and 50% NaOH (100 mL) were again added, and the mixture stirred overnight for a total reaction period of 24 h. The mixture was diluted with water (200 mL) and exhaustively extracted with $CH_2Cl_2$. The $CH_2Cl_2$ extracts were washed with brine (200 mL), dried ($MgSO_4$) and evaporated. The amorphous residue was triturated with hexane (300 mL) and filtered. The collected solid was washed with hexane (100 mL) and the combined filtrate and was concentrated, leaving 42.0 g of crude product. This was flash chromatographed over 900 mL of silica using 10% ethyl acetate in hexane as eluent. Fractions of 200 ml were taken after a forerun of 800 ml. Clean methyl 2,3,4-tri-O-ethyl-L-rhamnopyranoside (25.5 g, 82%) as a colorless oil was obtained from fractions 3–11: $^1$HNMR ($CDCl_3$) δ 4.64 (d, 1, H-1(α anomer)), 3.89 (dq,1, H-5), 3.50–3.80 (m, 8), 3.33 (s, 3, $OCH_3$), 3.23 (t,1, H-4), 1.30 (d,3, H-6), 1.15–1.25 (m,9, $CH_2CH_3$).

Example A83
2,3,4-Tri-O-ethyl-L-rhamnose

A solution of methyl 2,3,4-tri-O-ethyl-L-rhamnopyranoside (11.0 g, 0.042 mol) in 110 mL of 4:1 (v/v) trifluoroacetic acid:water was stirred at ambient temperature for 24 h. The solution was concentrated to near dryness at reduced pressure (~1.0 mm, 30–35° C.) and the residue diluted with $CH_2Cl_2$ (200 mL). The aqueous phase was separated and the organic extracts washed with sat. $NaHCO_3$ solution (40 mL), brine (40 mL) and then dried (MgSO4) and concentrated, leaving 11.0 g of crude product. This was flash chromatographed over 950 mL of silica using 25% ethyl acetate in hexane as eluent, giving 9.5 g (91%) of clean triethylrhamnose as a 9:1 mixture of α and β anomers as a nearly colorless oil: $^1$HNMR ($CDCl_3$) δ 5.18 (m, 1, H-1), 3.6–3.95 (m, 8), 3.25 (m, 1, H-4), 2.48 (d, 1, OH), 1.15–1.35 (m, 12).

Example A84
O-(2,3,4-Tri-O-ethyl-α-L-rhamnopyranosyl)-trichloroacetimidate

Freshly distilled trichloroacetonitrile (12.0 mL, 0.12 mmol) was added in one portion to a cold (0–5° C.), well stirred solution of triethylrhamnose (2.2 g, 8.86 mmol) in dry $CH_2Cl_2$ (80 mL). To this solution 60% sodium hydride in mineral oil (0.35 g, 8.87 mmol as 100%) was added in portions during 1–2 min. (Caution: foaming and $H_2$ evolution). After 20 min. reaction, the cooling bath was removed and the mixture was stirred at ambient temperature for 5.5 h. The mixture was then recooled to 0–5° C. and silica gel (6.0 g) was added in one portion. After stirring for 10 min., the mixture was filtered and the collected solids washed with $CH_2Cl_2$ (25 mL). The combined filtrate and wash was evaporated to dryness at reduced pressure (~25 mm, 30–35° C.) and the residue treated with hexane (80 mL), whereupon some flocculent solids separated. After standing for 30 min., the solids were filtered (Celite) and washed with hexane (25 mL). The combined filtrate and wash was then concentrated to dryness at reduced pressure (~25 mm, 30–35° C.), leaving 2.9 g (82%) of crude imidate as a pale yellow oil, which by $^1$HNMR spectros-copy was only the a anomer and was pure enough to be used without further purification (Note: the imidate proved unstable to chromatography over silica and decomposed upon attempted short-path distillation at reduced pressure (~0.1 mm)): 1HNMR (CDCl$_3$) δ 8.54 (s, 1, NH), 6.22 (s, 1, H-1), 3.6–3.95 (m, 9), 3.35 (t, 1, H-4), 1.34 (d, 3, H-6), 1.1–1.3 (m, 9).

Example A85
3'(E)-(carbomethoxy)methylene-3'-deoxy Spinosyn J (3'(Z)-(carbomethoxy)methylene-3'-deoxy Spinosyn J Compound 3'-keto Spinosyn J (609 mg, 0.851 mmol) was dissolved in dry toluene (25 ml). Carbomethoxymethylene triphenylphosphorane (2.2 g, an excess) was added. The reaction mixture was heated to reflux under nitrogen for 2 hrs. It was cooled to RT and directly chromatographed on a flash SiO$_2$ column (220 g/EtOAc). The fractions of expected polarity were combined and concentrated in vacuo to give the crude product (584 mg). This sample was separated by repeated RP C-18 HPLC (12% H$_2$O in methanol) to give: recovered starting 3'-keto Spinosyn J (49 mg), compound a) 3'(Z)-(carbomethoxy)methylene-3'-deoxy Spinosyn J; 45 mg, 7.5% $^1$H-NMR (CDCl$_3$) d 6.68 (1H, bs), 6.13 (1H, bs), 3.68 (3H, CH$_3$, s), 3.38 (3H, CH$_3$, s), 3.30 (3H, CH$_3$ s), 2.16 (6H, 2× CH$_3$, s) ppm, and compound b) 3'(E)-(carbomethoxy)methylene-3'-deoxy Spinosyn J; 242 mg,40% $^1$H-NMR (CDCl$_3$) δ 6.64 (1H, bs), 6.16 (1H, 1.8 Hz), 3.58 (3H, CH$_3$, s), 3.37 (3H, CH$_3$, s), 3.19 (3H, CH$_3$,s), 2.08 (6H, 2× CH$_3$, s) ppm.

Example A86
Spinosyn A 9-Psa

To a solution of 3'keto Spinosyn J (1.89 gm, 2.64 mmol) in MeOH (100 ml), K$_2$CO$_3$ (anhydrous; 1.82 gm, 13.2 mmol) was added and the mixture was stirred at room temperature for 1 hr. Et$_2$O (100 ml) was then added and the mixture was filtered. The filtrate was evaporated at room temperature giving a yellow solid. The yellow solid was dissolved in dichloromethane and washed with water, then brine, and dried with MgSO$_4$. The dichloromethane was then evaporated at reduced pressure, giving a colorless semi-solid (1.53 gm). This semi-solid was purified by flash chromatography with 5% MeOH in dichloromethane—10% MeOH in dichloromethane in a one-step gradient, giving Spinosyn A 9-Psa (1.09 gm, 76% yield) as an off white glass.

Example A87
3'-Keto Spinosyn D

The reaction was run as described above in Example A46 starting with Spinosin L (997.4 mg, 1.36 mmol), and gave 3'-keto Spinosyn D (850 mg) as a colorless semi-solid. NMR showed contamination of product with diisopropyl sulfide, but the product was used without further purification.

Example A88
Spinosyn D 9-Psa

The reaction was run as described in Example A86 starting with 3'-keto Spinosyn D (770 mg, 1.06 mmol) and gave Spinosyn D 9-Psa (246 mg, 42% yield) as a colorless glass.

Example A89
2'-Keto Spinosyn H

To a cold (−78° C.), nitrogen blanketed suspension of N-chlorosuccinimide (1.7 g, 12.73 mmol) in dichloromethane (60 mL), ethyl sulfide (1.8 mL, 16.74 mmol) was added dropwise during 2–3 min. The resulting solution was stirred at −78° C. for 30 min., then a solution of Spinosyn H(3.0 g, 4.18 mmol) in dichloromethane (25 mL) was added dropwise during 10 min. while maintaining a reaction temperature of <−65° C. After 3.5 h at −78° C., triethylamine (4.1 mL, 29.47 mmol) was added dropwise during 5 min. while maintaining a reaction temperature of <−65° C. The cooling bath was then removed and the reaction mixture allowed to warm to ambient temperature over 20 to 30 min. Dichloromethane (80 mL) was added and the solution washed with 0.2 N HCl (150 mL) and brine (100 mL) and dried (MgSO$_4$). Concentration left 4.2 g of semi-solid residue. This was flash chromatographed over silica (325 mL) with 3% methanol in dichloromethane as eluent and gave 2'-ketone of Spinosyn H (2.8 g, 93%) as a colorless foam: $^1$HNMR (CDCl$_3$) δ 4.68 (s, 1, H-1'), 4.12 (d, 1, H-3'), 3.97 (m, 1, H-5').

Example A90
Spinosyn A 9-Psa

A solution of 2'-keto Spinosyn H (1.0 g, 1.39 mmol), p-toluenesulfonhydrazide (0.32 g, 1.75 mmol) and tripropylamine (0.33 mL, 1.75 mmol) in 1,4-dioxane (40 mL) was heated at reflux with stirring, under nitrogen, for 30 h. The solvent was then removed in vacuo and the residue chromatographed over silica (100 mL) using 5% methanol in dichloromethane as eluent to give Spinosyn A 9-Psa as a colorless foam (0.39 g, 52%): $^1$HNMR (CDCl$_3$) δ 6.78 (br s, 1, H-13), 4.63 (m, 1, H-21), 4.43 (m, 2, H-1", H-9), 2.23 (s, 6, N(CH$_3$)$_2$.

Example A91
Spinosyn B 9-Psa

The reaction was run as described in Example 3 starting with Spinosyn M (199.3 mg, 0.28 mmol). After initial purification by chromatography on silica, eluting with 7% methanol in dichloromethane then 10% methanol in dichloromethane in 1 step. The product was isolated by preparative HPLC on a C$_{18}$ column, eluting with acetonitrile:methanol:0.1% NH$_4$OAc (30:30:40 to 32.5:32.5:35 in a 60 minute linear gradient). This gave Spinosyn B 9-Psa (49 mg ; 33% yield) as a white solid, FDMS, m/e (relative intensity) 530 (M$^+$, 60), 529 (100).

Example A92
(5R,6S)-5,6-Epoxy-3'-O-n-propyl Spinosyn L and (5S,6R)-5,6-epoxy-3'-O-n-propyl Spinosyn L Compound 3'-O-n-propyl Spinosyn L (1.07 g, 1.38 mmol) was dissolved in methylene chloride (25 mL) under a nitrogen atmosphere and m-CPBA (50%, 1.88 g, 5.44 mmol) was added and the reaction stirred for 24 h. The reaction mixture was diluted with ethyl acetate (50 mL) and extracted with 10% aqueous sodium sulfite (3×25 mL) followed by saturated aqueous sodium bicarbonate (3×25 mL) The organic layer was washed with brine (25 mL) and dried over anhydrous potassium carbonate to give a yellow solid (0.80 g). The crude product was purified by reverse-phase HPLC (methanol:0.1% aq ammonium hydroxide, 90:10) to give (5R,6S)-5,6-epoxy-3'-O-n-propyl Spinosyn L (26.6 mg, 2.4%): partial $^1$H NMR δ 6.68 (bs, 1H), 4.78 (s, 1H), 4.67 (m, 1H), 4.37 (d, 1H), 4.21 (q, 1H), 3.58 (m, 1H); and (5S,6R)-5,6-epoxy-3'-O-n-propyl Spinosyn L (114 mg, 10.4%): partial $^1$H NMR d 6.54 (bs, 1H), 4.78 (s, 1H), 4.63 (m, 1H), 4.38 (d, 1H),4.20 (m, 1H), 3.60 (m, 1H).

Example A93
3'-O,N-Bis(trideuteriomethyl) Spinosyn M

Spinosyn J (1.34 g, 1.87 mmol) was dissolved in CH$_2$Cl$_2$ (8 mL). Potassium carbonate (1.0 g) was added, followed by 20% aqueous NaOH solution (20 mL), tetrabutylammonium hydrogen sulfate (0.77 g) and trideuteriomethyl iodide (5.0 g). The reaction mixture was vigorously stirred for 20 h. After work-up the crude mixture was suspended in m-xylene (25 mL) and heated to reflux for 1 h. The mixture was then cooled and chromatographed on silica gel (ethyl acetate) to afford 3'-O,N-bis(trideuteriomethyl) Spinosyn M (0.883 g, 64%) as a white solid: MS m/z 737. Anal. Calcd for C$_{41}$H$_{59}$D$_6$NO$_{10}$: C, 66.73; H, 8.06; N, 1.90. Found: C, 66.92; H, 7.84; N, 2.13.

Example A94
3'-(Z)-(Carboxy)methylene Spinosyn J

Compound 3'-(Z)-(carbomethoxy)methylene Spinosyn J (80 mg, 0.104 mmol) was dissolved in THF (5 mL). Methanol (3 mL) and saturated aqueous LiOH solution (3 mL) were added. The mixture was stirred for 6 h under nitrogen and AcOH (2 mL) was added, then the mixture was concentrated. The residue was dissolved in ethyl acetate (50 mL) and washed three times with brine. The organic layer was dried over sodium sulfate, concentrated and purified by HPLC (80:20, MeOH/H$_2$O) to give 3'-(Z)-(carboxy) methylene Spinosyn J (42 mg, 53%) as an off-white solid: $^1$H NMR δ 6.68 (s, 1 H), 5.28 (s, 1 H), 3.41 (s, 3 H), 3.34 (s, 3 H).

Example A95
4'-Epi Spinosyn K

Compound 4'-keto spinosyn K (235 mg, 0.328 mmol) was dissolved in dry THF (10 mL). Dry Et$_2$O (10 mL) was added and the solution was cooled under nitrogen to 0° C. Upon vigorous stirring, lithium tri-t-butoxyaluminohydride (194 mg, 0.74 mmol) was added. After 30 minutes, saturated brine was carefully added, followed by Et$_2$O (100 ml). The mixture was washed three times with 2N NaOH/brine solution, then with 5% aqueous KHCO$_3$ solution. The organic layer was dried over potassium carbonate, filtered, concentrated and dried in vacuo to give 4'-epi spinosyn K (206 mg, 87%) as a white solid: $^1$H NMR δ 6.65 (s, 1 H), 4.84 (s, 1 H), 3.64 (m, 2 H), 3.40 (s, 3 H), 3.34 (s, 3 H).

Example A96
4'-Epi spinosyn A

Compound 4'-epi Spinosyn K (149 mg, 0.207 mmol) was reacted with MeI and then heated to reflux in m-xylene following the procedure described for the synthesis of compound 3'-O,N-bis(trideuteriomethyl) Spinosyn M, using potassium carbonate (1.2 g), 20% aqueous NaOH (25 ml), MeI (5.0 ml) and tetrabutylammonium hydrogen sulfate (0.80 g). Crude thermolysis product was purified by chromatography on silica gel (ethyl acetate) and additionally purified by HPLC (86:14, MeOH/H$_2$O). This gave compound 4'-epi Spinosyn A (74 mg, 49%) as a white solid: $^1$H NMR δ 6.67 (s, 1 H), 4.84 (s, 1 H), 3.74 (q, J=6.8 , 1 H), 3.46 (s, 3 H), 3.34 (s, 3 H), 3.37 (s, 3 H).

Example A97
4'-Trifluoromethyl-4'-epi Spinosyn K

Compound 4'-keto Spinosyn K (170 mg, 0.237 mmol) was dissolved in dry THF (10 mL). The solution was stirred at 0° C. under nitrogen and trifluoromethyl(trimethyl)silane (241 mg, 1.69 mmol) was added, followed by tetrabutylammonium fluoride (15% on alumina; 300 mg). Stirring at 0° C. was continued for 6 h. After work-up, the crude product was dissolved in methylene chloride (5 mL). Water (1 mL), benzyltriethylammonium chloride (100 mg) and KHF$_2$ (300 mg) were added and the mixture was stirred for 2 h. The usual work-up afforded crude product which was purified by flash chromatography on silica gel (ethyl acetate) and additionally purified by HPLC (88:12, MeOH/H$_2$O) to furnish 4'-trifluoromethyl-4'-epi Spinosyn K (65 mg, 35%) white solid: $^1$H NMR δ 6.70 (s, 1 H), 4.81 (d, J=2.2, 1 H), 3.85 (q, J=6.4, 1 H), 3.47 (s, 3 H), 3.44 (s, 3H); $^{13}$C NMR (APT) d 76.0 (q, J=26, quaternary).

Example A98
(5R,6S)-3'-Deoxy-5,6-epoxy-3'-methylene Spinosyn J and (5S,6R)-3'-Deoxy-5,6-epoxy-3'-methylene Spinosyn J Compound 3'-deoxy-3'-methylene Spinosyn J (640 mg, 0.896 mmol) was dissolved in methylene chloride (100 mL). The solution was cooled to 0° C. and m-CPBA (1.06 g, ca. 3 mmol) was added in a few portions. Stirring at 0° C. was continued for 1 h. 10% Aqueous NaHSO$_3$ solution (100 ml) was added, followed by methylene chloride (150 mL). After extraction, phases were separated and the organic phase was worked up in the usual manner. The crude product was purified over a silica gel column and then separated by HPLC (88:12, MeOH/H$_2$O) to give a) compound 5R,6S-3'-deoxy-5,6-epoxy-3'-methylene Spinosyn J (20 mg, 3%) white solid: $^1$H NMR δ 6.64 (s, 1 H), 5.23 (t, J=1.7, 1 H), 5.07 (d, J=1.5, 1 H), 4.69 (d, J=1.6, 1 H), 3.41 (s, 3 H), 3.26 (s, 3H); and compound 5S,6R-3'-deoxy-5,6-epoxy-3'-methylene Spinosyn J (170 mg, 26%) white solid: $^1$H NMR δ 6.47 (s, 1 H), 5.18 (s, 1 H), 5.02 (s, 1 H), 4.64 (s, 1 H), 3.36 (s, 3 H), 3.20 (s, 3H).

Example A99
3'''-(4'''(((Spinosyn J-3'-O-)yl)methyl) phenyl-3'''-trifluoromethyl)-3'''H-diazirine 3-(4-(Bromomethyl)phenyl-3-trifluoromethyl-3H-diazirine (6.0 g, 21.5 mmol) was dissolved in methylene chloride (6 mL). To this solution was added a solution of spinosyn J (1.75 g, 2.4 mmol) in methylene chloride (5 mL), followed by tetrabutylammonium hydrogen sulfate (1.1 g) and 25% aqueous NaOH (50 ml). The reaction mixture was vigorously stirred for 20 hrs. Work-up and chromatography on silica gel (ethyl acetate) furnished compound 3'''-(4''' (((Spinosyn J-3'-O-)yl) methyl)phenyl-3'''-trifluoromethyl)-3'''H-diazirine (1.393 g, 62%) as white solid: ESI MS m/z 916 (M+1). Anal. Calcd for C$_{49}$H$_{68}$F$_3$N$_3$O$_{10}$: C, 64.24; H, 7.48; N, 4.58. Found: C, 64.13; H, 7.60; N, 4.69.

Example A100
3'-O-Isopropenyl Spinosyn J

3'-O-Acetate of Spinosyn J (3.74 g, 4.92 mmol) was dissolved in dry THF (50 mL). Dry pyridine (10 mL) was added and the solution was cooled to −78° C. under nitrogen. 0.5 M Tebbe Reagent in toluene (25 mL, 12.5 mmol) was slowly added. After stirring at −78° C. for 30 min the temperature was raised to +25° C. and stirring was continued for one hour. The mixture was cooled to 0° C. and 15% aqueous NaOH solution (20 mL) was very slowly added. Afterwards, Et$_2$O (150 mL) was added. The usual work-up and chromatography on silica gel (ethyl acetate) furnished 3'-O-isopropenyl Spinosyn J (1.99 g, 53%) as a white solid: $^1$H NMR δ 6.65 (s, 1 H), 4.20 (m, 2H), 3.84 (m, 2H), 3.41 (s, 3 H), 3.34 (s, 3H), 1.75 (s, 3H). Anal. Calcd for C$_{43}$H$_{67}$NO$_{10}$: C, 68.13; H, 8.91; N, 1.85. Found: C, 68.10; H, 8.99; N, 2.09.

Example A101
3'-O-Isopropyl Spinosyn J

3'-O-Isopropenyl Spinosyn J (0.828 g, 1.09 mmol) was dissolved in dry toluene (12 mL). Triethylsilane (338 mg, 2.9 mmol) was added. The mixture was cooled to +10° C. under nitrogen and TFA (912 mg, 8 mmol) was added during one min. Stirring was continued for 5 min, then triethylamine (1.5 mL) was added. The ususal work-up and chromatography on silica gel gave product which was additionally purified by HPLC (90:10, MeOH/H$_2$O) to give 3'-O-isopropyl Spinosyn J (218 mg, 26%) as a white solid: $^1$H NMR δ 6.71 (s, 1 H), 3.73 (m, 1H), 3.51 (s, 3 H), 3.45 (s, 3H). Anal. Calcd for C$_{43}$H$_{69}$NO$_{10}$: C, 67.95; H, 9.15; N, 1.84. Found: C, 68.20; H, 9.08; N, 1.85.

Example A102
A mixture of compound 3'-O-n-propyl Spinosyn J (60%–85%) and compound 3'-O-n-propyl Spinosyn L (40%–15%)

A technical mixture of Spinosyn J (60%–85%) and Spinosyn L (40%–15%) (20.38 g) was dissolved in methylene chloride (50 mL). Potassium carbonate (12 g) and 20% aqueous NaOH solution (100 mL) were added, followed by n-propyl iodide (35 mL), tetrabutylammonium hydrogen sulfate (4.6 g) and DMSO (50 mL). The mixture was vigorously stirred for 72 h. The usual work-up and chromatography on silica gel (ethyl acetate) afforded a mixture of compound 3'-O-n-propyl Spinosyn J (60%–85%) and compound 3'-O-n-propyl Spinosyn L (40%–15%) (8.87 g) as a white solid: $^1$H NMR δ 6.65 (s, 1 H), 5.37 (s, ca. 0.2 H), 0.85 (t, J=7.4, 3 H).

Example A103

A mixture of compound 3'-O-n-propyl Spinosyn J (60%–85%) and compound 3'-O-n-propyl Spinosyn L (40%–15%) citrate salts A mixture of compound 3'-O-n-propyl Spinosyn J (60%–85%) and compound 3'-O-n-propyl Spinosyn L (40%–15%) (205 mg, 0.275 mmol) was dissolved in acetone (8 mL) and a solution of citric acid monohydrate (57.9 mg, 0.275 mmol) in acetone (3 mL) was added and the solution stirred for 2 h. The solvent was removed by rotary evaporation to give a mixture of compound 3'-O-n-propyl Spinosyn J (60%–85%) and compound 3'-O-n-propyl Spinosyn L (40%–15%) citrate salts (254 mg).

Example A104

A mixture of compound 5,6-dihydro-3'-O-n-propyl Spinosyn J (60%–85%) and compound 3'-O-n-propyl Spinosyn L (40%–15%)

A mixture of compound 3'-O-n-propyl Spinosyn J (60%–85%) and compound 3'-O-n-propyl Spinosyn L (40%–15%) (8.35 g) was dissolved in ethanol (250 mL). Cyclohexene (60 mL) was added. The mixture was cooled under nitrogen to 0° C. and 10% Pd/C catalyst (7.0 g) was added. The reaction mixture was gently heated to reflux for 3 h. It was then cooled to 0° C. and pyridine (2 mL) was added, the catalyst was filtered, the filtrate was concentrated, then dissolved in ethyl ether (300 mL). The usual work-up afforded a mixture of compound 5,6-dihydro-3'-O-n-propyl Spinosyn J (60%–85%) and compound 3'-O-n-propyl Spinosyn L (40%–15%) (7.40 g) as a white solid: $^1$H NMR δ 6.73 (s, ca. 0.8 H), 6.63 (s, ca. 0.2 H), 5.37 (s, ca. 0.2 H), 0.84 (t, J=7.4, 3 H).

Example A105

A mixture of compound 5,6-dihydro-3'-O-n-propyl Spinosyn J (60%–85%) and compound 3'-O-n-propyl Spinosyn L (40%–15%) citrate salts A mixture of compound 5,6-dihydro-3'-O-n-propyl Spinosyn J (60%–85%) and compound 3'-O-n-propyl Spinosyn L (40%–15%) (205 mg, 0.269 mmol) was dissolved in acteone (8 mL) and a solution of citric acid monohydrate (56.7 mg, 0.269 mmol) in acetone (3 mL) was added and the solution stirred for 2 h. The solvent was removed by rotary evaporation to give a mixture of compound 5,6-dihydro-3'-O-n-propyl Spinosyn J (60%–85%) and compound 3'-O-n-propyl Spinosyn L (40%–15%) citrate salts (211 mg).

Example A106

5,6-Dihydro-3'-O-isopropyl Spinosyn J

3'-O-Isopropenyl Spinosyn J (280 mg, 0369 mmol) was reacted during 20 min with triethylsilane (110 mg, 0.94 mmol) and TFA (340 mg, 3.0 mmol) following the procedure described for compound 3'-O-isopropyl Spinosyn J (Example A101). After HPLC (90:10, MeOH/H$_2$O) separation of the crude product, this gave 5,6-dihydro-3'-O-isopropyl Spinosyn J (47 mg, 17%) as a white solid: ESI MS m/z 763 (M+1).

Example A107

3'-O-Ethyl-N-formyl Spinosyn M and compound 3'-O-ethyl Spinosyn M

3-O-Ethyl Spinosyn J (2.20 g, 2.95 mmol) was dissolved in ethanol (25 mL). This solution was then added to a solution of NaOAc (10.3 g) in ethanol (50 mL) and water (20 mL) which was previously refluxed under nitrogen for 30 min. Iodine (4.8 g) was then added, after 5 min. followed by 0.2 N aqueous NaOH solution. Stirring was continued for 10 min at +50° C. The reaction mixture was combined with saturated aqueous NaHSO$_3$ solution (200 ml) and worked up in the usual manner. Flash chromatography on silica gel (ethyl acetate, then 30% EtOH in EtOAc) afforded a) 3'-O-ethyl-N-formyl Spinosyn M (0380 g, 17%) as yellowish glassy solid: ESI MS m/z 760 (M+1); and b) 3'-O-ethyl Spinosyn M (0.799 g, 37%) as an off-white solid: ESI MS m/z 732 (M+1).

Example A108

N-[2'''-(Carbomethoxy)vinyl]-3'-O-ethyl spinosyn M

3'-O-Ethyl Spinosyn M (455 mg, 0.622 mmol) was dissolved in dry methylene chloride (20 mL). Methyl propiolate (2.20 mL, an excess) was added and the mixture was stirred at ambient temperature under nitrogen. After 18 h it was worked up and purified over a silica gel column (ethyl acetate) to give N-[2'''-(carbomethoxy)vinyl]-3'-O-ethyl Spinosyn M (454 mg, 89%) as a white solid: ESI MS m/z 816 (M+1).

Example A109

3'''-(4'''(((Spinosyn H-2'-O-)yl)methyl) phenyl-3'''-trifluoromethyl)-3'''H-diazirine Spinosyn H (1.40 g, 1.95 mmol) and 3-(4-(bromomethyl) phenyl-3-trifluoromethyl-3H-diazirine (2.70 g, 9.7 mmol) were reacted following the procedure described for compound 3'''-(4'''(((Spinosyn J-3'-O-)yl)methyl) phenyl-3'''-trifluoromethyl)-3'''H-diazirine. This gave 3'''-(4'''(((Spinosyn H-2'-O-)yl)methyl) phenyl-3'''-trifluoromethyl)-3'''H-diazirine (251 mg, 14%) as an off-white solid: ESI MS m/z 916 (M+1).

Example A110

3'''-(4'''(((3'-O-Ethyl Spinosyn M-N-)yl)methyl)phenyl-3'''-trifluoromethyl)-3'''H-diazirine 3'-O-Ethyl Spinosyn M (79 mg, 0.108 mmol) was dissolved in dry DMF (5 mL). Triethylamine (0.50 mL) was added, followed by a solution of 3-(4-(bromomethyl)phenyl-3-trifluoromethyl-3H-diazirine (1.0 g, 3.6 mmol) in dry methylene chloride (4 ml). The mixture was stirred at ambient temperature, in darkness, and under nitrogen. After 20 h the mixture was worked up and chromatographed on silica gel (ethyl acetate) to furnish 3'''-(4'''(((3'-O-ethyl spinosyn M-N-)yl) methyl) phenyl-3'''-trifluoromethyl)-3'''H-diazirine (90 mg, 90%) as yellowish glassy solid: ESI MS m/z 930 (M+1).

Example A111

3'-Allyl-3'-epi Spinosyn J

3'-Keto Spinosyn J (3.40 g, 4.75 mmol) was dissolved in dry Et$_2$O (40 mL). To this solution, vigorously stirred under nitrogen at +10° C. was added allyltributyl tin (4.0 mL, an excess). After 5 min. lithium perchlorate (20.0 g) was slowly introduced. Vigorous stirring was maintained for 20 h. More ethyl ether (100 mL) was added and the mixture was worked up. The crude product was chromatographed on silica gel (ethyl acetate) to afford 3'-allyl-3'-epi Spinosyn J (2.23 g, 62%) as a white solid: $^1$H NMR δ 6.66 (s, 1 H), 5.72 (m, 3 H), 5.09 (m, 2 H), 3.45 (s, 3 H), 3.35 (s, 3 H). ESI MS m/z 758 (M+1).

Example A112

(14 R/S)-3'-Allyl-13,14-dihydro-3'-epi Spinosyn J

3'-Allyl-3'-epi Spinosyn J (1.14 g, 1.50 mmol) was dissolved in dry methylene chloride (12 mL). The solution was cooled to −78° C. under nitrogen and phenylselenenyl chloride (650 mg, 3.32 mmol) was added in one portion. After 10 min the mixture was warmed up to 0° C. After additional 10 min triethylamine (0.50 mL) was added and stirring at 0° C. was continued for another 10 min. Work-up and chromatography on silica gel (ethyl acetate) afforded a white solid (1.028 g). This material was dissolved in dry toluene (20 mL). Tri-n-butyltin hydride (1.80 mL, an excess) and AIBN (110 mg) were added. The mixture was heated to reflux under nitrogen for 15 min. After cooling to room temperature, the mixture was concentrated in vacuo and purified by chromatography on silica gel (ethyl acetate). Subsequent separation by HPLC (92:8, MeOH/H$_2$O) afforded (14R/S)-3'-allyl-13,14-dihydro-3'-epi spinosyn J (188 mg, 16%) as white solid: $^1$H NMR δ 5.45–5.75 (m, 3 H), 5.04 (m, 2 H). ESI MS m/z 760 (M+1).

Example A113
5,6-Dihydro-3'-epi-N-formyl-3'-propyl Spinosyn J and 5,6-dihydro-3'-epi-3'-propyl Spinosyn J Compound 3'-allyl-3'-epi Spinosyn J (218 mg, 0.287 mmol) was dissolved in ethanol (30 mL). The solution was cooled to 0° C. under nitrogen. 10% Pd/C (911 mg) was added, followed by cyclohexene (10 mL, not purified before use). The mixture was heated to reflux under nitrogen for 3 h. Triethylamine (1 mL) was added. After work-up and chromatography on silica gel, the crude product was separated on HPLC (94:6, MeOH/H$_2$O). This gave a) 5,6-dihydro-3'-epi-N-formyl-3'-propyl Spinosyn J (28 mg, 12%) as a yellowish glassy solid: $^1$H NMR δ 8.04 (s, 1H), 6.81 (s, 1 H), 3.47 (s, 3 H), 3.39 (s, 3 H), 2.71 (s, 1.5 H), 2.19 (s, ca. ca. 1.5 H). ESI MS m/z 766 (M+1) and b) 5,6-dihydro-3'-epi-3'-propyl Spinosyn J (94 mg, 43%) as a white solid: $^1$H NMR δ 6.75 (s, 1 H), 3.42 (s, 3 H), 3.34 (s, 3 H), 2.13 (s, 6 H).

Example A114
3'-O-Vinyl Spinosyn J

Spinosyn J (1.2 g, 1.67 mmol) was dissolved in ethyl vinyl ether (50 mL, an excess). Mercuric acetate (3.5 g) was added. The mixture was heated to reflux under nitrogen for 4 h. After work-up, chromatography on silica gel (ethyl acetate) afforded 3'-O-vinyl Spinosyn J (163 mg, 13%) as a white solid: ESI MS m/z 744 (M+1).

Example A115
3'-O-(N-Imidazol)sulfonyl Spinosyn J

Spinosyn J (2.40 g, 3.34 mmol) was dissolved in dry dimethylformamide (15 mL). The solution was cooled to 0° C. under nitrogen and imidazole (6.8 g, an excess) was added. The mixture was stirred for 10 min. Afterwards, sulfuryl chloride (1.90 mL) was slowly introduced via syringe, the mixture was warmed up to room temperature and stirring was continued for 16 h. The usual work-up and chromatography on silica gel (ethyl acetate) afforded 3'-O-(N-imidazol)sulfonyl Spinosyn J (1.52 g, 54%) as a white solid: ESI MS m/z 848 (M+1).

Example A116
4'-Nor-3'-(E)-(methoxy)methylene Spinosyn J

3'-O-(N-Imidazol)sulfonyl Spinosyn J (1.21 g, 1.43 mmol) was dissolved in dry toluene (20 mL). Benzyltriethylammonium chloride (5.0 g, an excess) was added and the mixture was heated to reflux under nitrogen. After 5 h, the mixture was concentrated in vacuo. The crude product was purified by chromatography on silica gel (ethyl acetate) and then separated by HPLC (90:10, MeOH/H$_2$O) to give 4'-nor-3'-(E)-(methoxy)methylene Spinosyn J (61 mg, 6%) as a white solid: $^1$H NMR δ 6.70 (s, 1 H), 6.15 (d, J=2.0, 1 H), 5.00 (s, 1 H), 4.68 (q, J=6.6, 1 H), 3.60 (s, 3 H), 3.20 (s, 3 H).

Example A117
5,6-Dihydro-3'-O-vinyl Spinosyn J 5,6-Dihydro-Spinosyn J (1.85 g, 2.57 mmol) was dissolved in butyl vinyl ether (50 mL, an excess). Mercuric acetate (4.2 g, an excess) was added. The reaction mixture was heated to reflux for 4 h. Solid potassium carbonate (10 g) was then added. The usual work-up and chromatography on silica gel (ethyl acetate) afforded 5,6-dihydro-3'-O-vinyl Spinosyn J (1.02 g, 53%) as a white solid: $^1$H NMR δ 6.74 (s, 1 H), 6.31 (dd, J$_1$=16.9, J$_2$=6.5, 1 H), 4.30 (m, 2 H), 3.90 (m, 2 H), 3.38 (s, 3 H), 3.36 (s, 3 H).

Example A118
2'-O-Vinyl Spinosyn H

Spinosyn H (2.03 g, 2.83 mmol) was reacted with butyl vinyl ether and isolated from the reaction mixture following the procedure described for 5,6-dihydro-3'-O-vinyl Spinosyn J. This gave 2'-O-vinyl Spinosyn H (1.09 g, 52%) as a white solid: ESI MS m/z 744 (M+1).

Example A119
3'-O-(Dimethyl)phosphate of Spinosyn J

Spinosyn J (0.903 g, 1.26 mmol) was dissolved in dry pyridine (2.5 mL). The solution was cooled to 0° C. under nitrogen and carbon tetrabromide (0.91 g, 2.75 mmol) was added. After stirring for 5 min, trimethyl phosphite P(OMe)$_3$ (0.38 mL, 3.12 mmol) was slowly introduced via syringe. The cooling bath was removed and the mixture was stirred for 3 h at room temperature. The usual work-up and chromatography on silica gel (15% EtOH in EtoAc) afforded 3'-O-(dimethyl)phosphate of Spinosyn J (0.910 g, 88%) as a white solid: ESI MS m/z 826 (M+1).

Example A120
2'-O-(Dimethyl)phosphate of Spinosyn H

Spinosyn H (0.65 g, 0.905 mmol) was reacted with CBr$_4$ (0.63 g, 1.90 mmol) and P(OMe)$_3$ (0.30 mL, 2.46 mmol) following the procedure described for 3'-O-(dimethyl)phosphate of Spinosyn J. This afforded 2'-O-(dimethyl)phosphate of Spinosyn H (0.230 g, 31%) as a white solid: ESI MS m/z 826 (M+1).

Example A121
(14S)-13,14-Dihydro-3'-O-ethyl Spinosyn M

3'-O-Ethyl Spinosyn M (810 mg, 1.106 mmol) was dissolved in dry Et$_2$O (80 mL). Lithium tri-tert-butoxyaluminohydride (97% powder, 1.48 g, 5.6 mmol) was added in one portion. The mixture was stirred at room temperature under nitrogen for 5 h. The solution was then cooled to 0° C. and slowly quenched with saturated brine (5 mL). More Et$_2$O (100 mL) was added and the mixture was extracted with 2N aqueous NaOH solution (two times) and with saturated aqueous NaHCO$_3$ solution (one time). The organic layer was dried over anhydrous potassium carbonate, filtered and concentrated. The crude product was chromatographed on silica gel (20% EtOH in EtOAc) to give (14S)-13,14-dihydro-3'-O-ethyl Spinosyn M (766 mg, 94%) as a white solid: $^1$H NMR δ 4.68 (s, 1 H), 4.60 (m, 1 H), 3.42 (s, 3 H), 3.35 (s, 3 H), 2.29 (s, 3 H), 0.98 (d, J=6.6, 3 H).

Example A122
(14S)-13,14-Dihydro-N,3'-O-diethyl Spinosyn M (14S)-13,14-Dihydro-3'-O-ethyl Spinosyn M (326 mg, 0.444 mmol) was dissolved in dry dimethylformamide (10 mL). Triethylamine (3.0 mL) and iodoethane (2.0 mL, an excess) were added. The mixture was stirred under nitrogen at room temperature for 4 h. The usual work-up and chromatography on silica gel (ethyl acetate) furnished (14S)-13,14-dihydro-N,3'-O-diethyl Spinosyn M (337 mg, 99%) as a white solid: ESI MS m/z 762 (M+1).

Example A123
(14S)-13,14-Dihydro-3'-O-n-propyl Spinosyn J, compound (1R/S,15R,21S)-15-deoxy-1,15-oxa-3'-O-n-propyl-1,21-seco Spinosyn J 1-hemiacetal, and compound (15R)-15-deoxy-15-hydroxy-3'-O-n-propyl Spinosyn J 3'-O-n-Propyl Spinosyn J (1.87 g, 2.46 mmol) was reacted with lithium tri-tert-butoxyaluminohydride (97% powder, 2.02 g, 7.71 mmol) in Et$_2$O (100 mL) during 16 hrs., according to the procedure given for (14S)-13,14-dihydro-3'-O-ethyl Spinosyn M. After work-up and chromatography on silica gel (ethyl acetate) this afforded: a) (14S)-13,14-dihydro-3'-O-n-propyl Spinosyn J (1.19 g, 63%) as a white solid: $^1$H NMR d 4.70 (s, 1H), 4.64 (m, 1H), 3.48 (s, 3 H), 3.41 (s, 3 H), 2.15 (s, 6 H), 1.04 (d, J=6.8, 3 H); and b) a mixture of compounds (0.66 g) which was further separated by HPLC (88:12, MeOH/H$_2$O) to give c) (1R/S,15R,21S)-15-deoxy-1,15-oxa-3'-O-n-propyl-1,21-seco Spinosyn J 1-hemiacetal (77 mg, 4%) as a white solid: $^1$H NMR δ 5.38 (s, 0.5 H), 5.03 (d, J=7, 0.5 H), 3.49 (s, 3 H), 3.40 (s, 3 H), 2.15 (s, 6 H), 1.02 (broadened d, J=6.8, 3 H). ESI MS m/z 764 (M+1); and d) (15R)-15-deoxy-15-hydroxy-3'-O-n-propyl Spinosyn J (44 mg, 2.3%) as a white solid: $^1$H NMR δ 5.79 (d, J=9.8, 1 H), 5.72 (s, 1 H), 5.70 (d, J=9.8, 1 H), (s, 1H), 4.64 (m, 1H), 3.47 (s, 3 H), 3.42 (s, 3 H), 0.90 (d, J=6.6, 3 H).

Example A124
(14S)-5,6,13,14-Tetrahydro-3'-O-n-propyl Spinosyn J 5,6-Dihydro-3'-O-n-propyl Spinosyn J (1.88 g, 2.47 mmol) was reacted with lithium tri-tert-butoxyaluminohydride (97% powder, 2.40 g, 9.16 mmol) in Et$_2$O (100 mL) during 3.5 hrs., according to the procedure given for (14S)-13,14-dihydro-3'-O-ethyl Spinosyn M. After work-up and chromatography on silica gel (ethyl acetate) this afforded (14S)-5,6,13,14-tetrahydro-3'-O-n-propyl Spinosyn J (1.440 g, 76%) as a white solid: $^1$H NMR δ 4.66 (d, J=1.4, 1 H), 4.64 (m, 1 H), 3.41 (s, 3 H), 3.34 (s, 3 H), 2.09 (s, 3 H), 1.00 (d, J=6.6, 3 H).

Example A125
3'-O-(2-Methoxyethyl)-Spinosyn J

Spinosyn J (718 mg, 1.00 mmol) was dissolved in a mixture of DMSO (1.4 mL) and CH$_2$Cl$_2$ (1.4 mL). Potassium carbonate (0.90 g, 6.5 mmol), 20% aqueous NaOH (5.2 mL), tetra-n-butlylammonium hydrogen sulfate (339 mg, 1.00 mmol) and 2-methoxyethyl bromide (1.00 mL, 10.6 mmol) were added sequentially. The mixture was stirred for 3 days at room temperature. The mixture was partitioned between Et$_2$O and water. The aqueous layer was extracted with Et$_2$O. The combined organic layers were washed with water (three time) and saturated aqueous sodium bicarbonate, dried over anhydrous potassium carbonate and evaporated to yield a yellow oil. This oil was chromatographed on a reversed-phase column (Kromasil' C18, Silica ODS, 100 Å, 10 m, spherical, 25 cm×20 mm) with 88% MeOH and 12% water (containing 0.1% v/v conc. aqueous NH$_4$OH) to yield a white amorphous solid (249 mg, 32%) $^1$H NMR d 3.78 (m, 2 H), 3.38 (s, 3 H).

Example A126
3'-Methoxymethyl-Spinosyn J

Spinosyn J (359 mg, 0.500 mmol) was dissolved in CH$_2$Cl$_2$ (2 mL) and the resulting solution cooled to 0° C. Diisopropylethylamine (105 mL, 0.600 mmol) was added in a single portion followed by bromomethyl methyl ether (90%, 50 mL, 0.55 mmol) in several portions. An immediate precipitate formed which redissolved in a few minutes. The mixture was stirred at 0° C. for 2.5 hrs. and at room temperature for an additional 2.5 hrs. The mixture was cooled to 0° C. and additional amine (0.32 mL, 1.8 mmol) and bromide (0.15 mL, 1.7 mmol) added. The mixture was stirred an additional hour. Saturated aqueous sodium bicarbonate (3 mL) was added and the mixture stirred at room temperature for 17 hrs. The mixture was diluted with CH$_2$Cl$_2$ and washed with saturated aqueous sodium bicarbonate, water (twice), saturated aqueous sodium bicarbonate and brine (twice). The mixture was dried over anhydrous potassium carbonate and evaporated to yield a yellow oil. The oil was chromatographed on a reversed-phase column (Kromasil' C18, Silica ODS, 100 Å, 10m, spherical, 25 cm×20 mm) with 85% MeOH and 15% water (containing 0.1% v/v conc. aqueous NH$_4$OH) to yield a white glassy solid (87 mg, 23%) $^1$H NMR d 3.45 (s, 3 H); MS m/z 762.6 (calc. for M+H, 762.5).

Example A127
5,6-Dihydro-3'-methoxymethyl-Spinosyn J

3'-methoxymethyl-Spinosyn J (243 mg, 0.319 mmol) and palladium on charcoal (10%, 200 mg) were placed in a 25-mL round-bottomed flask. Ethanol (7.25 mL) and cyclohexene (1.75 mL, 17.3 mmol) were added and the resulting solution was heated at reflux temperature for 3 hrs. The mixture was successively filtered through Celite and a PTFE filter (Gelman, Acrodisc 13 CR, 0.2 mm). The mixture was concentrated under reduced pressure and the residue chromatographed on a reversed-phase column (Kromasil' C18, Silica ODS, 100 Å, 10 m, spherical, 25 cm×20 mm) using 85% MeOH and 15% water (containing 0.1% v/v conc. aqueous NH$_4$OH) to yield an amorphous white solid (68 mg, 28%) MS m/z 764.7 (calc. for M+H 764.5)

Example A128
3'-O-Cyanomethyl-Spinosyn L and 3'-O-trimethylsilyl-Spinosyn L

Spinosyn L (366 mg, 0.500 mmol) was dissolved in DMF (1 mL) and the solution cooled to −15° C. A 1.0 M solution of sodium hexamethyldisilazane (0.53 mL, 0.53 mmol) was added dropwise. After the mixture was stirred for 5 min, bromoacetonitrile (38 mL, 0.55 mmol) was added dropwise to yield a very dark solution which was allowed to stand at 0° C. for 65 hrs. The reaction mixture was partitioned between EtOAc and saturated aqueous sodium bicarbonate. The organic layer was washed with dilute aqueous sodium bicarbonate, dilute aqueous sodium thiosulfate and brine. The mixture was dried over anhydrous MgSO$_4$ and the solvent removed under reduced to yield a dark oil (380 mg). This oil was chromatographed on a reversed-phase column (Kromasil' C18, Silica ODS, 100 Å, 10 m, spherical, 25 cm×20 mm) with 90% MeOH and 10% water (containing 0.1% v/v conc. aqueous NH$_4$OH) to yield two products 3'-O-cyanomethyl-Spinosyn L (48 mg, 12%), $^1$H NMR d 4.52, 4.44(ab q, J=14.9, 2 H); MS m/z 771.6 (calc. for M+H 771.5); and 3'-O-trimethylsilyl-Spinosyn L (241 mg, 60%) $^1$H NMR d 0.19 (s, 9 H); MS m/z 804.7 (calc. for M+H 804.5).

Example A129
3'-O-Carbo-t-butoxymethyl-Spinosyn J

Spinosyn J (718 mg, 1.00 mmol) and tetra-n-butylammonium hydrogen sulfate (34 mg, 0.10 mmol) were dissolved in CH$_2$Cl$_2$ (3.5 mL). t-Butyl bromoacetate (2.95 mL, 20.0 mL) and powdered KOH (1.0 g, 15 mmol) were added sequentially in single portions and the reaction mixture stirred at room temperature. After 40 min., additional tetra-n-butylammonium hydrogen sulfate (64 mg, 0.2 mmol) was added. After an additional 60 min., the mixture was dilute with water and extracted with CH$_2$Cl$_2$ (once) and EtOAc (once). The combined organic layers were washed with water (twice), saturated aqueous sodium bicarbonate and brine, dried over K$_2$CO$_3$ and MgSO$_4$ and evaporated to yield a yellow oil (4.13 g). The oil was placed under reduced pressure (0.9 Torr) for 2 h to yield an oil (2.30 g). This oil was chromatographed over silica gel (165 g) with EtOAc followed by 10% MeOH in EtOAc to yield a white foam (295 mg, 35%) $^1$H NMR d 4.24, 4.19 (ab q, J=16.5, 2 H), 1.49 (s 9 H); MS m/z 832.7 (calc. for M+H 831.5).

Example A130
4"-N-Desmethyl-4'-N-(2-fluoroethyl)-5,6-dihydro-3'-O-propyl Spinosyn J This compound was prepared according to the method in Example CZ from 1-bromo-2-fluoroethane (0.20 mL, 0.34 g, 2.7 mmol), NaI (0.04 g, 0.3 mmol), (i-Pr)$_2$NEt (0.40 mL, 0.30 g, 2.3 mmol), 4"-N-desmethyl-5,6-dihydro-3'-O-propyl Spinosyn J (0.300 g, 0.401 mmol), and DMF (2 mL). MPLC (25:75 to 50:50 EtOAc/hexane) gave 0.235 g (74%) of 4"-N-desmethyl-4"-N-(2-fluoroethyl)-5,6-dihydro-3'-O-propyl Spinosyn J as a white powder.

Example A131
4"-N-[3'-O-(9-Fluorenylmethoxycarbonyl)-β-alanyl] Spinosyn J and 3'-O-(β-alanyl) Spinosyn J Triethylamine (0.25 mL, 0.18 g, 1.8 mmol) and HC≡C(Me)OCOCl (0.10 mL,, 0.11 g, 0.92 mmol) were added sequentially to a 0° C. solution of Fmoc-N(H)-b-Ala-CO$_2$H (0.26 g, 0.84 mmol), Spinosyn J (0.502 g, 0.699 mmol), and DMAP (0.02 g, 0.2 mmol) in CH$_2$Cl$_2$ (4 mL). After 2 hrs., the mixture was warmed to ambient temperature for 20 h. The mixture was evaporated. MPLC (SiO$_2$, 0:100 to 20:80 MeOH/CH$_2$Cl$_2$) gave 0.17 g (24%) of 4"-N-[3'-O-(9-fluorenylmethoxycarbonyl)-β-alanyl] Spinosyn J as a white powder: MS (m+H$^+$) expected: 1011.6. Found: 1011.6 and 3'-O-(β-alanyl) Spinosyn J, 0.21 g (38%) as a white powder: MS (m+H$^+$ & m+2H$^+$/2) expected: 789.5 & 395.2. Found: 395.5. Facile deprotection of the Fmoc group under the reaction conditions may have accounted for the production of this compound.

Example A132
4"-N-Desmethyl-5,6-dihydro-3'-O-propyl Spinosyn J

F-TEDA (0.98 g, 2.8 mmol) was added to a solution of 5,6-dihydro-3'-O-n-propyl Spinosyn J (0.94 g, 1.23 mmol) in CH$_3$CN (10 mL). After 10 min, the mixture was partitioned between EtOAc and 0.1 M HCl. The organic layer was washed sequentially with NaHCO$_3$ and brine. The organic layer was dried (MgSO$_4$), filtered, and evaporated. MPLC (SiO$_2$, 5:95 to 10:90 MeOH/CH$_2$Cl$_2$) gave 0.64 g (70%) of 4"-N-desmethyl-5,6-dihydro-3'-O-propyl Spinosyn J as a white powder (5,6-dihydro-3'-O-n-propyl Spinosyn J, 0.25 g (27%) was also recovered).

Example A133
1'-epi-Spinosyn K

To a well stirred solution of spinosyn A 9-Psa (1.25 g. 2.30 mmol) and pyridinium p-toluenesulfonate (0.815 g, 3.24 mmol) in dry CH$_2$Cl$_2$ (120 mL) containing powdered 4A molecular sieves (2.0 g), a solution of O-(2,3-di-O-methyl-4-O-benzoyl-α-L-rhamno-pyranosyl)trichloroacetimidate (5.5 g, 11.5 mmol) in CH$_2$Cl$_2$ (60 mL) was added dropwise during 15 min. After stirring at ambient temperature for 4 days, the mixture was filtered through Celite, the Celite washed with CH$_2$Cl$_2$ (100 mL) and the combined filtrate and wash washed with sat. Na$_2$CO$_3$ (2×60 mL) and brine (75 mL) and dried (MgSO$_4$). Concentration left 8.2 g of residue which was flash chromatographed over silica (650 mL) using 3% MeOH in CH$_2$Cl$_2$ to yield 1.1 g (58%) of coupled product, a 3 α:1 β anomeric mixture, as a colorless foam. This material was dissolved in MeOH (30 mL) and to this solution was added anhy. K$_2$CO$_3$ (0.98 g, 7.1 mmol). This solution was stirred at ambient temperature for 6 h, acidified by the dropwise addition of 2N HCl (6.8 mL) and then concentrated to near dryness at reduced pressure. The residue was partitioned between water (40 mL) and CH$_2$Cl$_2$ (150 mL). The organic extracts were then washed with sat. NaHCO$_3$ (40 mL) and brine (40 mL) and dried (MgSO$_4$). Concentration left 0.72 g of crude debenzoylated product. This was purified by flash chromatography over silica (80 mL) using 4% MeOH in CH$_2$Cl$_2$ to yield 0.54 g of clean product as a 3:1 mixture of Spinosyn K and 1'-epi-spinosyn K. This mixture was separated by hplc in three portions of ~180 mg over a 41.4 mm (i.d.)×25 cm (1) Rainin reverse phase C18 (8 μm) column using 15% H$_2$O (containing 0.01% NH$_4$OH) in MeOH as eluent. The β-anomer, 1'-epi-spinosyn K elutes first: 110 mg; colorless foam; $^1$H NMR (CDCl$_3$) δ 6.79 (s, 1, H-13), 4.68 (m, 1, H-21), 4.45 (m, 3, H-1', H-1", H-9); MS m/z 435 (10), 175 (5), 142 (100), 71 (90).

Example A134
4'-O-Propionyl Spinosyn K

Propionic anhydride (0.1 mL, 0.77 mmol) was added in one portion to a well stirred solution of spinosyn K (72 mg, 0.1 mmol) and DMAP (~2 mg) in dry pyridine (1.0 mL) at ambient temperature and this mixture was stirred for 20 h. The pyridine was removed in vacuo, the residue was dissolved in CH$_2$Cl$_2$ (25 mL) and this CH$_2$Cl$_2$ solution washed with water (5 mL), sat. Na$_2$CO$_3$ (5 mL), brine (5 mL) and dried (MgSO$_4$). After filtration of the drying agent, the CH$_2$Cl$_2$ solution was concentrated to ~6 mL and stirred with polyvinylpyridine (0.3 g) for 15 min to neutralize any residual propionic acid salt of product. After filtration of the resin, the CH$_2$Cl$_2$ was evaporated leaving 85 mg of crude propionate. This was purified by flash chromatography over silica (30 mL) using 3% MeOH in CH$_2$Cl$_2$ to give 71 mg of 4'-O-propionyl Spinosyn K as a colorless foam: $^1$H NMR (CDCl$_3$) δ 6.76 (s, 1, H-13), 5.02 (t, 1, H-4'), 4.87 (s, 1, H-1'), 4.66 (m, 1, H-21), 4.42 (br d, 1, H-1"), 4.32 (m, 1, H-9); MS m/z 773 (2), 231 (15), 142 (70), 71 (100).

Example A135
(9-O-(2,3,4-Tri-O-methyl-D-rhamnopyranosyl) Analogs of Spinosyn A Compounds 9-O-(2,3,4-tri-O-methyl-D-rhamnopyranosyl) Spinosyn A, a 3.5 α:1 β anomeric mixture at position 1', was prepared in 82% yield by the same procedure as that used for Example A45 above from 0.54 g (1.0 mmol) Spinosyn A 9-Psa, 0.35 g (1.4 mmol) pyridinium p-toluenesulfonate, and 2.0 g (5.7 mmol) of O-(2,3,4-tri-O-methyl-α-D-rhamnopyranosyl)-trichloroacetimidate. The α and β anomers were separated by reversed phase hplc over C18 bonded silica gel using 10% H$_2$O (containing 0.1% NH$_4$OH) in MeOH. The β anomer elutes first. β anomer: 85 mg; colorless foam; $^1$H NMR (CDCl$_3$) δ 6.78 (s,1H,H-13), 4.66 (m, 1H, H-21), 4.40 (m, 3H, H-1", H-1', H-9). α anomer: 270 mg; colorless foam; $^1$H NMR (CDCl$_3$) δ 6.76 (s, 1H, H-13), 4.82 (s, 1H, H-1'), 4.66 (m, 1H, H-21), 4.40 (d, 1H, H-1"), 4.28 (m, 1H, H-9); MS m/z 449 (2), 189 (10), 142 (70), 71 (100).

Example A136
3'-O-(2,2,2-Trifluoroethyl)Spinosyn J

To a cold (0–5° C.), well stirred solution of Spinosyn J (500 mg, 0.7 mmol) in anhydrous THF (20 mL), a 60% suspension of NaH in mineral oil (224 mg, 5.6 mmol as 100%) was added in one portion. When H$_2$ evolution had ceased (after ~10 min.), trifluoroethyl triflate (*J. Org. Chem.* 1973, 38, 3673; *Tetrahedron* 1965, 21, 1) (0.9 g, 3.2 mmol) was added dropwise during 2–3 min. The cooling bath was removed after 1 h, and the reaction let stir at ambient temperature for 4 h. The mixture was recooled to 0–5° C., and water (20 ml) was added dropwise during 15 min. The mixture was extracted with ether (2×50 mL). The organic extracts were washed with brine (25 mL) and dried (MgSO4). Concentration, left 0.6 g of crude product which contained ~40 % starting Spinosyn J. This was partially purified by flash chromatography over Silica (120 ml) using 3% MeOH in CH$_2$Cl$_2$ as eluent. This partially purified product (150 mg) was purified by hplc over a 41.4 mm (i.d.)×25 cm (1) Rainin reverse phase C18 (8 μm) column using 10% water (containing 0.1% NH4OH) in MeOH as eluent, to afford 58 mg of clean 3'-O-(2,2,2-trifluoroethyl) Spinosyn J as a colorless foam: $^1$H NMR (CDCl$_3$) δ 6.76 (s, 1H, H-13), 4.81 (s, 1H, H-1'), 4.67 (m, 1H, H-21), 4.42 (d, 1H, H-1''), 4.30 (m, 1H, H-9), 4.06 (m, 2H, CF$_3$CH$_2$O).

Example A137

3'-O-(2,3,4-Tri-O-ethyl)-α-L-rhamnopyranosyl) Spinosyn J and 3'-O-(2,3,4-Tri-O-ethyl)-β-L-rhamnopyranosyl) Spinosyn J A 9:1 anomeric mixture of α:β at position 1'''(0.33 g, 62% yield) was obtained from the reaction of Spinosyn J (0.4 g, 0.56 mmol), pyridinium p-toluenesulfonate (0.18 g, 0.72 mmol) and O-(2,3,4-tri-O-ethyl-α-L-rhamnopyranosyl)-trichloroacetimidate (1.6 g, 4.08 mmol) by the same procedure as that used in Example A45. This mixture was separated by reversed-phase hplc over a C18 bonded silica (8 mm) column (41.4 mm (i.d.)×25 cm (1)) using 6% H$_2$O (containing 0.15% NH$_4$OH) in MeOH as eluent. The β-anomer elutes first. β anomer: 5 mg; colorless foam; $^1$H NMR (CDCl$_3$) δ 6.76 (s, 1H, H-13), 4.81 (d, J=2.2, 1H, H-1'), 4.67 (m, 1H, H-21), 4.49 (s, 1H, H-1'''), 4.42 (dd, J=8.8, 1.4, 1H, H-1''), 4.30 (m, 1H, H-9). α anomer: 85 mg; colorless foam; $^1$H NMR (CDCl$_3$) δ 6.76 (s, 1H, H-13), 5.02 (d, J=1.5, 1H, H-1'''), 4.79 (d, J=1.5, 1H, H-1'), 4.67 (m, 1H, H-21), 4.42 (dd, J=8.5, 1.5, 1H, H-1''), 4.27 (m, 1H, H-9); MS m/z 948 (100).

Example A138

4'-Dehydro-3'-deoxy-3'-enyl Spinosyn J 2,2,2-Trifluoroethanol (15 μL, 0.21 mmol) was added in one portion to a cold (0° C.) suspension of a 60% mineral oil dispersion of NaH (7.5 mg, 0.188 mmol) in dry DMF (2.5 mL) and this mixture was stirred in the cold for 20 min. To this now clear solution, 3'-O-trifluoromethanesulfonyl-3'-epi-spinosyn J (100 mg, 0.118 mmol), was added in one portion and this mixture then stirred at room temperature for 18 hrs. Silica gel (200 mg) was added, this mixture stirred for 10 min., then filtered and the collected silica washed with CH$_2$Cl$_2$. The combined filtrate and wash was concentrated to dryness at reduced pressure and the residue was dissolved in EtOAc (20 mL). This EtOAc solution was then washed with brine (10 mL) and dried (MgSO$_4$). Evaporation of the solvent left 76 mg of residue which was flash chromatographed over silica (10 mL) using 3% MeOH in CH$_2$Cl$_2$ as eluent to give 43 mg of 4'-dehydro-3'-deoxy-3'-enyl Spinosyn J as a colorless foam: $^1$H NMR (CDCl$_3$) δ 4.72 (d, J=3.3, 1H, H-3'); $^{13}$C NMR (CDCl$_3$) δ 160.0 (C-4'), 87.9 (C-3').

Example A139

3'-O-Propyl Spinosyn L

Powdered potassium hydroxide (1 g) was added to a suspension of Spinosyn L (0.732 g, 1.0 mmol), tetrabutylammonium bromide (0.1 mmol) and n-propyl bromide (2.7 g, 22.0 mmol) in dichloromethane (3 mL) and stirred under a N$_2$ atmosphere for 1.5 hrs. at 25° C. Water (10 mL) was added and layers separated. Aqueous layer was extracted with dichloromethane (3×20 mL) and the combined extracts were dried over sodium sulfate, filtered and concentrated. Trituration with pentane gave 3'-O-Propyl Spinosyn L (0.72 g, 93%) as a colorless glass. ESI MS, m/z 774.7 (M$^+$).

Example A140

3'-O-Propyl Spinosyn J & L

Powdered potassium hydroxide (1 g) was added to a suspension of Spinosyn J & L (0.732 g, 1.0 mmol), tetrabutylammonium bromide (0.032 g, 0.1 mmol) in propyl bromide (5 mL) and stirred under a N$_2$ atmosphere for 3 hrs. at 25° C. Ether (20 mL) and water (10 mL) was added and layers were separated. Aqueous layer was extracted with ether (2×20 mL) and the combined ether extracts were dried over sodium sulfate, filtered and concentrated. Trituration with pentane gave 3'-O-Propyl Spinosyn J & L (0.71 g, 92%) as a colorless glass. ESI MS, m/z 760.2 (M$^+$) for 3'-O-Propyl Spinosyn J and m/z 774.3 (M$^+$) for 3'-O-Propyl Spinosyn L.

Example A141

3'-O-Ethyl Spinosyn L

Powdered potassium hydroxide (1 g) was added to suspension of Spinosyn L (0.732 g, 1.0 mmol) and tetrabutylammonium bromide (0.032 g, 0.1 mmol) in bromoethane (5 mL) and stirred under a N$_2$ atmosphere for 0.5 hr. at 25° C. Ether (20 mL) and water (10 mL) was added and layers were separated. Aqueous layer was extracted with ether (2×20 mL), dried over sodium sulfate, filtered and concentrated. Trituration with pentane gave 3'-O-Ethyl Spinosyn L (0.72 g, 94%) as a colorless glass. ESI MS, m/z 760.3 (M$^+$)

Example A142

Synthesis of 3'-O-n-propyl Spinosyn Q

To a magnetically stirred 50 mL round-bottom flask was charged Spinosyn Q (732 mg, 1 mmol), tetrabutylphosphonium bromide (34 mg, 0.1 mmol), 1-bromopropane (4 mL, 24 mmol), and dichloromethane (1 mL). This solution was stirred in a room-temperature water bath and potassium hydroxide (500 mg, 7.5 mmol based on 85% pure, machine powdered before use) was added in one portion. The resulting mixture was stirred for 2 hours, and then worked up by partitioning between 25 mL ethyl ether and 5 mL water, separating the phases, washing the ether phase 1×5 mL water, 1×5 mL saturated sodium chloride, drying over magnesium sulfate, and removing the solvent on the rotovap. The residue was purified by chromatography over 30 g of silica gel, eluting with ethanol/ethyl acetate/hexanes (2:50:50) to give compound 3'-O-n-propyl Spinosyn Q as a white crunchy foam (610 mg, 97.5% pure by HPLC). $^1$H NMR (CDCl$_3$) d 6.75 (1H, bs), 5.48 (1H, bs), 4.78 (1H, S), 4.4 (1H, d, j=8 Hz), 4.28 (1H, br q, j=7.5 Hz), 0.91 (3H, t, j=7.5 Hz), 0.8 (3H, t, j=7.5 Hz). Mass spectra, M/E: 775 (M+1)

Part B Modification of the Psuedoaglycone by Replacement of Forosamine with Nonsugar Derivatives Example B1

17-O-Acetyl Spinosyn A 17-Psa

A solution of Spinosyn A (2.00 gms, 2.73 mmol) in glacial acetic acid (50 ml) was heated to reflux for 5 hours and then stirred at room temperature for 12 hours. The reaction mixture was evaporated to a small volumn, and then poured into saturated aqueous NaHCO$_3$. The aqueous mixture was extracted with ether. The ether was washed with brine, dried with K$_2$CO$_3$, and evaporated at room temperature under reduced pressure, giving a yellow glass (1.48 gms). The products were separated by chromatography on silica, eluting with 40% hexane in ethyl acetate. 17-O-acetyl Spinosyn A 17-Psa(478.9 mg; 28% yield) was isolated as a white solid, FDMS, m/e (relative intensity) 632 (M$^+$-H, 100), and Spinosyn A 17-Psa(846.2 mg; 52% yield) was isolated as a colorless glass.

Example B2

17-O-(3-Dimethylaminopropanoyl) Spinosyn A 17-Psa

Compound 17-O-(propenoyl) Spinosyn A 17-Psa (206.3 mg, 0.32 mmol) was dissolved in ice cold dimethylamine (5 ml) and the reaction mixture was capped and stirred at −5-C for 2 hours. The reaction mixture was then allowed to warm to room temperature while dimethylamine was distilled through an acid scrubber. The residue was dissolved in aqueous HCl and washed with ether. The aqueous was basified with 5 N NaOH and extracted with fresh ether. The ether from the base extract was washed with brine, dried with $K_2CO_3$ and evaporated at room temperature under reduced pressure. This gave 17-O-(3-dimethylaminopropanoyl) Spinosyn A 17-Psa(177.1 mg; 80% yield) as a colorless glass, FDMS, m/e (relative intensity) 689 ($M^+$, 100).

Example B3

17-O-(Propenoyl) Spinosyn A 17-Psa

To a solution of Spinosyn A 17-Psa 364.3 mg, 0.61 mmol) in chloroform (10 ml), acryloyl chloride (75 ml, 0.92 mmol) was added followed by diisopropylethylamine (160 ml, 0.92 mmol). The reaction mixture was heated to reflux for 6 hours; then additional acryloyl chloride (75 ml, 0.92 mmol) and diisopropylethylamine (160 ml, 0.92 mmol) were added and the mixture was refluxed another 12 hours. The reaction mixture was then cooled to room temperature and diluted with dichloromethane. The dichloromethane was washed with saturated aqueous $NaHCO_3$, dried with $K_2CO_3$ and evaporated at room temperature under reduced pressure, giving a yellow semi-solid (470.5 mg). The crude material was purified by chromatography on silica, eluting with 20% ethyl acetate in dichloromethane. This gave 17-O-(propenoyl) Spinosyn A 17-Psa (322 mg ; 82% yield) as a colorless glass, FDMS, m/e (relative intensity) 643 ($M^+$-H, 100).

Example B4

17-O-(Chloroacetyl) Spinosyn A 17-Psa

The reaction was run as described in Example B3 starting with Spinosyn A 17-Psa (205.4 mg, 0.35 mmol), and chloroacetyl chloride, and using 40% ethyl acetate in hexane as the chromatography eluent. This gave 17-O-(chloroacetyl) Spinosyn A 17-Psa (194.7 mg, 83% yield), as an off white glass, FDMS, m/e (relative intensity) 666 ($M^+$-H, 100), 190 (20).

Example B5

17-O-(4-Chlorobutanoyl) Spinosyn A 17-Psa

The reaction was run as described in Example B3 starting with Spinosyn A 17-Psa (206.4 mg, 0.35 mmol), and chlorobutyryl chloride, and using 35% ethyl acetate in hexane as the chromatography eluent. This gave 17-O-(4-chlorobutanoyl) Spinosyn A 17-Psa (224.3 mg, 92% yield), as an off white glass, FDMS, m/e (relative intensity) 696 (50), 694 ($M^+$, 100), 189 (20), 100 (30).

Example B6

17-O-(Dimethylaminoacetyl) Spinosyn A 17-Psa

The reaction was run as described in Example B2 starting with 17-O-(chloroacetyl) Spinosyn A 17-Psa (99.4 mg, 0.15 mmol). This gave 17-O-(dimethylaminoacetyl) Spinosyn A 17-Psa (79.1 mg, 78% yield) was a beige glass, FDMS, m/e (relative intensity) 675 ($M^+$-H, 100).

Example B7

17-O-(4-Iodobutanoyl) Spinosyn A 17-Psa

To a solution of 17-O-(4-chlorobutanoyl) Spinosyn A 17-Psa (91.9 mg, 0.13 mmol) in acetone (3 ml), sodium iodide (198 mg, 1.3 mmol) was added. The mixture was heated to reflux for 18 hours during which time a precipitate formed. The mixture was then cooled to room temperature, diluted with water and extracted with dichloromethane. The dichloromethane was dried with $K_2CO_3$ and evaporated at room temperature under reduced pressure. This gave 17-O-(4-iodobutanoyl) Spinosyn A 17-Psa (94.7 mg; 93% yield) as a beige glass, FDMS, m/e (relative intensity) 832 (10), 786 ($M^+$-H, 100), 704 (20), 377 (30).

Example B8

17-O-(4-Dimethylaminobutanoyl) Spinosyn A 17-Psa

The reaction was run as described in Example B2, starting with 17-O-(4-iodobutanoyl) Spinosyn A 17-Psa (216.9 mg, 0.28 mmol). This gave 17-O-(4-dimethylaminobutanoyl) Spinosyn A 17-Psa (155.7 mg; 79% yield) as a beige glass, FDMS, m/e (relative intensity) 704 ($M^+$, 100).

Example B9

17-O-(N'-Methyl-N-piperazinylacetate) Spinosyn A 17-Psa

To a solution of 17-O-(chloroacetyl) Spinosyn A 17-Psa (150.5 mg, 0.23 mmol) in chloroform (7 ml), diisopropylamine (59 µl, 0.34 mmol) was added followed by 1-methylpiperazine (38 µl, 0.34 mmol). The reaction mixture stirred at room temperature for 1 hour and was then heated to reflux for 2.5 hours. The mixture was then cooled to room temperature for 3 days. An additional amount of 1-methylpiperazine (0.5 ml) was then added and the mixture was heated to reflux for 4 hours. The reaction mixture was then cooled to room temperature and poured into saturated aqueous $NaHCO_3$, and extracted with ether. The ether was washed with brine, dried with MgSO4, and evaporated at room temperature under reduced pressure. Crude product was purified by chromatography on silica, eluting with 7% methanol in dichloromethane then 20% methanol in dichloromethane (1 step). This gave 17-O-(N'-methyl-N-piperazinylacetate) Spinosyn A 17-Psa (63.1 mg; 38% yield) as a colorless glass, FDMS, m/e (relative intensity) 730 ($M^+$, 100), 731 (80).

Example B10

17-O-(N-Morpholinylacetate)Spinosyn A 17-Psa

The reaction was run as described in Example B9 starting with 17-O-(chloroacetyl) Spinosyn A 17-Psa (152.3 mg, 0.23 mmol), and morpholine (0.5 ml in one addition). Refluxing for 14 hours and extracting with dichloromethane, gave 17-O-(N-morpholinylacetate)Spinosyn A 17-Psa (141.3 mg; 86% yield) was an off white glass, FDMS, m/e (relative intensity) 717 ($M^+$, 100).

Example B11

17-O-(2-(1-Imidazoyl)acetyl) Spinosyn A 17-Psa

To a suspension of sodium hydride (50% dispersion in mineral oil; 15.8 mg, 0.33 mmol) in THF (5 ml), imidizole (23.1 mg, 0.34 mmol) was added. To this mixture 17-O-bromoacetyl Spinosyn A 17-Psa (201.1 mg, 0.28 mmol) was added, and the reaction mixture stirred at room temperature for 2 hours. The mixture was then diluted with dichloromethane and washed with water. The dichloromethane was then washed with brine, dried with $K_2CO_3$, and evaporated at room temperature under reduced pressure, giving a yellow glass (191 mg). This crude material was purified by chromatography on silica, eluting with 5% ethanol in ethyl acetate. This gave 17-O-(2-(1-imidazoyl)acetyl) Spinosyn A 17-Psa (117 mg; 60% yield) as a colorless glass, FDMS, m/e (relative intensity) 699 ($M^+$, 100), 698 (40), 189 (40), 101 (70).

Example B12

17-O-(2-(4-(2-Pyrimidinyl)-1-piperizinyl)acetyl) Spinosyn A 17-Psa

The reaction was run as described in Example B11 starting with 17-O-bromoacetyl Spinosyn A 17-Psa (209.6 mg, 0.29 mmol), and 2-(1-piperazinyl)pyrimidine, and using 5% methanol in dichloromethane as chromatography eluent. This gave 17-O-(2-(4-(2-Pyrimidinyl)-1-piperizinyl)acetyl) Spinosyn A 17-Psa (223.6 mg; 97% yield) as an off white glass, FDMS, m/e (relative intensity) 795 ($M^+$, 60), 794 (100).

Example B13

17-O-(2-(4-Dimethylamino-1-piperidinyl)acetyl) Spinosyn A 17-Psa

The reaction was run as described in Example B11 starting with 17-O-bromoacetyl Spinosyn A 17-Psa (201.8 mg, 0.28 mmol), and 4-dimethylamino piperidine, stirring at room temperature for 3 days, and using 10% methanol in dichloromethane then 100% methanol (1-step) as eluent. This gave 17-O-(2-(4-dimethylamino-1-piperidinyl)acetyl) Spinosyn A 17-Psa (104.2 mg; 49% yield) as a white solid, FDMS, m/e (relative intensity) 759 ($M^+$, 100).

Example B14
17-O-(4-Pyridinecarbonyl) Spinosyn A 17-Psa

To a suspension of isonicotinic acid (50.7 mg, 0.41 mmol) in dichloromethane (10 ml), DMAP (48.5 mg, 0.4 mmol) and Spinosyn A17 Psa (202.1 mg, 0.34 mmol) were added, followed by DCC (107.8 mg, 0.52 mmol). The reaction mixture stirred at room temperature for 2.5 days, and was then diluted with ether and filtered. The filtrate was evaporated at room temperature under reduced pressure. The residue was purified by chromatography on silica, eluting with 50% ethyl acetate in hexane. This gave 17-O-(4-pyridinecarbonyl) Spinosyn A 17-Psa(176.1 mg, 74% yield) as a colorless glass, FDMS, m/e (relative intensity) 696 ($M^+$, 100), 694 (40).

Example B15
17-O-Piperazinoacetyl Spinosyn A 17-Psa

The reaction was run as described in Example B11 starting with 17-O-bromoacetyl Spinosyn A 17-Psa (206.4 mg, 0.29 mmol), and piperazine. This gave 7-O-piperazinoacetyl Spinosyn A 17-Psa (127.1 mg; 61% yield) as a beige solid, FDMS, m/e (relative intensity) 791 (40), 718 (100), 717 ($M^+$, 65).

Example B16
17-O-(N-Methyl-L-prolinyl) Spinosyn A 17-Psa

The reaction was run as described in Example B14 starting with Spinosyn A 17 Psa (207.7 mg, 0.35 mmol) and N-methyl proline (63.7 mg, 0.43 mmol). This gave 17-O-(N-Methyl-L-prolinyl) Spinosyn A 17-Psa (65.9 mg; 43% yield, based on recovered Spinosyn A 17-Psa), FDMS, m/e (relative intensity) 703 (95), 702 ($M^+$, 100).

Example B17
17-O-[N-(2-Piperidinoethyl)]aminoacetyl Spinosyn A 17-Psa

The reaction was run as described in Example B11 starting with 17-O-bromoacetyl Spinosyn A 17-Psa (205.1 mg, 0.29 mmol), and 1-(2-aminoethyl)-piperidine. After chromatography on silica, eluting with 10% methanol in dichloromethane, the product was further purified by preparative HPLC on a $C_{18}$ column, eluting with acetonitrile:methanol:0.1% $NH_4OAc$ (35:35:30 to 45:45:10 in a 60 minute linear gradient) to give 17-O-[N-(2-piperidinoethyl)] aminoacetyl Spinosyn A 17-Psa (11 mg; 5% yield) as a white solid, FDMS, m/e (relative intensity) 760 (90), 759 ($M^+$, 100).

Example B18
17-O-(Carboethoxyacetyl) Spinosyn A 17-Psa

The reaction was run as described in Example B3, starting with Spinosyn A 17-Psa (207.7 mg, 0.35 mmol), and ethyl malonyl chloride (484 ml, 3.78 mmol; only one addition). This gave 17-O-(carboethoxyacetyl) Spinosyn A 17-Psa (153.6 mg, 62% yield) was a colorless glass, FDMS, m/e (relative intensity) 704 ($M^+$-H, 100), 189 (15).

Example B19
17-O-Bromoacetyl Spinosyn A 17-Psa

The reaction was run as described in Example B3, starting with Spinosyn A 17-Psa (4.06 gm, 6.9 mmol), and bromo acetyl bromide, and using 10% ethyl acetate in dichloromethane as chromatography eluent. This gave 17-O-bromoacetyl Spinosyn A 17-Psa (2.92 gms; 59% yield) as an off white glass, FDMS, m/e (relative intensity) 712 ($M^+$, 50), 711 (100), 713 (85).

Example B20
17-O-(p-Aminobenzeneacetyl) Spinosyn A 17-Psa

Compound 17-O-(p-nitrobenzeneacetyl) Spinosyn A 17-Psa (101.6 mg, 0.134 mmol) was dissolved in ethanol (5 mL) and tin(II)chloride (142.6 mg, 0.75 mmol) was added. The yellow color of the solution immediately disappeared and was replaced by a white suspension. The reaction was heated to reflux for 3.5 h, cooled to room temperature, and allowed to stand over night. After work-up the residue was purified by chromatography on silica gel (ethyl acetate/hexane) to afford 17-O-(p-aminobenzeneacetyl) Spinosyn A 17-Psa (45.3 mg, 46%) as a white solid: FDMS m/z 723. Anal. Calcd for $C_{41}H_{57}NO_{10}$: C, 68.03; H, 7.94; N, 19.3. Found: C, 67.53; H, 7.91; N, 2.41.

Example B21
17-O-(o-Chlorobenzoyl) Spinosyn A 17-Psa

The compound was prepared following the procedure described in Example B46 using o-chlorobenzoic acid (51 mg, 0.32 mmol), DMAP (47 mg, 0.38 mmol), Spinosyn A 17-Psa (135 mg, 0.228 mmol), and DCC (49 mg, 0.23 mmol). This gave compound 17-O-(o-chlorobenzoyl) Spinosyn A 17-Psa (69 mg, 41%) as a white solid: FDMS m/z 729.

Example B22
17-O-(m-Chlorobenzeneacetyl) Spinosyn A 17-Psa

The compound was prepared following the procedure described in Example B46 using m-chlorobenzeneacetic acid (42.3 mg, 0.24 mmol), DMAP (45.2 mg, 0.37 mmol), Spinosyn A 17-Psa (134.4 mg, 0.22 mmol), and DCC (51.2 mg, 0.24 mmol). This gave compound 17-O-(m-chlorobenzeneacetyl) Spinosyn A 17-Psa (101.5 mg, 60%) as a white solid: FDMS m/z 742.

Example B23
17-O-Formyl spinosyn A 17-Psa

Compound Spinosyn A 17-Psa (104 mg, 0.18 mmol) was dissolved in benzene (5 mL) and dimethylformamide dimethylacetal (0.10 g, 0.84 mmol) was added. The solution was heated to reflux for 2 h, cooled to ambient temperature, and the solvent evaporated in vacuo. The residue was purified by chromatography on silica gel (ethyl acetate/hexane gradient, 20:80 to 50:50) to afford compound 17-O-formyl Spinosyn A 17-Psa (35.8 mg, 32.8%) as a white solid: FDMS m/z 618.

Example B24
17-O-((o-Benzoyl)benzoyl) Spinosyn A 17-Psa

The compound was prepared following the procedure described in Example B46 using 2-benzoylbenzoic acid (83 mg, 0.36 mmol), DMAP (38 mg, 0.31 mmol), Spinosyn A 17-Psa (150 mg, 0.25 mmol), and DCC (58 mg, 0.28 mmol). This gave compound 17-O-((o-benzoyl)benzoyl) Spinosyn A 17-Psa (37.6 mg, 18.5%) as a white solid: FDMS m/z 799.

Example B25
17-O-(o-Chlorobenzeneacetyl) spinosyn A 17-Psa

The compound was prepared following the procedure described in Example B46 using 2-chlorobenzeneacetic acid (69 mg, 0.40 mmol), DMAP (49 mg, 0.40 mmol), Spinosyn A 17-Psa (148 mg, 0.25 mmol), and DCC (64 mg, 0.31 mmol). This gave compound 17-O-(o-chlorobenzeneacetyl) Spinosyn A 17-Psa (92 mg, 49%) as a white solid: FDMS m/z 743, 745. Anal. Calcd for $C_{41}H_{55}O_{10}Cl$: C, 66.25; H, 7.46. Found: C, 66.23; H, 7.36.

Example B26
17-O-(o-Phenylbenzoyl) Spinosyn A 17-Psa

The compound was prepared following the procedure described in Example B46 using 2-phenylbenzoic acid (78 mg, 0.39 mmol), DMAP (37 mg, 0.30 mmol), Spinosyn A 17-Psa (142 mg, 0.24 mmol), and DCC (60 mg, 0.29 mmol). This gave compound 17-O-(o-phenylbenzoyl) Spinosyn A 17-Psa (70 mg, 38%) as a white solid: FDMS m/z 770.

Example B27
17-O-(o,p-Dichlorobenzeneacetyl) Spinosyn A 17-Psa

The compound was prepared following the procedure described in Example B46 using 2,4-dichlorobenzeneacetic acid (66 mg, 0.32 mmol), DMAP (52 mg, 0.42 mmol), Spinosyn A 17-Psa (142 mg, 0.24 mmol), and DCC (55 mg, 0.26 mmol). This gave compound 17-O-(o,p-dichlorobenzeneacetyl) Spinosyn A 17-Psa (108.5 mg, 57.9%) as a white solid: FDMS m/z 777.

Example B28
17-O-(o-Isopropylbenzoyl) Spinosyn A 17-Psa

The compound was prepared following the procedure described in Example B46 using 2-isopropylbenzoic acid (72 mg, 0.43 mmol), DMAP (43 mg, 0.35 mmol), Spinosyn A 17-Psa (171 mg, 0.28 mmol), and DCC (72 mg, 0.35 mmol). This gave compound 17-O-(o-isopropylbenzoyl) Spinosyn A 17-Psa (76.7 mg, 36.0%) as a white solid: FDMS m/z 737. Anal. Calcd for $C_{43}H_{60}O_{10}$: C, 70.08; H, 8.21. Found: C, 70.33; H, 8.28.

Example B29
17-O-(o,o-Dichlorobenzeneacetyl) Spinosyn A 17-Psa

The compound was prepared following the procedure described in Example B46 using 2,6-dichlorobenzeneacetic acid (61 mg, 0.30 mmol), DMAP (40.6 mg, 0.332 mmol), Spinosyn A 17-Psa (131 mg, 0.22 mmol), and DCC (59 mg, 0.28 mmol). This gave compound Compound 17-O-(o,o-dichlorobenzeneacetyl) Spinosyn A 17-Psa (101 mg, 58.5%) as a white solid: FDMS m/z 777.

Example B30
17-O-Benzyl Spinosyn A 17-Psa

Compound Spinosyn A 17-Psa (120 mg, 0.20 mmol) was dissolved in 5 mL dimethylformamide and silver oxide (50 mg, 0.21 mmol) and benzyl bromide (120 mg, 0.70 mmol) were added. The reaction was stirred for 1 h at which time additional benzyl bromide (200 mg, 1.4 mmol) and silver oxide (40 mg, 0.42 mmol) were added. The reaction was stirred for an additional 12 h after which time the reaction was heated to 80–90° C. and benzyl bromide (100 mg) and silver oxide (20 mg) were added every hour for 3 h. The reaction was cooled to ambient temperature and diluted with ether (50 mL), filtered, and the filtrate washed with deionized water (10 mL) followed by brine solution (10 mL). The ether solution was dried over magnesium sulfate and concentrated in vacuo. The residue was purified by chromatography on silica gel (ethyl acetate/hexane gradient 20:80 to 50:50) to afford compound Compound 17-O-benzyl Spinosyn A 17-Psa (6.3 mg, 4.5%) as a colorless glass: partial $^1$H NMR δ 7.41–7.36 (m, 5H), 6.78 (bs, 1H), 5.90 (dd, 1H), 5.81(dt, 1H), 5.18 (dd, 2H), 4.90 (m, 1H), 4.86 (dd, 1H), 4.68 (m, 1H), 4.33 (q, 1H).

Example B31
17-O-(o,m-Dichlorobenzeneacetyl) Spinosyn A 17-Psa

The compound was prepared following the procedure described in Example B46 using 3,4-dichlorobenzeneacetic acid (136 mg, 0.66 mmol), DMAP (70 mg, 0.57 mmol), Spinosyn A 17-Psa (170 mg, 0.29 mmol), and DCC (70 mg, 0.34 mmol). This gave compound 17-O-(o,m-dichlorobenzeneacetyl) Spinosyn A 17-Psa. (171.2 mg, 76.5%) as a white solid: FDMS m/z 776, 778, 779, 780. Anal. Calcd for $C_{41}H_{54}O_{10}Cl_2$: C, 63.32; H, 7.00: Cl, 9.12. Found: C, 63.37; H, 6.91; Cl, 9.31.

Example B32
17-O-(p-(N,N-Dimethylamino)benzoyl) Spinosyn A 17-Psa

The compound was prepared following the procedure described in Example B46 using 4-dimethylaminobenzoic acid (30 mg, 0.18 mmol), DMAP (22 mg, 0.18 mmol), Spinosyn A 17-Psa (98 mg, 0.16 mmol), and DCC (40 mg, 0.19 mmol). This gave compound 17-O-(p-(N,N-dimethylamino)benzoyl) Spinosyn A 17-Psa (39.5 mg, 32%) as a white solid: FDMS m/z 737, 738. Anal. Calcd for $C_{42}H_{59}NO_{10}$: C, 68.36; H, 8.06; N, 1.90. Found: C, 68.20; H, 7.90; N, 2.12.

Example B33
7-O-(p-Methoxybenzoyl) Spinosyn A 17-Psa

The compound was prepared following the procedure described in Example B46 using 4-methoxybenzoic acid (44 mg, 0.29 mmol), DMAP (41 mg, 0.33 mmol), Spinosyn A 17-Psa (108 mg, 0.18 mmol), and DCC (44 mg, 0.21 mmol). This gave compound 7-O-(p-methoxybenzoyl) Spinosyn A 17-Psa (101.7 mg, 76.4%) as a white solid: FDMS m/z 724, 725.

Example B34
17-O-Benzoyl Spinosyn A 17-Psa

The compound was prepared following the procedure described in Example B46 using benzoic acid (33 mg, 0.27 mmol), DMAP (28 mg, 0.23 mmol), Spinosyn A 17-Psa (98 mg, 0.17 mmol), and DCC (41 mg, 0.20 mmol). This gave compound 17-O-benzoyl Spinosyn A 17-Psa (71.0 mg, 61.7%) as a white solid: FDMS m/z 695. Anal. Calcd for $C_{40}H_{54}O_{10}$: C, 69.14; H, 7.83. Found: C, 69.35; H, 7.69.

Example B35
17-O-(p-Isopropylbenzoyl) Spinosyn A 17-Psa

The compound was prepared following the procedure described in Example B46 using 4-isopropylbenzoic acid (58 mg, 0.35 mmol), DMAP (51 mg, 0.41 mmol), Spinosyn A 17-Psa (129 mg, 0.21 mmol), and DCC (80 mg, 0.38 mmol). This gave compound 17-O-(p-isopropylbenzoyl) Spinosyn A 17-Psa (33.1 mg, 20.5%) as a white solid: FDMS m/z 736.

Example B36
17-O-Benzeneacetyl Spinosyn A 17-Psa

The compound was prepared following the procedure described in Example B46 using phenylacetic acid (30 mg, 0.22 mmol), DMAP (43 mg, 0.34 mmol), Spinosyn A 17-Psa (121 mg, 0.20 mmol), and DCC (47 mg, 0.22 mmol). This gave compound 17-O-benzeneacetyl Spinosyn A 17-Psa (86.0 mg, 59.3%) as a white solid: FDMS m/z 709. Anal. Calcd for $C_{41}H_{56}O_{10}$: C, 69.47; H, 7.96. Found: C, 69.28; H, 7.94.

Example B37
17-O-(p-Methoxybenzeneacetyl) Spinosyn A 17-Psa

The compound was prepared following the procedure described in Example B46 using 4-methoxyphenylacetic acid (39 mg, 0.23 mmol), DMAP (45 mg, 0.36 mmol), Spinosyn A 17-Psa (123 mg, 0.20 mmol), and DCC (67 mg, 0.32 mmol). This gave compound 17-O-(p-methoxybenzeneacetyl) Spinosyn A 17-Psa (97.8 mg, 63.5%) as a white solid: FDMS m/z 739.

Example B38
17-O-(p-Nitrobenzeneacetyl) Spinosyn A 17-Psa

The compound was prepared following the procedure described in Example B46 using 4-nitrophenylacetic acid (86 mg, 0.47 mmol), DMAP (66 mg, 0.54 mmol), Spinosyn A 17-Psa (255 mg, 0.43 mmol), and DCC (100 mg, 0.48 mmol). This gave compound 17-O-(p-nitrobenzeneacetyl) Spinosyn A 17-Psa (194.1 mg, 59.6%) as a white solid: FDMS m/z 753. Anal. Calcd for $C_{41}H_{55}NO_{12}$: C, 65.32; H, 7.35; N, 1.86. Found: C, 65.58; H, 7.54; N, 2.05.

Example B39
17-O-(m-Nitrobenzeneacetyl) Spinosyn A 17-Psa

The compound was prepared following the procedure described in Example B46 using 3-nitrophenylacetic acid (68 mg, 0.37 mmol), DMAP (62 mg, 0.50 mmol), Spinosyn A 17-Psa (185 mg, 0.31 mmol), and DCC (83 mg, 0.40 mmol). This gave compound 17-O-(m-nitrobenzeneacetyl) Spinosyn A 17-Psa (166.1 mg, 70.3%) as a white solid: Anal. Calcd for $C_{41}H_{55}NO_{12}$: C, 65.32; H, 7.35; N, 1.86. Found: C, 65.13; H, 7.49; N, 1.92.

Example B40

17-O-(m-Trifluromethylbenzeneacetyl) Spinosyn A 17-Psa

The compound was prepared following the procedure described in Example B46 using 3-trifluoromethylphenylacetic acid (101 mg, 0.49 mmol), DMAP (64 mg, 0.52 mmol), Spinosyn A 17-Psa (274 mg, 0.46 mmol), and DCC (109 mg, 0.52 mmol). This gave compound 17-O-(m-trifluromethylbenzeneacetyl) Spinosyn A 17-Psa (302.2 mg, 84.6%) as a white solid: MS(CI) m/z 777. Anal. Calcd for $C_{42}H_{55}O_{10}F_3$: C, 64.93; H, 7.14. Found: C, 65.07; H, 7.39.

Example B41

17-Epi-O-methyl Spinosyn A 17-Psa

The compound was prepared following the procedure described in Example B47 using compound 17-epi-spinosyn A 17-Psa (20 mg, 0.033 mmol), Proton Sponge® (5 mg, 0.03 mmol) and trimethyloxonium tetrafluoroborate (14 mg, 0.065 mmol). This gave compound 17-epi-O-methyl Spinosyn A 17-Psa (7.1 mg, 35%) as a white solid: partial $^1$H NMR δ 6.71 (bs, 1H), 5.88 (dd, 1H), 5.81 (dt, 1H), 4.90 (m, 1H), 4.84 (s, 1H), 4.32 (q, 1H), 4.77–4.62 (m, 2H), 3.56 (s, 3H) , 3.50 (s, 6H) , 3.45 (s, 3H)

Example B42

17-O-(m-Methoxybenzeneacetyl) Spinosyn A 17-Psa

The compound was prepared following the procedure described in Example B46 using 3-methoxyphenylacetic acid (98 mg, 0.59 mmol), DMAP (71 mg, 0.58 mmol), Spinosyn A 17-Psa (290 mg, 0.49 mmol), and DCC (112 mg, 0.54 mmol). This gave compound 17-O-(m-methoxybenzeneacetyl) Spinosyn A 17-Psa (308.7 mg, 85.1%) as a white solid: Anal. Calcd for $C_{42}H_{58}O_{11}$: C, 68.27; H, 7.91. Found: C, 68.25; H, 7.92.

Example B43

17-O-(Tetrahydropyran-2-yl) Spinosyn A C-17 Psa

A solution of Spinosyn A C-17 Psa (0.50 g, 0.85 mmol), 3,4-dihydro-2H-pyran (0.45 mL, 0.41 g, 4.9 mmol), and TsOH.HCl (0.01 g, 0.05 mmol) in $CH_2Cl_2$ (4 mL) was stirred for 24 h. The mixture was partitioned between $Et_2O$ and $NaHCO_3$. The organic layer was washed with brine, dried ($MgSO_4$), filtered, and evaporated. MPLC ($SiO_2$, 50:50 $Et_2O$/hexane) gave 0.35 g (61%) of 17-O-(tetrahydropyran- 2-yl) Spinosyn A C-17 Psa as a 1:1 mixture was diastereomers as a clear colorless glass Example B44

17-O-(4-Nitrobenzoyl)-17-epi-Spinosyn A 17-Psa

A solution of diethylazodicarboxylate (0.4 mL, 2.49 mmol) in benzene (2 mL) was added dropwise during 2–3 min at room temperature to a well stirred mixture of spinosyn A 17-Psa (0.3 g, 0.51 mmol), triphenylphosphine (0.65 g, 2.49 mmol) and p-nitrobenzoic acid (0.37 g, 2.20 mmol) in benzene (12 mL). The resulting solution was stirred at room temperature for 48 h. The solvent was removed and the residue flash chromatographed over silica (150 mL) using 2.5% acetone in $CH_2Cl_2$ as eluent to give 110 mg of 17-O-(4-nitrobenzoyl)-17-epi-Spinosyn A 17-Psa. A sample was recrystallized from 2:1 acetone/water as colorless needles, mp 159–161° C.; $^1$H NMR ($CDCl_3$) δ 7.32 (s, 1H, H-13), 5.59 (m, 1H, H-17), 4.97 (m, 1H, H-21), 4.87 (d, 1H, H-1'), 4.34 (m, 1H, H-9); MS m/z 740 (100).

Example B45

17-O-(4-Nitrophenylacetyl)-17-epi-spinosyn A 17-Psa 1,3-Dicyclohexylcarbodiimide (21 mg, 0.11 mmol) was added in one portion at room temperature to a stirred solution of 4-nitro-phenylacetic acid (20 mg, 0.11 mmol), 4-dimethylaminopyridine (3 mg, 0.024 mmol) and 17-epi-spinosyn A 17-psa (59 mg, 0.1 mmol) in $CH_2Cl_2$ (2 mL). The resulting mixture was stirred at room temperature fo 2 h, then diluted with more $CH_2Cl_2$ (2.0 mL) and filtered from insolubles. The filtrate was evaporated and the residue flash chromatographed over silica (25 mL) using 25% EtOAc in hexane as eluent to give 17-O-(4-nitrophenylacetyl)-17-epi-spinosyn A 17-Psa (70 mg) as a colorless foam: $^1$H NMR ($CDCl_3$) δ 8.23 (d, 2H), 7.50 (d,2H), 7.12 (s, 1H, H-13), 5.28 (m, 1H, H-17), 4.90 (m, 1H, H-21), 4.84 (d, 1H, H-1'), 4.30 (m, 1H, H-9), 3.78 (s, 2H, $CH_2CO_2$); MS m/z 752 (100).

Example B46

17-O-(p-Chlorobenzeneacetyl) Spinosyn A 17-Psa

Compound p-chlorobenzeneacetic acid (50 mg, 0.29 mmol), and dimethylaminopyridine (DMAP, 50 mg, 0.40 mmol) were dissolved in methylene chloride (8 mL) and to this solution was added Spinosyn A 17-Psa (164.7 mg, 0.279 mmol) followed by dicyclohexylcarbodiimide (DCC, 66 mg, 0.32 mmol). The reaction was stirred over night. Ether (25 mL) was added and the reaction stirred for 2 hrs. The reaction was filtered to remove solids and the filtrate evaporated in vacuo. The residual was purified by chromatography on silica gel (ethyl acetate/hexane gradient, 20:80 to 50:50) to afford 17-O-(p-chlorobenzeneacetyl) Spinosyn A 17-Psa (128.4 mg, 61.8%) as a white solid: FDMS m/z 743. Anal. Calcd for $C_{41}H_{55}O_{10}Cl$: C, 66.25; H, 7.46. Found: C, 65.98; H, 7.31.

Example B47

17-O-Methyl Spinosyn A 17-Psa

Compound Spinosyn A 17-Psa (267 mg, 0.452 mmol) was dissolved in methylene chloride (5 mL) and Proton Sponge® (107 mg, 0.50 mmol) and trimethyloxonium tetrafluoroborate (104 mg, 0.702 mmol) were added. The mixture was stirred for 3 h and worked-up to give a white fluffy solid (0.20 g). The solid was purified by reversed-phase chromatography (methanol/water 90:10) to afford 17-O-methyl Spinosyn A 17-Psa (135.8 mg, 49.6%) as a white solid: IR (film) 2969, 2933, 2825, 1722, 1661, 1458, 1377, 1103, 1034 $cm^{-1}$; $^{13}$C NMR δ 202.80, 172.31, 147.01, 143.71, 129.15, 128.78, 95.22, 82.19, 82.09, 80.86, 77.53, 76.05, 75.86, 67.75, 60.73, 58.80, 57.51, 57.33, 49.33, 47.42, 46.55, 46.11, 41.23, 40.91, 37.23, 36.11, 34.24, 30.93, 30.39, 27.88, 20.19, 17.61, 17.02, 9.19.

Part C Modifications within the Forosamine Substituent

Example C1

N- Acetyl Spinosyn B

To a solution of Spinosyn B (200 mg, 0.28 mmol) in chloroform (5 ml), diisopropylethylamine (72.7 μl, 0.42 mmol) was added followed by acetyl chloride (30 μl, 0.42 mmol). The reaction mixture was stirred at room temperature for 0.5 hrs. The mixture was then diluted with dichloromethane and washed with saturated aqueous $NaHCO_3$. The dichloromethane was dried with $K_2CO_3$, and evaporated at room temperature under reduced pressure. The product was purified by chromatography on silica, eluting with 5% methanol in dichloromethane. This gave N- acetyl Spinosyn B (239 mg; ~100% yield) as a colorless glass, FDMS, m/e (relative intensity) 759 ($M^+$-H, 10), 714 (60), 189 (50), 170 (50), 101 (100).

Example C2

N-Benzoyl Spinosyn B

The reaction was run as described in Example C1 with starting with Spinosyn B (200 mg, 0.28 mmol), and benzoyl chloride. This gave N-benzoyl Spinosyn B (227.4 mg; ~100% yield), as a pale yellow glass, FDMS, m/e (relative intensity) 821 ($M^+$-H, 5), 776 (20), 232 (30), 189 (35), 103 (100).

Example C3
N-Allyl Spinosyn B

The reaction was run as described in Example C1 starting with Spinosyn B (200 mg, 0.28 mmol), and allyl bromide. The reaction was stirred at room temperature for 4 days, then evaporated at room temperature under reduced pressure, and 40% ethyl acetate in hexane was used as the chromatography eluent. This gave N-allyl Spinosyn B (148.9 mg, 70% yield) as a colorless glass, FDMS, m/e (relative intensity) 757 ($M^+$-H, 100).

Example C4
N-Benzyl Spinosyn B

The reaction was run as described in Example C1 starting with Spinosyn B (200 mg, 0.28 mmol), and benzyl bromide. This gave N-benzyl Spinosyn B(216.6 mg, 96% yield) as a colorless glass, FDMS, m/e (relative intensity) 807 ($M^+$-H, 100).

Example C5
N-Methyl Spinosyn A iodide

To a solution of Spinosyn A (111.6 mg, 0.15 mmol) in chloroform (5 ml), methyl iodide (200 $\mu$l) was added. The reaction mixture was stirred at room temperature for 24 hours then additional methyl iodide (200 $\mu$l) was added, and the mixture stirred another 24 hours at room temperature. The solvent was then evaporated at room temperature under reduced pressure and the residue was triturated with ether. This gave N-methyl Spinosyn A iodide (101 mg; 76% yield) as an off white solid, FDMS, m/e (relative intensity) 747 ($M^+$, 100).

Example C6
N-Oxo Spinosyn A

To an ice cold solution of 82.1% pure Spinosyn A (2.07 gm, 2.83 mmol) in dichloromethane (100 ml), m-chloroperoxybenzoic acid (450 mg, 2.57 mmol) was added. The reaction mixture was allowed to warm to room temperature over 1 hour, and then stirred at room temperature for 5 hours. The reaction was quenched by addition of saturated aqueous $NaHCO_3$. The organic layer was separated, dried with $MgSO_4$, and evaporated at room temperature under reduced pressure. The product was purified by chromatography on silica eluting with 10% methanol in dichloromethane. This gave N-oxo Spinosyn A (1.59 gm; 92% yield) as a pale yellow glass, FDMS, m/e (relative intensity) 762.9 (20), 731.8 ($M^+$-O, 40), 686.8 (100), 401.7 (25).

Example C7
4"-Hydroxy Spinosyn A

The reaction was run as described in Example C13 starting with N-oxo Spinosyn A (509.8 mg, 0.68 mmol). A white precipitate formed in the reaction and was isolated by filtration. The precipitate was then triturated with ether. The ether was evaporated at room temperature under reduced pressure and the residue was dissolved in methanol (20 ml) and sodium borohydride (258 mg, 6.82 mmol) was added and the reaction mixture stirred at room temperature for 7 hours. The mixture was then evaporated at room temperature under reduced pressure to a small volume and diluted with ether. This ether was washed with water, brine, dried with $K_2CO_3$ and evaporated at room temperature under reduced pressure. The product was isolated by chromatography on silica, eluting with 70% ethyl acetate in hexane. This gave 4"-hydroxy Spinosyn A (92.1 mg; 19% yield) as a colorless glass in a 3:1 isomeric mixture, FDMS, m/e (relative intensity) 704 ($M^+$, 80), 591 (30), 190 (70), 115 (100).

Example C8
3",4"-Dehydro-4"-deamino Spinosyn C

N-oxo Spinosyn A (505.9 mg, 0.68 mmol) was heated to 120° C. under $N_2$. Gas evolution began at 115° C., and heating was continued until gas evolution ceased (~15 min). The mixture was then cooled slowly to room temperature. The products were purified by chromatography on silica, eluting with 5% methanol in dichloromethane. This gave 3",4"-dehydro-4"-deamino Spinosyn C (91 mg; 19% yield), FDMS, m/e (relative intensity) 696 ($M^+$, 10), 589 (20), 189 (50), 101 (100), N- formyl Spinosyn B (43.3 mg; 9% yield), Spinosyn A (102.1 mg; 21% yield), and spinosyn B (114.5 mg; 23% yield ) all as colorless glasses.

Example C9
N-(N'-Benzyl-3 -indolemethyl) Spinosyn C

To a solution of Spinosyn C (213.6 mg, 0.3 mmol) in methanol (2 ml), N-benzyl-3-indolecarboxaldehyde (83.7 mg, 0.36 mmol) was added. The reaction mixture was stirred at room temperature for 20 hours, and sodium cyanoborohydride (43.5 mg, 0.7 mmol) was added. The reaction mixture stirred at room temperature an additional 2 hours. TLC (eluting with 10% methanol in dichloromethane) showed reaction was incomplete, however. The solvent was evaporated to a small volume at room temperature under reduced pressure. The mixture was then diluted with dichloromethane. The dichloromethane was washed with water, brine, dried with $K_2CO_3$ and evaporated at room temperature under reduced pressure. The product was isolated by chromatography on silica, eluting with 70% ethyl acetate in hexane. This gave N-(N'-benzyl-3-indolemethyl) Spinosyn C (83.8 mg; 30% yield) as a pale yellow glass, FDMS, m/e (relative intensity) 1140 (15), 923 ($M^+$, 100).

Example C10
N-Demethyl-N-formyl Spinosyn J

To a solution of Spinosyn J (990.4 mg, 1.38 mmol) in anhydrous dichloromethane (25 ml), pyridinium dichromate (622.6 mg, 1.65 mmol) was added. The reaction mixture stirred at room temperature for 3.75 days and was then filtered through celite. The celite was rinsed with fresh dichloromethane. The dichloromethane was combined and evaporated at room temperature under reduced pressure. The product was purified by chromatography on silica, eluting with ethyl acetate. This gave N-demethyl-N-formyl Spinosyn J (360 mg; 36% yield) as a white solid, EIMS, m/e (relative intensity) 732 ($M^+$, 40), 715 (100), 175 (20), 101 (25).

Example C11
N-Benzyl Spinosyn A bromide salt

The reaction was run as described in Example C5 starting with Spinosyn A (100 mg, 0.14 mmol), and benzyl bromide and refluxing for 6 days. This gave N-benzyl Spinosyn A bromide salt (86.6 mg, 69% yield) as an off white solid, FDMS, m/e (relative intensity) 976 (10), 822 ($M^+$, 100), 189 (60), 142 (100).

Example C12
4"-Des-(dimethylamino)-4"-aziridinyl spinosyn A

To a solution of Spinosyn C (205.2 mg, 0.29 mmol) in acetonitrile (2 ml), chloroacetaldehyde (0.28 ml, 0.44 mmol) was added followed by commercial pH 5 buffer (2 ml), and then sodium cyanoborohydride (39.1 mg, 0.62 mmol). The reaction mixture stirred at room temperature for 2 days. Reverse phase HPLC (eluting with 44% acetonitrile, 44% methanol 12% (0.5%) aqueous $NH_4OAc$) showed the reaction was incomplete. The mixture was then diluted with saturated aqueous $NaHCO_3$ and extracted with dichloromethane. The dichloromethane was then washed with brine, dried with $K_2CO_3$ and evaporated at room temperature under reduced pressure, giving a colorless glass (199 mg). Product was isolate by preparative HPLC on a $C_{18}$ column, eluting with acetonitrile:methanol:0.1% $NH_4OAc$ (35:35:30 to 45:45:10 in a 90 minute linear gradient). This gave 4"-des-(dimethylamino)-4"-aziridinyl Spinosyn A (30 mg; 14% yield), as a white solid, FDMS, m/e (relative intensity) 729 (M+, 100).

Example C13

4"-Des-(dimethylamino)-4"-oxo Spinosyn A

To a solution of N-oxo spinosyn A (203.8 mg, 0.27 mmol) in benzene (10 ml), acetic anhydride (500 ml) was added. The reaction mixture was stirred at room temperature for 5 days. The mixture was then evaporated at room temperature under reduced pressure. The residue (after sitting at room temperature for 6 days) was seperate by chromatography on silica eluting with 2.5% methanol in dichloromethane. This gave compound a) 4"-des-(dimethylamino)-4"-oxo Spinosyn A (59.9 mg; 32% yield) as an unstable colorless glass, FDMS, m/e (relative intensity) 704 (MH+, 10), 592 (90), 190 (95), 101 (100), and compound b) N- acetyl Spinosyn B (69.2 mg; 34% yield) as a colorless glass.

Example C14

N-(N'-Methylcarbamyl) Spinosyn B

Compound Spinosyn B (200 mg, 0.278 mmol) and methyl isocyanate (0.30 g, 5.26 mmol) were combined in 10 mL toluene and the mixture stirred at RT for 3 days. Partitioned the reaction mixture between ether/water and separated layers. Extracted aqueous with 3×25 mL ether and combined ether extracts. Washed ether extracts with 5 mL brine solution, dried over anhydrous magnesium sulfate and concentrated in vacuo. The residue was chromatographed using a medium pressure $SiO_2$ column (230–400 m, $CH_2Cl_2$:$CH_3OH$, 95:5, V/V) to give compound N-(N'-methylcarbamyl) Spinosyn B (0.14 g, 66%). Elemental analysis for $C_{42}H_{66}N_2O_{11}$; Calc. C 65.09, H, 8.31, N 3.31, Found C 64.80, H 8.31, N 3.34; FAB MS (m/z) 775 (M+1).

Example C15

N-Methanesulfonyl Spinosyn B

Compound Spinosyn B(200 mg, 0.279 mmol), was dissolved in 5 mL methylene chloride and methanesulfonyl chloride (0.11 g, 0.96 mmol) and diisopropylethyl amine 0.13 g (1.00 mmol) were added. Stirred reaction at RT for 2 hrs. then pour into 10 mL each ether/water. Separated layers and extracted aqueous with 2×10 mL ether. Combined ether extracts, washed with 10 mL brine solution, dried over magnesium sulfate and concentrated in vacuo. The residue was chromatographed on a medium pressure $SiO_2$ column (230–400 m, $CH_2Cl_2$:$CH_3OH$, 95:5, V/V) to give compound N-methanesulfonyl Spinosyn B (0.14 g, 63%). Elemental Analysis for $C_{41}H_{65}NO_{12}S$; Calc. C 61.86, H 8.23, N 1.76; Found C 61.73, H 7.83, N 1.65.

Example C16

N-Ethoxylcarbonyl Spinosyn B

Compound Spinosyn B(214 mg, 0.298 mmol) was dissolved in 5 mL methylene chloride and ethyl chloroformate (0.15 g, 0.14 mmol) and diisopropylethyl amine (0.12 g, 0.93 mmol) were added. The reaction was stirred at RT for 2 hrs. Pour reaction into 10 mL water/10 mL ether and separated layers. Extracted aqueous layer with 2×10 mL ether. Combined ether extract and washed with 10 mL saturated sodium bicarbonate followed by 10 mL brine solution. Dried ether solution over anhydrous magnesium sulfate, filtered, and evaporated in vacuo. The residue was chromatographed on a medium pressure $SiO_2$ column (230–400 m, $CH_2Cl_2$:$CH_3OH$, 95:5, V/V) to give compound N-ethoxylcarbonyl Spinosyn B (0.19 g, 80%) Elemental Analysis for $C_{43}H_{67}NO_{12}$; calc. C 65.38, H 8.55, N 1.77; Found C 64.80, H 8.53, N 1.12; FAB MS (m/z) 790 (M+1).

Example C17

N-Trifluoromethylacetyl Spinosyn B

Compound Spinosyn B(118.9 mg, 0.165 mmol) was dissolved in 5 mL methylene chloride and diisopropylethyl amine (0.10 g, 0.77 mmol) and trifluoroacetic anhydride (0.10 g, 0.48 mmol) were added. The reaction was stirred at RT for 20 hrs. Poured reaction mixture into ether/saturated aqueous sodium bicarbonate and separated layers. Extrated aqueous layer with 2×25 mL ether. Combined ether extracts, washed extracts with 30 mL brine solution, dried over anhydrous magnesium sulfate, and concentrated in vacuo. The residue was chromatographed on a medium pressure $SiO_2$ column (230–400 m, ethylacetate/hexane, 40:60, V/V) to give compound N-trifluoromethylacetyl Spinosyn B (104.6 mg, 77.6%). Elemental Analysis for $C_{42}H_{62}NO_{11}F_3$; Calc. C 61.97, H 7.52, N 1.31, Found C 60.88, H 7.60, N 1.46; FD MS (m/z) 813 (M+).

Example C18

N-Formyl Spinosyn B

Compound Spinosyn B(107.3 mg, 0.150 mmol) was added to 10.0 mL ethyl formate and the mixture heated to reflux. After 1 hr. at reflux the reaction was cooled to RT and the solvent removed under vacuo. The residue was chromatographed on a medium presssure $SiO_2$ column (230–400 m, $CH_2Cl_2$:$CH_3OH$, 95:5, V/V) to give compound N-formyl Spinosyn B; 103.1 mg, 92.3%) Elemental analysis: for $C_{41}H_{63}NO_{11}$ calc. C 66.02, H 8.51, N 1.88; Found C 64.67, H 8.75, N 2.03; FD MS (m/z) 745 (M+).

Example C19

N-Carbamyl Spinosyn C

Silver cyanate (3.7 g, 24 mmol) was suspended in 10 mL benzene and silicon tetrachloride (1.0 g, 5.8 mmol) was added. The reaction changed color immediately from light grey to dark purple suspension. Heated reaction to reflux for 1 hr., cooled to RT and filtered away solids. The filtrate was concentrated in vacuo to give silicon tetracyanate as a colorless oil. Dissolved all silicon tetracyanate in 10 mL benzene and added compound Spinosyn C (93 mg, 0.132 mmol) as a solution in 2 mL benzene. The resulting solution was heated to reflux for 30 min. Cooled reaction to RT and concentrated in vacuo. To the residue was added 20 mL of 90% isopropanol/water and the reaction heated to reflux for 30 min. Cooled to RT and concentrated in vacuo. The residue was suspended in methylene chloride and filtered to remove solids. The filtrate was chromatographed on a gravity SiO2 column (230–400 m, $CH_2Cl_2$/$CH_3OH$, 95:5, V/V) to give compound N-carbamyl Spinosyn C (28.2 mg, 28.6%). Elemental Analysis for C40H62N2O11; Calc. C 64.32, H 8.37, N 3.75, Found C 64.04, H 8.12, N 4.04; FD MS (m/z) 746 (M+).

Example C20

N-Trifluoromethanesulfonyl Spinosyn B

Compound Spinosyn B(136 mg, 0.189 mmol) was dissolved in 5 mL methylene chloride and diisopropylethyl amine (0.10 g, 0.77 mmol) and trifluoromethanesulfonic anhydride (0.10 g, 0.35 mmol) were added. Stirred reaction for 1 hr. at RT then poured into 20 mL each ether/saturated aqueoues sodium bicarbonate. Separated the layers and extracted aqueous phase with 2×25 mL ether. Combined the ether extracts, washed with 25 mL brine solution, dried over anhydrous magnesium sulfate, and concentrated in vacuo. The residue was chromatographed on a medium presssure $SiO_2$ column (230–400 m, ethylacetate/hexane, 50:50, V/V) to give compound N-trifluoromethanesulfonyl Spinosyn B (116.9 mg, 72.6%). Elemental Analysis for $C_{41}H_{62}NO_{12}SF_3$; Calc. C 57.94, H 7.35, N 1.65, Found C 58.07, H 7.52, N 1.70; FD MS (m/z) 849 (M+).

Example C21

Spinosyn A ammonium N-[(E)-prop-1'''-eno]-3'''-ate, and Ethyl [Spinosyn B N-2'''-methyl-(Z)-prop-1'''-eno)]-3'''-ate Compound Spinosyn A (0.68 g, 0.929 mmol) was dissolved in $CH_2Cl_2$ (3 ml). Water (50 ml) was added. The mixture was stirred at 0° C. and ethyl propiolate (Aldrich, 2.20 g, 22.4 mmol) was added in one portion. The cooling bath was removed and the reaction mixture was stirred for 30 min., then it was sonicated (in a 50 W Fishers ultrasound cleaner) for 12 min. Afterwards, dioxane (400 ml) was added and the solvents were removed in vacuo. The residue was separated by flash column chromatography on silica gel (230–400 m, 80 g/THF, then MeOH, then 15% $H_2O$ in MeOH). Chromatographically pure fractions gave compound a) ethyl [Spinosyn B N-2'''-methyl-(Z)-prop-1'''-eno)]-3'''-ate (296 mg, 38%): IR v 1720, 1685, 1645 and 1610 $cm^{-1}$; $^1$H-NMR (CDCl$_3$) d 7.35 (1H, bs), 6,70 (1H, bs), 2.60 (3H, $CH_3$, bs), 1.95 (3H, $CH_3$, s) ppm, and compound b) Spinosyn A ammonium N-[(E)-prop-1'''-eno]-3'''-ate, (316 mg, 42%): IR n 1720, 1655, 1605 $cm^{-1}$; $^1$H-NMR (CDCl$_3$) d 7.04 (1H, d: 17 Hz), 6.72 (1H, bs), 6.47 (1H, d: 17 Hz), 3,35 (3H, $CH_3$, bs), 3.28 (3H, $CH_3$, bs) ppm.

Example C22

Methyl [Spinosyn B N-(2'''-methyl-(Z)-prop-1'''-eno)]-3'''-ate

Compound Spinosyn B(192 mg, 0.267 mmol) was dissolved in dry $CH_2Cl_2$ (25 ml). Methyl propiolate (Aldrich, 1.80 g, 21.4 mmol) was added in one portion. The reaction mixture was stirred at room temperature under nitrogen for 5 hrs. The solvent and excess of methyl propiolate were then removed in vacuo. The residue was purified on a flash silica gel column (230–400 m, 50 g/THF). Pure fractions gave compound methyl [Spinosyn B N-(2'''-methyl-(Z)-prop-1'''-eno)]-3'''-ate (205 mg, 95%): $^1$H-NMR (CDCl$_3$) d 7.38 (1H, d:12.8 Hz), 6.70 (1H, bs), 4.50 (1H, d: 12.8 Hz) ppm.

Example C23

N-(cyano)methyl Spinosyn B

Compound Spinosyn B(263 mg, 0.370 mmol) was dissolved in dimethylformamide (7 ml). The solution was stirred at room temperature under nitrogen. Triethylamine (1.0 ml) was added, followed by bromoacetonitrile (1.2 ml, an excess). The reaction mixture was stirred at RT for three days. EtOAC (50 ml) and PhH (50 ml) were added, the solution was washed successively with water (3×) and 5% aqueous $NaHCO_3$ (2×). The organic layer was dried over anh. $K_2CO_3$ and concentrated in vacuo. The residue was then dried at 0.005 torr for three hours to give compound N-(cyano)methyl Spinosyn B (260 mg, 94%): $^{13}$C-NMR (CDCl$_3$) d 117.8 (CN) and 43.8 (N—$CH_2$—CN) ppm.

Example C24

4''-N-Ethyl Spinosyn B

Alkylation Procedure A: A stirring solution of Compound Spinosyn B (0.50 g, 0.70 mmol) in DMF (1.5 mL) was treated sequentially with EtI (0.11 mL, 0.21 g, 1.4 mmol) and (i-Pr)$_2$NEt (0.36 mL, 0.27 g, 2.1 mmol) under an $N_2$ atmosphere. After 20 hrs., the mixture was treated with ca. 1 mL of a 1M solution of $Na_2S_2O_3$ to decompose any residual iodine. The resulting mixture was partitioned between Et$_2$O and a saturated aqueous solution of NaCl (brine). The organic layer was washed with brine, dried (MgSO$_4$), filtered, and evaporated in vacuo to yield 0.61 g. Purification of the residue by MPLC (SiO$_2$, 5:95 MeOH/EtOAc) gave 0.47 g (90%) of 4''-N-ethyl Spinosyn B white powder. Calc'd for $C_{42}H_{67}NO_{10}$: C, 67.62; H, 9.05; N, 1.88. Found: C, 67.11; H, 9.73; N, 1.92 and C, 67.17; H, 9.54; N, 1.98.

Example C25

4''-N-(1-Propyl) Spinosyn B

This compound was prepared according to Alkylation Procedure A as described in Example C24 using Spinosyn B (0.50 g, 0.70 mmol), DMF (1.5 mL), 1-iodopropane (0.14 mL, 0.24 g, 1.4 mmol), and (i-Pr)$_2$NEt (0.36 mL, 0.27 g, 2.1 mmol). Purification by MPLC (SiO$_2$, 2:98 MeOH/EtOAc) gave 0.41 g (77%) of 4''-N-(1-propyl) Spinosyn B as a white powder. Calc'd for $C_{43}H_{69}NO_{10}$: C, 67.96; H, 9.15; N, 1.84. Found: C, 68.06; H, 9.25; N, 1.97.

Example C26

4''-N-(2-Methylprop-1-yl) Spinosyn B

This compound was prepared according to Alkylation Procedure A from as described in Example C24 using Spinosyn B (0.95 g, 1.3 mmol), DMF (2.8 mL), 1-iodo-2-methylpropane (0.32 mL, 0.51 g, 2.8 mmol), and (i-Pr)$_2$NEt (0.73 mL, 0.54 g, 4.2 mmol). Purification by MPLC (SiO$_2$, 50:50 EtOAc/hexanes) gave 0.07 g (7%) of 4''-N-(2-methylprop-1-yl) Spinosyn B as a pale powder. Calc'd for $C_{44}H_{71}NO_{10}$: C, 68.28; H, 9.25; N, 1.81. Found: C, 68.33; H, 9.26; N, 1.88.

Example C27

4''-N-Cyclopropylmethyl Spinosyn B

This compound was prepared according to Alkylation Procedure A as described in Example C24 using Spinosyn B (0.95 g, 1.3 mmol), DMF (2.8 mL), cyclopropylmethylbromide (0.27 mL, 0.38 g, 2.8 mmol), NaI (0.05 g, 0.3 mmol), and (i-Pr)$_2$NEt (0.73 mL, 0.54 g, 4.2 mmol). Purification by MPLC (SiO$_2$, 2:98 MeOH/EtOAc) gave 0.34 g (33%) of 4''-N-cyclopropylmethyl Spinosyn B as a white powder. Calc'd for $C_{44}H_{69}NO_{10}$: C, 68.45; H, 9.01; N, 1.81. Found: C, 68.36; H, 9.22; N, 1.76.

Example C28

N-(N'-(1,1-Dimethylethoxycarbonyl)glycyl) Spinosyn B

Peptide Coupling Procedure A: A −15° C. stirring slurry of Boc-Gly-OH (0.16 g, 0.91 mmol) and BOP-Cl (0.23 g, 0.90 mmol) in $CH_2Cl_2$ (7 mL) was treated with N-methylmorpholine (0.12 mL, 0.11 g, 1.1 mmol) under an $N_2$ atmosphere. After 1.5 hrs., the mixture was treated sequentially with Spinosyn B (0.50 g, 0.70 mmol) and N-methylmorpholine (0.12 mL, 0.11 g, 1.1 mmol). The temperature was maintained at −15° C. for 4 hr., then the material was allowed to gradually warm to ambiant temperature for 10 hr. The mixture was evaporated in vacuo, and the residue was purified by MPLC (SiO$_2$, 50:50 AE 100:0

EtOAc/hexanes) to afford 0.61 g (99%) of N-(N'-(1,1-dimethylethoxycarbonyl)glycyl) Spinosyn B as a white powder. Calc'd for $C_{47}H_{74}N_2O_{13}$: C, 64.51; H, 8.52; N, 3.20. Found: C, 63.76; H, 8.62; N, 3.29 and C, 63.78; H, 8.60; N, 3.43.

Example C29

N-(N'-(1,1-Dimethylethoxycarbonyl)-β-alanyl) Spinosyn B

This compound was prepared according to Peptide coupling Procedure A as described in Example C28 using Boc-β-Ala-OH (0.17 g, 0.90 mmol), BOP-Cl (0.23 g, 0.90 mmol), $CH_2Cl_2$ (7 mL), N-methylmorpholine (2×0.12 mL, 0.22 g, 2.2 mmol), and Spinosyn B (0.50 g, 0.70 mmol). Purification by MPLC ($SiO_2$, 70:30→100:0 EtOAc/hexanes) gave 0.62 g (99%) of N-(N'-(1,1-dimethylethoxycarbonyl)-β-alanyl) Spinosyn B as a white powder. Calc'd for $C_{48}H_{76}N_2O_{13}$: C, 64.84; H, 8.62; N, 3.15. Found: C, 64.38; H, 8.67; N, 3.22.

Example C30

N-(N'-(Phenylmethoxycarbonyl)-L-Alanyl) Spinosyn B

This compound was prepared according to Peptide Coupling Procedure A as desrcibed in Example C28 using Cbz-L-Ala-OH (0.21 g, 0.94 mmol), BOP-Cl (0.24 g, 0.94 mmol), $CH_2Cl_2$ (7 mL), N-methylmorpholine (2×0.12 mL, 0.22 g, 2.2 mmol), and Spinosyn B (0.50 g, 0.70 mmol). Purification by MPLC ($SiO_2$, 75:25 EtOAc/hexanes) gave 0.68 g (99%) of N-(N'-(phenylmethoxycarbonyl)-L-alanyl) Spinosyn B as a white powder. Calc'd for $C_{51}H_{74}N_2O_{13}$: C, 66.36; H, 8.08; N, 3.03. Found: C, 2 rotamers: $^1$H NMR 7.3–7.4 (M,5H), [5.06+5.10 y 5.04 (5+2d, J=12.2 y 12.3, Σ=2H)], 2.87 y 2.76 (2S, Σ=3H)

Example C31

N-(N',N'-Dimethylglycyl) Spinosyn B

This compound was prepared according to Peptide Coupling Procedure A as described in Example C28 using N(Me$_2$)Gly-OH (0.09 g, 0.9 mmol), BOP-Cl (0.25 g, 0.98 mmol), $CH_2Cl_2$ (7 mL), N-methylmorpholine (2×0.12 mL, 0.22 g, 2.2 mmol), and Spinosyn B (0.50 g, 0.70 mmol). Purification by MPLC ($SiO_2$, 5:95 8:92 MeOH/$CH_2Cl_2$) gave 0.23 g (41%) of N-(N',N'-dimethylglycyl) Spinosyn B as a clear colorless glass. Calc'd for $C_{44}H_{70}N_2O_{11}$: C, 65.81; H, 8.79; N, 3.49. Found: C, M+H+ Calc'd 803.5, found 803.6.

Example C32

N-(N'-Methylthiocarbamyl) Spinosyn B

Spinosyn B (203 mg, 0.28 mmol) was dissolved in 10 mL toluene and methylisothiocyanate (100 mg, 1.36 mmol) was added and the solution stirred for 1 hr. After work-up the crude mixture was chromatographed on silica gel (1:1, ethyl acetate/hexane) to afford N-(N'-methylthiocarbamoyl Spinosyn B (0.14 g, 64%) as a white solid: MS m/z 791. Anal. Calcd for $C_{42}H_{66}N_2O_{10}S$: C, 63.77; H, 8.41; N, 3.54. Found: C, 63.57; H, 8.42; N 3.63.

Example C33

N-(N',N'-Dimethylformamidinyl) Spinosyn B

Spinosyn C (102 mg, 0.140 mmol) was dissolved in dimethylformamide dimethyl acetal (5 mL) and the solution heated to reflux for 30 min. The reaction was cooled to room temperature and the solvent evaporated in vacuo. The crude product was purified by chromatography on silica gel (95:5, MeOH/$CH_2Cl_2$) to afford N-(N',N'-dimethylformamidinyl) Spinosyn B (56.2 mg, 51%) as a tan solid: FDMS m/z 758.

Example C34

N-(N',N'-Dimethylcarbamyl) Spinosyn B

Spinosyn B (0.10 g, 0.14 mmol), dimethylcarbamyl chloride (0.10 g, 0.93 mmol), and N,N-diisopropylethylamine (0.10 g, 0.77 mmol) were dissolved in methylene chloride (10 mL) and stirred for 24 hrs. The solvent was evaporated in vacuo and the residue purified by chromatography on silical gel (95:5, $CH_2Cl_2$/MeOH). This gave N-(N',N'-dimethylcarbamyl) Spinosyn B (76.8 mg, 70%) as a white solid: FDMS m/z 788.

Example C35

N-octanoyl Spinosyn B

Compound Spinosyn B (98 mg, 0.14 mmol) was dissolved in methylene chloride (5 mL) and N,N-diisopropylethylamine (26 mg, 0.20 mmol) and octanoyl chloride (30 mg, 0.18 mmol) were added and the reaction stirred for 20 hrs. After work-up the residue was purified by chromatography on silica gel (ethyl acetate/hexane gradient, 40:60 to 60:40) to afford compound N-octanoyl Spinosyn B (61.9 mg, 53.8%): FDMS m/z 844. Anal. Calcd for $C_{48}H_{77}NO_{11}$: C, 68.29; H, 9.19; N, 1.65. Found: C, 68.03; H, 9.29; N, 1.84.

Example C36

N-Nitroso Spinosyn B

Compound Spinosyn B (1.01 g, 1.40 mmol) was suspended in water (10 mL) and cooled to 0° C. in an ice bath. To the cold suspension was added 1N HCl (10 mL) and the reaction stirred until all solids dissolved (note: a slight warming of the suspension was necessary to dissolve all solids). The solution was cooled back down to 0° C. and sodium nitrite (500 mg, 7.2 mmol) was added and the reaction stirred at 0° C. During the course of the reaction progress a white precipitate formed. After 2 hrs., additional sodium nitrite (500 mg, 7.2 mmol) was added and the reaction stirred for an additional 1 hr. The solid was collected by vacuum filtration and washed with cold water (2×20 mL). The solid was air dried to give compound N-nitroso Spinosyn B (1.00 g, 95%) as a white solid: FDMS m/z 748. Anal. Calcd for $C_{40}H_{62}N_2O_{11}$: C, 64.32; H, 8.37; N, 3.75. Found: C, 64.52; H, 8.26; N, 3.45.

Example C37

N-Benzenesulfonyl Spinosyn B

The compound was prepared following the procedure described in Example C78 using Spinosyn B (109 mg, 0.152 mmol), N,N-diisopropyldiethylamine (0.1 g, 0.8 mmol), and benzenesulfonyl chloride (26.8 mg, 0.15 mmol). This gave compound N-benzenesulfonyl Spinosyn B (78.6 mg, 60.5%) as a white solid: FDMS m/z 857.

Example C38

N-Benzylidenyl Spinosyn C

Compound Spinosyn C (106 mg, 0.15 mmol), benzaldehyde (0.1 g, 0.9 mmol) and camphorsulfonic acid (5 mg)

were dissolved in benzene (15 mL) and the reaction heated at reflux for 1 hr. The solvent was evaporated in vacuo and the residue purified by chromatography on silica gel (ethyl aceate/hexane gradient, 20:80 to 40:60) to afford compound N-benzylidenyl Spinosyn C (65.5 mg, 55.0%) as a white solid: FDMS m/z 746, 791.

Example C39

N,N-Diacetyl Spinosyn C

The compound was prepared following the procedure described in Example C78 using Spinosyn C (102 mg, 0.144 mmmol), N,N-diisopropyldiethylamine (0.1 g, 0.8 mmol), and acetyl chloride (0.1, 1 mmol). This gave compound N,N-diacetyl Spinosyn C (56.6 mg, 49.7%) as a white solid: FDMS m/z 787. Anal. Calcd for $C_{43}H_{65}N_1O_{12}$: C, 65.54; H, 8.31. Found: C, 65,64; H, 8.08.

Example C40

N-(N'-Methylcarbamyl) Spinosyn C

The compound was prepared following the procedure described in Example C79 using Spinosyn C (81 mg, 0.11 mmol), and methyl isocyanate (0.05 g, 0.9 mmol). This gave compound N-(N'-methylcarbamyl) Spinosyn C (61.8 mg, 71.0%) as a white solid: FDMS m/z 760. Anal. Calcd for $C_{41}H_{64}N_2O_{11}$: C, 64.71; H, 8.48; N, 3.68. Found: C, 64.48; H, 8.70; N, 3.59.

Example C41

4"-Des-(dimethylamino)-4"-[N-(E)-(2-hydroxy,3,5-di-t-butylphenyl)]imino Spinosyn A and 4"-des-(dimethylamino)-4"-[N-(Z)-(2-hydroxy,3,5-di-t-butylphenyl)]imino Spinosyn A Compound Spinosyn C (0.55 g, 0.78 mmol) was dissolved in methanol/tetrahydrofuran (6:1) and 1,3-di-t-butyl-1,2-benzoquinone (228 mg, 1.03 mmol) was added and the reaction stirred for 24 hrs. During this time the reaction changed from dark red to light yellow-green. The solvents were removed by rotary evaporation and the crude green solid purified by chromatography on silica gel (ethyl acetate/hexane, 1:1) to afford compounds 4"-des-(dimethylamino)-4"-[N-(Z)-(2-hydroxy,3,5-di-t-butylphenyl)]imino Spinosyn A (228 mg, 32.2%): partial $^1$H NMR d 6.78 (bs, 1H), 6.65 (s, 1H), 6.62 (s, 1H), 5.88 (dt, 1H), 5.80 (dt, 1H), 4.86 (s, 1H), 4.67 (m, 1H), 4.63 (d, 1H), 4.32 (q, 1H), 4.15 (bs, 1H), 3.70–3.62 (m, 2H); and 4"-des-(dimethylamino)-4"-[N-(E)-(2-hydroxy,3,5-di-t-butylphenyl)]imino Spinosyn A (343 mg, 48.5%): partial $^1$H-NMR δ 6.78 (bs, 1H), 6.74 (s, 1H), 6.63 (s, 1H), 5.88 (dd, 1H), 5.81 (dt, 1H), 4.86 (s, 1H), 4.69 (m, 1H), 4.63 (d, 1H), 4.32 (q, 1H), 3.68 (m, 1H).

Example C42

4"-Des-(dimethylamino)-4"-oxo Spinosyn A

Compound 4"-des-(dimethylamino)-4"-[N-(E)-(2-hydroxy,3,5-di-t-butylphenyl)]imino Spinosyn A (204 mg, 0.225 mmol) was suspended in methanol/tetrahydrofuran/water, 6:1:1 (8 mL) and the compound dissolved through the addition of tetrahydrofuran (6 mL). To this solution was added oxalic acid dihydrate (60 mg, 0.47 mmol) and the reaction stirred for 20 hrs. followed by heating at 50–60° C. for 4 hrs. After work-up the residue was purified by cycloytron chromatography on silica gel (ethyl acetate/hexane, 1:1) to afford compound 4"-des-(dimethylamino)-4"-oxo Spinosyn A (43.2 mg, 27.3%) as a white solid: partial $^1$H NMR δ 6.75 (bs, 1H), 5.86 (dd, 1H), 5.77 (dt, 1H), 4.96 (dd, 1H), 4.82 (s, 1H), 4.65 (m, 1H), 4.29 (q, 1H), 4.00 (q, 1H), 3.70 (m, 1H).

Example C43

(4"S)-4"-Des-(dimethylamino)-4"-hydroxy Spinosyn A

Compound 4"-des-(dimethylamino)-4"-oxo Spinosyn A (78 mg, 0.11 mmol) was dissolved in ether (10 mL) and cooled to 0° C. in an ice bath. To this cool solution was added lithium tri-t-butoxide aluminium hydride (48 mg, 0.19 mmol) and the reaction stirred for 20 min. The reaction was quenched with saturated aqueous sodium chloride (3 mL), worked-up, and purified by cyclotron chromatography on silica gel (ethyl acetate/hexane, 50:50) to afford compound (4"S)-4"-des-(dimethylamino)-4"-hydroxy Spinosyn A (46.6 mg, 59.7%) as a colorless glass: partial $^1$H NMR δ 6.78 (bs, 1H), 5.88 (dd, 1H), 5.81 (dt, 1H), 4.86 (s, 1H), 4.67 (m, 1H), 4.50 (d, 1H), 4.32 (q, 1H), 3.66 (m, 1H), 3.34–3.23 (m, 3H); $^{13}$C NMR δ 202.81, 172.55, 147.54, 144.12, 129.33, 128.80, 103.14, 95.45, 82.27, 81.06, 80.85, 77.72, 76.68, 76.06, 75.71, 71.54, 67.94, 60.94, 59.01, 57.70, 49.44, 47.60, 46.04, 41.52, 41.16, 37.38, 36.28, 34.32, 34.19, 31.42, 30.62, 30.12, 28.39, 21.53, 18.01, 17.80, 16.21, 9.35.

Example C44

(4"S)-4"-Des-(dimethylamino)-4"-acetoxy Spinosyn A

Compound (4"S)-4"-des-(dimethylamino)-4"-hydroxy Spinosyn A (10 mg, 0.14 mmol) was dissolved in methylene chloride and acetic anhydride (0.05 g, 0.5 mmol) and pyridine (0.1 g, 1 mmol) were added and the reaction stirred for 2 h. Work-up gave compound (4"S)-4"-des-(dimethylamino)-4"-acetoxy Spinosyn A (5.7 mg, 57%) as a colorless glass; partial $^1$H NMR δ 6.75 (bs, 1H), 5.86 (dd, 1H), 5.77 (dt, 1H), 4.83 (s, 1H), 4.66 (m, 1H), 4.49 (dd, 1H), 4.42 (ddd, 1H, J=11.0, 9.4, 4.7), 4.29 (q, 1H), 3.63 (m, 1H); $^{13}$C NMR δ 147.64, 129.33, 128.77, 103.02, 95.39, 82.24, 81.01, 80.74, 77.68, 76.77, 76.01, 73.13, 72.82, 67.92, 60.95, 59.01, 57.71, 49.42, 47.58, 46.01, 41.48, 41.14, 37.35, 36.25, 34.27, 34.17, 30.12, 30.03, 29.68, 28.39, 27.76, 21.53, 21.17, 17.99, 17.79, 16.13, 9.34.

Example C45

N-Demethyl-N-formyl Spinosyn D

Compound N-demethyl Spinosyn D (1.08 g, 1.47 mmol) was dissolved in ethyl formate (25 mL) and the solution heated at reflux for 14 h. The solvent was removed by rotary evaporation and the residue purified by reverse-phase HPLC (methanol/0.1% aq ammonium hydroxide, 85:15) to afford N-demethyl-N-formyl Spinosyn D (645.6 mg, 57.6%) as white foam: partial $^1$H NMR δ 8.09 & 8.06 (s, 1H), 6.77 (bs, 1H), 5.49 (bs, 1H), 4.86 (s, 1H), 4.67 (m, 1H), 4.50 (d, 1H), 4.30 (q, 1H), 3.60 (m, 1H).

Example C46

4"-N-[(2,4-Difluorophenyl)aminocarbonyl] Spinosyn B

This compound was prepared according to the method in Example C80 from 2,4-difluorophenyl isocyanate (75 mL, 98 mg, 0.63 mmol) and Spinosyn B (0.30 g, 0.42 mmol). MPLC (SiO$_2$, 50:50 EtOAc/hexane) gave 0.36 g (99%) of 4"-N-[(2,4-difluorophenyl)aminocarbonyl] Spinosyn B as a white powder: MS (m+H$^+$) expected: 873.5. Found: 873.8.

Example C47

4"-N-[(3,4-Dichlorophenyl)aminocarbonyl] Spinosyn B

This compound was prepared according to the method in Example C80 from 3,4-dichlorophenyl isocyanate (0.12 g, 0.64 mmol) and Spinosyn B (0.30 g, 0.42 mmol). MPLC (SiO$_2$, 60:40 to 100:0 EtOAc/hexane) gave 0.38 g (99%) of 4"-N-[(3,4-dichlorophenyl)aminocarbonyl] Spinosyn B as a white powder: MS (m+H$^+$) expected: 905.4. Found: 905.6.

Example C48

4"-N-[(4-methoxyphenyl)aminocarbonyl] Spinosyn B

This compound was prepared according to the method in Example C80 from 4-methoxyphenyl isocyanate (81 mL, 93 mg, 0.63 mmol) and Spinosyn B (0.30 g, 0.42 mmol). MPLC (SiO$_2$, 60:40 EtOAc/hexane) gave 0.36 g (99%) of 4"-N-[(4-methoxyphenyl)aminocarbonyl] Spinosyn B as a white powder: MS (m+H$^+$) expected: 867.5. Found: 867.8.

Example C49

4"-N-(1-Propyl) Spinosyn B

This compound was prepared according to the method in Example C81 from 1-iodopropane (0.14 mL, 0.24 g, 1.4 mmol), (i-Pr)$_2$NEt (0.36 mL, 0.27 g, 2.1 mmol), Spinosyn B (0.50 g, 0.70 mmol), and DMF (1.5 mL). MPLC (SiO$_2$, 50:50 EtOAc/hexane) gave 0.41 g (77%) of 4"-N-(1-propyl) Spinosyn B as a white powder. Anal. Calcd for C$_{43}$H$_{69}$NO$_{10}$: C, 67.96; H, 9.15; N, 1.84. Found: C, 68.06; H, 9.25; N, 1.97.

Example C50

4"-N-(2-Methyl-1-propyl) Spinosyn B

This compound was prepared according to the method in Example C81 from 1-iodo-2-methylpropane (0.32 mL, 0.51 g, 2.8 mmol), (i-Pr)$_2$NEt (0.73 mL, 0.54 g, 4.2 mmol), Spinosyn B (0.95 g, 1.3 mmol), and DMF (2.8 mL). MPLC (SiO$_2$, 50:50 EtOAc/hexane) gave 0.07 g (7%) of 4"-N-(2-methyl-1-propyl) Spinosyn B as a white powder (Spinosyn B, 0.71 g (75%) was also recovered): MS (m+H$^+$) expected: 774.5. Found: 774.6. Anal. Calcd for C$_{44}$H$_{71}$NO$_{10}$: C, 68.28; H, 9.25; N, 1.81. Found: C, 68.33; H, 9.26; N, 1.88.

Example C51

4"-N-[(Cyclopropyl)methyl] Spinosyn B

This compound was prepared according to the method in Example C81 from (bromomethyl)cyclopropane (0.27 mL, 0.38 g, 2.8 mmol), NaI (0.05 g, 0.3 mmol), (i-Pr)$_2$NEt (0.73 mL, 0.54 g, 4.2 mmol), Spinosyn B (0.95 g, 1.3 mmol), and DMF (2.8 mL). MPLC (50:50 EtOAc/hexane) gave 0.34 g (33%) of 4"-N-[(cyclopropyl)methyl] Spinosyn B as a white powder (Spinosyn B, 0.40 g (42%) was also recovered). Anal. Calcd for C$_{44}$H$_{69}$NO$_{10}$: C, 68.45; H, 9.01; N, 1.81. Found: C, 68.36; H, 9.22; N, 1.76.

Example C52

4"-N-Ethyl-5,6-dihydro Spinosyn B

This compound was prepared according to the method in Example C81 from iodoethane (60 mL, 0.12 g, 0.75 mmol), (i-Pr)$_2$NEt (0.20 mL, 0.15 g, 1.1 nmol), 5,6-dihydro Spinosyn B (0.27 g, 38 mmol), and DMF (2 mL). MPLC (40:60 EtOAc/hexane) gave 0.22 g (79%) of 4"-N-ethyl-5,6-dihydro Spinosyn B as a white powder. Anal. Calcd for C$_{42}$H$_{69}$NO$_{10}$: C, 67.44; H, 9.30; N, 1.87. Found: C, 67.52; H, 9.07; N, 1.78.

Example C53

5,6-Dihydro-4"-N-(2-methyl-1-propyl) Spinosyn B

This compound was prepared according to the method in Example C81 from 1-iodo-2-methylpropane (0.10 mL, 0.16 g, 0.87 mmol), (i-Pr)$_2$NEt (0.23 mL, 0.17 g, 1.3 mmol), 5,6-dihydro Spinosyn B (0.31 g, 0.43 mmol), and DMF (2 mL). MPLC (SiO$_2$, 40:60 EtOAc/hexane) gave 0.16 g (48%) of 5,6-dihydro-4"-N-(2-methyl-1-propyl) Spinosyn B as a white powder. Anal. Calcd for C$_{44}$H$_{73}$NO$_{10}$: C, 68.10; H, 9.48; N, 1.80. Found: C, 68.10; H, 9.37; N, 1.87.

Example C54

4"-N-(2-Fluoroethyl) Spinosyn B

This compound was prepared according to the method in Example C81 from 1-bromo-2-fluoroethane (0.10 mL, 0.17 g, 1.3 mmol), NaI (0.04 g, 0.3 mmol), (i-Pr)$_2$NEt (0.36 mL, 0.27 g, 2.1 mmol), Spinosyn B (0.48 g, 0.67 mmol), and DMF (2 mL). MPLC (30:70 to 40:60 EtOAc/hexane) gave 0.30 g (59%) of 4"-N-(2-fluoroethyl) spinosyn B as a white powder. Anal. Calcd for C$_{42}$H$_{66}$FNO$_{10}$: C, 66.03; H, 8.71; N, 1.83. Found: C, 65.89; H, 9.11; N, 1.92.

Example C55

4"-N-(2,2,2-Trifluoroethyl) Spinosyn B

This compound was prepared according to the method in Example C81 from 2,2,2-trifluoroethyl trifluoromethanesulfonate (0.34 g, 1.5 mmol), (i-Pr)$_2$NEt (0.36 mL, 0.27 g, 2.1 mmol), Spinosyn B (0.38 g, 0.53 mmol), and DMF (2 mL). MPLC (30:70 EtOAc/hexane) gave 0.32 g (76%) of 4"-N-(2,2,2-trifluoroethyl) Spinosyn B as a white powder. Anal. Calcd for C$_{42}$H$_{64}$F$_3$NO$_{10}$: C, 63.06; H, 8.06; N, 1.75. Found: C, 62.78; H, 7.97; N, 1.66.

Example C56

4"-N-[2-(N',N'-Dimethylamino)ethyl] Spinosyn B

This compound was prepared according to the method in Example C81 from Me$_2$(CH$_2$)$_2$Cl.HCl (0.30 g, 2.1 mmol), (i-Pr)$_2$NEt (0.50 mL, 0.37 g, 2.9 mmol), Spinosyn B (0.50 g, 0.70 mmol), and DMF (2 mL). MPLC (20:80 MeOH/CH$_2$Cl$_2$) gave 0.04 g (7%) of 4"-N-[2-(N',N'-dimethylamino)ethyl] Spinosyn B as a white powder (Spinosyn B, 0.44 g (88%) was also recovered): MS (m+H$^+$) expected: 789.5. Found: 789.8.

Example C57

4"-N-(2-Propyl) Spinosyn B

This compound was prepared according to the method in Example C81 from 2-iodopropane (0.11 mL, 0.19 g, 1.1 mmol), (i-Pr)$_2$NEt (0.30 mL, 0.22 g, 1.7 mmol), Spinosyn B (0.40 g, 0.56 mmol), and DMF (2 mL). MPLC (SiO$_2$, 50:50 EtOAc/hexane) gave 0.09 g (21%) of 4"-N-(2-propyl) Spinosyn B as a white powder: MS (m+H$^+$) expected: 760.5. Found: 760.6. Anal. Calcd for C$_{43}$H$_{69}$NO$_{10}$: C, 67.96; H, 9.15; N, 1.84. Found: C, 68.04; H, 9.32; N, 1.85.

Example C58

4"-N-(1-Butyl) Spinosyn B

This compound was prepared according to the method in Example C81 from 1-iodobutane (0.13 mL, 0.21 g, 1.1 mmol), (i-Pr)$_2$NEt (0.30 mL, 0.22 g, 1.7 mmol), Spinosyn B (0.40 g, 0.56 mmol), and DMF (2 mL). MPLC (SiO$_2$, 50:50 EtOAc/hexane) gave 0.41 g (95%) of 4"-N-(1-butyl) Spinosyn B as a white powder: MS (m+H$^+$) expected: 774.5. Found: 774.7.

Example C59

4"-N,4"-N-(But-1,4-diyl) Spinosyn B Iodide Salt

This compound was prepared according to the method in Example C81 from 1,4-diiodobutane (0.11 mL, 0.26 g, 0.83 mmol), (i-Pr)$_2$NEt (0.30 mL, 0.22 g, 1.7 mmol), Spinosyn B (0.30 g, 0.42 mmol), and DMF (1 mL). MPLC (SiO$_2$, 25:75 MeOH/CH$_2$Cl$_2$) gave 0.18 g (47%) of 4"-N,4"-N-(but-1,4-diyl) Spinosyn B iodide salt as a tan powder.

Example C60

4"-N,4"-N-(Pent-1,5-diyl) Spinosyn B Iodide Salt

This compound was prepared according to the method in Example C81 from 1,5-diiodopentane (0.12 mL, 0.26 g, 0.81 mmol), (i-Pr)$_2$NEt (0.30 mL, 0.22 g, 1.7 mmol), Spinosyn B (0.30 g, 0.42 mmol), and DMF (1 mL). MPLC (SiO$_2$, 25:75 MeOH/CH$_2$Cl$_2$) gave 0.10 g (26%) of 4"-N,4"-N-(pent-1,5-diyl) Spinosyn B iodide salt as a tan powder.

Example C61

4"-N,4"-N-(But-1,4-diyl) Spinosyn C

This compound was prepared according to the method in Example C81 from 1,4-diiodobutane (0.22 mL, 0.52 g, 1.7 mmol), (i-Pr)$_2$NEt (0.44 mL, 0.33 g, 2.5 mmol), Spinosyn C (0.60 g, 0.57 mmol), and DMF (4 ml). MPLC (SiO$_2$, 5:95 MeOH/CH$_2$Cl$_2$) gave 0.10 g (23%) of 4"-N,4"-N-(but-1,4-diyl) Spinosyn C as a white powder: MS (m+H$^+$) expected: 758.5. Found: 758.6.

Example C62

4"-N,4"-N-(Pent-1,5-diyl) Spinosyn C

This compound was prepared according to the method in Example C81 from 1,5-diiodopentane (0.25 mL, 0.54 g, 1.7 mmol), (i-Pr)$_2$NEt (0.44 mL, 0.33 g, 2.5 mmol), Spinosyn C (0.60 g, 0.57 mmol), and DMF (4 ml). MPLC (SiO$_2$, 50:50 EtOAc/hexane) gave 0.31 g (70%) of 4"-N,4"-N-(pent-1,5-diyl) Spinosyn C as a white powder: MS (m+H$^+$) expected: 772.5. Found: 772.7.

Example C63

4"-N,4"-N-Diethyl Spinosyn C

This compound was prepared according to the method in Example C81 from iodoethane (0.23 mL, 0.45 g, 2.9 mmol), (i-Pr)$_2$NEt (0.60 mL, 0.45 g, 3.4 mmol), Spinosyn C (0.40 g, 0.57 mmol), and DMF (2 mL). MPLC (SiO$_2$, 50:50 EtOAc/hexane) gave 0.38 g (88%) of 4"-N,4"-N-diethyl Spinosyn C as a white powder: MS (m+H$^+$) expected: 760.5. Found: 760.7. Anal. Calcd for C$_{43}$H$_{69}$NO$_{10}$: C, 67.96; H, 9.15; N, 1.84. Found: C, 68.01; H, 9.47; N, 1.83.

Example C64

4"-N,4"-N-(2-Buten-1,4-diyl) Spinosyn C and 4"-N,4"-N-(butadien-1,4-diyl) Spinosyn C These compounds were prepared according to the method in Example C81 from 1,4-dichlorobut-2-ene (0.10 mL, 0.12 g, 0.95 mmol), NaI (0.02 g, 0.1 mmol), (i-Pr)$_2$NEt (0.22 mL, 0.16 g, 1.3 mmol), Spinosyn C (0.29 g, 0.41 mmol), and DMF (1.5 ml). MPLC (SiO$_2$, 20:80 to 100:0 EtOAc/CH$_2$Cl$_2$) gave 0.11 g (35%) of 4"-N,4"-N-(2-buten-1,4-diyl) Spinosyn C as a white powder: MS (m+H$^+$) expected: 756.5. Found: 756.6 and 4"-N,4"-N-(butadien-1,4-diyl) Spinosyn C: 0.11 g (35%) as a white powder: MS (m+H$^+$) expected: 754.5. Found: 754.8. Facile ambient oxidation may have accounted for the production of this product.

Example C65

4"-N-[(6-Chloro-3-pyridyl)methyl] Spinosyn B

This compound was prepared according to the method in Example C81 from (6-chloro-3-pyridyl)chloromethane (0.14 g, 0.86 mmol), (i-Pr)$_2$NEt (0.22 mL, 0.16 g, 1.3 mmol), Spinosyn B (0.30 g, 0.42 mmol), and DMF (1 mL). MPLC (25:75 to 75:25 EtOAc/hexane) gave 0.30 g (86%) of 4"-N-[(6-Chloro-3-pyridyl)methyl] Spinosyn B as a white powder.

Example C66

4"-N-[N'-(2,2-dimethylethoxycarbonyl)-β-alanyl] Spinosyn B

This compound was prepared according to the method in Example C77 from NMM (2×0.12 mL, 0.22 g, 2.2 mmol), Boc-N(H)-β-Ala-CO$_2$H (0.17 g, 0.90 mmol), BOP-Cl (0.23 g, 0.90 mmol), Spinosyn B (0.50 g, 0.70 mmol), and CH$_2$Cl$_2$ (7 mL). MPLC (SiO$_2$, 70:30 to 100:0 EtOAc/hexane) gave 0.62 g (99%) of 4"-N-[N'-(2,2-dimethylethoxycarbonyl)-β-alanyl] Spinosyn B as a white powder: MS (m+H$^+$) expected: 889.5. Found: 889.7. Anal. Calcd for C$_{48}$H$_{76}$N$_2$O$_{13}$: C, 64.84; H, 8.62; N, 3.15. Found: C, 64.38; H, 8.67; N, 3.22.

Example C67

4"-N-[N'-(Phenylmethoxycarbonyl)-L-alanyl] Spinosyn B

This compound was prepared according to the method in Example C77 from NMM (2×0.12 mL, 0.22 g, 2.2 nmol), Cbz-N(H)-L-Ala-CO$_2$H (0.21 g, 0.94 mmol), BOP-Cl (0.24 g, 0.94 mmol), Spinosyn B (0.50 g, 0.70 mmol), and CH$_2$Cl$_2$ (7 mL). MPLC (SiO$_2$, 75:25 EtOAc/hexane) gave 0.68 g (99%) of 4"-N-[N'-(Phenylmethoxycarbonyl)-L-alanyl] Spinosyn B as a white powder: MS (m+H$^+$) expected: 923.5. Found: 923.7.

Example C68

4"-N-[N',N'-Dimethylglycyl] Spinosyn B

This compound was prepared according to the method in Example C77 from NMM (2×0.12 mL, 0.22 g, 2.2 mmol), N(Me)$_2$-Gly-CO$_2$H (0.09 g, 0.9 mmol), BOP-Cl (0.25 g, 0.98 mmol), Spinosyn B (0.50 g, 0.70 mmol), and CH$_2$Cl$_2$ (7 mL). MPLC (SiO$_2$, 5:95 to 8:92 MeOH/CH$_2$Cl$_2$) gave 0.43 g (77%) of 4"-N-[N',N'-dimethylglycyl] Spinosyn B as a white powder: MS (m+H$^+$) expected: 803.5. Found: 803.6.

Example C69

4"-N-[N',N'-(Pent-1,5-diyl)-β-alanyl] Spinosyn B

This compound was prepared according to the method in Example C77 from NMM (2×0.12 mL, 0.22 g, 2.2 mmol), N,N(CH$_2$)$_5$-β-Ala-CO$_2$H (0.14 g, 0.89 mmol), BOP-Cl (0.26 g, 1.0 mmol), Spinosyn B (0.50 g, 0.70 mmol), and CH$_2$Cl$_2$ (7 mL). MPLC (SiO$_2$, 5:95 to 10:90 MeOH/CH$_2$Cl$_2$) gave 0.54 g (90%) of 4"-N-[N',N'-(pent-1,5-diyl)-β-alanyl] Spinosyn B as a white powder: MS (m+H$^+$) expected: 857.6. Found: 857.8.

Example C70

4"-N-[N',N'-Diethyl-β-alanyl] Spinosyn B

This compound was prepared according to the method in Example C77 from NMM (0.24 mL, 0.22 g, 2.2 mmol & 0.12 mL, 0.11 g, 1.1 mmol), N,N(Et)$_2$-β-Ala-CO$_2$H.HCl (0.16 g, 0.88 mmol), BOP-Cl (0.26 g, 1.0 mmol), Spinosyn B (0.50 g, 0.70 mmol), and CH$_2$Cl$_2$ (7 mL). MPLC (SiO$_2$, 5:95 to 10:90 MeOH/CH$_2$Cl$_2$) gave 0.46 g (78%) of 4"-N-[N',N'-diethyl-β-alanyl] Spinosyn B as a white powder: MS (m+H$^+$) expected: 845.6. Found: 845.8.

Example C71

4"-N-[N'-(9-Fluorenylmethoxycarbonyl)-β-alanyl] Spinosyn B and 4"-N-(β-alanyl) Spinosyn B This compound was prepared according to the method in Example C77 from NMM (2×0.12 mL, 0.22 g, 2.2 mmol), Fmoc-N(H)-β-Ala-CO$_2$H (0.26 g, 0.84 mmol), BOP-Cl (0.23 g, 0.90 mmol), Spinosyn B (0.502 g, 0.699 mmol), and CH$_2$Cl$_2$ (7 mL). MPLC (SiO$_2$, 0:100 to 20:80 MeOH/CH$_2$Cl$_2$) gave 0.03 g (4%) of 4"-N-[N'-(9-fluorenylmethoxycarbonyl)-β-alanyl] Spinosyn B as a white powder: MS (m+H$^+$) expected: 1011.6. Found: 4"-N-(β-alanyl) Spinosyn B, 0.27 g (49%) as a white powder: MS (m+H$^+$) expected: 789.5. Found: 789.7. Facile deprotection of the Fmoc group under the reaction conditions may have accounted for the production of this product.

Example C72

4"-N-(Diethoxyphosphoryl) Spinosyn B (EtO)$_2$P(O)Cl (91 mL, 0.11 g, 0.63 mmol) and (i-Pr)$_2$NEt (0.22 mL, 0.16 g, 1.3 mmol) were added sequentially to a solution of Spinosyn B (0.30 g, 0.42 mmol) in CH$_2$Cl$_2$ (4 mL). After 2 day, the mixture was partitioned between CH$_2$Cl$_2$ and NaHCO$_3$. The organic layer was washed with brine, dried (Na$_2$SO$_4$), filtered, and evaporated. MPLC (SiO$_2$, EtOAc) gave 0.27 g (75%) of 4"-N-(diethoxyphosphoryl) Spinosyn B as a white powder.

Example C73

N-Trifluoroacetyl-N-demethyl Spinosyn D

Trifluoroacetic anhydride (0.16 mL, 1.1 mmol) was added in one portion to a cold (0° C.), well stirred solution of N-demethyl Spinosyn D (0.4 g, 0.54 mmol) and triethylamine (0.2 mL, 1.5 mmol) in EtOAc. The cooling bath was removed and this solution stirred at room temperature for 40 min. then poured on to ice water (40 mL). The product was extracted into EtOAc (3×15 mL) and the organic extracts were washed with saturated NaHCO$_3$ (6 mL), brine (6 mL) and dried (MgSO$_4$). Evaporation of the solvent left 0.4 g of clean N-trifluoroacetyl-N-demethyl Spinosyn D as a colorless foam: $^1$H NMR (CDCl$_3$) δ 6.76 (s, 1H, H-13), 5.49 (s, 1H, H-5), 4.86 (d, 1H, H-1'), 4.66 (m, 1H, H-21), 4.51 (d, 1H, H-1"), 4.30 (m, 1H, H-9), 3.0 and 2.88 (s, total 3H, N(CH$_3$)); MS m/z 189 (70), 224 (100).

Example C74

N-(2,2,2-Trichloroethoxy)carbon-yl-N-demethyl Spinosyn A

Anhydrous K$_2$CO$_3$ (0.12 g, 0.87 mmol) was added to a well stirred solution of Spinosyn A (1.5 g, 2.0 mmol) and 2,2,2-trichloroethyl chloroformate (0.8 mL, 5.5 mmol) in dry benzene (20 mL). The resulting mixture was heated at reflux for 48 hrs., then cooled to room temperature and poured on to ice water (100 mL). The organics were extracted into EtOAc (3×40 mL) and the extracts washed with brine (40 mL) and dried (MgSO$_4$). The residue (2.7 g) left after evaporation of the solvent was flash chromatographed over silica (170 mL) using 2:1 Hexane/EtOAc as eluent to give N-(2,2,2-trichloroethoxy)carbon-yl-N-demethyl Spinosyn A (1.3 g) as a colorless foam: $^1$H NMR (CDCl$_3$) δ 6.76 (s, 1H, H-13), 4.86 (d, 1H, H-1'), 4.75 (m, 3H, Cl$_3$CCH$_2$, H-21), 4.48 (m, 1H, H-1"), 4.32 (m, 1H, H-9); MS m/z 189 (100), 302 (28), 591 (32), 893 (77).

Example C75

N-(2,2,2-trichloroethoxy)carbonyl-N-demethyl Spinosyn D

A soluton of 2,2,2-trichloroethyl chloroformate (0.07 mL, 0.51 mmol) in CH$_2$Cl$_2$ (2 mL) was added dropwise during 2–3 min. to a stirred solution of N-demethyl Spinosyn D (0.15 g, 0.20 mmol) and pyridine (0.3 mL) in CH$_2$Cl$_2$ (4 mL). This solution was stirred at room temperature for 6 hrs., then diluted with water (5 mL). The organic layer was separated and washed successively with 1N HCl (5 mL), saturated NaHCO$_3$ (5 mL) and brine (5 mL) and dried (MgSO$_4$). Concentration left 0.42 g of residue which was flash chromatographed over silica (90 mL) using 2:1 hexane/EtOAc to give 0.15 g (80%) of N-(2,2,2-trichloroethoxy) carbonyl-N-demethyl Spinosyn D as a colorless foam: $^1$H NMR (CDCl$_3$) δ 6.76 (s, 1H, H-13), 5.48 (s, 1H, H-5), 4.86 (d, 1H, H-1'), 4.76 (m, 2H, Cl$_3$CCH$_2$), 4.66 (m, 1H, H-21), 4.48 (m, 1H, H-1"), 4.30 (m, 1H, H-9), 2.87 and 2.85 (s, total 3H, NCH$_3$).

Example C76

N-(2,2,2-Trichloroethoxy)-carbonyl-N-demethyl-7-hydroxy Spinosyn D

A suspension of 5% SeO2 on silica (0.21 g) and tert-butyl-hydroperoxide (90%, 0.07 mL) in CH$_2$Cl$_2$ (3 mL) was stirred at room temperature for 15 min. To this mixture, a solution of N-tri-chloroethoxycarbonyl-N-demethyl Spinosyn D (0.15 g, 0.16 mmol) in CH$_2$Cl$_2$ (2 mL) was added dropwise during 2–3 min. This mixture was stirred at room temperature for 1.5 hrs., then filtered. The collected solids were washed with CH$_2$Cl$_2$ (10 mL) and the combined filtrate and wash washed with water (5 mL) and brine (5 mL) and dried (MgSO$_4$). Concentration left 0.11 g of residue which was chromatographed over silica using 4% MeOH in CH$_2$Cl$_2$ to give 63 mg of N-(2,2,2-trichloroethoxy)-carbonyl-N-demethyl-7-hydroxy Spinosyn D as a white foam: $^1$H NMR (CDCl$_3$) δ 6.76 (s, 1H, H-13), 5.58 (s, 1H, H-5), 4.6–4.9 (m, 4H, H-1', H-21, Cl$_3$CCH$_2$), 4.48 (m, 1H, H-1"), 4.40 (m, 1H, H-9).

Example C77

4"-N-[N'-(2,2-Dimethylethoxycarbonyl)glycyl] Spinosyn B

4-Methylmorpholine (NMM) (0.12 mL, 0.11 g, 1.1 mmol) was added to a −15° C. solution of Boc-N(H)-Gly-CO$_2$H (0.16 g, 0.91 mmol) and BOP-Cl (0.23 g, 0.90 mmol) in CH$_2$Cl$_2$ (7 mL). After 1.5 hrs., the volume was reduced approx. by half in vacuo. Spinosyn B (0.50 g, 0.70 mmol) and NMM (0.12 mL, 0.11 g, 1.1 mmol) were added sequentially. The mixture was warmed to ambient temperature over 20 hrs.; the mixture was evaporated. MPLC ($SiO_2$, 50:50 to 100:0 EtOAc/hexane) gave 0.61 g (99%) of 4"-N-[N'-(2,2-dimethylethoxycarbonyl)glycyl] Spinosyn B as a white powder: MS (m+H$^+$) expected: 875.5. Found: 875.9.

Example C78

N-Chloroacetyl Spinosyn B

Compound Spinosyn B (104.4 mg, 0.145 mmol) was dissolved in methylene chloride (5 mL) and N,N-diisopropylethylamine (0.1 g, 0.8 mmol) and chloroacetyl chloride (0.1 g, 0.9 mmol) were added and the reaction stirred for 1 h. After work-up the residue was purified by chromatography on silica gel (ethyl acetate/hexane, 50:50) to afford compound N-chloroacetyl Spinosyn B (79.1 mg, 68%) as a colorless glass: FDMS m/z 794. Anal. Calcd for $C_{42}H_{64}NO_{11}Cl$: C, 63.50; H, 8.12; N, 1.76. Found: C, 63.32; H, 8.04; N, 1.58.

Example C79

N-(N'-Ethylthiocarbamyl) Spinosyn B

Compound Spinosyn B (97.8 mg, 0.136 mmol) was dissolved in toluene (4 mL) and ethylisothiocyanate (0.05 g, 0.6 mmol) was added and the reaction heated at reflux for 2 hrs. The toluene solvent was removed in vacuo and the residue purified by chromatography on silica gel (ethyl acetae/hexane gradient 20:80 to 50:50) to afford compound N-(N'-ethylthiocarbamyl) Spinosyn B (80.6 mg, 73.4%) as a colorless glass: FDMS m/z 804, 805.

Example C80

4"-N-[[4-(Trifluoromethoxy)phenyl]aminocarbonyl] Spinosyn B 4-(Trifluoromethoxy)phenyl isocyanate (94 mL, 0.13 g, 0.63 mmol) and DMF (3 mL, 3 mg, 0.04 mmol) were added sequentially to a 0° C. solution of Spinosyn B (0.30 g, 0.42 mmol) in $Et_2O$ (4 mL). The mixture was allowed to warm to ambient temperature for 15 min. The excess isocycante was decomposed via addition of MeOH (1 mL) and the mixture was evaporated. MPLC ($SiO_2$, 50:50 EtOAc/hexane) gave 0.37 g (97%) of 4"-N-[[4-(Trifluoromethoxy)phenyl] aminocarbonyl] Spinosyn B as a white powder: MS (m+H$^+$) expected: 921.5. Found: 921.6.

Example C81

4"-N-Ethyl Spinosyn B

Iodoethane (0.11 mL, 0.21 g, 1.4 mmol) and (i-Pr)$_2$NEt (0.36 mL, 0.27 g, 2.1 mmol) were added sequentially to a solution of Spinosyn B (0.50 g, 0.70 mmol) in DMF (1.5 mL). The progress of the reaction was monitored by TLC ($SiO_2$) and HPLC ($C_{18}$). After sufficient conversion was noted (1–5 day), the mixture was evaporated. The residue was partitioned between EtOAc and $NaHCO_3$. The organic layer was washed with brine, dried ($MgSO_4$), filtered, and evaporated. MPLC ($SiO_2$, 50:50 EtOAc/hexane) gave 0.55 g (89%) of 4"-N-ethyl Spinosyn B as a white powder: MS (m+H$^+$) expected: 746.5. Found: 746.7.

Example C82

(4"S)-4"-Des-(dimethylamino)-4"-methoxy Spinosyn A

Compound (4"S)-4"-des-(dimethylamino)-4"-hydroxy Spinosyn A (2.21 g; 3.08 mmol) is dissolved in $CH_2Cl_2$ (60 ml). Water (20 ml), 10% aq NaOH (25 ml) and solid $K_2CO_3$ (5 g) are added, followed by dimethyl sulfate (8 ml, an excess). The reaction mixture is stirred vigorously at ambient temperature under nitrogen for 48 hrs. Water (50 ml) and $CH_2Cl_2$ (50 ml) are added, layers are separated, the organic layer is washed with $H_2O$ (2×), dried over $K_2CO_3$ and concentrated in vacuo. The residue is separated by a flash $SiO_2$ column chromatography (230–400 m, 250 g/ethyl acetate).

Example C83

4"-(S)-4"-Des-(dimethylamino)-4"-ethoxy Spinosyn A

Compound (4"S)-4"-des-(dimethylamino)-4"-hydroxy Spinosyn A (2.21 g; 3.08 mmol) is dissolved in $CH_2Cl_2$ (60 ml). Water (20 ml), 10% aq NaOH (25 ml) and solid $K_2CO_3$ (5 g) are added, followed by diethyl sulfate (8 ml, an excess). The reaction mixture is stirred vigorously at ambient temperature under nitrogen for 48 hrs. Water (50 ml) and $CH_2Cl_2$ (50 ml) are added, layers are separated, the organic layer is washed with $H_2O$ (2×), dried over $K_2CO_3$ and concentrated in vacuo. The residue is separated by a flash $SiO_2$ column chromatography (230–400 m, 250 g/ethyl acetate).

Example C84

4"-(S)-4"-Des-(dimethylamino)-4"-propoxy Spinosyn A

Compound 4"-(S)-4"-des-(dimethylamino)-4"-hydroxy Spinosyn A (1.22 g, 1.70 mmol) is dissolved in $CH_2Cl_2$ (20 ml). Water (10 ml) and 25% aqueous NaOH (15 ml) are added, followed by $K_2CO_3$ (2 g), tetrabutylammonium chloride (1.2 g) and benzyltriethylammonium chloride (1.5 g). Compound 1-iodopropane (10 ml) is added and the reaction mixture is vigorously stirred at ambient temperature under $N_2$ for 48 hrs. Dichloromethane (20 ml) is added and the phases are separated. The organic layer is washed with water (2×), dried over $K_2CO_3$, and concentrated in vacuo. The residue is purified over a flash $SiO_2$ column (120 g/ethyl acetate).

Example C85

4"-(S)-4"-Des-(dimethylamino)-4-chloromethyl Spinosyn A

Compound 4"-(S)-4"-des-(dimethylamino)-4"-hydroxy Spinosyn A (510 mg, 0.71 mmol) is dissolved in $CH_2Cl_2$ (5.0 ml) and $K_2CO_3$ (1.10 g) is added. The reaction flask is immersed in a water bath (10° C.) and 15% aqueous NaOH (10 ml) is added with vigorous stirring, followed by benzyltriethylammonium chloride (1.20 g). Chloroiodomethane (5.0 ml) is added and the reaction mixture is vigorously stirred at ambient temperature under $N_2$ for 72 hrs. Dichloromethane (100 ml) and water (50 ml) are added. The phases are separated. The organic layer is washed with water (2×), dried over $K_2CO_3$ and concentrated in vacuo. The residue is purified over a flash $SiO_2$ column (70 g/ethyl acetate).

Example C86

4"-(S)-4"-Des-(dimethylamino)-4"-trimethylsiloxy Spinosyn A

Compound (4"-(S)-4"-des-(dimethylamino)-4"-hydroxy Spinosyn A (510 mg, 0.71 mmol) is dissolved in $CH_2Cl_2$ (10 ml). Dimethylaminopyridine (0.80 g) is added. The mixture is stirred at ambient temperature under nitrogen. Trimethylsilyl triflate (0.90 ml, an excess) is slowly introduced via a syringe and stirring is continued for 1 hr. Ethyl acetate (50 ml) and benzene (50 ml) are added. The solution is washed with 5% aq NaHCO$_3$ solution (3×). The organic layer is dried over K$_2$CO$_3$ and concentrated in vacuo. The residue is purified on a flash SiO$_2$ column (100 g/ethyl acetate).

Example C87

(4"S)-4"-Des-(dimethylamino)-4"-acetoxy Spinosyn A

Compound(4"S)-4"-des-(dimethylamino)-4"-hydroxy Spinosyn A (10 mg, 0.14 mmol) is dissolved in methylene chloride and acetic anhydride (0.05 g, 0.5 mmol) and pyridine (0.1 g, 1 mmol) are added and the reaction stirred for 2 hrs. Work-up gives compound (4"S)-4"-des-(dimethylamino)-4"-acetoxy Spinosyn A.

Example C88

4"-(S)-4"-Des-(dimethylamino)-4"-chloroacetoxy Spinosyn A

Compound 4"-(S)-4"-des-(dimethylamino)-4"-hydroxy Spinosyn A (306 mg, 0.43 mmol) is dissolved in dry pyridine (5 ml). Chloroacetic chloride (0.50 ml) is added dropwise. The reaction mixture is stirred at ambient temperature under nitrogen. After 3 hrs., toluene (50 ml) and ethyl acetate (50 ml) are added. The solution is washed successively with brine, 5% NaHCO$_3$ (2×) and water. The organic phase is dried over anhydrous Na$_2$SO$_4$ and concentrated in vacuo. The residue is separated on a flash SiO$_2$ column (80 g/ethyl acetate).

Example C89

Compound 3",4"-dehydro-4"-desamino-5,6-dihydro Spinosyn A 5,6-Dihydro Spinosyn A N-oxide (1.26 g, 1.68 mmol) was dissolved in dry THF (10 ml). The solution was cooled to −78° C. and pyridine (5 ml) was added. Upon stirring, trifluoroacetic anhydride (1.8 ml, 2.67 g, 12.7 mmol) was added. After 16 hrs. Et$_2$O (120 ml) was added, the mixture was extracted with diluted brine (2×), then with 10% aqueous KHCO$_3$ (2×), dried over K$_2$CO$_3$ and concentrated in vacuo. The residue was separated over a flash SiO$_2$ column (Et$_2$O) to give 3",4"-dehydro-4"-desamino-5,6-dihydro Spinosyn A (122 mg, 10.5%) as a white solid: $^1$H NMR d 6.82 (bs, 1H), 5.61 (m, 1H), 5.53 (bd, J=10 Hz, 1 H), 4.66 (q, J=6 Hz, 1 H), 1.23 (d, J=6.3 Hz, 3 H), 1.19 (d, J=6.6 Hz, 3H), 1.15 (d, J=7.0 Hz, 3H).

Example C90

Compound 5,6-dihydro-N-formyl Spinosyn B and compound 4"-desamino-5,6-dihydro-4"-keto Spinosyn C 5,6-Dihydro spinosyn A (1.43 g, 1.95 mmol) was dissolved in methylene chloride (25 ml) and pyridine (6.0 ml) was added. The flask was cooled at +10° C. Bromine (3.0 ml) was added with vigorous stirring under N$_2$. After 30 min. water (2.0 ml) was added and stirring was continued for 1 hr. Et$_2$O (200 ml) was added, the mixture was successively extracted with: water, 10% aqueous NaHSO$_3$, water, and 10% aqueous KHCO$_3$, dried over anh. K$_2$CO$_3$, filtered and concentrated. The crude product was divided into two equal parts. One part was purified by flash chromatography (SiO$_2$/ Et$_2$O) and separated by repeated RP (C-18) HPLC (92:8, MeOH/H$_2$O) to give a) 5,6-dihydro-N-formyl spinosyn B (230 mg, 31%) as a white solid: $^1$H NMR d 7.96 (bs) and 7.93 (bs, total 1 H), 6.74 (bs, 1 H), 2.64 (s, 3 H), 1.14 (d, J=5.8 Hz, 3 H), 1.05 (d, J=6.9 Hz, 3 H), 1.02 (d, J=6.3 Hz, 3 H) and b) fractions enriched to ca. 50% in 4"-desamino-5,6-dihydro-4"-keto spinosyn C (168 mg, ca. 12%). The above procedure was repeated on a 5-times larger scale, which led to pure 4"-desamino-5,6-dihydro-4"-keto spinosyn C (212 mg, 3.1%), a white solid: $^1$H NMR d 6.79 (bs, 1 H), 4.90 (dd, J=8.2 Hz, 2.5 Hz), 3.95 (q, J=6.7 Hz); $^{13}$C NMR d 208.7, 203.2, 172.6, 149.6, 145.1, 100.9, 95.4, 17.6 (CH$_3$), 16.1 (CH$_3$), 15.3 (CH$_3$), 9.2 (CH$_3$).

Example C91

Compound 4"-desamino-5,6-dihydro-4"(S)-hydroxy Spinosyn C

4"-Desamino-5,6-dihydro-4"-keto Spinosyn C (192 mg, 0.273 mmol) was dissolved in dry Et$_2$O (50 ml). The solution was cooled to 0° C. and lithium tri-t-butoxyaluminohydride (97%, 145 mg, 0.55 mmol) was added in one portion. Stirring at the same temperature was continued for 15 min. The reaction mixture was then carefully quenched with brine. Ethyl ether (100 ml) was added and the mixture was extracted with aqueous 2N NaOH (2×), then with 10% aq. KHCO$_3$, dried over K$_2$CO$_3$ and concentrated. The crude product was purified over a flash SiO$_2$ column (EtOAc) and separated by RP (C-18) HPLC (92:8, MeOH/H$_2$O) to give 4"-desamino-5,6-dihydro-4"(S)-hydroxy spinosyn C (91 mg, 47%) as a white solid: $^1$H NMR d 6.81 (bs, 1 H), 4.43 (bd, J=7.4 Hz, 1 H), 3.57 (m, 1 H), 1.21 (d, J=6.1 Hz, 6H), 1.12 (d, J=6.9 Hz, 3H).

Example C92

Compound 4"-desamino-5,6-dihydro-4"(S)-methoxy Spinosyn C

4"-Desamino-5,6-dihydro-4"(S)-hydroxy Spinosyn C (66 mg, 0.093 mmol) was dissolved in methylene chloride (1.5 ml). Iodomethane (2.0 ml) was added, followed by 40% aqueous NaOH solution (3.0 ml) and tetrabutylphosphonium bromide (320 mg). The reaction mixture was vigorously stirred at RT/N$_2$ and powdered KOH (0.60 g) was added. Stirring was continued for 2 hrs. Water (10 ml) and Et$_2$O (100 ml) were added, the mixture was washed with water, then with 10% aq. KHCO$_3$ solution (2×). The organic phase was dried over anh. K$_2$CO$_3$, filtered and concentrated in vacuo. The residue was purified over a flash SiO$_2$ column (CH$_2$Cl$_2$-Et$_2$O, 8:2) to afford 4"-desamino-5,6-dihydro-4" (S)-methoxy Spinosyn C (40.0 mg, 59%) as a white solid: $^1$H NMR δ 6.82 (bs, 1 H), 4.43 (dd, J=9.4 Hz, 1.9 Hz), 3.52 (s, 3 H), 3.46 (s, 3 H), 3.45 (s, 3 H), 3.32 (s, 3 H), 1.25 (d, J=6.3 Hz, 3 H), 1.20 (d, J=6.1, 3 H), 1.14 (d, J=6.8 Hz, 3 H), 0.77 (t, J=7.4 Hz, 3 H).

Part D Modification of the 13' and 14' Position on the Tricyclic Portion of the Compound in Formula 1

Example D1

(14R)-13,14-Dihydro Spinosyn A

To a solution of Spinosyn A (1.0 gms, 1.37 mmol) in absolute ethanol (20 ml) under nitrogen atmosphere, sodium borohydride (520 mg, 13.7 mmol) was added in portions over 0.5 hour. The reaction mixture was stirred at room temperature for 45 min., then quenched by addition of saturated aqueous ammonium chloride. The mixture was then diluted with water and extracted with dichloromethane. The dichloromethane was dried with $K_2CO_3$, and evaporated at room temperature under reduced pressure. The product was purified by chromatography on silica, eluting with 5% methanol in chloroform. This gave a poor separation so chromatography was repeated, after recovery of product, eluting with ethyl acetate. This gave (14R)-13,14-dihydro Spinosyn A (567.5 mg; 57% yield) as a colorless glass, FDMS, m/e (relative intensity) 734 ($M^+$, 100), 733 (60).

Example D2

(14S)-5,6,13,14-Tetrahydro Spinosyn A

The reaction was run as described in Example D5 starting with Spinosyn A (106.8 mg, 0.15 mmol). This gave (14S)-5,6,13,14-tetrahydro Spinosyn A(85.5 mg; 80% yield) as a colorless, slightly sticky solid, FDMS, m/e (relative intensity) 736 ($M^+$, 100).

Example D3

(14R)-5,6,13,14-Tetrahydro Spinosyn A

To a solution of (14R)-13,14-dihydro Spinosyn A (210.3 mg, 0.29 mmol) in benzene (9 ml), tris(triphenylphosphine) rhodium(I) chloride (47.2 mg, 0.05 mmol) was added and the reaction mixture was placed under one atmosphere of hydrogen. The mixture stirred at room temperature for 4 days, then the solvent was evaporated at room temperature under reduced pressure. The product was purified by chromatography on silica, eluting with 5% methanol in dichloromethane. Product was further purified by chromatography on silica, eluting with 70% ethyl acetate in dichloromethane. This gave (14R)-5,6,13,14-tetrahydro Spinosyn A(93.3 mg; 44% yield) as as colorless glass, FDMS, m/e (relative intensity) 735 ($M^+$, 100).

Example D4

(13R,14S)-13,14-Epoxy Spinosyn A

To an ice cold solution of Spinosyn A (200.7 mg, 0.27 mmol) in methanol (3 ml), 30% aqueous $H_2O_2$ (41 ml, 1.35 mmol) followed by sodium hydroxide (19 mg, 0.33 mmol) were added. The reaction mixture was stirred at 0° C. for 1 hour and then warmed to room temperature. After stirring at room temperature for 3 hours, the mixture was diluted with dichloromethane. The dichloromethane was then washed with water, 5% aqueous sodium thiosulfate, dried with $K_2CO_3$, and evaporated at room temperature under reduced pressure. This gave (13R,14S)-13,14-epoxy Spinosyn A (200.2 mg; 99% yield), as colorless glass, FDMS, m/e (relative intensity) 747 ($M^+$, 100).

Example D5

(14S)-5,6,13,14-Tetrahydro-3'-deoxy Spinosyn J

To a solution of 3'-deoxy Spinosyn J (108.8 mg, 0.16 mmol) in ethyl acetate (50 ml), 5% palladium on aluminum oxide (100 mg) was added. The reaction mixture was placed under 60 psi of hydrogen and stirred at room temperature for 8 hour. After filtration of the catalyst, the solvent was evaporated at room temperature under reduced pressure. The residue was purified by chromatography on silica, eluting with 2.5% ethanol in ethyl acetate. This gave (14S)-5,6,13,14-tetrahydro-3'-deoxy Spinosyn J(50.5 mg; 45% yield) as a white solid, FDMS, m/e (relative intensity) 707 (65), 706 ($MH^+$, 100).

Example D6

(14S)-13,14-Dihydro Spinosyn A

Compound Spinosyn A (454 mg, 0.620 mmol) was dissolved in $Et_2O$ (50 ml). To this solution, vigorously stirred under nitrogen at room temperature, was added lithium tri-t-butoxyaluminohydride (475 mg, 97%, 1.81 mmol). Stirring was continued for 18 hrs. The reaction mixture was then diluted with EtOAc (70 ml) and toluene (50 ml) and carefully quenched with brine. The resulting mixture was rinsed with brine (2×), and then with 5% aq. $NaHCO_3$ (2×). The organic layer was dried over anh. $K_2CO_3$ and concentrated in vacuo. The residue was purified on a flash $SiO_2$ column (30 g; 0.05% pyridine in EtOAc) to give compound (14S)-13,14-dihydro Spinosyn A(421 mg, 92%) needles ($Et_2O$-hexane) m.p. 150–152° C.; $[\alpha]_{589}=-77.4°$ ($CHCl_3$); $^1$H-NMR ($CDCl_3$, 300 MHz) d 3.56 (1H, m), 3.00 (1H, dd: 9.0, 9.0 Hz), 2.32 (1H, m), 2.14 (6H, 2×$CH_3$, s) ppm; HR FAB MS ($MH^+$) Calc. for $C_{41}H_{68}NO_{10}$: m/z 734.4843; Found: m/z 734.4853; Anal. Calcd. for $C_{41}H_{67}NO_{10}$: C 67.09, H 9.20, N 1.91; Found: C 67.30, H 9.39, N 1.95.

Example D7

13-(N-Hydroxy)amino-13,14-ene Spinosyn A

Compound Spinosyn A(3.45 g; 4.71 mmol) was dissolved in EtOH (80 ml). 10% Aqueous NaOH (15 ml) was added, immediately followed by hydroxylamine hydrochloride (2.0 g, an excess). The reaction mixture was stirred for 45 min. EtOAc (50 ml) and toluene (100 ml) were added. The solution was extracted with brine, then with 5% aq. $NaHCO_3$ (3×). The organic layer was dried over $K_2CO_3$ and concentrated in vacuo. The residue was well dried in vacuo and dissolved in $CH_2Cl_2$ (50 ml). Triethylamine (5 ml) was added followed by methanesulfonyl chloride (2.5 ml). After stirring for 30 min. toluene (70 ml) and EtOAc (50 ml) were added. The solution was washed with 5% $NaHCO_3$ (3×). The organic phase was dried over $K_2CO_3$ and concentrated in vacuo. The residue was dissolved in dry toluene (30 ml). DBU (4.0 ml) was added and the reaction mixture was heated under reflux (under nitrogen) for 30 min. The solution was cooled, toluene (50 ml) was added and the solution was extracted with water (4×). The organic phase was dried over $K_2CO_3$ and concentrated in vacuo. The residue was separated by flash column chromatography ($SiO_2$/EtOAc) and then by preparative HPLC (C-18 coated silica, 10% water in methanol as mobile phase) to give compound 13-(N-hydroxy)amino-13,14-ene Spinosyn A (1.45 g, 40%) IR v 1722, 1618, 1120 $cm^{-1}$; CI MS m/z 763 (M+1); $^1$H-NMR ($CDCl_3$, 300 MHz) d 3.55 (1H, m), 2.60 (1H, dd: 9.0, 9.0 Hz), 2.36 (1H, bd: 5.0 Hz), 2.13 (6H, 2×$CH_3$, s) ppm; $^{13}$C-NMR ($CDCl_3$, 300 MHz) d 200.7 (conjugated C=O), 166.5 (quarternary C), 107.8 (quarternary C) ppm.

Example D8

(13R)-13-Cyano-14,15(E)-en-15-O-trimethylsilyl Spinosyn A

Compound Spinosyn A(5.68 g, 7.76 mmol) was dissolved in DMSO (40 ml). The solution was stirred at RT (water bath) under nitrogen. Trimethylsilyl cyanide (3.0 ml) was added. After 5 min. of stirring, LiCN (1.1 g, an excess) was added in a few portions. Stirring was continued for 30 min. EtOAc (50 ml) and PhH (100 ml) were added. The solution was extracted with 10% aq. $K_2CO_3$ (3×). The organic phase was dried over anh. $K_2CO_3$ and concentrated in vacuo. The residue was purified over a flash $SiO_2$ column (220 g/EtOAc). Evaporation of pure fractions furnished compound (13R)-13-cyano-14,15(E)-en-15-O-trimethylsilyl Spinosyn A; 5.33 g, 82%) $^1$H-NMR (CDCl$_3$, 300 MHz) d 5.73 (2H, m), 4.74 (2H, m), 4.22 (2H, m), 3.53 (1H, m), 3.14 (1H, bs), 2.13 (6H, 2×CH$_3$, s), 0.09 (9H, 3×CH$_3$, s); Anal. Calcd. for $C_{45}H_{74}N_2O_{10}Si$: C 65.03, H 8.97, N 3.37; Found: C 64.88, H 8.95, N 3.68.

Example D9

(13R,14R)-13-Cyano-17-deoxy-13,14-dihydro-16,17 (E)-ene Spinosyn A X509471 and (13R,14R)-13-cyano-13,14-dihydro Spinosyn A X509488

Compound (13R)-13-cyano-14,15(E)-en-15-O-trimethylsilyl Spinosyn H (557 mg, 0.67 mmol) was dissolved in $CH_2Cl_2$ (30 ml). Water (50 ml) and $KHF_2$ (5.0 g) were added, followed by tetrabutylammonium chloride (1.36 g). The reaction mixture was stirred at RT under nitrogen for 1 hr. Methylene chloride (70 ml) and water (50 ml) were added. Phases were separated and the organic phase was washed with water (2×), dried over $K_2CO_3$ and concentrated in vacuo. The residue was separated on a flash $SiO_2$ column (230–400 m, 100 g/EtOAc) to give compound a) (13R,14R)-13-cyano-17-deoxy-13,14-dihydro-16,17(E)-ene Spinosyn A; 132 mg, 33%) $^1$H-NMR (CDCl$_3$, 300 MHz) d 6.80 (1H, dd: 10.2, 4.4 Hz), 4.30 (3H, m), 3.00 (1H, dd: 9.2, 9.3 Hz), 1.69 (3H, CH$_3$, s); Anal. Calcd. for $C_{34}H_{49}NO_8$: C 68.09, H 8.23, N 2.33; Found: C 67.87, H 8.42, N 2.48 and compound b) (13R,14R)-13-cyano-13,14-dihydro Spinosyn A; 290 mg, 57%) $^1$H-NMR (CDCl$_3$, 300 MHz) d 4.26 (4H, m), 2.96 (1H, dd: 9.3, 9.1 Hz), 2.06 (6H, 2×CH$_3$, s), 0.88 (3H, d: 6.4 Hz); Anal. Calcd. for $C_{42}H_{66}N_2O_{10}$: C 66.46, H 8.76, N 3.69; Found: C 66.62, H 8.39, N 3.64.

Example D10

(13R)-13-Cyano-14,15(E)-en-2'-O-trifluoromethanesulfonyl-15-O-trimethylsilyl Spinosyn H X507995

Compound 2'-O-trifluoromethanesulfonyl Spinosyn H (663 mg, 0.78 mmol) was dissolved in dry DMSO (7 ml). The solution was stirred at RT under nitrogen and trimethylsilyl cyanide (1.0 ml, an excess) was added. Cooling of the reaction mixture to ambient temperature was necessary at this point. After 5 min. of stirring, lithium cyanide anh. powder (310 mg, 9.4 mmol) was added in one portion. Vigorous stirring was continued for another 30 min. EtOAc (50 ml) and PhH (100 ml) were added. The solution was successively extracted with brine, diluted brine and 5% aq. NaHCO$_3$ (2×). The organic layer was dried over $K_2CO_3$ and concentrated in vacuo. The residue was purified over a flash $SiO_2$ column (100 g/EtOAc) to give compound (13R)-13-cyano-14,15(E)-en-2'-O-trifluoromethanesulfonyl-15-O-trimethylsilyl Spinosyn H, 507 mg, 69% IR v 2238, 1734, 1670, 1206, 1149, 1066 cm$^{-1}$; $^1$H-NMR (CDCl$_3$, 300 MHz) d 5.76 (2H, m), 4.80 (3H, m), 4.24 (2H, m), 3.19 (1H, bs), 2.18 (6H, 2×CH$_3$, s), 0.14 (9H, 3×CH$_3$, s).

Example D11

(13R,14R)-13,14-Dihydro-13-(hydroxy)amino Spinosyn A

Compound Spinosyn A (1.0 g, 1.3 mmol) was dissolved in 10 mL methanol and hydroxylamine hydrochloride (0.23 g, 3.3 mmol) added. To this solution was added potassium hydroxide (0.15 g, 2.6 mmol) and the reaction stirred at RT. Within a few minutes the colorless solution turned cloudy supporting a white precipitate. The reaction was stirred overnight at RT. After stirring at RT for 18 hr, the white suspension was poured into a separatory funnel containing 30 mL saturated aqueous sodium bicarbonate and 30 mL ether. The layers were separated and the aqueous extracted with 2×50 mL ether. The ether extracts were combined, washed with 30 mL brine solution, dried over anhydrous magnesium sulfate and concentrated in vacuo. This gave compound (13R,14R)-13,14-dihydro-13-(hydroxy)amino Spinosyn A; 0.92 g, 88% as a white solid. Anal. Calc. for $C_{41}H_{68}N_2O_{11}$: C 64.37, H 8.96, N 3.66; Found: C 64.12, H 8.84, N 3.50; MS m/z (FD) 764 (M+); IR v 3445, 3263, 2936, 2972, 1722; $^1$H-NMR (CDCl$_3$, 300 Mz) d 5.81 (1H, d), 5.75 (1H, dd), 4.81(1H, s), 3.22 (1H, d), 3.06 (1H, t).

Example D12

(13R,14R)-13,14-Dihydro-13-(N-methyl-N-hydroxy)amino Spinosyn A

Compound Spinosyn A (1.01 g, 1.36 mmol) was dissolved 5 mL methanol and N-methylhydroxylamine hydrochloride (195 mg, 2.34 mmol) added. Potassium hydroxide (148 mg, 2.63 mmol) was added and then reaction let stir at RT. The reaction became cloudy after 1 min. Let the reaction stir at RT for 18 hrs. and poured contents into a separatory funnel containing 30 mL saturated aqueous sodium bicarbonate and 30 mL methylene chloride. The layers were separated and the aqueous extracted with 2×25 mL methylene chloride. The methylene chloride extracts were combined, washed with 30 mL brine solution, dried over anhydrous magnesium sulfate and concentrated in vacuo. This gave compound (13R,14R)-13,14-dihydro-13-(N-methyl-N-hydroxy)amino Spinosyn A; 0.89 g, 83% as a white solid. Anal. Calc. for $C_{42}H_{70}N_2O_{11}$: C 64.76, H 9.06, N 3.60; Found: C 64.88, H 9.03, N 3.78; MS m/z (FD) 779 (M+1).

Example D13

(13R,14R)-13,14-Dihydro-13-(hydroxy)amino Spinosyn A 17-Psa

The procedure described in Example D11 was used with Spinosyn A 17-Psa (207 mg, 0.35 mmol), hydroxylamine hydrochloride (96.0 mg, 1.38 mmol), potassium hydroxide (74.6 mg, 1.32 mmol), and 5 mL methanol. This gave compound (13R,14R)-13,14-dihydro-13-(hydroxy)amino Spinosyn A 17-Psa, 115 mg, 53%. Anal. Calc. for $C_{33}H_{53}NO_{10}$ C 63.54, H 8.56, N 2.25; Found: C 62.66, H 9.76, N 2.11. MS m/z (CI) 624 (M+1). $^1$H-NMR (CDCl$_3$, 300 Mz) d 5.90 (1H, d), 5.77 (1H, dd), 4.85 (1H, s), 4.83 (1H, m), 4.34 (1H, m), 3.80 (1H, m), 3.30 (1H, d).

Example D14

(13R,14R)-13,14-Dihydro-13-(N-benzylidenyl-N-oxo)amino Spinosyn A

Compound (13R,14R)-13,14-Dihydro-13-(hydroxy) amino Spinosyn A (139 mg, 0.181 mmol) was dissolved in 5 mL toluene and benzaldehyde (44 mg, 0.41 mmol) added. The reaction was heated to reflux for 1 hr, cooled to RT, and concentrated in vacuo. The residue was purified by medium pressure $SiO_2$ column (CH$_2$Cl$_2$:CH$_3$OH, 97:03 (V/V)) to give compound (13R,14R)-13,14-dihydro-13-(N-benzylidenyl-N-oxo)amino Spinosyn A (84 mg, 54%. Anal.

Calc. for $C_{48}H_{72}N_2O_{11}$: C 67.58, H 8.51, N 3.28; Found: C 67.31, H 8.43, N 3.11; $^1$H-NMR (CDCl$_3$, 300 Mz) d 8.26 (2H, m), 7.44 (3H, t), 5.90 (1H, d), 5.76 (1H, dt), 4.84(1H, s).

Example D15

(13R,14R)-13,14-Dihydro-13-(N-methyl-N-hydroxy)amino Spinosyn D

Compound Spinosyn D (0.53 g, 0.71 mmol) was suspended in 10 mL methanol and N-methylhydroxylamine (103 mg, 1.24 mmol) was added. To this stirring suspension was added potassium hydroxide (103 mg, 1.83 mmol) and the reaction stirred at RT. After stirring for 1 min. the reaction grew visibly more cloudy. The reaction was stirred at RT for 48 hr. Poured reaction into a separatory funnel containing 25 mL methylene chloride and 30 mL saturated aqueous sodium bicarbonate. Separated layers and extracted aqueous with 2×25 mL methylene chloride. Combined methylene chloride extracts, washed with 30 mL brine solution, dried over magnesium sulfate, and concentrated in vacuo. The residue was purified by HPLC (C18, CH$_3$OH:H$_2$O, 95:5 (V/V)). This gave compound (13R,14R)-13,14-dihydro-13-(N-methyl-N-hydroxy)amino Spinosyn D; 180 mg, 32%. Note: compound (13R,14R)-13,14-dihydro-13-(N-methyl-N-hydroxy)amino Spinosyn D partially decomposes back to compound Spinosyn D during chromatography purification. Anal. Calc. for C43H72N2O11: C 65.12, H 9.15, N 3.53; Found: C 64.96, H 8.97, N 3.32. $^1$H-NMR (CDCl$_3$, 300 mZ) d 5.43 (1H, bs), 4.86 (1H, s), 4.80 (1H, m), 4.42 (1H, m), 4.28 (1H, m), 3.68 (1H, m).

Example D16

(14S)-13,14-Dihydro Spinosyn A 17-Psa

Compound (14S)-13,14-dihydro Spinosyn A (380 mg, 0.518 mmol) was suspended in 10 mL water and 2 mL 1N H$_2$SO$_4$ added. Upon the addition of the acid no change in the reaction was observed. The reaction was heated to 95–100° C. during which time the solids dissolved giving a colorless solution. After heating for 1 hr a white precipitate formed and the reaction cooled to RT. The solid was collected by vacuum filtration, washed with 3×10 mL cold water and air dried. This gave compound (14S)-13,14-dihydro Spinosyn A 17-Psa, 284 mg, 93%. Anal. Calc. for $C_{33}H_{52}O_9$: C 66.86, H 8.84; Found: C 66.29, H 9.19; $^1$H-NMR (CDCl$_3$, 300 Mz) d 5.90 (1H, d), 5.79 (1H, dt), 5.85 (1H, s), 4.76 (1H, m), 4.32 (1H, q), 3.82 (1H, m).

Example D17

(14R)-13,14-Dihydro Spinosyn A 17-Psa

Compound (14R)-13,14-dihydro Spinosyn A (397 mg, 0.541 mmol) was suspended in 10 mL water and 2 mL 1N H$_2$SO$_4$ added. Upon addition of acid, the solids dissolved giving a colorless solution. This solution was heated to 95–100° C. After heating for 20 min. a white precipitate began to form which re-dissolved after 1 hr. Cooled reaction to RT upon which a glassy solid formed. Extracted glassy solid with 2×25 mL ether, washed with 20 mL brine, dried over magnesium sulfate and concentrated in vacuo. This gave compound (14R)-13,14-dihydro Spinosyn A 17-Psa; 226 mg, 71%. Anal. Calc. for $C_{33}H_{52}O_9$: C 66.86, H 8.84; Found C66.84, H 8.90; $^1$H-NMR (CDCl$_3$, 300 Mz) d 5.88 (1H, d), 5.67 (1H, dt), 4.85 (1H, s), 4.83 (1H, m), 4.34 (1H, q), 4.01 (1H, m).

Example D18

(13R,14S)-13,14-Dihydro-13-methyl Spinosyn A

Cuprous iodide (1.34 g, 7.0 mmol) was suspended in 20 mL anhydrous ether under a nitrogen atmosphere. The reaction was cooled to 0° C. in an ice bath and methyl lithium 1.4M solution in ether (9.0 mL, 12.6 mmol) was added slowly over 3 min. Gave a pale yellow solution which was stirred at 0° C. for 20 min. Compound Spinosyn A(2.04 g, 2.80 mmol) in 5 mL ether was added slowly to the reaction over 10 min. Gave a bright yellow solution which gradually lost its color and gave a precipitate. After 30 min. poured reaction into separatory funnel containing 25 mL saturated aqueous sodium bicarbonate and 25 mL ether. Separated layers and extracted aqueous with 2×50 mL ether. Filtered ether to removed suspended solids and washed with 25 mL brine, dried over magnesium sulfate and concentrated in vacuo. The residue was purified by HPLC (C18, CH$_3$OH:H$_2$O, 95:5, V/V) to give compound (13R,14S)-13,14-dihydro-13-methyl Spinosyn A, 0.56 g, 27%). Anal. Calc. for $C_{42}H_{69}NO_{10}$: C 67.44, H 9.30, N 1.87; Found: 67.47, H 9.20, N 1.93. MS m/z (CI) 748 (M+1); $^1$H-NMR (CDCl$_3$, 300 Mz) d 5.85 (1H, d), 5.80 (1H, dt), 4.85 (1H, s), 4.78 (1H, m), 4.42(1H, d), 4.33 (1H, q), 3.66 (1H, m).

Example D19

(13R,14S)-13,14-Dihydro-13-n-butyl Spinosyn A

Cuprous iodide (1.0 g, 5.2 mmol) was suspended in 20 mL anhydrous ether under nitrogen atmosphere. The suspension was cooled to 0° C. and n-butyl lithium 1.6M solution in hexane (7.0 mL, 11 mmol) was added slowly over 5 min. This gave a dark brown solution which was stirred at 0° C. for 30 min. Compound Spinosyn A (2.13 g, 2.9 mmol) in 5 mL ether was slowly added to this solution over 5 min. After stirring reaction for 15 min., poured into separatory funnel containing 50 mL 50% aqueous conc. ammonium hydroxide and extracted with 3×30 mL ether. Combined ether extracts, washed with 50 mL conc. aqueous ammonium hydroxide and 30 mL saturated aqueous sodium bicarbonate. Dried ether solution over magnesium sulfate and concentrated in vacuo. The residue was purified by HPLC (C18, CH$_3$OH:H$_2$O, 95:5, V/V). This gave compound (13R,14S)-13,14-dihydro-13-n-butyl Spinosyn A, 0.53 g, 23%). Anal. Calc. for $C_{45}H_{75}NO_{10}$: C 68.41, H 9.57, N 1.77; Found C 68.07, H 9.51, N 1.82; MS m/z (DCI) 790 (M+1); $^1$H-NMR (CDCl$_3$, 300 Mz) d 5.85 (1H, d), 5.80(1H, dt), 4.85 (1H, s), 4.79 (1H, m), 4.43 (1H, d), 4.29(1H, q), 3.67 (1H, m).

Example D20

(14S, 15S)-13,14-dihydro-15-hydroxy Spinosyn

Spinosyn A (600 mg, 0.820 mmol) was dissolved in dry Et$_2$O (100 ml). Lithium tri-t-butoxyaluminum hydride (296 mg, 97%, 1.13 mmol) was added. After stirring for 5 min. under N$_2$, the reaction mixture was cooled to −78° C. and LiAlH$_4$ (29 mg, 0.763 mmol) was added in one portion. Stirring at −78° C./N$_2$ was continued for 25 min. The cooling bath was then changed to 0° C. and stirring was continued for 2 hrs. Brine (10 ml) was then slowly introduced and Et$_2$O (70 ml) was added. After extraction phases were separated. The organic layer was washed with brine (3×), dried over K$_2$CO$_3$, filtered and concentrated in vacuo. The residue was purified over a flash SiO$_2$ column (20 g/EtOAc) and then subjected to Chromatotron separations (1.0 mm, 10% EtOH/EtOAc). These procedures furnished compound (14S, 15S)-13,14-dihydro-15-hydroxy Spinosyn A, 78 mg,13%: $^1$H-NMR (CDCl$_3$, 300 MHz) d 4.80 (1H, d: 1.2 Hz), 4.37 (2H, m), 4.25 (2H, m), 3.62 (1H, m), 3.51 (3H, CH$_3$, s), 3.45 (6H, 2×CH$_3$, bs), and 2.19 (6H, 2×CH$_3$, s) ppm.

Example D21

(14S,15S,17S,21S)-1,21-Deoxy-13,14-dihydro-1,21-seco-1,15,21-tri-hydroxy Spinosyn A and [(15S)-hydroxy Spinosyn A Spinosyn A (446 mg, 0.610 mmol) was dissolved in dry Et$_2$O (60 ml). Lithium tri-t-butoxyaluminum hydride (148 mg, 0.583 mmol) was added with stirring, at room temperature under N$_2$. After 10 min., LiAlH$_4$ (19 mg, 0.50 mmol) was added and stirring at RT/N$_2$ was continued for 50 min. The mixture was cooled to 0° C. and brine was added dropwise to quench remaining hydrides. Et$_2$O (70 ml) was added, after extraction layers were separated, the organic layer was washed with brine (3×), dried over K$_2$CO$_3$, filtered and concentrated in vacuo. The residue was separated on a flash SiO$_2$ column (25 g/5% EtOH in EtOAc) to give: compound a) [(14S,15S,17S,21S)-1,21-deoxy-13,14-dihydro-1,21-seco-1,15,21-tri-hydroxy Spinosyn A, 71 mg, 15%: $^1$H-NMR (CDCl$_3$, 300 MHz) d 4.86 (1H, d: 1.2 Hz), 4.48 (1H, bd: 7.5 Hz), 4.30 (2H, m), 3.84 (1H, m), 3.45 (3H, CH$_3$, s), 3.46 (3H, CH$_3$, s), 3.52 (3H, CH$_3$, s) and 2.21 (6H, 2×CH$_3$, s) ppm, and (b) a mixture of products (313 mg) which was further repeatedly separated on a Chromatotron rotating plate (1.0 mm, 15% EtOH/EtOAc). These separations furnished compound b) [(15S)-hydroxy Spinosyn A, 79 mg, 17%: $^{13}$C-NMR (CDCl$_3$, 75 MHz, downfield region) d 172.22, 144.73, 130.94, 129.73, 128.70, 103.37, 95.47, 84.49, 82.25, 81.01, 79.03 and 77.70 ppm.

Example D22

(14R)-13,14-Dihydro-15-hydroxy Spinosyn A

Compound Spinosyn A (2.17 g, 2.96 mmol) was dissolved in ethanol (75 mL) and sodium borohydride (1.1 g, 29 mmol) was added cautiously over 5 min. The reaction was stirred for 3 hr. and quenched cautiously with 1N HCL (15 mL). After work-up the crude material (1.68 g) was purified by chromatography on silica gel (methylene chloride/methanol, 95:5) to afford (14R)-13,14-dihydro Spinosyn A (635 mg, 29.2%) and (14R)13,14-dihydro-15 -hydroxy Spinosyn A (317 mg, 14.6%) as white solids. Compound (14R)13,14-dihydro-15-hydroxy Spinosyn A: $^{13}$C NMR d 174.75, 131.52, 128.50, 104.16, 95.34, 83.28, 82.26, 80.99, 77.74, 76.15, 76.15, 73.66, 70.29, 67.80, 64.82, 60.83, 58.94, 57.66, 44.90, 44.54, 44.54, 44.26, 42.93, 40.65, 40.38, 39.89, 37.74, 36.84, 34.91, 34.41, 33.84, 31.65, 31.17, 28.07, 19.06, 19.06, 18.36, 17.75, 9.51, 8.77; partial $^1$H NMR d 7.31 (s, 1H), 5.75 (dd, 1H), 5.67 (dt, 1H), 4.81 (s, 1H), 4.80 (m, 1H), 4.40–4.25 (m 2H), 3.95 (m, 1H).

Example D23

(13R,14S,15R/S)-15-Hydroxy-13,14-epoxy Spinosyn A

Compound (13R,14S)-13,14-epoxy Spinosyn A (0.53 g, 0.71 mmol) was dissolved in ethanol (10 mL) and sodium borohydride (36 mg, 0.96 mmol) was added and the reaction stirred for 3 hr. Additional sodium borohydride (100 mg, 2.64 mmol) was added and the reaction stirred for 72 hr. The reaction was quenched with acetone (5 mL), followed by 1N HCl (1 mL) and worked-up to give a residue which was purified by reverse-phase HPLC (methanol/0.1% aq ammonium hydroxide, 90:10). This gave compounds (13R,14S, 15S)-15-hydroxy-13,14-epoxy Spinosyn A (78.9 mg, 14.8%): partial $^1$H NMR d 5.8 (d, 1H), 5.60 (dt, 1H), 4.80 (s, 1H), 4.43 (d, 1H), 4.30 (q, 1H), 4.09 (d, 1H),4.01 (m, 1H), 3.78 (m, 1H); and (13R,14S,15R)-15-hydroxy-13,14-epoxy Spinosyn A (70 mg, 13%): MS m/z 750.6.

Example D24

(14S)-13,14-Dihydro Spinosyn D

Compound Spinosyn D (1.00 g, 1.34 mmol) was dissolved in anhydrous tetrahydrofuran (25 mL) under nitrogen and lithium tri-t-butoxide aluminium hydride (1.01 g, 3.97 mmol) was added and the reaction stirred for 24 hr. The reaction was quenched with ethyl acetate (40 mL) and brine (10 mL) and the phases separated. The aqueous phase was extracted with ethyl acetate (25 mL) and the layers separated after filtration through filter paper. The ethyl acetate extracts were combined and washed with brine (35 mL), dried over anhydrous potassium carbonate and concentrated in vacuo. The residue (360 mg) was purified by reverse-phase HPLC (methanol/0.1% aq ammonium hydroxide, 95:5) to give compound (14S)-13,14-dihydro spinosyn D (189 mg, 18.9%) as a white solid: MS m/z 748.7. Anal. Calcd for C$_{42}$H$_{69}$NO$_{10}$: C, 67.44; H, 9.30; N, 1.87. Found: C, 67.21; H, 9.20; N, 1.69.

Example D25

1,21-Deoxy-1,21-seco-1,15,21-trihydroxy Spinosyn A, (15R/S)-15-hydroxy Spinosyn A, (14R,16,17Z)-17-deoxy-16,17-dehydro-13,14-dihydro Spinosyn A 17-Psa, and (14R)-13,14-dihydro Spinosyn A Compound Spinosyn A (5.12 g, 7.00 mmol) was dissolved in anhydrous ether (75 mL) and cooled to 0° C. A solution of lithium aluminium hydride (0.5M in ethylene glycol dimethyl ether, 15.0 mL, 7.5 mmol) was added and the reaction was immediately quenched by adding water (0.30 mL), followed by 15% aqueous sodium hydroxide (0.30 mL), and water (1.0 mL). The suspended solids were filtered off and the filtrate rotary evaporated in vacuo to afford a white solid (4.62 g). The crude product was purified by reverse-phase HPLC (methanol/0.1% aq ammonium hydroxide, 90:10) to afford compounds 1,21-deoxy-1,21-seco-1,15,21-trihydroxy Spinosyn A (792 mg, 15.4%): partial $^1$H NMR δ 5.88–5.72 (m, 2H), 4.82 (s, 1H), 4.40 (d, 1H), 4.35–4.23 (m, 2H), 4.13 (m, 1H), 3.85–3.67 (m, 3H); MS m/z 738.7 (M+1), and (15R/S)-15-hydroxy Spinosyn A (1.13 g, 22.1%): (first isomer) partial $^1$H NMR d 5.89 (dd, 1H), 5.78–5.72 (m, 2H), 4.81 (s, 1H), 4.44–4.31 (m, 2H), 4.26 (q, 1H), 4.04 (t, 1H), 3.83 (m, 1H); $^{13}$C NMR δ 173.53, 145.22, 132.34, 130.14, 128.29, 103.01, 95.46, 82.26, 81.03, 77.72, 76.24, 73.76, 67.89, 64.78, 60.89, 58.97, 57.66, 47.65, 46.91, 46.90, 41.39, 40.64, 39.62, 37.39, 36.39, 31.20, 30.73, 28.37, 27.21, 20.68, 19.00, 18.33, 17.75, 10.15, 9.80; MS m/z 734.7 (m+1). Anal. Calcd for C$_{41}$H$_{67}$NO$_{10}$: C, 67.09; H, 9.20; N, 1.91. Found: C, 66.96; H, 9.14; N, 1.94, (second isomer) partial $^1$H NMR δ 5.89 (d, 1H), 5.85–5.74 (m, 2H), 4.84 (s, 1H), 4.46–4.35 (m, 2H), 4.33–4.25 (m, 2H), 3.67 (m, 1H); $^{13}$C NMR δ 172.24, 144.75, 130.96, 129.77, 128.69, 103.80, 95.40, 84.50, 82.27, 81.03, 79.35, 76.71, 76.20, 73.80, 67.83, 64.65, 60.87, 58.95, 57.66, 48.00, 47.78, 46.54, 44.71, 41.27, 40.63, 37.44, 36.94, 36.36, 32.02, 31.36, 29.65, 27.10, 19.54, 19.05, 18.34, 17.73, 10.15, 7.40; MS m/z 734.7 (m+1). Anal.

Calcd for $C_{41}H_{67}NO_{10}$: C, 67.09; H, 9.20; N, 1.91. Found: C, 66.65; H, 9.16; N, 1.85, and (14R,16,17Z)-17-deoxy-16,17-dehydro-13,14-dihydro Spinosyn A 17-Psa (54 mg, 1.0%): partial $^1$H NMR δ 6.78 (dd, 1H), 5.86 (d, 1H), 5.66 (dt, 1H), 4.83 (s, 1H), 4.55 (m, 1H), 4.30 (q, 1H), 3.91 (m, 1H); MS (EI) m/z 574, and (14R)-13,14-dihydrospinosyn A (901, 17.6%).

Example D26

(15R,14S)-15-Deoxy-15-hydroxy-5,6,13,14-tetrahydro Spinosyn A and compound (1R/S,14S, 15R,21S)-15-deoxy-1,15-oxa-1,21-seco-5,6,13,14-tetrahydro Spinosyn A 1-hemiacetal (14S)-5,6,13,14-Tetrahydro Spinosyn A (2.60 g, 3.53 mmol) was dissolved in dry $Et_2O$ (90 mL). The solution was cooled to 0° C. under nitrogen and $LiAlH_4$ (95% powder, 268 mg, 6.8 mmol) was added. The mixture was stirred at 0° C. for 10 min and then carefully quenched with saturated $NH_4Cl$ solution in 10% aqueous $NH_4OH$ (10 mL). The usual work-up and chromatography on silica gel (ethyl acetate, then 15% EtOH in EtOAc) afforded a) (15R,14S)-15-deoxy-15-hydroxy-5,6,13,14-tetrahydro Spinosyn A (1.261 g, 48%) as a white solid: $^1$H NMR δ 4.71 (d, J=1.2, 1 H), 4.47 (d, J=7.5, 1 H), 4.17 (m, 1 H), 4.08 (m, 2 H), 3.43 (s, 3 H), 3.37 (s, 6 H), 0.72 (d, J=6.8, 3 H). Anal. Calcd for $C_{41}H_{71}NO_{10}$: C, 66.73; H, 9.70; N, 1.90. Found: C, 66.44; H, 9.71; N, 1.82; and b) (1R/S,14S,15R,21S)-15-deoxy-1,15-oxa-1,21-seco-5,6,13,14-tetrahydro Spinosyn A 1-hemiacetal (0.561 g, 21%) as a white solid: ESI MS m/z 740 (M+1).

Example D27

(14S)-15-Deoxy-15,16(E)-ene-5,6,13,14-tetrahydro Spinosyn A,(14S, 15R/S)-15-deoxy-15-fluoro-5,6, 13,14-tetrahydro Spinosyn A, and (14S)-15-deoxy-15,16(E)-ene-5,6,13,14-tetrahydro Spinosyn A (15R,14S)-15-Deoxy-15-hydroxy-5,6,13,14-tetrahydro Spinosyn A (0.484 g, 0.65 mmol) was dissolved in dry methylene chloride (4 mL). The solution was cooled to 0° C. under nitrogen and morpholinosulfur trifluoride (0.50 mL, 4.1 mmol) was slowly added. The cooling bath was removed and stirring was continued at room temperature for 4 h. The usual work-up and chromatography on silica gel (ethyl acetate) afforded a mixture of products which was further separated by HPLC (90:10, MeOH/$H_2O$). This gave: a) (14S)-15-deoxy-15,16(E)-ene-5,6,13,14-tetrahydro Spinosyn A (48 mg, 10%) as a white solid: $^1$H NMR δ 5.28 (d, J=9.9, 1 H), 4.83 (s, 1 H), 4.72 (m, 1 H), 4.21 (m, 4H), 3.52 (s, 3 H), 3.47 (s, 3 H), 3.46 (s, 3 H), 1.41 (s, 3 H); b) (14S,15R/S)-15-deoxy-15-fluoro-5,6,13,14-tetrahydro Spinosyn A (60 mg, 12%) as a white solid: $^1$H NMR δ 4.96 (d, J=46.8, 0.4 H), 4.19 (dd, $J_1$=66, $J_2$=9, 0.6 H), 4.83 (d, J=1.2, 0.6 H), 4.81 (d, J=1.2, 0.4 H), 3.53 (s, 3 H), 3.46 (s, 6 H); and c) (14S)-15-deoxy-15,16(E)-ene-5,6,13,14-tetrahydro Spinosyn A (152 mg, 32%) as a white solid: $^1$H NMR δ 5.24 (d, J=10.8, 1 H), 4.80 (d, J=1.2, 1 H), 4.79 (m, 1 H), 4.34 (d, J=7.4, 1 H), 4.20 (m, 3 H), 3.51 (s, 3 H), 3.45 (s, 6 H), 1.66 (s, 3 H).

Example D28

13,14-a-Methano-Spinosyn A

Sodium hydride (60% dispersion in oil, 52 mg, 1.3 mmol) was weighed into a dry flask and placed under a dry nitrogen atmosphere. The dispersion was stirred briefly with pentane (2 mL) and the pentane removed by pipet. The residual pentane was evaporated under a stream of nitrogen. The dried NaH was suspended in DMSO (4 mL), the resulting slurry cooled to 15° C. and trimethylsulfoxonium iodide (286 mg, 1.3 mmol) was added in a single portion (caution-vigorous gas evolution initially). The reaction mixture was stirred at that temperature for 40 min, at which time the mixture was a clear solution. A solution of Spinosyn A (827 mg, 1.13 mmol) in dry toluene (1 mL) and DMSO (1 mL) was added dropwise over 5 min. The resulting solution was stirred at room temperature for 2 h. The reaction mixture was cooled to 0° C., diluted with $Et_2O$ and quenched with saturated aqueous sodium bicarbonate and water. The mixture was partitioned between $Et_2O$ and saturated aqueous sodium bicarbonate. The aqueous layer was extracted with $Et_2O$ and the combined ether phases washed with water (three times), dilute aqueous sodium bicarbonate and brine. The mixture was dried over anhydrous potassium carbonate and the solvent removed under a stream of dry nitrogen to yield a white solid (812 mg). This solid was chromatographed on silica gel (81 g) with EtOAc followed by 2% MeOH in EtOAc to yield a white solid (785 mg, 93%) $^1$H NMR δ loss of 6.85 (br s, 1 H); MS m/z 746.5 (calc. for M+H, 746.5).

Example D29

13,14-Epoxy-15-Hydroxy Spinosyn A

Compound 13,14-epoxy Spinosyn A (250 mg, 0.3 mmol) was dissolved in $Et_2O$ (20 mL). To this solution, vigorously stirred under nitrogen at room temperature, was added lithium tri-t-butoxyaluminohydride (153 mg, 0.6 mmol). Stirring was continued for 18 h. The reaction mixture was quenched with brine and extracted with ether (3×20 mL). Combined ether extracts were dried over anh. $Na_2SO_4$ and concentrated in vacuo. The residue was purified on a prep. TLC (EtOAc) to give compound 13,14-epoxy-15-hydroxy Spinosyn A (140 mg, 56%) as a white solid. m.p. 90–91° C.; MS m/z 750; $^1$H-NMR (CDCl$_3$, 300 MHz) 5.81 (1H, d), 5.62 (1H, d), 4.80 (1H, s), 4.42 (1H, d), 4.30 (1H, m); 13C-NMR (CDCl$_3$, 300 MHz) 172.2 (lactone C=O), 85.2 (C-OH)

Example D30

13,14-Dihydro-2-Phenylseleno Spinosyn A

To a –30° C. solution of diisopropylamine (1.01 mL, 7.7 mmol) in THF (20 mL) under nitrogen was added n-butyl lithium (4.8 mL, 7.7 mmol) and HMPA (1.0 mL) cooled to –40° C. A solution of Spinosyn A (1.0 g, 1.4 mmol) in THF (10 mL) was added over 10 min period to this reaction mixture and stirred for 1 h. The reaction mixture was quenched with $NH_4Cl$ solution (10 mL) and extracted with ether (3×40 mL). Combined ether extracts were dried over anh. $Na_2SO_4$, filtered and concentrated in vacuo. The residue was purified on a prep HPLC on a C18 column, eluting with 10% water (0.1% NH4OH) in methanol to give compound 13,14-dihydro-2-phenylseleno Spinosyn A (0.24 g, 19%) as an off-white solid. $^1$H-NMR (CDCl$_3$, 300 MHz) 7.55 (2H, m), 7.25 (3H, m), 6.01 (1H, m), 5.85 (1H, m), 3.97 (1H, d)

Example D31

3,14-Dehydro Spinosyn A

Compound (2Z)-2,3-dehydro Spinosyn A (20 mg, 0.03 mmol) was dissolved in $Et_2O$ (5 mL). To this solution, vigorously stirred under nitrogen at room temperature, was added lithium tri-t-butoxyaluminohydride (7.6 mg, 0.03 mmol). After stirring for 18 h, additional amount of lithium tri-t-butoxyaluminohydride (7.6 mg, 0.03 mmol) was added. Stirring was continued for 1 h. The reaction mixture was diluted with brine and extracted with ether (3×15 mL). Combined ether extracts were dried over anh. $Na_2SO_4$ and concentrated in vacuo. The residue was purified on a prep HPLC on a C18 column, eluting with 10% water (0.1% $NH_4OH$) in methanol to give compound 3,14-dehydro Spinosyn A (11 mg, 50%) as an off-white flaky solid. 1H NMR ($CDCl_3$, 300 MHz) 5.95 (2H, m), 4.91(1H, s), 4.70 (1H, s); 13C NMR ($CDCl_3$, 300 MHz) 206.1 (C=O), 168.9 (lactone C=O), 144.7 (quaternary C=), 138.0 (quaternary C=); MS m/z 732.

Part E Modification of the Pseudoaglycone at the C-17 Position of the Tricyclic Portion of the Compound Formula 1

Example E1

17-Deoxy-17-amino Spinosyn A 17-Psa

To a solution of 17-keto Spinosyn A 17-Psa (318.7 mg, 0.54 mmol) in methanol (6 ml), ammonium acetate (417.1 mg, 5.4 mmol) was added followed by sodium cyanoborohydride (45 mg, 0.76 mmol). The reaction mixture stirred at room temperature for 5 days. The solvent was evaporated at room temperature under reduced pressure. The residue was dissolved in 1N HCl and washed with ether. The aqueous was then basified with 5N NaOH, and saturated with sodium chloride. The aqueous was then extracted with fresh ether. This ether was washed with brine, dried with $K_2CO_3$ and evaporated at room temperature under reduced pressure. This gave 17-deoxy-17-amino Spinosyn A 17-Psa (68.2 mg; 21% yield) as a colorless glass, in a 7 to 1 mixture of isomers, FDMS, m/e (relative intensity) 744 (5), 591 (20), 590 ($MH^+$, 40), 112 (100).

Example E2

(16,17Z)-17-Deoxy 16,17-dehydro Spinosyn A 17-Psa

To a suspension of N-Methyl Spinosyn A iodide (203.7 mg, 0.23 mmol) in THF (9 ml), sodium hydride (50% dispersion in mineral oil, 42.9 mg, 0.89 mmol) was added. The reaction mixture was heated to reflux for 1 hour, and then cooled to room temperature. The mixture was then poured into water, and extracted with ether. The ether was washed with brine, dried with $K_2CO_3$, and evaporated at room temperature under reduced pressure. The crude product was purified by chromatography on silica, eluting with hexane and then 40% ethyl acetate in hexane in a one step gradient. This gave (16,17Z)-17-deoxy 16,17-dehydro Spinosyn A 17-Psa (89.5 mg; 67% yield) was a white glass, FDMS, m/e (relative intensity) 1144 (20), 573 ($M^+$, 60), 101 (100).

Example E3

(16,17E)-17-Deoxy 16,17-dehydro Spinosyn A 17-Psa,(17,18E)-17-deoxy 17,18-dehydro Spinosyn 17-Psa and (16,17Z)-17-deoxy 16,17-dehydro Spinosyn A 17-Psa The reaction was run as described in Example E2 starting with Spinosyn A (5.1 gm, 6.97 mmol). The products were seperated by preparative HPLC on a $C_{18}$ column, eluting with acetonitrile:methanol:0.1% $NH_4OAc$ (20:40:40). This gave (16,17E)-17-deoxy 16,17-dehydro Spinosyn A 17-Psa (119 mg; 3% yield), FDMS, m/e (relative intensity) 572 ($M^+$, 100), (17,18E)-17-deoxy 17,18-dehydro Spinosyn 17-Psa (634 mg; 16% yield), FDMS, m/e (relative intensity) 572 ($M^+$, 100), and (16,17Z)-17-deoxy 16,17-dehydro Spinosyn A 17-Psa (689 mg; 17% yield) all as white solids.

Example E4

(5R,6R)-5-(2-Hydroxyethoxy)-6-bromo Spinosyn A 17-Psa

To a suspension of Spinosyn A (154.1 mg, 0.21 mmol) in ethylene glycol (5 ml), N-bromosuccinimide (79.8 mg, 0.45 mmol) was added. The reaction mixture was heated to 80° C. for 1.5 hour and then cooled to room temperature. The mixture was diluted with dichloromethane and washed with water. The dichloromethane was then washed with brine, dried with $K_2CO_3$, and evaporated at room temperature. The products were seperated by chromatography on silica, eluting with 70% ethyl acetate in hexane and then 5% methanol in dichloromethane. This gave compound a) Spinosyn A 17-Psa (41.7 mg; 34% yield) as a colorless glass. (5R,6R)-5-(2-hydroxyethoxy)-6-bromo Spinosyn A 17-Psa was further purified by chromatography on silica, eluting with 70% ethyl acetate in hexane. This gave pure compound b) (5R, 6R)-5-(2-hydroxyethoxy)-6-bromo Spinosyn A 17-Psa (50.2 mg; 33% yield) as a colorless glass, FDMS, m/e (relative intensity) 734 (65), 732 ($MH^+$, 60), 189 (100).

Example E5

(5S,6R)-5,6-Epoxy-17-O-trimethylsilyl Spinosyn A 17-Psa

To a solution of (5S,6R)-5,6-epoxy Spinosyn A 17-Psa (503.7 mg, 0.83 mmol) in ether (20 ml), chlorotrimethyl silane (211 ml, 1.66 mmol) and diisopropylethylamine (289 ml, 1.66 mmol) were added. The reaction mixture was stirred at room temperature for 23 hours, then additional chlorotrimethyl silane (105 ml, 0.83 mmol) and diisopropylethylamine (144 ml, 0.83 mmol) were added. The reaction mixture continued to stir at room temperature another 18 hours. The ether was then decanted and the residue precipitate was triturated with fresh ether. The ether was combined, washed with aqueous saturated $NaHCO_3$, dried with $K_2CO_3$ and evaporated at room temperature under reduced pressure. The crude product was purified by chromatography on silica, eluting with 50% ethyl acetate in hexane. This gave (5S,6R)-5,6-epoxy-17-O-trimethylsilyl Spinosyn A 17-Psa (521.1 mg; 92% yield) as a colorless glass, FDMS, m/e (relative intensity) 679 (75), 678 ($M^+$, 100), 190 (30), 100 (35).

Example E6

(5S,6R)-5,6-Epoxy Spinosyn A 17-Psa

To a solution of Spinosyn A 17-Psa (1.0 gm, 1.71 mmol) in dichloromethane (45 ml), m-chloroperoxybenzoic acid (591.7 mg, 3.34 mmol) was added. The reaction mixture stirred at room temperature for 23 hour. The mixture was then diluted with dichloromethane and washed with aqueous saturated $NaHCO_3$, dried with $K_2CO_3$, and evaporated at room temperature under reduced pressure. The product was purified by chromatography on silica, eluting with 15% acetone in dichloromethane. This gave (5S,6R)-5,6-epoxy Spinosyn A 17-Psa (1.04 gm; ~100% yield) as a colorless glass, FDMS, m/e (relative intensity) 607 (M$^+$, 70), 190 (100), 101 (99).

Example E7

17-Keto Spinosyn A 17-Psa

To a −78° C. suspension of N-chlorosuccinimide (108.6 mg, 0.81 mmol) in dichloromethane (2.6 ml), diisoproplysulfide (125 ml, 0.86 mmol) was added. The reaction mixture was stirred at −78° C. for 30 minutes then Spinosyn A 17-Psa (150.1 mg, 0.25 mmol) in dichloromethane (1 ml) was added slowly. The reaction mixture continued to stir at −78° C. for 3 hours then triethylamine (109 ml, 0.78 mmol) was added and the mixture was warmed to room temperature while the color became red. The mixture was then diluted with dichloromethane. The dichloromethane was washed with 0.1N HCl, brine, dried with $MgSO_4$, and evaporated at room temperature under reduced pressure. The product was purified by chromatography on silica, eluting with 40% ethyl acetate in hexane. This gave 17-keto Spinosyn A 17-Psa (84.7 mg; 58% yield) as a colorless glass, FDMS, m/e (relative intensity) 588 (M$^+$, 100).

Example E8

17-Deoxy-16,17-dehydro Spinosyn A Ag

The reaction was run as described in Example 3 starting with Spinosyn J (15.02 gm, 21 mmol). After treatment with $K_2CO_3$ in methanol, the reaction mixture was filtered, then evaporated at room temperature under reduced pressure. The residue was kept at room temperature without further purification for 24 hours, then triturated with dichloromethane. The dichloromethane was then evaporated at room temperature under reduced pressure. The crude product was purified by chromatography on silica, eluting with 5% methanol in dichloromethane. This gave crude 17-deoxy-16,17-dehydro Spinosyn A Ag, as a yellow semi-solid and Spinosyn A 9-Psa (1.02 gm; 9% yield) as a colorless glass. The crude 17-deoxy-16,17-dehydro Spinosyn A Ag was further purified by preparative HPLC on a $C_{18}$ column, eluting with acetonitrile:methanol:0.5% $NH_4OAc$ (35:35:30) giving pure 17-deoxy-16,17-dehydro Spinosyn A Ag (1.81 gm; 22% yield) as a white glass, FDMS, m/e (relative intensity) 460 (10), 385 (M$^+$, 55), 384 (100).

Example E9

17-Deoxy-17-cyano-13,14-dihydro-13-cyano Spinosyn A 17-Psa

Compound Spinosyn A (97 mg, 0.13 mmol) was dissolved in 5 mL methanol and potassium cyanide (59.8 mg, 0.92 mmol) was added and the reaction stirred over night. After work-up the the crude product (0.05 g) was purified by chromatography on silica gel (ethyl acetate/hexane 20:80 to 50:50 gradient) to afford compound 17-deoxy-17-cyano-13,14-dihydro-13-cyano Spinosyn A 17-Psa (16.9 mg, 20.2%) as a white solid: IR (KBr) 3019, 2971, 2933, 2828, 2240, 1723, 1461, 1104, 1038, 732 cm$^{-1}$; $^{13}$C NMR δ 171.86, 131.87, 126.64, 121.49, 120.18, 96.01, 82.72, 81.61, 78.36, 75.96, 68.65, 61.42, 59.61, 58.36, 56.37, 48.30, 47.09, 46.75, 44.58, 43.41, 41.80, 37.48, 36.57, 34.15, 33.53, 30.23, 28.63, 27.47, 22.97, 22.22, 18.32, 13.26, 10.42; FDMS m/z 626. Anal. Calcd for $C_{42}H_{66}N_2O_{10}$: C, 66.46; H, 8.76. Found: C, 65.84; H, 8.14.

Example E10

17-Deoxy-3'-O-[2'''-(dimethylamino)ethyl]-16,17-(Z)-ene Spinosyn J 17-Psa

Spinosyn J (1.20 g, 1.67 mmol) was reacted with 1-chloro-2-dimethylaminoethane (generated in situ from its hydrochloride) following the procedure described for 3'-O, N-bis(trideuteriomethyl) Spinosyn M. Chromatography on silica gel (ethyl acetate) and HPLC separation (88:12, $MeOH/H_2O$) furnished 17-deoxy-3'-O-[2'''-(dimethylamino)ethyl]-16,17-(Z)-ene Spinosyn J 17-Psa (109 mg, 10%) as white solid: $^1$H NMR δ 6.39 (s, 1 H), 5.63 (m, 1 H), 2.18 (s, 6H), 1.84 (s, 3H).

Example E11

(13R,14S)-13,14-Epoxy Spinosyn A, compound (13R,14S)-16,17-dehydro-17-deoxy-16,17(Z)-ene-13,14-epoxy Spinosyn A 17-Psa, and compound (13R,14S,16S,17R)-17-deoxy-13,14-epoxy-16,17-epoxy Spinosyn A 17-Psa Spinosyn A (5.06 g, 6.91 mmol) was dissolved in ethanol (35 mL). Tetrahydrofuran (15 mL) was added followed by 10% aqueous NaOH solution (15 mL) and 30% aqueous hydrogen peroxide solution (6 mL, an excess). The reaction mixture was stirred at RT for 4 h. The usual work-up and chromatography on silica gel (ethyl acetate) gave: a) (13R, 14S)-13,14-epoxy Spinosyn A (3.18 g, 61.5%) as a white solid: ESI MS m/z 748 (M+1); and b) a mixture of less polar compounds, which was separated by flash silica gel column chromatography (7% $Et_2O$ in methylene chloride) to give: c) (13R,14S)-16,17-dehydro-17-deoxy-16,17(Z)-ene-13,14-epoxy Spinosyn A 17-Psa (260 mg, 6.4%) as a white solid: $^1$H NMR δ 5.40 (m, 1 H), 3.45 (s, 3 H), 3.39 (s, 3 H), 3.38 (s, 3 H), 1.72 (s, 3 H); and d) (13R,14S,16S,17R)-17-deoxy-13,14-epoxy-16,17-epoxy Spinosyn A 17-Psa (97 mg, 2.3%) as a white solid: $^1$H NMR δ 4.47 (m, 1 H), 3.81 (s, 1 H),3.43 (s, 3 H), 3.38 (s, 6 H), 1.37 (s, 3 H).

Example E12

(2R/S)-16,17-Dehydro-17-deoxy-16,17(E/Z)-ene-2-ethyl Spinosyn F 17-Psa

Diisopropyl amine (0.658 mL, 5.0 mmol) was dissolved in dry THF (10 mL). The solution was cooled to −23° C. under nitrogen and n-BuLi (2.5M solution in hexanes, 2.0 mL, 5.0 mmol) was added dropwise. Stirring at −23° C. was continued for 30 min and the mixture was cooled to −78° C. A solution of Spinosyn F (1.03 g, 1.434 mmol) in dry THF (3 mL) was added dropwise to the reaction mixture. After 5 min the temperature was raised to −23° C. After 40 min iodoethane (1.25 mL, 15.6 mmol) was introduced. With stirring, the temperature was allowed to raise to room temperature during 2.5 h. The usual work-up and chromatography on silica gel (ethyl acetate) gave a product (441 mg), which was repeatedly chromatographed on silica gel (methylene chloride). This afforded (2R/S)-16,17-dehydro-17-deoxy-16,17(E/Z)-ene-2-ethyl Spinosyn F 17-Psa (152 mg, 18%) as a white solid: $^1$H NMR δ 6.60 (m, 0.33 H), 6.50 (s, 0.33 H), 6.29 (s, 0.33 H), 5.60–6.06 (m, 3 H), 4.78 (s, 1 H), 3.46 (s, 3 H), 3.40 (s, 6 H), 0.75–0.92 (3×t, 6 H). ESI MS m/z 587 (M+1).

Example E13

17-epi-spinosyn A 17-Psa

Sodium borohydride (14.2 mg, 0.37 mmol) was added in one portion to a cold (−20° C.) solution of 17-keto Spinosyn A 17-psa (220 mg, 0.37 mmol) and cerium(III) chloride heptahydrate (140 mg, 0.37 mmol) in MeOH (6 mL) (Caution: foaming and $H_2$ evolution). This mixture was stirred at −20° C. for 20 min, then quenched at that temperature, by the dropwise addition of 1N HCl (0.5 mL) during 2–3 min. The mixture was then diluted with ether (40 mL) and the organic phase washed with brine (2×5 mL) and dried (MgSO$_4$). Concentration left 290 mg of solid residue which was flash chromatographed over silica (40 mL) using 3% MeOH in CH$_2$Cl$_2$ as eluent to give 220 mg of white powder which was a 4:1 mixture of 17-epi-spinosyn A 17-psa and Spinosyn A 17-psa. This mixture was separated by reversed-phase hplc over a C18 bonded silica column (41.4 mm (i.d.)×25 cm (1)) using 15% H$_2$O in MeOH as eluent. Spinosyn A 17-psa elutes first. 17-epi-spinosyn A 17-psa: 106 mg; white powder; $^1$H NMR (CDCl$_3$) δ 6.78 (s, 1H, H-13), 4.86 (d, 1H, H-1'), 4.83 (m, 1H, H-21), 4.32 (m, 1H, H-9), 3.90 (m, 1H, H-17).

Part F Modification of the C-5 and C-6 Positions of the Tricyclic Portion of Compound Spinosyn A Example F1

(5R,6R)-5-(2-Hydroxyethoxy)-6-bromo Spinosyn A

To a suspension of Spinosyn A (1.0 gm, 1.37 mmol) and N-bromosuccinimide (289.5 mg, 1.63 mmol) in ethylene glycol (20 ml), 5N HCl (295 μl, 1.47 mmol) was added. The reaction mixture turned yellow and was stirred at room temperature for 1.5 hour, during which time the color faded to clear. The mixture was poured into saturated aqueous NaHCO$_3$, and extracted with ether. The ether was dried with MgSO$_4$ and evaporated at room temperature under reduced pressure. This gave crude (5R,6R)-5-(2-hydroxyethoxy)-6-bromo Spinosyn A(896.8 mg, 75% yield). The compound could be purified by chromatography on silica, eluting with 5% methanol in dichloromethane, giving (5R,6R)-5-(2-hydroxyethoxy)-6-bromo Spinosyn A as a white glass, FDMS, m/e (relative intensity) 873 (100), 871 (M$^+$, 80).

Example F2

(5S,6R)-5,6-Dihydroxy-5,6-dihydro Spinosyn A

To a suspension of Spinosyn A (487.8 mg, 0.67 mmol) and trimethylamine-N-oxide dihydrate (108 mg, 0.97 mmol), in t-butylalcohol (3 ml) with water (0.5 ml), pyridine (60 ml, 0.74 mmol) was added followed by osmium tetroxide (0.1M; 40 ml, 0.004 mmol). The reaction mixture was heated to reflux under a nitrogen atmosphere for 19 hours. The dark colored mixture was then cool to room temperature and poured into aqueous 20% NaHSO$_3$, and extracted with ether. The ether was washed with brine, dried with MgSO$_4$, and evaporated at room temperature under reduced pressure. The product was purified by chromatography on silica, eluting with 7% methanol in dichloromethane. This gave (5S,6R)-5,6-dihydroxy-5,6-dihrdro Spinosyn A (282.1 mg; 55% yield) as a beige solid, FDMS, m/e (relative intensity) 766 (M$^+$, 60), 765 (100).

Example F3

(5R)-5-(2-Hydroxyethoxy)-6,7-dehydro Spinosyn A

To a solution (5R,6R)-5-(2-hydroxyethoxy)-6-bromo Spinosyn A (299.9 mg, 0.34 mmol) in anhydrous THF (10 ml), sodium hydride (50% dispersion in mineral oil; 69.3 mg, 1.44 mmol) was added and gas evolved. The reaction mixture stirred at room temperature for 3.5 hour, and was then poured into water. The water was extracted with ether. The ether was washed with brine, dried with K$_2$CO$_3$ and evaporated at room temperature under reduced pressure. The product was purified by chromatography on silica, eluting with 5% methanol in dichloromethane. This gave unreacted (5R,6R)-5-(2-hydroxyethoxy)-6-bromo Spinosyn A (27.6 mg) and (5R)-5-(2-hydroxyethoxy)-6,7-dehydro Spinosyn A (123.9 mg; 50% yield, based on recovered starting material) as a pale yellow glass, FDMS, m/e (relative intensity) 791.8 (M$^+$, 100), 419.5 (30).

Example F4

(5S,6R)-Spinosyn A carbonate

To a solution of (5S,6R)-5,6-dihydroxy Spinosyn A (85 mg, 0.11 mmol) and ethylene carbonate (109.2 mg, 1.2 mmol) in benzene (3 ml), anhydrous K$_2$CO$_3$ (40.2 mg, 0.29 mmol) was added and the mixture was heated to relfux. After 2.5 hours the mixture was cooled to room temperature and diluted with dichloromethane. The dichloromethane was washed with water, brine, dried with K$_2$CO$_3$ and evaporated at room temperature under reduced pressure. The product was purified by chromatography on silica, eluting with 7% methanol in dichloromethane. This gave (5S,6R)-Spinosyn A carbonate (65.1 mg; 75% yield) as a white solid, FDMS, m/e (relative intensity) 792 (M$^+$, 70), 791 (100).

Example F5

(5S,6S)-5-Acetoxy-6-bromo Spinosyn A and (5R,6R)-5-Acetoxy-6-bromo-5,6-dihydro Spinosyn A To a solution of Spinosyn A (511.7 mg, 0.7 mmol) in glacial acetic acid (5 ml), N-bromosuccinimide (152.9 mg, 0.86 mmol) was added. The reaction mixture was stirred at room temperature for 24 hours and was then slowly poured into 5N NaOH (35 ml). The aqueous mixture was then saturated with NaCl, and extracted with ether. The ether was washed with brine, dried with K$_2$CO$_3$, and evaporated at room temperature under reduced pressure. This gave a crude mixture (544.2 mg). The mixture could be purified by chromatography on silica, eluting with 7% methanol in dichloromethane, and the isomers seperated by preparative HPLC on a C$_{18}$ column, eluting with acetonitrile:methanol:0.1% NH$_4$OAc (41:41:18 to 42:42:16 in a 60 minute linear gradient). This gave pure (5S,6S)-5-acetoxy-6-bromo Spinosyn A, FDMS, m/e (relative intensity) 874 (50), 873 (98), 872 (48), 871 (M$^+$, 100) and (5R,6R)-5-acetoxy-6-bromo-5,6-dihydro Spinosyn A, FDMS, m/e (relative intensity) 874 (60), 873 (90), 872 (45), 871 (M$^+$, 100) as white solids.

Example F6

5,6-Dibromo Spinosyn A 17-Psa

To a solution of Spinosyn A (257.2 mg, 0.35 mmol) in carbon tetrachloride (10 ml), bromine (18 ml, 0.35 mmol) was added. The reaction mixture was stirred at room temperature for 20 hours, during which time the reaction color faded to a light yellow. Solvent was then evaporated at room temperature under reduced pressure, however, tlc (eluting with 10% methanol in dichloromethane) showed the reaction to be incomplete. The residue was redissolved in carbon tetrachloride (10 ml) and bromine (18 μl, 0.35 mmol) was added. The reaction mixture was stirred at room temperature for 3 days, in which time the reaction color faded. The mixture was then diluted with dichloromethane and washed with aqueous 5% sodium thiosulfate. The dichloromethane was dried with MgSO$_4$ and evaporated at room temperature under reduced pressure. The product was purified by chromatography on silica, eluting with 3% methanol in dichloromethane. This gave 5,6-dibromo Spinosyn A 17-Psa (142.9 mg; 54% yield) as a white solid, FDMS, m/e (relative intensity) 750 ($M^+$, 10), 189 (30), 101 (100).

Example F7

5,6-Dihydro Spinosyn A(246088)

To a solution of Spinosyn A (504 mg; 0.69 mmol) in dry benzene (30 ml), tris(triphenylphosphine)rhodium chloride (50.6 mg; 0.055 mmol) was added and mixture was place in an atmospheric hydrogenator under hydrogen. After magnetic stirring (temperature was not monitored) 6 hr and then standing under $N_2$ atmosphere for 19 hr, the NMR of a small aliquot showed that reaction was about ⅔ complete. An additional tris(triphenylphosphine)rhodium chloride (50 mg; 0.055 mmol) was added and the mixture was replaced under hydrogen atmosphere. After magnetic stirring and additional 24 hr the mixture was evaporated at room temperature under reduced pressure. The residue was intially purified by flash chromatography on silica with 5% MeOH in dichloromethane, giving the crude product (489.1 mg) as a yellow glass. The product was further purified by delta-prep reverse phase HPLC eluting with $CH_3CN$ [38%]: MeOH [38%]: 0.05% $NH_4OAc$ [24%] with a gradient to $CH_3CN$ [45%]: MeOH [45%]: 0.05% $NH_4OAc$ [10%]. This gave 5,6-dihydro Spinosyn A (275.4 mg; 54% yield) as a pale yellow glass. Partial $^1$H-NMR ($CDCl_3$) δ 6.82(1H, bs), 4.79(1H, s), 4.61(1H, m), 4.39(1H, bd), 4.17(1H, bq), 3.23 (1H, m), 2.90(1H, m), 2.76(1H, m), 2.50(1H, m), 0.97(1H, m), 0.64(1H, m).

Example F8

(5S,6R)-5,6-Epoxy Spinosyn A and (5R,6S)-Epoxy Spinosyn A

To a solution of a 6:1 mixture of (5S,6R) and (5R,6S)-epoxy Spinosyn A, N-oxide(2.6 gms; 3.4 mmol) in 300 ml chloroform under nitrogen, triphenylborane (823 mg, 3.4 mmol) was added and the mixture stirred at room temperature for 6 hr. The reaction was then diluted with dichloromethane and washed with 1N NaOH. The dichloromethane was dried with $K_2CO_3$, and evaporated under reduced pressure giving an off white glass (2.57 gms). The crude material was purified by delta-prep reverse phase HPLC eluting with MeOH [42%]:$CH_3CN$ [42%]:0.25% $NH_4OAc$ [16%] for 22 minutes and then MeOH [45%] :$CH_3CN$ [45%]:0.25% $NH_4OAc$ [10%] for 14 minutes. This gave (5R,6S)-epoxy Spinosyn A (0.26 gms, 11%) partial $^1$H-NMR ($CDCl_3$) d 6.71(1H, bs), 4.86(1H, s), 4.71(1H, m), 4.42(1H, bd), 4.30(1H, bq), 2.56(1H, dt), 2.47(1H, dd) and (5S,6R)-5,6-epoxy Spinosyn A (1.3 gms; 54% yield) partial $^1$H-NMR ($CDCl_3$) δ 6.59(1H, bs), 4.86(1H, s), 4.68(1H, m), 4.42(1H, bd), 4.23(1H, bq), 2.59(1H, dt), 2.45(dd) both as white solids.

Example F9

(5S,6R)-Epoxy Spinosyn D and (5R,6S)-Epoxy Spinosyn D

The reaction was run as described in Example F8, starting with a 6:1 mixture of (5S,6R) and (5R,6S)-epoxy Spinosyn D, N-oxide (450 mg , 0.58 mmol). This gave (5R,6S)-epoxy Spinosyn D (16.4 mg, 4%) partial $^1$H-NMR($CDCl_3$) δ 6.71(1H, bs), 4.59(1H, m), 1.40(3H, s), and (5S,6R)-epoxy Spinosyn D (82.1 mg; 19% yield) partial 1H-NMR ($CDCl_3$) δ 6.59(1H, bs), 4.85(s), 4.68(1H, m), 4.42(1H, bd), 4.23(1H, bq), 2.56(1H, dt), 2.41(1H, dd), 1.39(3H, s) both as white solids. Low yields are due to loss on reverse phase HPLC column.

Example F10

Mixture of (5S,6R) and (5R,6S)-Epoxy Spinosyn A, N-oxide

To a solution of Spinosyn A (212.2 mg, 0.238 mmol; 82.1% purity) in 10 ml of dichloromethane, m-chloroperoxybenzoic acid (135 mg, 0.771 mmol) was added and the mixture stirred at room temperature for 3 days. The reaction was partitioned between saturated $NaHCO_3$ and dichloromethane. The phases were seperated and the aqueous was extracted with fresh dichloromethane. The organics were combined, dried with $MgSO_4$, and solvent was evaporated under reduced pressure, giving a white solid (246.8 mg). The crude product was purified by chromatography on silica eluting with 10% MeOH in dichloromethane going to 20% MeOH in dichloromethane in a one step gradient. This gave a 6:1 mixture of (5S,6R) and (5R,6S)-epoxy Spinosyn A, N-oxide as a white solid (181.2 mg; ~100%); partial $^1$H-NMR ($CDCl_3$) δ 6.71 and 6.60(1H, s), 4.87(1H, s), 4.76(m, 1H), 4.70(1H, m), 4.32(1H, m), 4.26(1H, m), 3.42(s), 3.31(s), 3.24(s)

Example F11

(5S,6R) and (5R,6S)-Epoxy Spinosyn D, N-oxide

The reaction was run as described in Example F10 starting with Spinosyn D (517.9 mg, 0.70 mmol). This gave a 6:1 mixture of (5S,6R) and (5R,6S)-epoxy Spinosyn D, N-oxide (450.4 mg; 83% yield) as a yellow glass Partial $^1$H-NMR ($CDCl_3$) δ 6.71 and 6.60(1H, s),1.40(3H, s).

Example F12

(5R,6R)-5,6-Dibromo-4"-keto Spinosyn A and (5R, 6R)-5,6-dibromo Spinosyn B

Compound Spinosyn A (1.98 g, 2.70 mmol) was dissolved in $CH_2Cl_2$ (90 ml). Triethylamine (10 ml) was added and the reaction mixture was cooled to 0° C. Bromine (5.0 g, 27.8 mmol) was added with vigorous stirring. After 15 min. the temperature was raised to RT and stirring was continued for another 30 min. The mixture was diluted with $CH_2Cl_2$ (100 ml) and washed successively with water (2x) and 10% aqueous $NaHSO_3$ (2x). The organic layer was dried over $K_2CO_3$ and concentrated in vacuo. The residue was chromatographed on a flash $SiO_2$ column (230–400 m, 120 g/EtOAc, then EtOH) to give: a) compound (5R,6R)-5,6-dibromo-4"-keto Spinosyn A (342 mg, 15%) IR (KBr) ν 1720, 1660, 740, 595 $cm^{-1}$; $^1$H-NMR ($CHCl_3$) d: 6.70 (1H, bs), 4.90 (1H, dd: 7.7, 2.9 Hz), 4.72 (3H, m:$W_{H/2}$=12 Hz, 3.95 (1H, q: 6.6 Hz) and b) compound (5R,6R)-5,6-dibromo Spinosyn B; 1.22 g, 51%) IR (KEr) ν 3410, 1720, 1665 $cm^{-1}$; $^1$H-NMR ($CHCl_3$) δ: 6.71 (1H, bs), 4.78 (3H, m: $W_{H/2}$=12 Hz), 2.50 (3H, $CH_3$, s).

Example F13

5-Chloro Spinosyn A and 6-chloro Spinosyn A

Compound Spinosyn A (2.62 g, 3.58 mmol) was dissolved in dry $CH_2Cl_2$ (30 ml). The solution was cooled to 0° C. under nitrogen. Phenylselenenyl chloride (Aldrich, 98%; 0.909 g, 4.65 mmol) was added in one portion, with vigorous stirring. After 7 min. m-CPBA (Aldrich, 50%; 4.46 g, 12.9 mmol) was introduced in one portion. CH$_2$Cl$_2$ (50 ml) was added and stirring at 0° C. was continued for 15 min. Afterwards, Et$_3$N (5.0 ml) was added. After additional stirring for 10 min. the reaction mixture was further diluted with CH$_2$Cl$_2$ (100 ml). The solution was washed with 10% aqueous NaHSO$_3$ (2×). The organic phase was successively washed with water (1×), 5% aqueous NaHCO$_3$ (3×), 5% aqueous K$_2$CO$_3$ (1×) and water (1×), then it was dried over anh. K$_2$CO$_3$, filtered and concentrated in vacuo. The residue was purified over a flash SiO$_2$ column (230–400 m, 120 g; EtOAc as eluent). Concentration in vacuo of fractions homogeneous by TLC afforded a white solid (2.23 g). This material was subsequently purified by preparative reversed phase HPLC [two Millipore RCM 40 mm cartridges, C18-coated 6 m silica; eluent: 10% water (containing 0.05 v/v % NH$_4$OH) in MeOH]. Collected fractions gave 5-chloro Spinosyn A as a white glassy solid (1.188 g, 43%). An analysis of $^1$H-NMR and H,H-COSY spectra indicated that this material contained as an admixture ca. 15% of the 6-chloro Spinosyn A 6. Separation of a 235 mg sample of this mixture was accomplished using a Rainin reversed phase column with spherical 5 m, 100 A, C-18 coated packing, and with 15% water (containig 0.05 v/v % NH$_4$OH) in methanol as the mobile phase. Compounds that were obtained were the following: compound a) 5-chloro Spinosyn A (91 mg, 39%) CI MS m/z (M+3): 769.25, (M+2): 768.10, (M+1) 767.10; $^1$H-NMR (CDCl$_3$) δ: 6.71 Hz (1H, bs), 5.96 (1H, bs), 2.86 (dd: 14.2, 3.2 Hz) ppm; IR (CHCl$_3$) v 1721, 1663, 1100, 605 cm$^{-1}$ and compound b) 6-chloro Spinosyn A (35 mg, 15%) CI MS: m/z 766 (M+1), 768 (M+3). $^1$H-NMR (CDCl$_3$) d: 6.65 (1H, bs), 5.84 (1H, dd: 3.1, 3.1 Hz). Elemental analysis: for C$_{41}$H$_{64}$NO$_{10}$Cl calc. C 64.25, H 8.42, N 1.83; found C 64.29, H 8.41, N 1.79.

Example F14

5,6-cis Dihydroxy-5,6-dihydro Spinosyn B (a 2:1 mixture of, respectively (5S,6R) and (5R,6R) isomers)

Compound Spinosyn A (3.26 g, 4.45 mmol) was dissolved in acetone (70 ml). Water (30 ml) was added, followed by N-methylmorpholine-N-oxide (645 mg. 5.5 mmol). After the N-oxide dissolved, OsO$_4$ was added (160 mg of a 2.5% solution in t-BuOH, 0.0015 mmol). The reaction mixture was stirred at RT. After 24 hrs. EtOAc (100 ml) and benzene (100 ml) were added. The mixture was successively washed with 10% aq. NaHSO$_3$ solution (1×), water (1×) and 5% aq. NaHCO$_3$ solution (1×). The organic layer was dried over K$_2$CO$_3$ and concentrated in vacuo. The residue was separated over a flash SiO$_2$ column (EtOAc, then 10% MeOH in EtOAc) to give a mixture of 5,6-cis dihydroxy-5,6-dihydro Spinosyn A (a 2:1 mixture of (5S,6R) and (5R,6S) isomers, 2.236 g, 66%) and a mixture of 5,6-cis dihydroxy-5,6-dihydro Spinosyn B (a 2:1 mixture of (5S,6R) and (5R,6S) isomers (339 mg, 10%) $^1$H-NMR (CDCl$_3$) d: 6.72 (1H, bs), 4.76 (1H, bs), 3.92 (0.65 H, m), 3.85 (0.35 H, m), 2.34 (3H, CH$_3$, s).

Example F15

Dichloroketene acetal of (5S,6R)-5,6-dihydroxy Spinosyn A (5S,6R)-5,6-bis(trichloro-acetoxy) Spinosyn A (5S,6R)-5,6-dihydroxy-5,6-dihydro Spinosyn A (376 mg, 0491 mmol) was dissolved in dry CH$_2$CL$_2$ (10 ml). Pyridine (3 ml) was added, followed by N,N-dimethylaminopyridine (600 mg). The reaction mixture was stirred at RT under nitrogen and trichloroacetyl chloride (1.00 ml, an excess) was added. After 1 hr. the mixture was diluted with EtOAc (100 ml) and PhH (50 ml). The solution was successively washed with brine (1×) and 5% aq. NaHCO$_3$ (2×) and dried over Na$_2$SO$_4$. The organic layer was concentrated in vacuo. The residue was separated by flash column chromatography on a flash SiO$_2$ column (60 g/EtOAc) to give: compound a) dichloroketene acetal of (5S,6R)-5,6-dihydroxy Spinosyn A (104 mg, 25%) IR (CHCl$_3$) v: 1805, 1722, 1660 cm$^{-1}$; $^1$H-NMR (CDCl$_3$) d: 6.62 (1H, bs), 4.96 (1H, dd: 7.8, 3.3 Hz), 4.85 (1H, dd:7.8, 3.9 Hz), 2.20 (6H, 2×CH$_3$, s) and compound b) (5S,6R)-5,6-bis(trichloro-acetoxy) Spinosyn A (129 mg, 25%) IR (CHCl$_3$) v 1772, 1720, 1662 cm$^{-1}$; $^1$H-NMR (CDCl$_3$): 6.76 (1H, bs), 5.66 (1H, m: W$_{H/2}$=8 Hz), 5.50 (1H, dd: 5.7, 3.3 Hz)2.19 (6H, 2×CH$_3$, s) ppm; CI MS m/z 1056 (M+1).

Example F16

5-Keto-6,7-en-6-hydroxy Spinosyn A

A 2:1 mixture of (5S,6R) and (5R,6S) 5,6-cis dihydroxy-5,6-dihydro Spinosyn A (1.51 g, 1.97 mmol) was dissolved in dry CH$_2$Cl$_2$ (5 ml). Separately, N-chlorosuccinimide (0.793 g, 5.91 mmol) was dissolved in dry CH$_2$Cl$_2$ (15 ml). Diethyl sulfide (0.83 ml, 7.68 mmol) was added to the solution of NCS at −78° C. and the mixture was stirred at −78° C. for 30 min. The solution of the diols was then introduced and stirring at −78° C. was continued for 1.5 hrs. Triethylamine (2 ml, dry) was then added and the solution was slowly allowed to reach RT, during 2 hrs and under nitrogen. EtOAc (50 ml) and PhH (100 ml) were added. The solution was successively washed with 5% aq. NaHCO$_3$ (3×) and water (1×), then dried over K$_2$CO$_3$ and concentrated in vacuo. The residue was purified by flash SiO$_2$ chromatography (230–400 m, 120 g, EtOAc, then 10% EtOH in EtOAc) to give 1.20 g of slightly contaminated, which readily crystallized from Et$_2$O to give pure compound 5-keto-6,7-en-6-hydroxy Spinosyn A (1.01 g, 67%) IR (CHCl$_3$) v 1720, 1665, 1648 cm$^{-1}$; $^1$H-NMR (CDCl$_3$) d: 6.68 (1H, bs), 3.84 (1H, dd: 9.2, 9.0 Hz), 2.13 (6H, 2×CH$_3$, s); CI MS m/z 762 (M+1).

Example F17

(5R,6R)-5,6-Dibromo Spinosyn A

Compound Spinosyn A (1.59 g, 2.17 mmol) was dissolved in dry CH$_2$Cl$_2$ (30 ml). The solution was stirred at RT under nitrogen. Phenylselenenyl bromide (98%, 1.05 g, 4.34 mmol) was added in one portion. After 30 min. of stirring the solution was cooled to 0° C. MCPBA (2.5 g, ca. 7 mmol) was added. Stirring at 0° C. was continued for 30 min. Triethylamine (3 ml) was then added and after stirring for 10 min., the mixture was diluted with benzene (150 ml) and EtOAc (50 ml). The solution was washed successively with 10% aqueous NaHSO$_3$ (2×), brine (1×) and 5% aqueous NaHCO$_3$ (2×). The organic phase was dried over K$_2$CO$_3$ and concentrated in vacuo. The residue was purified by flash column chromatography (SiO$_2$/EtOAc) and then by HPLC (C-18 coated, 6 m, 100 A packing; 5% H$_2$O in MeOH as mobile phase). Pure fractions afforded a) unreacted compound Spinosyn A and b) compound (5R,6R)-5,6-dibromo Spinosyn A (297 mg, 16%) $^1$H-NMR (CDCl$_3$) d: 6.69 (1H, bs), 4.74 (3H, m: W$_{H/2}$=12 Hz), 2.17 (6H, 2×CH$_3$, s) ppm; CI MS m/z 894 (M+3), 892 (M+1).

Example F18

5-Keto-6,7-en-6-(p-chloro)benyloxy Spinosyn A

Compound 5-keto-6,7-en-6-hydroxy Spinosyn A (556 mg, 0.73 mmol) was dissolved in dry CH$_2$Cl$_2$ (10 ml).

Pyridine (5 ml) and DMAP (300 mg) were added. The solution was stirred at RT under nitrogen and p-chlorobenzoyl chloride (1.0 ml, an excess) was added. After 15 min. the reaction mixture was diluted with EtOAc (50 ml) and PhH (100 ml). The solution was washed successively with brine (2×), water (1×) and aqueous 5% $NaHCO_3$ (2×). The organic phase was dried over $Na_2SO_4$ and concentrated in vacuo. The residue was purified by flash column chromatography ($SiO_2$/EtOAc) to give compound 5-keto-6,7-en-6-(p-chloro)benyloxy Spinosyn A (634 mg, 96%) $^1$H-NMR ($CDCl_3$) d: 8.03 (2H, bd: 8.4 Hz), 7.41 (2H, bd: 8.4 Hz), 6.73 (1H, bs), 4.09 (1H, dd: 9.3, 9.0 Hz), 2.20 (6H, 2×$CH_3$, s) ppm.

Example F19

5,6-Bis(trimethylsilyloxy)-5,7(8)-diene Spinosyn A

Compound 5-keto-6,7-en-6-hydroxy Spinosyn A (91.40 g, 1.84 mmol) was dissolved in dry $CH_2Cl_2$ (15 ml). To the solution stirred at RT under nitrogen was added triethylamine (dry, 3 ml). After 15 min. was introduced trimethylsilyl triflate (1.5 ml) and the reaction mixture was stirred for 1 hr. at RT. The mixture was diluted with PhH (50 ml) and EtOAc (100 ml). The solution was extracted successively with brine (1×), 5% aqueous $NaHCO_3$ (3×) and $H_2O$ (1×). The organic layer was dried over $K_2CO_3$ and concentrated in vacuo. The residue was separated on a flash $SiO_2$ column (120 g/EtOAc+0.2% Py) to give compound 5,6-bis(trimethylsilyloxy)-5,7(8)-diene Spinosyn A (1.312 g, 79%) $^1$H-NMR ($CDCl_3$) d: 6.69 (1H, bs), 5.48 (1H, dd: 1.9, 0.7 Hz), 0.13 (9H, 3×$CH_3$, s), 0.04 (9H, 3×$CH_3$, s); Elemental Analysis: for $C_{47}H_{79}NO_{12}Si_2$ calc. C 62.29, H 8.79, N 1.55; found C 62.10, H 8.84, N 1.41.

Example F20

5-Keto-6,7-en-6-t-butyldi-methylsilyloxy Spinosyn A

Compound 5-keto-6,7-en-6-hydroxy Spinosyn A (1.025 g, 1.345 mmol) was dissolved in $CH_2Cl_2$ (dry, 20 ml). Pyridine (2 ml) was added. To the solution stirred at RT under nitrogen was added t-BDMS triflate (98%, 471 ml, 2.01 mmol). Stirring was continued for 14 hrs. The mixture was diluted with EtOAc (80 ml) and PhH (50 ml). The solution was washed with 5% aqueous $NaHCO_3$ (2×). The organic layer was dried over $K_2CO_3$ and concentrated in vacuo. The residue was purified by flash column chromatography (230–400 m $SiO_2$, 100 g, EtOAc) to give compound 5-keto-6,7-en-6-t-butyldi-methylsilyloxy Spinosyn A (1.030 g, 87%) $^1$H-NMR ($CDCl_3$) d: 6.66 (1H, bs), 3.81 (1H, 9.5, 9.3 Hz), 0.84 (9H, 3×$CH_3$, s), 0.09 (3H, $CH_3$, s), 0.05 (3H, $CH_3$, s).

Example F21

(5S)-5,6-Dihydro-5-hydroxy Spinosyn A(6S)-5,6-Dihydro-6-hydroxy Spinosyn A (6R)-5,6-Dihydro-6-hydroxy Spinosyn A Mercuric trifluroactetate (1.12 g, 2.62 mmol) was suspended in 30 mL THF:water, 2:1 (V/V). To this yellow suspension was added compound Spinosyn A (0.98 g, 1.34 mmol). The reaction was then allowed to stir at RT for 30 min. The reaction was treated with 7 mL 1N NaOH followed by 2.5 mL 0.5M $NaBH_4$ in 3M NaOH. Reaction turned black supporting a precipitate. Allowed solids to settle to bottom of flask and decanted off liquid into a separatory funnel containing 50 mL ether. Separated layers and extracted aqueous with 2×25 mL ether. Combined ether extracts, washed with 30 mL saturated aqueous $NaHCO_3$, dried over $K_2CO_3$ and concentrated in vacuo. The residue was purified by medium pressure liquid chromatogrpahy {230–400 m $SiO_2$, $CH_2Cl_2$:MeOH, 95:5 (V/V} to give: compound a) (5S)-5,6-dihydro-5-hydroxy Spinosyn A (349.7 mg, 30.4%) partial $^1$H-NMR ($CDCl_3$) d 6.80 (1H, bs), 4.00 (1H, m), 2.95 (1H, m) 0.68 (1H, m); partial $^{13}$C-NMR ($CDCl_3$) d 148.64, 67.40, 45.79, 43.01 35.16 and a mixture of compounds (6S)-5,6-dihydro-6-hydroxy Spinosyn A and (6R)-5,6-dihydro-6-hydroxy Spinosyn A. Compounds (6S)-5,6-dihydro-6-hydroxy Spinosyn A and (6R)-5,6-Dihydro-6-hydroxy Spinosyn A were separated by HPLC (C-18 coated, 6 m, 100 A packing; 10% $H_2O$ in MeOH as mobile phase) to give compound b) (6R)-5,6-dihydro-6 -hydroxy Spinosyn A (7.1 mg, 1%) partial $^1$H-NMR ($CDCl_3$) d 6.84 (1H, bs), 3.48 (1H, m) 2.92 (1H, m) 0.85 (1H, m); $^{13}$C-NMR ($CDCl_3$) d 148.64, 72.66, 44.86, 43.96, 34.52 and compound c) (6S)-5,6-dihydro-6-hydroxy Spinosyn A (11.4 mg, 1%) partial $^1$H-NMR ($CDCl_3$) d 6.80 (1H, bs), 4.11 (1H, m) 2.78 (1H, m) 1.40 (1H, m); $^{13}$C-NMR ($CDCl_3$) d 148.46, 66.52, 38.18, 37.65, 32.95.

Example F22

(5R,6R)-5-Acetoxy-6-thiomethoxy Spinosyn A

Compound Spinosyn A (2.64 g, 3.61 mmol) was dissolved in $CH_3CN$ (dry, cont 1% of diethyl sulfide; 30 ml). To this solution maintained at RT was added dimethyl(methylthio)sulfonium tetrafluoroborate (1.10 g, 5.61 mmol) and the mixture was sonicated (50 W ultrasound cleaner) for 10 min. Anhydrous sodium acetate powder (2.5 g, an excess) was then added and the mixture was sonicated for 1 hr. The solution was diluted with EtOAc (50 ml) and PhH (100 ml) and successively washed with 5% aqueous $K_2CO_3$, 5% aq. $NaHCO_3$ and $H_2O$. The organic layer was dried over $Na_2SO_4$, and concentrated in vacuo. The residue was purified by flash column chromatography on $SiO_2$ and then by preparative HPLC (C-18 coated, 6 m, 100 A packing; 8% $H_2O$ in MeOH as mobile phase). Pure fractions afforded compound (5R,6R)-5-acetoxy-6-thiomethoxy Spinosyn A (2.07 g, 68%) $^1$H-NMR ($CDCl_3$) d: 6.69 (1H, bs), 5.31 (1H, dd: 2.4, 2.2 Hz), 2.16 (6H, 2×$CH_3$, s), 2.11 (3H, $CH_3$, s), 2.01 (3H, $CH_3$, s); Elemental Analysis: for $C_{44}H_{71}NO_{12}S$ calc. C 63.06, H 8.54, N 1.67; found C 63.15, H 8.77, N 1.76.

Example F23

(5R,6R)-5-Acetoxy-6-methylsulfonyl Spinosyn A

Compound (5R,6R)-5-acetoxy-6-thiomethoxy Spinosyn A (1.05 g, 1.25 mmol) was dissolved in $CH_2Cl_2$ (100 ml). The solution was cooled to 0° C. and, upon stirring, m-CPBA (50%, 1.95 g, 5.6 mmol) was added in a few portions. After 40 min. the reaction mixture was diluted with $CH_2Cl_2$ (50 ml). The solution was washed successively with 10% aqueous $NaHSO_3$ (2×), water (1×) and 5% aq. $NaHCO_3$ (2×). The organic layer was dried over $Na_2SO_4$ and concentrated in vacuo. The residue was purified by a flash column chromatography (230–400 m $SiO_2$/EtOAc, then 10% EtOH in EtOAc) to give compound (5R,6R)-5-acetoxy-6-methylsulfonyl Spinosyn A (966 mg,89%) IR ($CHCl_3$) v 1740, 1724, 1662, 1320, 1135 cm$^{-1}$; $^1$H-NMR ($CDCl_3$) d: 6.57 (1H, bs), 5.52 (1H, dd:4.5, 4.0 Hz), 2.78 (3H, $CH_3$, s), 2.17 (6H, 2×$CH_3$, s), 1.98 (3H, $CH_3$, s).

Example F24

(5R,6R)-6-Bromo-5-hydroxy Spinosyn J

Compound Spinosyn A (1.33 g, 1.82 mmol) was dissolved in DMSO (15 ml). Water (5 ml) was added, causing precipitation. Upon stirring was introduced conc. $H_2SO_4$ (1.8 mmol). The precipitate dissolved immediately. The solution was cooled to 0° C. and N-bromosuccinimide (322 mg, 1.8 mmol) was added. After stirring at 0° C. for 15 min., the reaction mixture was poured onto 50 ml sat. aq. $NaHCO_3$. The mixture was extracted with $Et_2O$ (3×). Combined organic extracts were washed with brine, dried over $K_2CO_3$ and concentrated in vacuo. The residue was purified by reversed phase HPLC (C-18 Dynamax column, 20% water in MeOH as mobile phase) to give compound (5R,6R)-6-bromo-5-hydroxy Spinosyn J (1.30 g, 86%) CI MS m/z 828 (M+1); $^1$H-NMR ($CDCl_3$) d: 6.56 (1H, bs), 4.24 (2H, m: $W_{H/2}$=14 Hz), 3.85 (1H, dd: 3.5, 3.5 Hz), 2.05 (6H, 2×$CH_3$, s).

Example F25

5,6-Dihydro Spinosyn A 9-Psa

Compound Spinosyn A 9-Psa (46.5 mg, 0.0856 mmol) was dissolved in 5 mL toluene. To this solution was added tris-triphenylphoshine rhodium(I) chloride (8.5 mg, 0.0092 mmol). Evacuated the flask head space and introduced nitrogen three times. Evacuated and introduced hydrogen three times. Maintained flask under hydrogen with balloon and heated reaction to 110–120° C. After 3.5 hr cooled flask to RT and evacuated hydrogen and replaced with nitrogen. Evaporated off toluene solvent and replaced with 20 mL ether. Extracted ether solution with 3×10 mL 1N HCl. Combined acid extracts and neutralized with 10 ml 4N NaOH. Extracted neutralized suspension with 3×10 mL ether, combined ether extracts, washed with 20 mL brine, dried over $K_2CO_3$, and evaporated in vacuo. Gave compound 5,6-dihydro Spinosyn A 9-Psa (29.5 mg, 63%) partial $^1$H-NMR ($CDCl_3$) d 6.84 (1H, bs), 1.01 (1H, m), 0.68 (1H, m).

Example F26

5,6-Dihydro Spinosyn A 17-Psa

The procedure described above in Example F25 was applied to compound Spinosyn A 17-Psa (270.8 mg, 0.458 mmol) with 32.8 mg [$(Ph)_3P]_3RhCl$. After evaporation of toluene the compound was purified directly by medium pressure liquid chromatography (230–400 m $SiO_2$, $CH_2Cl_2$:MeOH, 95:5 (V/V). Gave compound 5,6-dihydro Spinosyn A 17-Psa (188.1 mg, 69.2%) partial $^1$H-NMR ($CDCl_3$) d 6.84 (1H, bs), 3.63 (1H, m), 1.02 (1H, m), 0.68 (1H, m); partial $^{13}$C-NMR ($CDCl_3$) d 149.28, 72.48, 46.55, 27.00.

Example F27

5,6-Dihydro Spinosyn J

The procedure described above in Example F25 was applied to compound Spinosyn J (1.00 g, 1.39 mmol) using 91.3 mg [$(Ph)_3P]_3RhCl$ in 20 mL of toluene. This gave compound 5,6-dihydro Spinosyn J (0.70 g, 70%) partial $^1$H-NMR ($CDCl_3$) d 6.84 (1H, bs) 3.82 (1H, dt), 1.01 (1H, m), 0.69 (1H, m).

Example F28

5,6-Dihydro Spinosyn H

Compound Spinosyn H (2.57 g, 3.58 mmol) was dissolved in 20 mL toluene in a 250 mL round bottom flask. To this colorless solution was added a solution of [$Ph_3P]_3RhCl$ (169.2 mg, 0.183 mmol) in 5 mL toluene. The flask was fitted with a reflux condensor and the flask head space was evacuated three times and nitrogen gas introduced. The nitrogen was evacuated three times and hydrogen gas introduced. The flask was maintained under 1 atm hydrogen with a balloon and heated to 100–110° C. in an oil bath. After 10 hr., the heat was removed and the flask evacuated three times with nitrogen gas being introduced after each evacuation. The contents of the flask was filtered hot under a nitrogen atmosphere through a 3" column of celite. The celite was washed with 100 mL ether to elute the remaining compound. The filtrate was extracted with 3×50 mL 1N HCl. The acid extracts were combined, back extracted with 25 mL ether, and basified with 50 mL 4N NaOH. The white solid which precipitated was extracted into ether (2×25 mL) and the ether extracts washed with 25 mL brine solution. The ether solution was filtered through a plug of celite and evaporated in vacuo. This gave compound 5,6-dihydro Spinosyn H (2.24 g, 87.1%). Anal. Calcd. for $C_{40}H_{65}NO_{10}$: C 66.73, H 9.10, N 1.95; Found C 66.31, H 9.01, N 2.02. CI MS (m/z) 721 (M+1).

Example F29

5,6-Dihydro Spinosyn A Hemiglutarate salt

Compound 5,6-dihydro Spinosyn A (232.2 mg, 0.316 mmol) was dissolved in 3 mL acetone. A solution of glutaric acid (20.8 mg, 0.157 mmol) in 3 mL acetone was added and the solution stirred at RT overnight. Removed the solvent in vacuo to give compound 5,6-dihydro Spinosyn A hemiglutarate salt (250.8 mg). Anal calcd for $C_{41}H_{67}NO_{10}·½(C_5H_8O_4)$ C 65.31, H 8.94, N 1.75; Found C 65.14, $H_{8.78}$, N 1.87; mp. 83–92° C.

Example F30

5,6-Dihydro Spinosyn B

Hydrogenation Procedure A: A solution of Spinosyn B (1.10 g, 1.53 mmol) and $(Ph_3P)_3RhCl$ (0.05 g, 0.09 mmol) in PhMe (15 mL) was placed on a Parr apparatus and maintained under an $H_2$ atmosphere (45–50 psi) for 2 h at 104–107° C. After cooling to room temperature, the mixture was evaporated in vacuo and the residue was decolorized ($Et_2O$/charcoal) and filtered. The filtrate was evaporated in vacuo and the residue was purified by MPLC ($SiO_2$, 5:95→10:90 MeOH/$CH_2Cl_2$) to give 0.90 g (82%) of 5,6-dihydro Spinosyn B as a white powder. Calcd for $C_{40}H_{65}NO_{10}$: C, 66.73; H, 9.10; N, 1.95. Found: C, 66.53; H, 9.14; N, 2.15.

Example F31

Synthesis of compound (5S,6R)-Epoxy-Spinosyn Q

Spinosyn Q (970 mg, 1.32 mmol) was dissolved in methylene chloride (150 ml). The solution was cooled to 0° C. and m-CPBA (1.19 g of ca. 50% reagent, ca. 3.45 mmol) was added in one portion. Immediately after m-CPBA dissolved, the reaction mixture was set aside in a refrigerator. After 40 hrs. the reaction mixture was extracted with 10% aqueous solution of $NaHSO_3$ (2×), with water (1×) and with 5% aq. solution of $NaHCO_3$ (2×). The organic layer was dried over anh. $K_2CO_3$, filtered and concentrated in vacuo. The residue was separated over a flash $SiO_2$ column (230–400 m, 70 g/EtOAc). Concentration in vacuo of chromatographically homogenous fractions gave a white solid (694 mg). A white solid (88 mg) precipitated from a solution of this material upon attempted crystallization from dry Et$_2$O. The ether solution, upon evaporation, gave compound (5S,6R)-epoxy-Spinosyn Q, 606 mg, 61%) $^1$H-NMR d 6.51 (1H, bs), 4.73 (1H, d: 1.2 Hz), 3.87 (1H, dd: 1.2, 1.8 Hz), 2.16 (6H, bs 2×CH$_3$), 1.31 (3H, s, CH$_3$) ppm.

Example F32

Mixture of (5S,6R)-5,6-dihydro-5,6-dihydroxy Spinosyn A (65%) and (5R,6R)-5,6-dihydro-5,6-dihydroxy Spinosyn A (35%)

Spinosyn A (3.26 g, 4.45 mmol) was dissolved in acetone (70 mL). Water (30 mL) was added, followed by N-methylmorpholine N-oxide (645 mg, 5.5 mmol), and osmium tetroxide (2.5% solution in 2-methyl-2-propanol; 160 mg, 0.015 mmol). After 1 h another portion of OsO$_4$ (300 mg) was added. After 24 h the mixture was combined with 10% aqueous NaHSO$_3$ solution (200 mL) and worked up. The crude product was purified over a short flash column with silica gel (10% MeOH in EtOAc) to furnish an unseparable mixture of (5S,6R)-5,6-dihydro-5,6-dihydroxy Spinosyn A (65%) and (5R,6R)-5,6-dihydro-5,6-dihydroxy Spinosyn A (35%) (2.24 g, 66%) as a white solid: $^1$H NMR d 6.71 (s, 1 H), 3.93 (m, 0.65 H), 3.88 (m, 0.35 H), 2.11 (s, 6 H).

Example F33

5,6-Dihydro Spinosyn B

A solution of Spinosyn B (1.10 g, 1.53 mmol) and (Ph$_3$P)$_3$RhCl (0.08 g, 0.09 mmol) in PhMe (15 mL) was subjected to an H$_2$ atmosphere (45–50 psi) at 104–107° C. on a Parr apparatus. After 2 h, the mixture was filtered, and evaporated. The residue was dissolved into Et$_2$O and slurried with charcoal. This slurry was filtered and evaporated. MPLC (5:95 MeOH/CH$_2$Cl$_2$) gave 0.90 g (82%) of 5,6-dihydro Spinosyn B as a white powder. Anal. Calcd for C$_{40}$H$_{65}$NO$_{10}$: C, 66.73; H, 9.10; N, 1.95. Found: C, 66.53; H, 9.14; N, 2.15.

Example F34

5,6-dihydro Spinosyn D

To a solution of Spinosyn D (2.5 g, 3.4 mmol) in absolute ethanol (60 mL), 10% Pd/C and cyclohexene was added in a 100 ml Parr vessel. This suspension was heated at 120° C. for 48 h. After cooling, the reaction mixture was filtered through a pad of celite and concentrated in vacuo to give 2.4 g of 2:1 mixture of 5,6-dihydro Spinosyn D and Spinosyn D respectively. The residue (200 mg) was dissolved in dichloromethane (20 mL) and cooled to 0° C. MCPBA (95 mg, 0.45 mmol) was added to the reaction mixture and stirred at 25° C. for 16 h. The reaction mixture was quenched with sodium bicarbonate solution and layers separated. Aqueous layer was extracted with dichloromethane (2×20 mL). The combined extracts were stirred with 10% NaHCO$_3$ for 3 h, washed with brine, dried over anh. Na$_2$SO$_4$ and concentrated in vacuo. The residue was purified on a prep HPLC on a C18 column, eluting with 10% water (0.1% NH$_4$OH) in methanol to give compound 5,6-dihydro Spinosyn D (10 mg). MS m/z 748. $^1$H NMR (CDCl$_3$, 300 MHz) 6.85 (1H, s), 4.82 (1H, s), 4.65 (1H, m), 4.42 (1H, d), 4.20 (1H, m), 0.95 (3H, d).

Part G Modification by Replacement of the Forosamine with a Different Sugar

Example G1

17-O-(2-iodo-2-deoxy-3,4-di-O-acetyl-α-L-rhamnosyl) Spinosyn A 17-Psa

To a solution of Spinosyn A 17-Psa(105.4 mg, 0.18 mmol) in acetonitrile (0.86 ml), 3,4-di-O-acetyl-6-deoxyl-L-glucal (Aldrich, 52 µl, 0.35 mmol) was added followed by N-iodosuccinimide (80.6 mg, 0.36 mmol). The reaction mixture was stirred at room temperature for 19 hours. The dark colored mixture was then diluted with dichloromethane and washed with aqueous saturated NaHSO$_3$, and then aqueous 5% sodium thiosulfate. The dichloromethane was dried with MgSO$_4$ and evaporated at room temperature under reduced pressure. The product was purified by preparative HPLC, eluting with 45:45:10/acetonitrile:methanol:0.05% aqueous NH$_4$OAc. This gave 17-O-(2-iodo-2-deoxy-3,4-di-O-acetyl-α-L-rhamnosyl) Spinosyn A 17-Psa (49 mg; 29% yield) as a colorless glass, FDMS, m/e (relative intensity) 930 (M$^+$-H, 20), 929 (30), 190 (100).

Example G2

17-O-(2-Deoxy-α-L-rhamnosyl) Spinosyn A 17-Psa

The reaction was run as described below in Example G3 starting with 17-O-(2-deoxy-3,4-di-O-acetyl-α-L-rhamnosyl) Spinosyn A 17-Psa (271.2 mg, 0.34 mmol). This gave 17-O-(2-deoxy-α-L-rhamnosyl) Spinosyn A 17-Psa (187 mg; 77% yield) as a white glass, FDMS, m/e (relative intensity) 1432 (20), 752 (30), 720 (M$^+$, 100), 206 (50).

Example G3

17-O-(2-Iodo-2-deoxy-α-L-rhamnosyl) Spinosyn A 17-Psa

To a solution of 17-O-(2-iodo-2-deoxy-3,4-di-O-acetyl-α-L-rhamnosyl) Spinosyn A 17-Psa (107.8 mg, 0.12 mmol) in methanol (9 ml), saturated ammonia in methanol (2 ml) was added. The reaction mixture was capped and stirred at room temperature for 19 hours. The mixture was then evaporated at room temperature under reduced pressure. The product was purified by chromatography on silica, eluting with 5% methanol in dichloromethane. This gave 17-O-(2-iodo-2-deoxy-α-L-rhamnosyl) Spinosyn A 17-Psa (74 mg; 75% yield) as a colorless glass, FDMS, m/e (relative intensity) 848 (MH$^+$, 20), 591 (100), 189 (65), 101 (90).

Example G4

17-O-(2-Deoxy-3,4-di-O-acetyl-α-L-rhamnosyl) Spinosyn A 17-Psa

To a solution of 17-O-(2-iodo-2-deoxy-3,4-di-O-acetyl-α-L-rhamnosyl) Spinosyn A 17-Psa (515.3 mg, 0.55 mmol) in toluene (85 ml), tri-n-butylsilane (780 µl, 2.85 mmol) followed by a trace amount of AIBN was added. The reaction mixture was heated to reflux for 30 minutes, and then cooled to room temperature for 1.5 hour. The mixture was then evaporated at room temperature under reduced pressure. The residue was purified by chromatography on silica, eluting with 40% ethyl acetate in hexane. This gave 17-O-(2-deoxy-3,4-di-O-acetyl-α-L-rhamnosyl) Spinosyn A 17-Psa (321.5 mg; 73% yield) as an off white glass, FDMS, m/e (relative intensity) 804 (M$^+$-H, 100), 190 (55), 101 (70).

Example G5

3'-Desmethoxy Spinosyn C

The reaction was run as described in Example H1 below starting with 3'desmethoxy Spinosyn B (240 mg, 0.35 mmol). This gave 3'-desmethoxy Spinosyn C (126.1 mg; 54% yield) as a pale yellow solid, FDMS, m/e (relative intensity) 676 (40), 675 (100), 674 (M$^+$, 80), 673 (35).

Example G6

3'-Desmethoxy-17-keto Spinosyn A 17-Psa

The reaction was run as described in Example E7 above starting with 3'-desmethoxy Spinosyn A 17-Psa (809.8 mg, 1.4 mmol). This gave 3'-desmethoxy-17-keto Spinosyn A 17-Psa (501.4 mg; 64% yield) as a colorless glass, FDMS, m/e (relative intensity) 559 (M$^+$, 45), 558 (100), 159 (10).

Example G7

17-O-(2-acetamido-2-deoxy-3,4,6-tetra-O-acetyl-β-D-glucopyranosyl) Spinosyn A 17-Psa A solution of Spinosyn A 17-psa (1.0 g, 1.70 mmol), 2-methyl-(3,4,6-tri-O-acetyl-1,2-dideoxy-α-D-glucopyrano)-[2,1-d]-2-oxazoline (Nakabayashi, S.; Warren, C. D.; Jeanloz, R. W. *Carbohydr. Res.* 1986, 150, C7) (0.56 g, 1.70 mmol) and pyridinium-p-toluenesulfonate (75 mg, 0.30 mmol) in 1,2-dichloroethane (65 mL) was heated at reflux with stirring for 48 h then cooled to room temperature. Saturated $Na_2CO_3$ (2 mL) was then added and this mixture stirred at room temperature for 5 min. and then diluted with water (15 mL) and $CH_2Cl_2$ (30 mL). The aqueous layer was separated and washed with $CH_2Cl_2$ (30 mL) and this wash combined with the organic layer. The combined organic extracts were then washed with brine (25 mL), dried ($MgSO_4$) and concentrated. The residue (1.4 g) was flash chromatographed over silica (160 mL) using 3% MeOH in $CH_2Cl_2$ as eluent to give 0.6 g of crude glycosylated product. This was purified in three portions of 200 mg by reversed-phase hplc over a Rainin microsorb C18 column (41.4 mm (i.d.)×25 cm (1)) using 10% water in MeOH as eluent to give 151 mg of 17-O-(2-acetamido-2-deoxy-3,4,6-tetra-O-acetyl-β-D-glucopyranosyl) Spinosyn A 17-Psa. A sample was recrystallized from 1:2 EtOAc/hexane as colorless needles, mp 199–200° C.; $^1$H NMR (CDCl$_3$) d 6.76 (s, 1H, H-13), 5.66 (d, 1H, NH), 5.18 (dd, 1H, H-3"), 5.02 (t, 1H, H-4"), 4.83 (d, 1H, H-1'), 4.62 (m, 1H, H-21), 4.60 (d, J=8.2, 1H, H-1"), 4.28 (m, 1H, H-9), 4.14 (m, 2H, H-6"), 3.98 (m, 1H, H-2").

Example G8

17-O-(2-acetamido-2-deoxy-β-D-glucopyranosyl) Spinosyn A 17-Psa

To a solution of 17-O-(2-acetamido-2-deoxy-b-D-glucopyranosyl) Spinosyn A 17-psa (35 mg, 0.038 mmol) in MeOH (5 mL) a 60% mineral oil dispersion of NaH (2 mg) was added in one portion. The resulting solution was stirred at room temperature for 25 min. and then was neutralized with glacial acetic acid. The solvent was evaporated and the residue flash chromatographed over silica (25 mL) using 12% MeOH in $CH_2Cl_2$ as eluent to give 17-O-(2-acetamido-2-deoxy-β-D-glucopyranosyl) Spinosyn A 17-Psa (27 mg) as a colorless foam: $^1$H NMR (CDCl$_3$) δ 6.83 (s, 1H, H-13), 4.83 (s, 1H, H-1'), 4.63 (m, 1H, H-21), 4.58 (d, 1H, H-1"), 4.32 (m, 1H, H-9); MS m/z 102 (100), 189 (75), 573 (30), 794 (M$^+$+H, 12).

Example G9

2-O-Acetyl-α-D-desosaminylbromide Hydrobromide

Diacetyl desosamine hydrochloride (Flynn, E. H.; Sigal, M. V., Jr.; Wiley, P. F.; Gerzon, K. *J. Am. Chem. Soc.* 1954, 76, 3120) (0.9 g, 3.05 mmol) was added at room temperature to a well stirred solution prepared from acetic anhydride (0.75 mL) and 30% HBr in acetic acid (3.75 mL). This solution was stirred at room temperature for 1 h, then ether (45 ml) was added in portions of 4–5 mL each during 10 min. to precipitate the product hydrobromide; this initially oiled out but solidified with scratching and continued stirring. The hygroscopic hydrobromide was filtered under nitrogen and washed with ether (3×40 mL), then dried at 30° C. at reduced pressure (~30 mm) on a rotary evaporator to yield 2-O-acetyl-α-D-desosaminylbromide hydrobromide (1.1 g) as an off-white powder. This was used directly in the glycosylation reactions. $^1$H NMR (CDCl$_3$) δ 6.67 (d, 1H, H-1), 4.92 (dd, 1H, H-2), 2.84 (d, 6H, N(CH$_3$)$_2$), 2.33 (s, 3H, CH$_3$C=O), 1.37 (d, 3H, H-6).

Example G10

17-O-(β-D-Desosaminyl) Spinosyn A 17-Psa

2-O-Acetyl-α-D-desosaminylbromide hydrobromide (1.1 g, 3.0 mmol) was added in one portion to a well stirred solution of Spinosyn A 17-Psa (0.5 g, 0.85 mmol) and lutidine (0.26 mL, 2.2 mmol) in 1,2-dichloroethane. This solution was then heated to 60–65° C. and kept in that temperature range for 24 hr., after which it was cooled to 25° C. and treated with 0.5N HCl (5.2 mL). This mixture was stirred at 25° C. for 10 min. and then diluted with $CH_2Cl_2$ (20 mL). The organic layer was separated and washed with water (5 mL), saturated NaHCO$_3$ (6 mL) and brine (5 mL) and dried (MgSO$_4$). Concentration left 0.6 g of residue which was flash chromatographed over silica (150 mL) using 3% MeOH in $CH_2Cl_2$ as eluent to give 0.25 g of 17-O-(2-O-acetyl-β-D-desosaminyl) Spinosyn A 17-Psa, a 4β:1α anomeric mixture, as a white foam. This was dissolved in MeOH (7 mL) and 0.1M NaOMe in MeOH (1.5 mL) was added. This solution was stirred at room temperature for 6 h, then acetic acid (10 μL) was added and this solution stirred for 10 min. Evaporation of the solvent left 200 mg of 17-O-(β-D-desosaminyl) Spinosyn A 17-Psa as a 4:1 β/α anomeric mixture. The β-anomer (80 mg, white foam) was isolated by reversed-phase hplc in three portions over a Rainin C-18 column (41.4 mm (i.d.)×25 cm (1)) using 45:45:10 CH$_3$CN/MeOH/2% NH$_4$OAc as eluent: $^1$H NMR (CDCl$_3$) δ 6.78 (s, 1H, H-13), 4.84 (s, 1H, H-1'), 4.66 (m, 1H, H-21), 4.36 (d, J=7.1, 1H, H-1"), 4.30 (m, 1H, H-9); MS m/z 748 (2), 329 (30), 313 (50), 218 (45), 200 (100), 189 (15), 158 (70), 147 (20).

Example G11

α-D-Forosaminylbromide Hydrobromide

D-Forosamine (Boeck, L. D.; Chio, H.; Eaton, T. E.; Godfrey, O. W., Jr.; Michel, K. H.; Nakatsukasa, W. M.; Yao, R. C -F. European Patent, 0 375 316 A1 (1990)) (0.1 g, 0.63 mmol) was added in one portion to 1 mL of a well stirred, chilled (~10° C.) 5:1 (v/v) mixture of 30% HBr in acetic acid:acetic anhydride. The resulting solution was stirred for 10 min in the cold, then at ambient temperature for 1 hr. Ether (7 mL) was then added in 1.0 mL portions over 5 min. Product hydrobromide initially oils out but solidifies with scratching and continued stirring. The highly hygroscopic hydrobromide was collected by filtration under nitrogen, washed with ether (4×10 mL) and dried at reduced pressure on a rotary evaporator at ~30° C. This was used immediately in the glycosylation reactions. Yield of α-D-forosaminylbromide hydrobromide: 0.17 g (89%) as an off-white powder: $^1$H NMR (CDCl$_3$) δ 6.60 (s, 1H, H-1), 4.22 (m, 1H, H-5), 2.94 (d, 3H, NCH$_3$), 2.87 (m, 1H, H-4), 2.83 (d, 3H, NCH$_3$), 2.30 (m, 4H, H-2, H-3), 1.68 (d, 3H, H-6).

Example G12

1"-epi-Spinosyn A

A suspension of $HgBr_2$ (0.1 g, 0.28 mmol) in $CH_2Cl_2$ (10 mL) was rapidly stirred at ambient temperature for 10 min. (~⅔ of the $HgBr_2$ dissolves during this time). Powdered 4A molecular sieves (0.15 g) and Spinosyn A 17-Psa (0.11 g, 0.18 mmol) were then added and this mixture stirred for 10 min, after which a solution of α-D-forosaminylbromide hydrobromide (0.17 g, 0.56 mmol) in $CH_2Cl_2$ (4.0 mL) was added dropwise during 1 h. After stirring an additional 3 h, saturated $Na_2CO_3$ (4 mL) was added and this mixture stirred for 10 min. The mixture was then filtered through Celite and the collected solids washed with $CH_2Cl_2$ (15 mL) and water (5 mL). The organic layer of the combined filtrate and wash was separated and the aqueous layer washed with $CH_2Cl_2$ (15 mL). The combined organic extracts were then washed successively with 10% aq. KI solution (2×4 mL), 10% $NaHCO_3$ (5 mL) and brine (10 mL) and dried ($MgSO_4$). Evaporation left 0.15 g of residue which was flash chromatographed over silica (40 mL) using 4% MeOH in $CH_2Cl_2$ as eluent to give clean glycosylated product (49 mg) as an ~3:1 mixture of 1"-epi-Spinosyn A to Spinosyn A. This mixture was dissolved in $CH_3CN$ (1.5 mL) and the anomers were separated by hplc over two analytical 4.6 mm (i.d.)× 250 mm (1) Apex phenyl columns arranged in series with 40:40:20 $CH_3CN$/MeOH/2% $NH_4OAc$ as eluent and a flow rate of 1.5 mL/min. Approximately thirty injections of 40–45 μL, each containing ~1.5 mg of the mixture were made. Pure 1"-epi-spinosyn A was obtained as a colorless foam: $^1H$ NMR ($CDCl_3$) δ 6.75 (s, 1H, H-13), 4.80 (s, 2H, H-1', H-1"), 4.59 (m, 1H, H-21), 4.28 (m, 1H, H-9); MS m/z 732 ($M^+$+1, 1), 189 (25), 142 (100).

Example G13

17-O-(2,3,4,6-Tetra-O-acetyl-β-D-glucopyranosyl) Spinosyn A 17-Psa

A solution of Spinosyn A 17-Psa (0.3 g, 0.5 mmol) and $HgBr_2$ (90 mg, 0.25 mmol) in 1,2-dichloroethane (20 mL) containing powdered 4A molecular sieves was heated with stirring to reflux and 3 mL of solvent was collected by distillation. To this refluxing mixture, a solution of 2,3,4,6-tetra-O-acetyl-α-D-glucopyranosyl bromide (0.48 g, 1.17 mmol) in dichloroethane (5 mL) was added dropwise during 10 min. More solvent (3 mL) was collected and refluxing then continued for 20 h. More bromide (0.15 g) and $HgBr_2$ (90 mg) were then added and refluxing was continued for 5 hr. The reaction mixture was then cooled to room temperature and filtered through Celite. The collected solids were washed with $CH_2Cl_2$ (20 mL) and the combined filtrate and wash washed successively with 10% KI (2×10 mL), water (15 mL) and brine (15 mL) and then dried (MgSO4). Evaporation left 0.75 g of residue which was flash chromatographed over silica (90 mL) using 3% MeOH in $CH_2Cl_2$ to give 0.2 g of 17-O-(2,3,4,6-tetra-O-acetyl-β-D-glucopyranosyl) Spinosyn A 17-Psa as a colorless foam: $^1H$ NMR ($CDCl_3$) δ 6.78 (s, 1H, H-13), 5.20 (m, 1H, H-3"), 5.05 (m, 1H, H-4"), 4.86 (d, 1H, H-1'), 4.66 (m, 1H, H-21), 4.59 (d, 1H, H-1"), 4.30 (m, 1H, H-9), 4.14 (m, 2H, H-6"); MS m/z 921 ($M^+$+1, 2), 331 (100), 189 (90).

Part H Aglycone, Pseudoaglycone and Manufacture of other Alkylated Spinosyns

Example H1

Synthesis of Spinosyn C from Spinosyn B

A solution of Spinosyn B (1.00 gms, 1.4 mmol) in methanol (45 ml) was cooled to 3° C. under nitrogen. Freshly prepared 1M sodium methoxide in methanol solution (7.1 ml, 7.1 mmol) was added followed by iodine (1.8 gms, 7.1 mmol), as a solid in one portion. The reaction was stirred at 3° C. for 4.5 hr. (HPLC showed the reaction to be 80% complete) and was then poured into a 5% sodium thiosulfate/dilute ammonium hydroxide solution and extracted with diethyl ether. The ether extract was washed with brine, dried ($K_2CO_3$) and evaporated at ambient temperature under vacuum. The crude product was purified by reversed phase HPLC on a $C_{18}$ column, eluting with methanol:acetonitrile:0.05% ammonium acetate (45:45:10), giving Spinosyn C (361 mg). The product was identical (MS, and $^1H$ NMR) to a naturally produced sample of Spinosyn C.

Example H2

Spinosyn D Ag

To a suspension of Spinosyn D 9-Psa (132 mg, 0.24 mmol) in water (5 ml), 1N $H_2SO_4$ was added dropwise to a pH of 1.7 and the mixture became homogeneous. This solution was heated to 80° C. for 3.75 hr, during which time an oil separated from the solution. The mixture was cooled to room temperature and dichloromethane was added to dissolve the oil. The aqueous was separated and extracted with fresh dichloromethane. The dichloromethane was combined, washed quickly with 1N $H_2SO_4$, dried with $K_2CO_3$ and evaporated at room temperature giving a pale yellow glass (82.9 mg). The product was purified by flash chromatography with 5% MeOH in dichloromethane, giving Spinosyn D Ag (63.6 mg, 63% yield) as a colorless glass.

Example H3

Synthesis of Spinosyn B from Spinosyn A

A suspension of Spinosyn A (5.0 gms, 5.13 mmol) and sodium acetate trihydrate (4.68 gms, 34.4 mmol) in 80% methanol/water (125 ml) was heated to 47° C. under nitrogen. The pH dropped from 10 to 8 on addition of iodine (1.75 gms, 68.0 mmol) as a solid in one portion, giving a brown color. The pH was maintained at 8–9 by periodic addition of 1N sodium hydroxide. The reaction was heated for 2.75 h (during which time the color faded to pale yellow), and was then cooled to ambient temperature. The solution was poured into a solution of water (250 ml) and ammonium hydroxide (50 ml), and extracted with diethyl ether. The ether extract was washed with brine, dried ($K_2CO_3$), and evaporated at ambient temperature under vacuum. The crude product was purified by reversed phase HPLC on a $C_{18}$ column, eluting with methanol:acetonitrile:0.05% ammonium acetate (45:45:10) giving Spinosyn B (2.52 gms) which was identical (MS, $^1H$ NMR, $^{13}C$ NMR, IR, and OR) to a naturally produced sample of Spinosyn B.

Example H4

N-Demethyl Spinosyn J

The reaction was run as described in Example H3 starting with Spinosyn J(105.4 mg, 0.15 mmol); however, the extractive work up was done with dichloromethane rather than ether. This gave N-demethyl Spinosyn J (57.3 mg; 54%) as a pale yellow glass.

Example H5

N-Demethyl Spinosyn L

The reaction was run as described in Example H4 starting with Spinosyn L (102.5 mg, 0.14 mmol). This gave N-demethyl Spinosyn L (66.5 mg; 66%) as a white glass.

Example H6

N-Demethyl Spinosyn K

The reaction was run as described in
Example H4 starting with Spinosyn K (101.5 mg, 0.14 mmol). This gave N-demethyl Spinosyn K (79.3 mg; 81%) as a white glass.

Example H7

N-Demethyl Spinosyn D

A suspension of Spinosyn D (5.10 gms, 6.84 mmol) and sodium acetate (10.3 gm, 125 mmol) in 80% methanol/water (500 ml) was heated to 50° C. while bubbling nitrogen through the solution for 15 min. (pH=8.96). The pH dropped to pH 8 on the addition of iodine (3.15 gms, 12.4 mmol) as a solid in one portion, giving a brown color. The pH was maintained at 8–9 by periodic addition of 1N sodium hydroxide. The reaction was heated for 1.5 hr. (during which time the color faded to pale yellow), and was then cooled to ambient temperature. Added 10% aqueous sodium bisulfite (100 mL) to neutralize unreacted iodine. Concentrated the reaction to a total volume of 150 mL on rotary evaporator and extracted solution with 3×100 mL ethyl acetate. Combined ethyl acetate extracts and washed with brine solution (100 mL). Dried ethyl acetate solution over anhydrous potassium carbonate and concentrated on a rotary evaporator. Gave 5.0 gm yellow oil. The crude product was purified by flash chromatography (500 mL $SiO_2$, $CH_2Cl_2$:$CH_3OH$, 95:05) to give N-demethyl Spinosyn D (3.79 gms,75.8%): partial $^1$H-NMR(CDCl$_3$, 300 Mz) d 6.68 (1H, bs), 5.50 (1H, bs), 4.86 (1H, s), 4.67 (1H, m), 4.46 (1H, bd), 4.30 (1H, bd), 2.43 (6H, s), 1.72(3H, s).

Example H8

N,N-Didemethyl Spinosyn K

The reaction was run as described in Example H1 starting with N-demethyl Spinosyn K (891 mg, 1.27 mmol), however the extractive work up was done with EtOAc rather that $Et_2O$. This gave N,N-didemethyl Spinosyn K (463.6 mg) as a colorless glass.

Example H9

Spinosyn F 17-Psa

This compound was prepared as described for Spinosyn E 17-Psa, Example H10, from 35 mg (0.049 mmol) Spinosyn F. Spinosyn F 17-Psa, 24 mg (88%), as a colorless foam was obtained: $^1$H NMR (CDCl$_3$) δ 6.75 (br s, 1H, H-13), 5.83 (d, 1H, H-5), 5.75 (dt, 1H, H-6), 4.82 (s, 1H, H-1') 4.65 (m, 1H, H-21), 4.28 (m, 1H, H-9), 4.15 (m, 1H, H-17), 3.52 (s, 3H, 4'-OCH$_3$), 3.46 (s, 6H, 2'-,3'-OCH$_3$), 1.25 (d, 3H, H-6'); MS m/z 576 (2).

Example H10

Spinosyn E 17-Pseudoaglycone

To a well-stirred suspension of 35 mg of Spinosyn E in water (0.7 mL), 1N $H_2SO_4$ (0.1 mL) was added in one portion. The resulting solution was heated to 90–100° C. and kept at that temperature range for 24 h. The pseudoaglycone separates during this period. The mixture was then cooled to ambient temperature and the crude product extracted into dichloromethane. The organic extracts were then washed with sat. NaCl solution and dried (MgSO$_4$). Evaporation left crude 17-pseudoaglycone which was purified by chromatography over silica gel using 4% methanol in $CH_2Cl_2$ as eluent giving 26 mg (92%) Spinosyn E 17-pseudoaglycone as a colorless foam: $^1$H NMR (CDCl$_3$) δ 6.74 (br s, 1H, H-13), 5.83 (d, 1H, H-5), 5.75 (dt, 1H, H-6), 4.81 (s, 1H, H-1') 4.72 (m, 1H, H-21), 4.28 (m, 1H, H-9), 3.52 (s, 3H, 4'-OCH$_3$), 3.46 (s, 6H, 2'-,3'-OCH$_3$), 1.13 (d, 3H, H-22); MS m/z 576 (2).

Part I DEOXY Rhamnose Derivatives

Example I1

N-Demethyl-2'-deoxy Spinosyn Q

Compound 2'-deoxy Spinosyn Q (940 mg, 1.31 mmol) was dissolved in hot 70% MeOH/30% pH 9 buffer (40 ml). Sodium acetate trihydrate (1.3 gms, 9.6 mmol) was added, and the suspension was heated to 47° C. Iodine (438 mg, 1.7 mmol) was then added as a solid. After stirring at 47° C. for 4 hr, additional Iodine (150.8 mg, 0.59 mmol) was added. The mixture was stirred at 47° C. another 4 hr, and was then cooled to room temperature and stirred an additional 12 hr. The solution was poured into 5% sodium thiosulfate and extracted with $Et_2O$. The $Et_2O$ was washed with brine, dried ($K_2CO_3$), and evaporated at room temperature. The residue was chromatographed on a silica gel column (5% MeOH/ $CH_2Cl_2$) to afford N-demethyl-2'-deoxy Spinosyn Q (462.7 mg; 56% yield, based on recovered starting material as a pale pink solid. FDMS, m/z (relative intensity) 702(100), 159(10).

Example I2

N-demethyl-3'-deoxy Spinosyn J

Reaction was run as described in Example I1 starting with 3'-deoxy Spinosyn J (1.51 gms, 2.16 mmol). This gave N-demethyl-3'-deoxy Spinosyn J (937.6 mg; 63% yield) as a white solid; FDMS, m/e (relative intensity) 687(100) 159(10).

Example I3

3'-Deoxy Spinosyn J 17-Psa

3'-deoxy Spinosyn J (257.2 mg, 0.37 mmol) was suspended in 1N $H_2SO_4$ (5 ml) and heated to reflux for 2.25 hr. The mixture was then cooled to room temperature, diluted with $CH_2Cl_2$ and washed with water. The $CH_2Cl_2$ was then washed with brine, dried ($K_2CO_3$) and evaporated at room temperature. The residue was chromatographed on a silica gel column (50% EtOAc/Hexane) to afford 3'-deoxy Spinosyn J 17-Psa (112 mg; 54% yield); FDMS.m/e,(relative intensity) 560(100), 159(16).

Example I4

9-O-(1-Tetrahydropyranosyl) Spinosyn A 9-Psa (mixture of α and β isomers)

Compound Spinosyn A 9-Psa (106.6 mg, 0.20 mmol) was dissolved in benzene (10 ml) and dihydropyran (21 ml, 0.23 mmol) was added follow by a catalytic amount of p-toluenesulfonic acid. The mixture was heated to reflux for 16 hr. Since no reaction was observed, more dihydropyran (200 ml) was added and the mixture was refluxed with a Dean/Stark trap for 6 hr then cooled to room temperature. The mixture was diluted with $CH_2Cl_2$ and washed with 1N NaOH. The CH$_2$Cl$_2$ was washed with brine, dried (K$_2$CO$_3$) and evaporated at room temperature. The residue (105 mg, mostly Spinosyn A 9-Psa) was dissolved is benzene (10 ml), and dihydropyran (200 ml, 2.2 mmol) was added followed by p-toluenesulfonic acid (42.9 mg, 0.23 mmol). The mixture was stirred at room temperature for 1 hr, and was then diluted with Et$_2$O. The Et$_2$O was washed with saturated NaHCO$_3$, brine, dried (K$_2$CO$_3$) and evaporated at room temperature. The residue was chromatographed on a silica gel chromatotron plate (100% EtOAc, then 10% EtOH/EtOAc, then 100% MeOH, in 2 steps) to afford 9-O-(1-tetrahydropyranosyl) Spinosyn A 9-Psa (mixture of α and β isomers) (116.8 mg; 93% yield); FDMS m/e (relative intensity) 628 (100), 142(5).

Example I5

3'-O-Acetyl Spinosyn J

Compound Spinosyn J (207.9 mg, 0.29 mmol) was dissolved in pyridine (2 ml) and acetic anhydride (140 ml, 1.5 mmol) was added. The mixture was stirred at room temperature for 24 hr, and then evaporated at room temperature. The residue was chromatographed on a silica gel column (7% MeOH/CH$_2$Cl$_2$) to afford 3'-O-acetyl Spinosyn J (148.8 mg, 68% yield) as a colorless glass. FDMS, m/e (relative intensity) 759(100), 283(4), 142(7).

Example I6

2'-O-Acetyl Spinosyn H

The reaction was run as described in Example I5 starting with Spinosyn H (211.9 mg, 0.29 mmol). This gave 2'-O-acetyl Spinosyn H (175.2 mg, 80% yield) as a colorless glass. FDMS, m/e (relative intensity) 759(100), 142(6)

Example I7

4'-O-Acetyl Spinosyn K

The reaction was run as described in Example I5 starting with Spinosyn K (207.0 mg, 0.29 mmol). This gave 4'-O-acetyl Spinosyn K (204.9 mg, 93% yield) as a white glass. FDMS, m/e (relative intensity) 759(100).

Example I8

4'-O-[(S-Methyl)dithiocarbonyl] Spinosyn K

Spinosyn K (201.0 mg, 0.28 mmol) and imidizole (catalytic amount) were dissolved in anhydrous THF (2 ml), and stirred at room temperature under nitrogen. Sodium hydride (50% in mineral oil; 25 mg, 0.52 mmol) was added to the solution, followed by carbon disulfide (90 ml, 1.5 mmol) and then methyl iodide (90 ml, 1.44 mmol). After stirring at room temperature for 1 hr acetic acid (90 ml) was added, and the mixture was poured into saturated NaHCO$_3$. This aqueous solution was then extracted with CH$_2$Cl$_2$. The CH$_2$Cl$_2$ was washed with brine, dried (MgSO$_4$) and evaporated at room temperature to afford 4'-O-[(S-methyl)dithiocarbonyl] Spinosyn K (218.1 mg, 97% yield) as a yellow glass. FDMS, m/e (relative intensity) 808(100).

Example I9

3'-O-[(S-Methyl)dithiocarbonyl] Spinosyn J

The reaction was run as described in Example I8 starting with Spinosyn J (207.1 mg, 0.29 mmol). This gave 3'-O-[(S-methyl)dithiocarbonyl] Spinosyn J (224.0 mg, 96% yield) as a yellow glass. FDMS, m/z (relative intensity) 808(100).

Example I10

2'-O-[(S-Methyl)dithiocarbonyl] Spinosyn H

The reaction was run as described in Example I8 starting with Spinosyn H (204.0 mg, 0.28 mmol). This gave 2'-O-[(S-methyl)dithiocarbonyl] Spinosyn H (218.8 mg, 97% yield) as a yellow glass. FDMS, m/z (relative intensity) 808(100).

Example I11

2'-O-[(S-Methyl)dithiocarbonyl] Spinosyn Q

The reaction was run as described in Example I8 starting with Spinosyn Q (1.00 gms, 1.4 mmol). This gave 2'-O-[(S-methyl)dithiocarbonyl] Spinosyn Q (1.13 gms, 98% yield) as a yellow glass. FDMS, m/z, relative intensity 822(100).

Example I12

3'-O-(S-Methyl)dithiocarbonyl) Spinosyn L

Spinosyn L (1.65 gms, 2.2 mmol) was dissolved in anhydrous THF (50 ml) and cooled in an ice bath under nitrogen. Imidizole (21.2 mg, 0.3 mmol) was added to the solution, followed by sodium hydride (60% in mineral oil; 105.0 mg, 2.6 mmol) then carbon disulfide (700 ml, 11.64 mmol) and methyl iodide (700 ml, 11.1 mmol). This mixture was stirred for 1 hr at room temperature, then a slight amount of NaH was added and stirring continued for 1 hr. The mixture was poured into saturated ammonium chloride and extracted with CH$_2$Cl$_2$. The CH$_2$Cl$_2$ was dried (K$_2$CO$_3$) and evaporated at room temperature to afford 3'-O-(S-methylthionocarbonyl) Spinosyn L (1.86 gms, 100% yield) as a yellow solid. FDMS, m/e (relative intensity) 821(100), 160(4).

Example I13

4'-Deoxy Spinosyn K

Compound 4'-O-[(S-methyl)dithiocarbonyl] Spinosyn K (182.5 mg, 0.23 mmol) was dissolved in toluene (10 ml). Tributyltin hydride (93 ml, 0.35 mmol) and AIBN (catalytic amount) were added and the solution was refluxed. After 2 hr more tributyltin hydride (100 ml) was added. The mixture was refluxed an additional 12 hr, and then stirred at room temperature for 5 hr. Solvent was then evaporated to a small volume, and the residue was chromatographed on a silica gel column (80% EtOAc/Hexane) to afford 4'-deoxy Spinosyn K (59.9 mg, 37% yield) as a colorless glass. FDMS, m/e (relative intensity 702(100).

Example I14

3'-Deoxy Spinosyn J

Compound 3'-O-[(S-methyl)dithiocarbonyl] Spinosyn J(849.1 mg, 1.05 mmol) was dissolved in anhydrous toluene (50 ml). Fresh tributyltin hydride (500 ml, 1.6 mmol) and AIBN (10.2 mg) were added and the mixture was refluxed. After 8 hr. additional AIBN (32.8 mg) was added, and refluxing continued for 2 hr. After sitting at 5° C. for 48 hrs., the solvent was evaporated to a small volume. The residue was chromatographed on a silica gel column (3.5% MeOH/

CH$_2$Cl$_2$) to afford 3'-deoxy Spinosyn J (557.0 mg, 76% yield) as a colorless glass. FDMS, m/z (relative intensity) 701(100).

Example I15

2'-Deoxy Spinosyn H

Compound 2'-O-[(S-methyl)dithiocarbonyl] Spinosyn H(1.15 gms, 1.4 mmol) was dissolved in anhydrous toluene 50 ml. Fresh tributyltin hydride (750 ml, 2.8 mmol) and AIBN (30 mg) were added and the mixture was refluxed. After 2.5 hr more AIBN (20.5 mg) was added and refluxing continued for 5 hr. After stirring at room temperature for 11.5 hr, the solvent was evaporated to a small volume and the residue chromatographed on a silica gel column (3.5% MeOH/CH$_2$Cl$_2$) to afford 2'-deoxy Spinosyn H (821.5 mg, 84% yield) as a colorless glass. FDMS, m/z (relative intensity) 701(100).

Example I16

2'-Deoxy Spinosyn Q

Compound 2'-O-[(S-methyl)dithiocarbonyl] Spinosyn Q(1.08 gms, 1.3 mmol) was dissolved in anhydrous toluene (50 ml). Fresh tributyltin hydride (750 ml, 2.8 mmol) and AIBN (47.5 mg) were added and the mixture was reluxed 2.5 hr, and then cooled to room temperature. After 20 hr, the solvent was evaporated and the residue was chromatographed on a silica gel column (3.5% MeOH/CH$_2$Cl$_2$) to afford 2'-deoxy Spinosyn Q (912.9 mg, 98% yield) as a colorless glass. FDMS, m/z (relative intensity) 716(100).

Example I17

3'-deoxy Spinosyn L

The reaction was run as described in Example I16 starting with 3'-O-(S-methylthionocarbonyl) Spinosyn L(1.85 gms, 2.25 mmol). This gave 3'-deoxy Spinosyn L (1.16 gms, 74% yield) as a colorless glass. FDMS, m/e (relative intensity) 716(100).

Example I18

9-O-(α-L-3,4-di-O-acetylrhamnosyl) Spinosyn A 9-Psa

Spinosyn A 9-Psa (1.56 gms, 2.9 mmol) and 1-Bromo-2,3,4-tri-O-acetylrhamnose[1] (1.52 gms, 4.3 mmol) were dissolved in CH$_2$Cl$_2$ (75 ml; anhydrous). Tetramethyl urea (1.0 ml, 8.4 mmol) was added, followed by silver trifluoromethanesulfonate (823.8 mg, 3.2 mmol), and the reaction flask was covered with foil. After stirring 24 hr. at room temperature in the dark, the reaction mixture was filtered through celite, and the celite was washed with fresh CH$_2$Cl$_2$. The filtrate was then collected and washed with saturated NaHCO$_3$, dried (MgSO$_4$), and evaporated at room temperature. The residue was placed under high vacuum to yield a thick yellow oil 3.29 gms. This material was chromatographed on a silica gel column (5% EtOH/CH$_2$Cl$_2$, washing column with 100% EtOH) to afford product 9-O-(α-L-3,4-di-O-acetylrhamnosyl) Spinosyn A 9-Psa(259.6 mg, 15% based on recovered Spinosyn A 9-Psa as a colorless glass). IR (KBr, cm$^{-1}$) 3480.99 (OH), 2938.92, 1747.73, 1661.89, 1457.41, 1373.49, 1232.67, 1164.19, 1125.61, 1042.66, 988.64, 902.80. FDMS (m/z, rel inten) 774 (100). Anal (C$_{42}$H$_{63}$NO$_{12}$) calc, C: 65.18, H: 8.20, N: 1.81; found, C: 64.94, H: 8.28, N: 1.97.

Example I19

3,4-Di-O-ethyl-6-deoxy-L-glucal

Ethyl iodide (32 mL, 0.40 mol), 3,4-di-O-acetyl-6-deoxy-L-glucal (4.28 g, 0.20 mol), 50% aqueous NaOH (43 mL, 0.81 mol) and DMSO (11.4 mL, 0.16 mol) were added sequentially to a 300-mL round-bottom, three-neck flask equipped with an overhead stirrer. Stirring was begun and tetrabutylammonium hydrogen sulfate (2.04 g, 0.006 mol) added in a single portion. Stirring was continued for 66 h. The mixture was partitioned between water and Et$_2$O. The aqueous layer was extracted twice with Et$_2$O (20 mL) and a final time with 1:1 Et$_2$O-CH$_2$Cl$_2$ (20 mL). The organic layers were combined, washed successively with water, dilute aqueous sodium thiosulfate, water and brine and dried over sodium sulfate and potassium carbonate and concentrated under reduced pressure. A white solid precipitated during evaporation. The mixture was diluted with pentane and the solid removed by filtration. The solvent was removed from the filtrate under reduced pressure to yield a pale yellow oil (3.2 g, 87%) which was sufficiently homogeneous to use in subsequent reactions without additional purification. $^1$H NMR d 6.32 (dd, J=6.1, 0.6, 1 H), 4.78 (dd, J=6.1, 1.2, 1 H), 1.36 (d, J=6.4, 3 H), 1.22 (t, J=7.0, 6 H).

Example I20

3,4-Di-O-n-propyl-6-deoxy-L-glucal n-Propyl iodide (39 mL, 0.40 mol), 3,4-di-O-acetyl-6-deoxy-L-glucal (4.28 g, 0.20 mol), 50% aqueous NaOH (43 mL, 0.81 mol) and DMSO (11.4 mL, 0.16 mol) were added sequentially to a 300-mL round-bottom, three-neck flask equipped with an overhead stirrer. Stirring was begun and tetrabutylammonium hydrogen sulfate (2.04 g, 0.006 mol) added in a single portion. The mixture was stirred for 17 h. at room temperature. The mixture was partitioned between water and pentane. The aqueous layer was extracted with additional pentane. The combined organic layers were successively washed with water (three times), dilute aqueous sodium thiosulfate, dilute sodium bicarbonate and brine. The solvent was removed under reduced pressure (20 Torr followed by 0.1 Torr) to yield a pale yellow oil (4.0 g, 94%) that could be used without further purification. $^1$H NMR d 6.31 (dd, J=6.1, 1.4, 1 H), 4.78 (dd, J=6.1, 2.4, 1 H), 1.60 (m, 4 H), 1.37 (d, J=6.4, 3 H), 0.93 (t, J=6.3, 3 H), 0.94 (t, J=6.3, 3 H).

Example I21

3,4-Di-O-i-propyl-6-deoxy-L-glucal i-Propyl iodide (40 mL, 0.40 mol), 3,4-di-O-acetyl-6-deoxy-L-glucal (4.28 g, 0.20 mol), 50% aqueous NaOH (43 mL, 0.81 mol) and DMSO (11.4 mL, 0.16 mol) were added sequentially to a 300 mL round-bottom, three-neck flask equipped with an overhead stirrer. Stirring was begun and tetrabutylammonium hydrogen sulfate (2.04 g, 0.006 mol) added in a single portion. The mixture was stirred for 67 h. at room temperature and for 24 h at reflux temperature. The mixture was cooled to room temperature and partitioned between water and pentane. The aqueous layer was extracted with additional pentane. The combined organic layers were successively washed with water (four times), dilute aqueous sodium thiosulfate, water, and saturated sodium bicarbonate. The solvent was removed under reduced pressure (20 Torr followed by 0.1 Torr) to yield a light yellow oil (1.2 g, 28%) that could be used without further purification. $^1$H NMR d 6.29 (dd, J=6.1, 1.4, 1 H), 4.70 (dd, J=6.1, 2.4, 1 H), 1.35 (d, J=6.4, 3 H), 1.21 (d, J=6.4, 3 H), 1.18 (d, J=6.4, 6 H), 1.17 (d, J=6.4, 3 H).

Example I22

9-(2-Deoxy-3-O,4-O-di-n-propyl-1-a-rhamnosyl)-spinosyn A 9-pseudoaglycone and 9-(2-deoxy-3-O,4-O-di-n-propyl-1-β-rhamnosyl)-spinosyn A 9-pseudoaglycone Used the same procedure and work-up as in Example I29 with the following amounts: Spinosyn A 9-pseudoaglycone (544 mg, 1.00 mmol), $CH_2Cl_2$ (4 mL), 3,4-Di-O-n-propyl-6-deoxy-L-glucal (429 mg, 2.00 mmol) and camphorsulfonic acid (279 mg, 1.20 mmol). The crude product was chromatographed on silica gel (80 g) with 3% MeOH in $CHCL_3$ and on a reversed-phase column (Kromasil' C18, Silica ODS, 100 Å, 10 m, spherical, 25 cm×20 mm) with 90% MeOH and 10% water (containing 0.1% v/v conc. aqueous $NH_4OH$) to yield both anomeric products as white foams; α-anomer (307 mg, 41%) $^1H$ NMR d 4.85 (br d, J=2.9, 1 H), 0.94 (t, J=7.5, 3 H), 0.92 (t, J=7.5, 3 H) and β-anomer (80 mg, 10%) $^1H$ NMR d 4.42 (m, 2 H), 0.93 (t, J=7.3, 3 H), 0.92 (t, J=7.3, 3 H).

Example I23

9-(2-Deoxy-3-O,4-O-di-i-propyl-1-α-rhamnosyl)-Spinosyn A 9-pseudoaglycone

Used the same procedure and work-up as in Example I29 with the following amounts: Spinosyn A 9-pseudoaglycone (543 mg, 1.00 mmol), $CH_2Cl_2$ (4 mL), 3,4-Di-O-n-propyl-6-deoxy-L-glucal (428 mg, 2.00 mmol) and camphorsulfonic acid (279 mg, 1.20 mmol). The crude product was chromatographed on silica gel (100 g) with EtOAc and on a reversed-phase column (Kromasil' C18, Silica ODS, 100 Å, 10 m, spherical, 25 cm×20 mm) with 90% MeOH and 10% water (containing 0.1% v/v conc. aqueous $NH_4OH$) to yield a white powder (306 mg, 40%). $^1H$ NMR d 4.84 (br d, J=2.9, 1 H), 1.40–1.13 (m, 25 H).

Example I24

1-(O,O-Diethyldithiophosphoryl)-2-deoxy-3,4-di-O-acetyl-rhamnose 3,4-Di-O-acetyl-6-deoxy-L-glucal (2.14 g, 10.0 mmol) was dissolved in benzene (20 mL). A solution of O,O-diethyldithiophosphoric acid (1.96 g, 10.5 mmol) in benzene (10 mL) was added over 5 min and the resulting mixture stirred at room temperature for 18 h. Additional dithiophosphoric acid was added (0.10 g, 0.54 mmol) and the mixture stirred an additional 20 h. The mixture was extracted with dilute aqueous sodium bicarbonate (two times), water and brine. The mixture was dried with $Na_2SO_4$ and $MgSO_4$ and the solvent removed under reduced pressure to yield a yellow oil (4.03 g, 101%).

Example I25

9-(2-Deoxy-3-O,4-O-diacetyl-1-α-rhamnosyl)-spinosyn A 9-pseudoaglycone

Powdered 4 Å molecular sieves (500 mg) and AgF (685 mg, 5.40 mmol) were suspended in acetonitrile (2 mL). A solution of 1-(O,O-diethyldithiophosphoryl)-2-deoxy-3,4-di-O-acetyl-rhamnose (400 mg, 1.00 mmol) in acetonitrile was added in a single portion. The resulting dark greenish brown mixture was stirred at room temperature for 6 days. The mixture was filtered through Celite to remove a black precipitate, the solvent evaporated and the residue dissolved in a 1:1 mixture of $EtOAc-Et_2O$ (20 mL). The mixture was washed successively with dilute aqueous NaOH (twice), water (twice) and brine. The solvent was evaporated and the residue chromatographed on a reversed-phase column (Kromasil' C18, Silica ODS, 100 Å, 10 m, spherical, 25 cm×20 mm) using 90% MeOH and water (containing 0.1% v/v conc. aqueous $NH_4OH$) to yield an amorphous white solid (36 mg, 9%). $^1H$ NMR d 4.85 (br d, J=2.9, 1 H), 2.08 (s, 3 H), 2.01 (s, 3 H).

Example I26

9-(2H-5-R-Acetoxy-5,6-dihydro-6-S-methyl-2-a-pyranyl)-spinosyn A 9-pseudoaglycone Spinosyn A 9-pseudoaglycone (272 mg, 0.500 mmol) and 3,4-di-O-acetyl-6-deoxy-L-glucal (214 mg, 1.00 mmol) were dissolved in $CH_2CL_2$ (3 mL). Molecular sieves (4 Å, 40 mg) and camphorsulfonic acid (128 mg, 0.550 mmol) were added. After 18 h additional camphorsulfonic acid (20 mg, 0.086 mmol) was added. The mixture was stirred for 3 days. The mixture was diluted with $CH_2Cl_2$ (10 mL) and washed with a 1:1:1 mixture of water-saturate aqueous sodium bicarbonate-1.0N NaOH. The aqueous layer was extracted with $CH_2Cl_2$ (twice) and the combined organic phases washed with water, dried with anhydrous sodium sulfate and evaporated to yield a dark oil. The residue was chromatographed on a reversed-phase column (Kromasil' C18, Silica ODS, 100 Å, 10 m, spherical, 25 cm×20 mm) using 90% MeOH and 10% water (containing 0.1% v/v conc. aqueous $NH_4OH$) to yield a white foam (44 mg, 11%). $^1H$ NMR d 5.92–5.73 (m, 4 H), 5.01 (br s, 1 H), 2.09 (s, 3 H).

Example I27

5,6-Dihydro-9-(2-deoxy-3-O,4-O-diethyl-1-α-rhamnosyl)-spinosyn A 9-pseudoaglycone 9-(2-deoxy-3-O,4-O-diethyl-1-a-rhamnosyl)-spinosyn A 9-pseudoaglycone (200 mg, 273 mmol) and cyclohexene (0.40 mL, 3.95 mmol) were dissolved in absolute ethanol (4 mL). Palladium on charcoal (10%, 20 mg, 19 mmol) was added cautiously and the resulting mixture heated at reflux temperature for 3 hr. The mixture was stirred an additional 17 hr. at room temperature. The mixture was filtered through Celite and evaporated under a stream of nitrogen. The residue was chromatographed on a reversed-phase column (Kromasil' C18, Silica ODS, 100 Å, 10 m, spherical, 25 cm×20 mm) with 90% MeOH and 10% water (containing 0.1% v/v conc. aqueous $NH_4OH$) to yield a glassy solid (45 mg, 22%) $^1H$ NMR d 6.83 (br s, 1 H), 2H-multiplet at 5.9–5.7 absent.

Example I28

5,6-Dihydro-9-(2-deoxy-3-O,4-O-di-n-propyl-1-α-rhamnosyl)-spinosyn A 9-pseudoaglycone Cyclohexene (3.0 mL, 28.6 mmol) and palladium on charcoal (10%, 43 mg) were added to absolute ethanol (3 mL). A solution of 9-(2-deoxy-3-O,4-O-di-n-propyl-1-a-rhamnosyl)-spinosyn A 9-pseudoaglycone (188 mg, 0.248 mmol) in ethanol (2 mL) was added and the mixture heated at reflux temperature for 5.5 h. Additional palladium on charcoal was added to the reaction mixture at 1 h (38 mg)

and at 4.5 h (67 mg). The mixture was cooled, filtered through Celite and concentrated to a thick oil. The residue was dissolved in $Et_2O$ and washed with concentrated aqueous sodium bicarbonate and brine, dried over anhydrous potassium carbonate and evaporated to yield a light gray foam. This material was chromatographed on a reversed-phase column (Kromasil' C18, Silica ODS, 100 Å, 10 m, spherical, 25 cm×20 mm) with 92% MeOH and 8% water (containing 0.1% v/v conc. aqueous $NH_4OH$) to yield a white amorphous powder (80 mg, 42%). $^1H$ NMR d 6.73 (br s, 1 H), 2H-multiplet at 5.9–5.7 absent.

Example I29

9-(2-Deoxy-3-O,4-O-diethyl-1-α-rhamnosyl)-Spinosyn A 9-pseudoaglycone

Spinosyn A 9-pseudoaglycone (136 mg, 0.250 mmol) was dissolved in $CH_2Cl_2$ (1 mL). 3,4-Di-O-ethyl-6-deoxy-L-glucal (93 mg, 0.50 mmol) and camphorsulfonic acid (70 mg, 0.30 mmol) were added sequentially in single portions. The reaction mixture was stirred at room temperature for one hour. Saturated aqueous sodium bicarbonate was added and the mixture diluted with EtOAc (5 mL). The mixture was partitioned between a mixture of saturated aqueous sodium bicarbonate (10 mL) and 1.0N NaOH (2 mL) and EtOAc (10 mL). The aqueous layer was extracted with additional EtOAc. The combined organic layers were washed with successively with saturated aqueous sodium bicarbonate and brine and dried over anhydrous $Na_2SO_4$. The solvent was removed under reduced pressure and the residue chromatographed on a reversed-phase column (Kromasil' C18, Silica ODS, 100 Å, 10 m, spherical, 25 cm×20 mm) using 90% MeOH and 10% water (containing 0.1% v/v conc. aqueous $NH_4OH$) to yield an amorphous white solid (74 mg, 40%). $^1H$ NMR d 4.84 (br d, J=2.9, 1H), 1.21 (t, J=7.1, 3 H), 1.20 (t, J=7.2, 3 H).

Part J Modification of Pseudoaglycone A2 by Replacement of Rhamnose Sugar

Example J1

9-O-[(1'S,2'S,3'S)-2-Methyl-4-(1',2'-bis-acetoxy-3'-hydroxybutyl)-5-hydroxy-1,3-dioxolan-2-yl] Spinosyn A 9-Psa mixture at position 2 and 5 of dioxalane ring To a solution of Spinosyn A 9-Psa (100.8 mg, 0.19 mmol) in dichloromethane (5 ml), 1-bromo-2,3,4-tri-O-acetyl-rhamnose[1] (67.9 mg, 0.19 mmol) followed by silver triflate (52.3 mg, 0.2 mmol) and then diisopropylethylamine (35 µl, 0.2 mmol) were added. The reaction mixture was stirred at room temperature in the dark for 3.5 hours. The mixture was then diluted with dichloromethane and washed with water. The dichloromethane was then washed with brine, dried with MgSO4 and evaporated at room temperature under reduced pressure. The product was seperated from unreacted starting material by chromatography on silica, eluting with 5% methanol in dichloromethane. This gave 9-O-[(1'S,2'S,3'S)-2-Methyl-4-(1',2'-bis-acetoxy-3'-hydroxybutyl)-5-hydroxy-1,3-dioxolan-2-yl] Spinosyn A 9-Psa mixture at position 2 and 5 of dioxolane ring (75.2 mg; 49% yield), FDMS, m/e (relative intensity) 816 ($M^+$, 70), 815 (100), 585 (10).

Example J2

9-O-[(1'S,2'S,3'S)-2-Methyl-4-(1',2'-3'-trihydroxybutyl)-5-hydroxy-1,3-dioxolan-2-yl] Spinosyn A 9-Psa mixture at position 2 and 5 of dioxalane ring To a solution of 9-O-[(1'S,2'S,3'S)-2-Methyl-4-(1',2'-bis-acetoxy-3'-hydroxybutyl)-5-hydroxy-1,3-dioxolan-2-yl] Spinosyn A 9-Psa mixture at position 2 and 5 of dioxalane ring (104.2 mg, 0.12 mmol) in methanol (4 ml), a slight amount of sodium hydride (60% dispersion in mineral oil) was added with gas evolution. The reaction mixture was stirred at room temperature of 15 min. The mixture was then diluted with dichloromethane and washed with aqueous saturated ammonium chloride. The dichloromethane was then washed with brine, dried with $MgSO_4$, and evaporated at room temperature under reduced pressure. This gave 9-O-[(1'S,2'S,3'S)-2-Methyl-4-(1',2'-3'-trihydroxybutyl)-5-hydroxy-1,3-dioxolan-2-yl] Spinosyn A 9-Psa mixture at position 2 and 5 of dioxalane ring (44.2 mg; 50% yield) as a beige solid, FDMS, m/e (relative intensity) 733 (95), 732 ($M^+$, 100), 543 (10).

Example J3

9-O-(2-Methoxyethoxymethyl) Spinosyn A 9-Psa

To a solution of Spinosyn A 9-Psa (474.3 mg, 0.87 mmol) in dichloromethane (20 ml), diisopropylethylamine (225 µl, 1.3 mmol) and 2-methoxyethoxymethyl chloride (100 µl, 0.87 mmol) were added. The reaction mixture was heated to reflux for 24 hours and then stirred at room temperature for 2 days. The mixture was then diluted with dichloromethane, and washed with aqueous saturated $NaHCO_3$. The dichloromethane was dried with $K_2CO_3$, and evaporated at room temperature under reduced pressure. The product was separated from unreacted starting material by chromatography on silica, eluting with 4% methanol in dichloromethane, then 10% methanol in dichloromethane in 1 step. This gave 9-O-(2-methoxyethoxymethyl) Spinosyn A 9-Psa (226.5 mg; 56% yield, based on recover starting material) as a colorless glass, FDMS, m/e (relative intensity) 632 ($M^+$, 40), 631 (100).

Example J4

9-O-Methyl Spinosyn A 9-Psa

To a solution of Spinosyn A 9-Psa (200.1 mg, 0.37 mmol) in THF (2 ml), sodium hydride (50% dispersion in mineral oil; 34.6 mg, 0.72 mmol) was added followed by iodomethane (90 µl, 1.4 mmol). The reaction mixture stirred at room temperature, while slow evaporation took place over 3.5 hour. The mixture was then diluted with ether and washed with water. The ether was then washed with brine, dried with $K_2CO_3$ and evaporated at room temperature under reduced pressure. The product was seperated from unreacted starting material by chromatography on silica, eluting with 7% methanol in dichloromethane. This gave 9-O-methyl Spinosyn A 9-Psa (75.6 mg; 37% yield) as a white glass, FDMS, m/e (relative intensity) 558 ($M^+$, 60), 557 (100).

Example J5

9-O-[(2R,3S,4S,5R,9R)-2-Methyl-3-acetoxy-4-dimethylamino-7-methyl-1,6,8-trioxo[4.3.0]bicyclononan-7-yl] Spinosyn A 9-Psa To a solution of Spinosyn A 9-Psa (564.5 mg, 1.04 mmol) and 1-bromo-2,4-di-O-acetylmycaminose hydrobromide[2] (487.4 mg, 1.15 mmol) in anhydrous dichloromethane (30 ml), tetramethyl urea (358 ml, 3.0 mmol) and silver triflate (298.4 mg, 1.16 mmol) were added. The reaction mixture stirred at room temperature in the dark for 20 hours. The mixture was then diluted with dichloromethane and washed with 1N NaOH. The dichloromethane was then washed with brine, dried with $K_2CO_3$ and evaporated at room temperature under reduced pressure. The product was separated from unreacted starting material by chromatography on silica, eluting with 5% methanol in dichloromethane. This gave 9-O-[(2R,3S,4S,5R,9R)-2-methyl-3-acetoxy-4-dimethylamino-7-methyl-1,6,8-trioxo[4.3.0]bicyclononan-7-yl] Spinosyn A 9-Psa (101.9 mg; 13% yield, based on recovered starting material) as a mixture of isomers, FDMS, m/e (relative intensity) 828 (20), 800 ($M^+$-H, 100), 759 (20), 543 (30).

[2]Tatsuka, K.; Tanaka, A.; Fujimoto, K.; Kinoshita, M.; Umezawa, S. *J. Am. Chem. Soc.* 1977, 99(17), 5826.

Example J6

9-O-Acetyl Spinosyn A 9-Psa

To a solution of Spinosyn A 9-Psa (167.3 mg, 0.31 mmol) in chloroform (5 ml), diisopropylethylamine (220 μl, 1.26 mmol) followed by acetyl chloride (220 ml, 3.1 mmol) were added. The reaction mixture was stirred at room temperature for 2 hour. The mixture was then diluted with ether and washed with 1N NaOH, then with brine, dried with $K_2CO_3$ and evaporated at room temperature under reduced pressure. The product was purified by chromatography on silica, eluting with 50% ethyl acetate in hexane. This gave 9-O-acetyl Spinosyn A 9-Psa (110.6 mg; 61% yield) as an off white glass, FDMS, m/e (relative intensity) 586 (50), 585 ($M^+$, 100).

Example J7

9-O-Carboethoxyacetyl Spinosyn A 9-Psa

The reaction was run as described in Example J6 starting with Spinosyn A 9-Psa (177 mg, 0.33 mmol) and ethyl malonyl chloride. This gave 9-O-carboethoxyacetyl Spinosyn A 9-Psa (124.4 mg; 57% yield) was an off white glass, FDMS, m/e (relative intensity) 658 ($MH^+$, 100).

Example J8

9-O,N-Dimethyl Spinosyn A 9-Psa Iodide

To a solution of Spinosyn A 9-Psa (101.1 mg, 0.19 mmol) in DMF (0.5 ml), silver (II) oxide (81.9 mg, 0.35 mmol) and iodomethane (35 μl, 0.56 mmol) were added. The reaction mixture stirred at room temperature in the dark for 7 days. The mixture was then diluted with ether and filtered. The precipitate was dissolve in water and washed with fresh ether. The water was then freeze dried, and the residue was triturated with ether, and dried under a stream of nitrogen. This gave 9-O,N-dimethyl Spinosyn A 9-Psa iodide (13.5 mg; 10% yield) as a tan solid, FDMS, m/e (relative intensity) 761 (10), 573 (30), 572 ($M^+$, 100), 188 (25).

Example J9

9-O-[(S-Methyl)dithiocarbonyl] Spinosyn A 9-Psa

To a solution of Spinosyn A 9-Psa (205.5 mg, 0.38 mmol) and a crystal of imidizole, in anhydrous THF (2 ml), sodium hydride (50% dispersion in mineral oil; 33.8 mg, 0.7 mmol) followed by carbon disulfide (90 μl, 1.5 mmol) and then iodomethane (90 μl, 1.4 mmol) were added. The reaction mixture was stirred at room temperature for 2 hours then glacial acetic acid (90 μl) was added. The mixture was then poured into aqueous saturated $NaHCO_3$ and extracted with dichloromethane. The dichloromethane was washed with brine, dried with $MgSO_4$ and evaporated at room temperature under reduced pressure. This gave 9-O-[(S-methyl)dithiocarbonyl] Spinosyn A 9-Psa (230 mg; 95% yield) as a yellow glass, FDMS, m/e (relative intensity) 634 ($M^+$, 60), 633 (100), 142 (50).

Example J10

9-O-[(2R,3S,4S,5R,9R)-2-Methyl-3-hydroxy-4-dimethylamino-7-methyl-1,6,8-trioxo[4.3.0] bicyclononan-7-yl] Spinosyn A 9-Psa The reaction was run as described in Example J2 starting with 9-O-[(2R,3S,4S,5R,9R)-2-methyl-3-acetoxy-4-dimethylamino-7-methyl-1,6,8-trioxo[4.3.0]bicyclononan-7-yl] Spinosyn A 9-Psa (40 mg, 0.05 mmol). This gave 9-O-[(2R,3S,4S,5R,9R)-2-methyl-3-hydroxy-4-dimethylamino-7-methyl-1,6,8-trioxo[4.3.0]bicyclononan-7-yl] Spinosyn A 9-Psa (15.2 mg; 40% yield), FDMS, m/e (relative intensity) 759 ($M^+$, 100), 543 (35).

Example J11

9-O-m-Methoxybenzoyl-spinosyn A 9-pseudoaglycone

Same procedure as used for Example J18, except pyrrolidinopyridine added immediately and $Et_2O$ used in place of EtOAc in workup. The same chromatographic conditions were used to yield an amorphous white solid (110 mg, 54%), $^1$H NMR d 7.61 (dd, J=7.7, 0.9, 1 H), 7.54 (t, J=2, 1 H) 7.34 (t, J=7.8 1 H), 7.10 (dd, J=8.2, 2.0), 3.86 (s, 3 H).

Example J12

9-O-p-Methoxybenzoyl spinosyn A 9-pseudoaglycone

Same procedure as used for Example J18, except pyrrolidinopyridine added immediately and $Et_2O$ used in place of EtOAc in workup. The same chromatographic conditions were used to yield an amorphous white solid (100 mg, 49%), $^1$H NMR d 7.98 (d, J=8.9, 2 H), 6.92 (d, J=8.9, 2 H), 3.87 (s, 3 H).

Example J13

9-Epi-9-O-phenoxyacetyl-spinosyn A 9-pseudoaglycone

Spinosyn A 9-pseudoaglycone (544 mg, 1.00 mmol) and triphenylphosphine (525 mg, 2.00 mmol) were dissolved in benzene (5 mL) and the solution cooled to 4° C. Diethyl azodicarboxylate (0.31 mL, 2.00 mmol) was added dropwise at such a rate that the temperature remained below 5° C. and the color of the reagent was discharged between drops. The mixture was stirred for an additional 20 min while maintaining the temperature at 5° C.–11° C. and then 60 min. without cooling. The reaction was quenched with water and dilute aqueous sodium bicarbonate and partitioned between EtOAc and dilute aqueous sodium bicarbonate. The aqueous layer was extracted with EtOAc (twice). The combined organic layers were washed successively with dilute aqueous sodium bicarbonate (twice) and brine. The mixture was dried over anhydrous sodium sulfate and evaporated to yield an oily solid. This solid was dissolved in $Et_2O$ and extracted with dilute HCl (three times). The milky appearing aqueous layers were combined and extracted with $Et_2O$. The pH of the aqueous layer was adjusted to approximately 10 with 1.0N NaOH and extracted with EtOAc (two times). The combined EtOAc portions were washed with brine (twice)

and dried over anhydrous sodium sulfate. The solvent was evaporated and the residue chromatographed on a reversed-phase column (Kromasil' C18, Silica ODS, 100 Å, 10 m, spherical, 25 cm×20 mm) with 90% MeOH and 10% water (containing 0.1% v/v conc. aqueous NH$_4$OH) to yield a white amorphous solid (0.54 g, 79%) $^1$H NMR d 7.26 (t, J=8.4, 2 H), 6.95 (t, J=8.4, 1 H), 6.87 (d, J=8.4, 2 H), 5.35 (br q, J=6.0, 1 H), 4.58 (s, 2 H).

Example J14

9-O-(2,3,5-Tri-O-methyl)-α-L-ribofuranosyl) Spinosyn A 9-Psa and 9-O-(2,3,5-Tri-O-methyl)-b-L-ribofuranosyl) Spinosyn A 9-Psa A 9:1 mixture of α:β 9-O-(2,3,5-tri-O-methyl)-α-L-ribofuranosyl) Spinosyn A 9-Psa was obtained in 84% yield from the reaction of Spinosyn A 9-psa (0.33 g, 0.63 mmol), pyridinium p-toluenesulfonate (0.2 g, 0.8 mmol) and O-(2,3,5-tri-O-methyl-β-L-ribofuranosyl)trichloroacetimidate (1.6 g, 4.75 mmol) by the same procedure as that used in Example J18. The α and β anomers were separated by hplc over a 41.4 mm (i.d.)×25 cm (1) reverse phase C18 column. The α-anomer elutes first. α anomer: 100 mg; colorless foam; $^1$H NMR (acetone-d6, 400 MHz) δ 7.06 (s, 1H, H-13), 5.10 (d, J=4.1, 1H, H-1'), 4.66 (m, 1H, H-21), 4.47 (dd, J=10, 2, 1H, H-1"), 4.32 (m, 1H, H-9); MS m/z 719 (100). β anomer: 11 mg; colorless foam; $^1$H NMR (acetone-d6, 400 MHz) δ 7.05 (s, 1H, H-13), 4.99 (d, J=1.2, 1H, H-1'), 4.66 (m, 1H, H-21), 4.47 (dd, J=10, 2, 1H, H-1"), 4.32 (m, 1H, H-9); MS m/z 719 (100).

Example J15

9-O-(2,3,4,6-Tetra-O-methyl)-α-L-mannopyranosyl) Spinosyn A 9-Psa and 9-O-(2,3,4,6-Tetra-O-methyl-β-L-mannopyranosyl) Spinosyn A 9-Psa A 1.9:1 anomeric mixture of α and β 9-O-(2,3,4,6-tetra-O-methyl)-α-L-mannopyranosyl) Spinosyn A 9-Psa (0.4 g, 71% yield) was obtained from the reaction of Spinosyn A 9-psa (0.4 g, 0.74 mmol), pyridinium p-toluenesulfonate (0.25 g, 1.0 mmol) and O-(2,3,4,6-tetra-O-methyl-α-L-mannopyranosyl)tri-chloroacetimidate (1.7 g, 4.49 mmol) by the same procedure as that described in Example J18. The anomers were separated by reversed-phase hplc in two portions over a C18 bonded silica (8 μm) column (41.4 mm (i.d.)×25 cm (1)) using 10% H$_2$O (containing 0.1% NH$_4$OH) in MeOH as eluent. The β-anomer elutes first. β anomer: 18 mg; colorless foam; $^1$H NMR (CDCl$_3$) δ 6.74 (s, 1H, H-13), 4.63 (m, 1H, H-21), 4.42 (m, 2H, H-9, H-1"), 4.38 (s, 1H, H-1'); MS m/z 762 (100). α anomer: 95 mg; colorless foam; $^1$H NMR (CDCl$_3$) δ 6.75 (s, 1H, H-13), 4.93 (d, J=1.2, 1H, H-1'), 4.63 (m, 1H, H-21), 4.42 (d, J=7.5, 1H, H-1"), 4.34 (m, 1H, H-9); MS m/z 762 (100).

Example J16

9-O-(N-Demethyl-N-(2,2,2-trichloroethoxycarbonyl)-α-D-forosaminyl) Spinosyn A 9-Psa and 9-O-(N-Demethyl-N-2,2,2-trichloroethoxycarbonyl)-β-D-forosa-minyl) Spinosyn A 9-Psa Trimethylsilyl trifluoromethanesulfonate (0.7 mL, 3.6 mmol) was added in one portion to a cold (−40° C.), well stirred suspension of N-demethyl-N-(2,2,2-trichloroethoxy)carbonyl-1-O-(4-nitrobenzoyl)-D-forosamine (as an ~6α:1β anomeric mixture) (0.7 g, 1.49 mmol) and 4A molecular sieves (beads, 8–12 mesh, 2.0 g) in a mixture of CH$_2$Cl$_2$ (30 mL) and Et$_2$O (30 mL). The mixture was allowed to warm to −10° C. over 20 min., then while maintaining a reaction temperature of −10° C., a solution of Spinosyn A 9-Psa (0.5 g, 0.92 mmol) in CH$_2$Cl$_2$ (30 mL) was added dropwise during 20 min. After stirring at 10° C. for 4 hr., the whole mixture was poured on to a well stirred mixture of sat. NaHCO$_3$ (240 mL) and ice (~100 g). The organic layer was separated and the aqueous layer extracted with CH$_2$Cl$_2$ (2×75 mL). The combined organic extracts were washed with more sat. NaHCO$_3$ (75 mL) then brine (75 mL) and dried (MgSO4). Concentration left 1.1 g of residue which was flash chromatographed over silica (175 mL) using 3% MeOH in CH$_2$Cl$_2$ as eluent to give 0.6 g (77%) of clean glycosylated 9-O-(N-demethyl-N-(2,2,2-trichloroethoxycarbonyl)-α-D-forosaminyl) Spinosyn A 9-Psa, a 3:1 anomeric mixture of α to β, as a colorless foam. This mixture was separated by reversed-phase hplc over a C18 bonded silica column (41.4 mm (i.d.)×25 cm (1)) using 5% H$_2$O (containing 0.15% NH$_4$OH) in MeOH to give each of the pure anomers. The β-anomer elutes first. β anomer: 140 mg; colorless foam; $^1$H NMR (CDCl$_3$) δ 6.77 (s, 1H, H-13), 4.74 (m, 3H, H-21, CCl$_3$CH$_2$O), 4.40 (m, 3H, H-9, H-1', H-1"), 2.87 and 2.83 (s, total 3H, 4'-N(CH$_3$)). α anomer: 285 mg; colorless foam; $^1$H NMR (CDCl$_3$) δ 6.76 (s, 1H, H-13), 4.75 (m, 4H, H-1', H-21, CCl$_3$CH$_2$O), 4.43 (d,1H, H-1"), 4.30 (m, 1H, H-9), 2.87 and 2.85 (s, total 3H, 4'-N(CH$_3$)).

Example J17

9-O-(N-Demethyl-β-D-forosaminyl) Spinosyn A 9-Psa

This compound was prepared by the procedure used in Example J20. From 100 mg of 9-O-(N-demethyl-N-2,2,2-trichloroethoxycarbonyl)-β-D-forosaminyl) Spinosyn A 9-Psa was obtained 37 mg of 9-O-(N-demethyl-β-D-forosaminyl) Spinosyn A 9-Psa as a white foam: $^1$H NMR (CDCl$_3$) δ 6.78 (s, 1H, H-13), 4.66 (m, 1H, H-21), 4.42 (m, 2H, H-1', H-1"), 3.62 (m, 1H, H-9), 2.42 (s, 3H, NH(CH$_3$)), 2.23 (s, 6H, N(CH$_3$)$_2$); MS m/z 671 (M+H, 10), 377 (100), 357 (95), 336 (24).

Example J18

9-O-o-Methoxybenzoyl Spinosyn A 9-pseudoaglycone

Spinosyn A 9-pseudoaglycone (163 mg, 0.300 mmol) was dissolved in CH$_2$Cl$_2$ (0.6 mL). o-Methoxybenzoyl chloride (56 ul, 0.38 mmol) and triethylamine (53 ul, 0.38 mmol) were added. After 3 hr. 4-pyrrolidinopyridine (3 mg, 0.02 mmol) was added and stirring continued for 15 hr. The reaction mixture was partitioned between EtOAc (5 mL) and 0.5N aqueous NaOH (5 mL). The organic layer was washed successively with 0.5N aqueous NaOH and brine, dried over anhydrous MgSO$_4$ and concentrated under reduced pressure. The residue was chromatographed on a reversed-phase column (Kromasil' C18, Silica ODS, 100 Å, 10 m, spherical, 25 cm×20 mm) using 90% MeOH and 10% H$_2$O (containing 0.1% v/v conc. aqueous NH$_4$OH) to yield an amorphous white solid (110 mg, 54%), $^1$H NMR d 7.76 (dd, J=8.0, 1.8, 1 H), 7.47 (t, J=8.0, 1 H), 3.90 (s, 3 H).

Example J19

9-O-(2,3,4-Tri-O-methyl-L-lyxopyranosyl) Spinosyn A 9-Psa

To a well stirred solution of Spinosyn A 9-Psa (0.4 g, 0.74 mmol) and pyridinium p-toluenesulfonate (0.25 g, 1.0 mmol) in dry CH$_2$Cl$_2$ (50 mL) containing powdered 4 Å molecular sieves (0.8 g), a solution of O-(2,3,4-tri-O-methyl-a-L-lyxopyranosyl)tri-chloroacetimidate (2.3 g, 6.8 mmol) in CH$_2$Cl$_2$ (10 mL) was added dropwise during 20 min. The reaction mixture was stirred for 72 h then filtered through Celite, the collected solids washed with CH$_2$Cl$_2$ (25 mL) and the combined filtrate and wash washed with sat. Na$_2$CO$_3$ (2×20 mL) and brine (20 mL) and dried (MgSO4). Concentration left 2.8 g of residue which was flash chromatographed over Silica (240 mL) using 3% MeOH in CH$_2$Cl$_2$ to yield 0.45 g (85%) of clean coupled product as a 1.5:1 anomeric mixture of β:α 9-O-(2,3,4-tri-O-methyl-L-lyxopyranosyl) Spinosyn A 9-Psa. This mixture was separated by hplc in three portions of ~150 mg over a 41.4 mm (i.d.)×25 cm (1) reverse phase C18 column using 10% H$_2$O (containing 0.15% NH$_4$OH) in MeOH as eluent. The β-anomer elutes first. β anomer: 102 mg; colorless foam; $^1$H NMR (CDCl$_3$) δ 6.78 (s, 1H, H-13), 4.68 (m, 1H, H-21), 4.55 (d, J=1.4, 1H, H-1'), 4.44 (d, J=7.7, 1H, H-1"), 4.38 (m, 1H, H-9); MS m/z 435 (2), 175 (10), 142 (30), 71 (100). α anomer: 60 mg; colorless foam; $^1$H NMR (CDCl$_3$) d 6.79 (s, 1H, H-13), 4.84 (d, J=2.9, 1H, H-1'), 4.67 (m, 1H, H-21), 4.41 (d, J=7.3, 1H, H-1"), 4.31 (m, 1H, H-9); MS m/z 435 (2), 175 (10), 142 (50), 71 (100).

Example J20

9-O-(N-Demethyl-a-D-forosaminyl) Spinosyn A 9-Psa

Activated Zn powder (0.4 g) was added to a well stirred solution of 9-O-(N-demethyl-N-(2,2,2-trichloroethoxycarbonyl)-a-D-forosaminyl) Spinosyn A 9-Psa (0.1 g, 0.12 mmol) in THF (3 mL), MeOH (0.5 mL) and 1M NH$_4$OAc and this mixture was stirred at room temperature for 3 days. The solids were removed by filtration and washed with THF (5 mL). The combined filtrate and wash was evaporated to dryness and the residue taken up in CH$_2$Cl$_2$ (30 mL). This CH$_2$Cl$_2$ solution was washed with saturated Na$_2$CO$_3$ (5 mL) and brine and dried (MgSO$_4$). Concentration left 66 mg of residue which was chromatographed over silica (20 mL) using 8% MeOH in CH$_2$Cl$_2$ to give 42 mg of 9-O-(N-demethyl-α-D-forosaminyl) Spinosyn A 9-Psa as a white foam: $^1$H NMR (CDCl$_3$) δ 6.76 (s, 1H, H-13), 4.78 (d, J=1.9, 1H, H-1'), 4.66 (m, 1H, H-21), 4.41 (d, J=8.1, 1H, H-1"), 4.28 (m, 1H, H-9); MS m/z 671 (M+H, 12), 544 (20), 377 (44), 357 (100), 336 (40).

Part K Modification of Pseudoaglycone A2 at C9 of the Tricyclic Portion of A83543

Example K1

9-epi Spinosyn A 9-Psa

To a solution of 9-Keto Spinosyn A 9-Psa (207.9 mg, 0.38 mmol) in anhydrous methanol (10 ml), sodium borohydride (23 mg, 0.61 mmol) was added. The reaction mixture stirred at room temperature for 40 minutes, then diluted with dichloromethane and washed with water. The dichloromethane was washed with brine, dried with K$_2$CO$_3$, and evaporated at room temperature under reduced pressure. The products were separated by preparative HPLC on a C$_{18}$ column, eluting with acetonitrile:methanol:0.1% NH$_4$OAc (35:35:30 to 40:40:20 in a 60 minute linear gradient). This gave 9-epi Spinosyn A 9-Psa (57 mg; 28% yield), FDMS, m/e (relative intensity) 1084 (15), 544 (M$^+$, 45), 543 (100) and Spinosyn A 9-Psa (42 mg; 20% yield).

Example K2

(9S) and (9R)-9-Methyl Spinosyn A 9-Psa

To a solution of 9-Keto Spinosyn A 9-Psa (336.8 mg, 0.62 mmol) in anhydrous THF (7 ml), methylmagnesium chloride (3.0M; 250 µl, 0.75 mmol) was added. The reaction mixture warmed to reflux, during addition of the grignard reagent, then stirred at room temperature for 1 hour. Additional methylmagnesium chloride (500 µl, 1.5 mmol) was added and the mixture was stirred at room temperature for another hour. The mixture was then diluted with ether and washed with water. The ether was filtered through celite to remove magnensium salts, washed with brine, dried with K$_2$CO$_3$, and evaporated at room temperature under reduced pressure. The products were separated by preparative HPLC on a C$_{18}$ column, eluting with acetonitrile:methanol:0.1% NH$_4$OAc (30:30:40 to 45:45:10 in a 60 minute linear gradient). This gave (9S)-9-methyl Spinosyn A 9-Psa (93 mg; 27% yield), FDMS, m/e (relative intensity) 558 (M$^+$, 30), 557 (100) and (9R)-9-methyl Spinosyn A 9-Psa (55 mg; 16% yield), FDMS, m/e (relative intensity) 558 (M$^+$, 40), 557 (100).

Example K3

9-Deoxy Spinosyn A 9-Psa and 9-Deoxy-8,9-dehydro Spinosyn A 9-Psa

To a solution of 9-O-[(S-methyl)dithiocarbonyl] Spinosyn A 9-Psa (219.7 mg; 0.35 mmol) in toluene (10 ml), tributyltin hydride (250 ml, 1.0 mmol) and a trace amount of AIBN were added. The reaction mixture was heated to reflux for 20 hours, with no apparent reaction. Some additional AIBN (trace amount) was added and the heating was continued for 28 hours. The mixture then stirred at room temperature for 4 days and the solvent was then evaporated at room temperature under reduced pressure. The products were initially purified by chromatography on silica, eluting with 5% methanol in dichloromethane, then separated from unreacted starting material by preparative HPLC on a C$_{18}$ column, eluting with acetonitrile:methanol:0.1% NH$_4$OAc (40:40:20 to 45:45:10 in a 90 minute linear gradient). This gave 9-deoxy-8,9-dehydro Spinosyn A 9-Psa (8 mg; 4% yield), FDMS, m/e (relative intensity) 526 (M$^+$, 65), 525 (100) and 9-deoxy Spinosyn A 9-Psa (34 mg; 18% yield), FDMS, m/e (relative intensity) 528 (M$^+$, 55), 527 (100) both as white solids.

Example K4

9-O-Methyl Spinosyn A Ag

The reaction was run as described in Example 2 starting with 9-O-methyl Spinosyn A 9-Psa (188.8 mg, 0.34 mmol). This gave 9-O-methyl Spinosyn A Ag(126.9 mg; 90% yield) as a white solid, FDMS, m/e (relative intensity) 417 (M$^+$, 40), 416 (100).

Example K5

9-Deoxy-9-(N-morpholinyl) Spinosyn A 9-Psa

To a solution of 9-keto Spinosyn A 9-Psa (154.4 mg, 0.28 mmol) in anhydrous methanol (7 ml), morpholine (244 µl, 2.8 mmol) was added. The reaction mixture stirred at room temperature for 45 minutes, then sodium cyanoborohydride (84.5 mg, 1.3 mmol) was added. The mixture continued to stir at room temperature for 7 hour, and was then diluted with ether. The ether was washed with water, then brine, dried with MgSO$_4$, and evaporated at room temperature under reduced pressure. The product was separated from an unknown impurity by chromatography on silica, eluting with 5% methanol in dichloromethane. This gave 9-deoxy-9-(N-morpholinyl) Spinosyn A 9-Psa (48.5 mg; 28% yield)

Example K6

9-Deoxy Spinosyn A Ag

The reaction was run as described in Example 2 starting with 9-deoxy Spinosyn A 9-Psa (335 mg, 0.63 mmol). This gave 9-deoxy Spinosyn A Ag (129.5 mg; 53% yield) as a white solid, FDMS, m/e (relative intensity) 387 ($M^+$, 45), 386 (100).

Example K7

9-Keto Spinosyn A 9-Psa

N-chlorosuccinimide (1.4 g, 10.5 mmol) was suspended in $CH_2Cl_2$ (35 ml) and cooled to −70° C. under nitrogen. Dimethylsulfide (825 ul, 11.2 mmol) was added and after stirring at −70° C. for 30 min, Spinosyn A 9-Psa (2.0 g, 3.7 mmol) in $CH_2Cl_2$ (13 ml) was added slowly. After stirring at −70° C. for 2 hr, triethylamine (1.4 ml, 10 mmol) was added and the reaction was allowed to warm to room temperature. After stirring 20 hr at room temperature, and sitting at 0° C. for 24 hr, the solution was diluted with $CH_2Cl_2$ and washed with $H_2O$. The $CH_2Cl_2$ was then washed with brine, dried ($MgSO_4$), and evaporated at room temperature under vacuum. The residue was chromatographed on a silica gel column (7% $MeOH/CH_2Cl_2$) to afford 9-keto Spinosyn A 9-Psa (1.83 g, 91%) as a white glass. FDMS, m/e (relative intensity) 541(100).

Example K8

1"-α/β-9-O-Phenoxyacetyl-Spinosyn A 9-pseudoaglycone

Spinosyn A 9-pseudoaglycone (163 mg, 0.300 mmol) and 4-pyrrolidinopyridine (6 mg, 0.04 mmol) were dissolved in $CH_2Cl_2$ (1 mL). Phenoxyacetyl chloride (55 mL, 0.40 mmol) was added in a single portion. The mixture was stirred at room temperature for 18 h. The mixture was quenched with solid sodium bicarbonate and partitioned between EtOAc and aqueous sodium bicarbonate. The organic layer was washed with water and brine and dried over anhydrous sodium sulfate. The solvent was evaporated and the residue chromatographed on a reversed-phase column (Kromasil' C18, Silica ODS, 100 Å, 10 m, spherical, 25 cm×20 mm) with 90% MeOH and water (containing 0.1% v/v conc. aqueous $NH_4OH$) to yield a white solid (108 mg, 53%). $^1H$ NMR d (t, J=8.4, 2 H), 6.95 (t, J=8.4, 1 H), 6.87 (d, J=8.4, 2 H), 4.85, (br s, 0.5 H), 4.61 (s, 2 H), 4.42 (br d, J=7.8, 0.5 H).

Example K9

9-Epi-Spinosyn A 9-pseudoaglycone

9-Epi-9-O-phenoxyacetyl-Spinosyn A 9-pseudoaglycone (0.44 g, 0.65 mmol) was suspended in a mixture of MeOH (9 mL) and water (1 mL). To this resulting slurry was added potassium carbonate (135 mg, 0.97 mmol). Three milliliters of 9:1 MeOH-water was added to wash down the sides of the flask. After 4 h the homogeneous solution was partitioned between EtOAc and 1:1 water-saturated aqueous sodium bicarbonate. The aqueous phase was extracted with EtOAc and the combined organic phases washed successively with dilute aqueous sodium bicarbonate (twice) and brine. The mixture was dried over anhydrous sodium sulfate and the solvent removed under reduced pressure to yield a glassy solid (366 mg, 104%) $^1H$ NMR d 4.50 (br q, J=6.0, 1 H).

Example K10

9-Epi-9-(2-O,3-O,4-O-triethyl-1-α-rhamnosyl)-Spinosyn A 9-pseudoaglycone and 9-epi-9-(2-O,3-O,4-O-triethyl-1-β-rhamnosyl)-Spinosyn A 9-pseudoaglycone 9-Epi-Spinosyn A 9-pseudoaglycone (340 mg, 0.625 mmol) dissolved in $CH_2Cl_2$ (6 mL). To this solution was added molecular sieves (4 Å; 420 mg) and pyridinium tosylate (210 mg, 0.837 mmol). This mixture was cooled to 0° C. and maintained at that temperature while a solution of 1-(α/β)-2-O,3-O,4-O-triethyl-rhamnosyl trichloroacetimidate (1.23 g, 3.13 mmol) in $CH_2Cl_2$ (5 mL) was added dropwise over 10 min. The mixture was stirred at 0° C. for 40 min and for 18 hr. at room temperature. The reaction mixture was partitioned between $CH_2Cl_2$ and dilute aqueous sodium bicarbonate. The organic layer was washed with dilute aqueous sodium bicarbonate, water (twice) and brine. The solvent was removed at reduced pressure and the residue chromatoghraphed on silica gel (60 g) with 3% MeOH in $CH_2Cl_2$. The product containing fractions were pooled and the solvent removed under reduced pressure. The residue was chromatographed on a reversed-phase column (Kromasil' C18, Silica ODS, 100 Å, 10 m, spherical, 25 cm×20 mm) with 92% MeOH and 8% water (containing 0.1% v/v conc. aqueous $NH_4OH$) to yield, separately, the two anomers as amorphous white solids; α-(142 mg, 29%) $^1H$ NMR d 4.75 (d, J=1.4, 1 H), 1.32–1.15 (m, 22 H); β-(70 mg, 14%) $^1H$ NMR d 4.31 (br s, 1 H), 1.35–1.13 (m, 22 H).

Part L. Modification By Formation of Spinosyn Dimers

Example L1

Bis[(Spinosyn J-3'-O-)yl]-methane [formaldehyde bis(Spinosyn J-3'-O-) acetal]

Spinosyn J (0.93 g, 1.29 mmol) was reacted with $CH_2Br_2$ following the procedure described for compound 3'-O,N-bis (trideuteriomethyl) Spinosyn M using potassium carbonate (3.0 g), tetrabutylammonium hydrogen sulfate (1.80 g), 15% aqueous NaOH solution (50 mL) and $CH_2Br_2$ (4.5 mL). After work-up, the crude product was purified by chromatography on silica gel and then separated by HPLC (88:12, $MeOH/H_2O$) to give formaldehyde bis(Spinosyn J-3'-O-) acetal (47 mg, 5%) as a white solid: ESI MS m/z 1448 (M+1).

Example L2

[S]R/S-Bis[(Spinosyn J-3'-O)-yl] sulfite

Spinosyn J (2.70 g, 3.76 mmol) was dissolved in dry pyridine (10 mL). Dry methylene chloride (4 mL) was added. The mixture was stirred under nitrogen and cooled to −78° C. Thionyl chloride (0.90 mL, 12.3 mmol) was slowly added. The mixture was warmed up to room temperature and stirred for 20 h. The usual work-up and chromatography on silica gel (ethyl acetate, then 10% EtOH in EtOAc) afforded [S]R/S-bis[(Spinosyn J-3'-O)-yl] sulfite (1180 mg, 42%) as a white solid: ESI MS m/z 1482 (M+1).

Example L3

4"-N-Pentamethylene-bridged Spinosyn B Dimer and 4"-N,4"-N-(Pent-1,5-diyl) Spinosyn B Bromide Salt These compounds were prepared according to the method in Example C24 from 1,5-dibromopentane (38 mL, 64 mg, 0.28 mmol), (i-Pr)$_2$NEt (0.30 mL, 0.22 g, 1.7 mmol), Spinosyn B (0.40 g, 0.56 mmol), and DMF (1.5 mL). MPLC (0:100 to 20:80 MeOH/CH$_2$Cl$_2$) gave 0.07 g (17%) of 4"-N-pentamethylene-bridged Spinosyn B dimer as a white powder (Spinosyn B, 0.16 g (40%) was also recovered): MS (m+H$^+$ & m+2H$^+$/2) expected: 1504.0 & 752.5. Found: 1504.1 & 753.1 and; 4"-N,4"-N-(Pent-1,5-diyl) Spinosyn B Bromide Salt, 0.17 g (35%): MS (m-Br$^-$) expected: 786.5. Found: 786.7.

Part M Modification of Position 2 on the Macrocyclic Portion in Formula I

Example M1

2-Ethyl Spinosyn A

The procedure described above for the preparation of the 2-methyl analog of Spinosyn A, Example M23, was followed, substituting iodoethane (1.0 g, 6.4 mmol) for iodomethane. Thus, 1 g of Spinosyn A yielded 0.35 g of isomerically pure 2-ethyl Spinosyn A following preparative reverse phase chromatography. Anal. Calcd for C$_{43}$H$_{69}$NO$_{10}$: C, 67.96; H, 9.15; N, 1.84. Found: C, 67.65; H, 9.01; N, 1.96.

Example M2

2-Ethoxycarbonyl Spinosyn A

The procedure described above for the preparation of the 2-methyl analog of Spinosyn A, Example M23, was followed, substituting ethyl cyanoformate (0.69 g, 6.98 mmol) as the electrophile. Preparative reverse-phase chromatography (C-18, gradient elution using 85–98% methanol: 0.1% NH$_4$OH/water) gave 0.14 g of 2-ethoxycarbonyl Spinosyn A. Anal. Calcd. for C$_{44}$H$_{69}$NO$_2$: C, 65.72; H, 8.65; N, 1.74. Found: C, 65.77; H, 8.38; N, 1.79.

Example M3

2-Methylthio Spinosyn A

The procedure described above for the preparation of the 2-methyl analog of Spinosyn A, Example M23, was followed, substituting dimethyl sulfide (0.66 g, 6.98 mmol) as an electrophile at −70° C. Preparative reverse-phase chromatography (C-18, gradient elution using 85–98% methanol: 0.1% NH$_4$OH/water) gave 0.20 g of 2-methylthio Spinosyn A. $^1$H NMR (300 MHz, CDCl$_3$) d 2.2 (s, 3H, S-C H$_3$). Anal. Calcd. for C$_{42}$H$_{67}$NO$_{10}$S: C, 64.83; H, 8.68; N, 1.80; S, 4.1 Found: C, 65.18; H, 10.43; N, 1.76; S, 3.66.

Example M4

2-Bromo Spinosyn A

The procedure described above for the preparation of the 2-methyl analog of Spinosyn A, Example M23, was followed, substituting 1,2-dibromotetrafluoroethane (0.9 g, 3.47 mmol) as an electrophile at −70° C. Preparative reverse-phase chromatography (C-18, gradient elution using 85–98% methanol: 0.1% NH$_4$OH/water) gave 0.5 g of 2-bromo Spinosyn A. Anal. Calcd. for C$_{41}$H$_{64}$NO$_{10}$Br: C, 60.73; H, 7.95; N, 1.72. Found: C, 62.14; H, 7.93; N, 1.79.

Example M5

R and S isomers of 2-(2'-Hydroxy)ethyl Spinosyn A

The procedure described above for the preparation of the 2-methyl analog of Spinosyn A, Example M23, was followed, substituting acetaldehyde (0.19 mL, 3.47 mmol) as an electrophile at −70° C. Preparative reverse-phase chromatography (C-18, gradient elution using 85–98% methanol: 0.1% NH$_4$OH/water) gave two isomers (each 0.25 g) of 2-(2'-Hydroxy)ethyl Spinosyn A. Isomer 1: Anal. Calcd. for C$_{43}$H$_{69}$NO$_{11}$: C, 66.55; H, 8.96; N, 1.80. Found: C, 66.48; H, 10.6; N, 1.84. Isomer 2: Anal. Calcd. for C$_{43}$H$_{69}$NO$_{11}$: C, 66.55; H, 8.96; N, 1.80. Found: C, 65.82; H, 10.07; N, 1.72.

Example M6

2-Phenylthio Spinosyn A

The procedure described above for the preparation of the 2-methyl analog of Spinosyn A, Example M23, was followed, substituting diphenylsulfide (1.52 g, 6.98 mmol) as an electrophile at −70° C. Preparative reverse-phase chromatography (C-18, gradient elution using 85–98% methanol: 0.1% NH$_4$OH/water) gave 0.71 g of 2-phenylthio Spinosyn A. Anal. Calcd. for C$_{47}$H$_{69}$NO$_{10}$S: C, 67.19; H, 8.28; N, 1.67; S, 3.81. Found: C, 67.12; H, 9.51; N, 1.65; S, 3.34.

Example M7

2-Formyl Spinosyn A

This was prepared similarly to Example M23 except ethyl formate (0.56 mL, 6.98 mmol) was added as an electrophile at −70° C. Preparative reverse-phase chromatography (C-18, gradient elution using 85–98% methanol: 0.1% NH$_4$OH/ water) gave 0.5 g of 2-formyl spinosyn A. Anal. Calcd. for C$_{42}$H$_{66}$NO$_{11}$: C, 66.37; H, 8.75; N, 1.84. Found: C, 63.77; H, 8.46; N, 1.88.

Example M8

2-Methanesulfinyl Spinosyn A, N-oxide

A stirred solution of 2-Methylthio Spinosyn A (1.0 g, 1.3 mmol) in 10 mL of anhydrous methanol was cooled to 0° C. and treated portion-wise with m-chloroperbenzoic acid (50%, 0.67 g, 1.9 mmol). An exotherm to 10° C. was observed. After stirring for 1 hour the reaction mixture was poured into 10% HCl and washed 2× with ether. The aqueous was layer basified with NaHCO$_3$ and concentrated under reduced pressure to a solid. The solid was triturated with 3×25 mL ether, and 2×25 mL of EtOAc. The organics were combined and concentrated. Preparative reverse-phase chromatography (C-18, gradient elution using 85–98% methanol: 0.1% NH$_4$OH/water) gave 0.36 g of 2-methanesulfinyl Spinosyn A, N-oxide as a light yellow solid foam. Anal. Calcd. for C$_{42}$H$_{67}$NO$_{12}$S : C, 62.27; H, 8.34; N, 1.73; S, 3.95. Found: C, 58.63; H, 8.07; N, 1.64; S, 4.12.

Example M9

2-Methanesulfinyl Spinosyn A

A stirred solution of 2-Methylthio Spinosyn A (0.5 g, 0.65 mmol) in 10 mL of anhydrous methanol was cooled to −30° C. To this solution was added a 5.5M solution (in methanol) of m-chloroperbenzoic acid (50%, 0.67 g, 1.9 mmol) via syringe. After allowing the solution to stir for 10 minutes, 10% HCl was added to the reaction mixture. The solution was concentrated via rotovap, then the residue was dissolved in 10 mL of 10% HCl and the washed 2× with 30 mL of Et$_2$O. The aqueous layer was basified with NaHCO$_3$ and extracted 3× with ether/EtOAc, dried, and concentrated on rotovap to give 0.45 g of an oil. Preparative reverse-phase chromatography (C-18, gradient elution using 85–98% methanol: 0.1% $NH_4OH$/water) gave 0.36 g of 2-methanesulfinyl spinosyn A. Anal. Calcd. for $C_{42}H_{67}NO_{11}S$: C, 63.53; H, 8.50; N, 1.76; S, 4.02. Found: C, 63.17; H, 9.50; N, 1.77; S, 4.02.

Example M10

2-Hydroxymethyl Spinosyn A and 2-N-piperidinylmethyl Spinosyn A

Piperidine (0.06 g, 0.7 mmol) was added to a solution of compound 2-formyl Spinosyn A (0.44 g, 0.6 mmol) in 25 mL of MeOH at 20° C. After 15 min the solution was cooled to 0° C. and sodium cyanoborohydride (0.5 g, 0.9 mmol) was added portion wise so as to maintain temperature below 10° C. After 20 minutes the reaction was poured into ice/10% HCl and washed 2× with $Et_2O$. The aqueous layer was basified with $NaHCO_3$ and extracted 3× with EtOAc. The combined organic layers were dried and concentrated via rotovap to an oil. Preparative reverse-phase chromatography (C-18, gradient elution using 85–98% methanol: 0.1% $NH_4OH$) gave 0.1 g of 2-hydroxymethyl spinosyn A and 0.1 g of 2-N-piperidinylmethyl spinosyn A. For 2-hydroxymethyl Spinosyn A: Anal. Calcd. for $C_{42}H_{67}NO_{11}$: C, 66.19; H, 8.86; N, 1.84. Found: C, 64.95; H, 8.65; N, 1.83. For 2-N-piperidinylmethyl Spinosyn A: Anal. Calcd. for $C_{47}H_{76}N_2O_{10}$: C, 68.08; H, 9.24; N. 3.38. Found: C, 67.89; H, 9.31; N, 3.13.

Example M11

2-(1-Methoxy-1-hydroxymethyl) Spinosyn A

The enolate of Spinosyn A (4.1 mmol) was prepared according to the general procedure described above in Example M23. Ethyl formate (1.5 g, 20 mmol) was added drop-wise over 10 minutes to the cooled (−70° C.) solution, which was then allowed to warm slowly to −30° C. The solution was then poured onto a stirred, cooled (0° C.) solution of saturated aqueous $NH_4Cl$ (75 mL) and ether (75 mL). The organic layer was separated and washed with brine, dried and concentrated to an oil. HPLC reverse-phase chromatrography (80–98% MeOH: 0.1% $NH_4OH$) gave 1.5 g of pure hemiacetal. Anal. $C_{43}H_{69}NO_{12}$ requires C, 65.21; H, 8.78; N, 1.77. Found: C, 65.16; H, 8.65; N, 1.83.

Example M12

2-Phenylseleno Spinosyn A

The procedure described above for the preparation of the 2-methyl analog of Spinosyn A, Example M23, was followed, substituting phenylselenyl chloride (0.26 g, 1.37 mmol) for iodomethane. Thus, 1 g of Spinosyn A yielded the two (R and S) isomers of 2-phenylseleno Spinosyn A (0.19 g and 0.06 g) following preparative reverse phase chromatography (C-18, gradient elution using 85–98% methanol: 0.1% $NH_4OH$). Major isomer: $^1H$ NMR (300 MHz, $CDCl_3$) d 7.7 (m, 2H); 7.25 (m, 3H); 4.05 (br s, 1H). Anal. Calcd for $C_{47}H_{69}NO_{10}Se$: C, 63.64; H, 7.84; N, 1.58. Found: C, 63.57; H, 7.85; N, 1.53. Minor isomer: $^1H$ NMR (300 MHz, $CDCl_3$) d 7.6 (m, 2H); 7.25 (m, 3H); 6.82 (br s, 1H); 4.55 (d, J=4.2 Hz, 1H).

Example M13

(R and S) 2-Ethoxycarbonylmethyl Spinosyn A

The enolate of Spinosyn A (1.37 mmol) was prepared according to the general procedure described above in Example M23. Ethyl bromoacetate (0.76 g, 4.5 mmol) was added at −60° C., and the solution was allowed to warm slowly to 0° C. The solution was then poured into saturated $NH_4Cl$ solution and extracted with 2×50 mL of $Et_2O$. The combined organic phase was extracted with 50 mL of 0.1N HCl, then the acidic aqueous layer was bade basic with saturated $NaHCO_3$ and reextracted with 2×50 mL of $Et_2O$. The combined organic layer was dried and concentrated to yield 1 g of an oil which was subjected to reverse-phase chromatography. Gradient elution with 85→98% methanol:0.1% $NH_4OH$ furnished two isomers of 2-ethoxycarbonylmethyl Spinosyn A (0.17 g, 17% and 0.13 g, 13%). Spinosyn A (0.2 g) was also recovered.

Example M14

2-Phenylselenoxy Spinosyn A and 2,3-dehydro Spinosyn A

A solution of 2-phenylseleno Spinosyn A (major isomer; 0.20 g, 0.22 mmol) in 10 mL of dry MeOH was cooled to −60° C. under $N_2$ and stirred magnetically while MCPBA (0.06 g, about 0.25 mmol of 57–85% pure MCPBA) was added in three portions over 15 min. The solution was allowed to warm to ambient temperature over 1 h, then it was diluted with 50 mL of $Et_2O$ and washed with saturated $NaHCO_3$ solution. The organic layer was then extracted with 30 mL of 1N HCl. The acidic aqueous layer was then made basic (pH 9) with saturated $NaHCO_3$ solution and re-extracted with 2×25 mL of $Et_2O$. The organic layer was dried over $MgSO_4$ and concentrated to an oil. Chromatography (C-18, gradient elution using 85–90% methanol:0.1% $NH_4OH$) to furnish two new materials. The first (0.06 g) was identified as 2-phenylselenoxy Spinosyn A. The second product (0.02 g) was 2,3-dehydro Spinosyn A. The selenoxide (0.4 g, 0.44 mmol) was taken up in 10 mL of toluene and heated to reflux for 30 min. The solution was then cooled, diluted with ether and washed with 25 mL of 1N HCl. The aqueous layer was separated, the pH adjusted to 9 with aqueous NaHCO3 solution, and re-extracted with 2×50 mL of $Et_2O$. The combined organic layer was dried, concentrated and chromatographed (C-18, gradient elution using 85–90% methanol:0.1% $NH_4OH$) to give 0.10 g of 2,3-dehydro Spinosyn A. For 2-phenylselenoxy Spinosyn A: $^1H$ NMR (300 MHz, $CDCl_3$) δ 7.9–8.0 (m, 2H); 7.45 (m, 3H); 6.77 (br s, 1H); (br d, J=11 Hz, 1H); 5.05 (br d, J=11 Hz, 1H); 4.87 (m, 1H; 4.75 (s, 1H); 4.4 (d, J=7Hz, 1H); 4.18 (m, 1H). For 2,3-dehydro Spinosyn A: $^1H$ NMR (300 MHz, $CDCl_3$) δ 6.85 (br s, 1H); 5.97 (br d, J=10 Hz,. 1H); 5.82 (br d, J=10 Hz, 1H); 5.65 (s, 1H); 4.82 (s, 1H); 4.65 (d, J=7Hz, 1H);4.25–4.4 (m, 2H); 4.1 (m, 1H).; 4.87 (m, 1H; 4.75 (s, 1H); 4.4 (d, J=7Hz, 1H); 4.18 (m, 1H). M.S. M+H 730.9.

Example M15

2-Phenylselenoxy Spinosyn A and 2,3-dehydro Spinosyn A

A solution of 2-phenylseleno Spinosyn A (minor isomer; 0.22 g, 0.25 mmol) in 10 mL of dry methanol was cooled to −60° C. under $N_2$ and stirred magnetically while MCPBA (0.065 g, about 0.25 mmol of 57–85% pure MCPBA) was added in three portions over 15 min. The solution was allowed to warm to ambient temperature over 1 h, then it was diluted with 50 mL of diethyl ether and washed with saturated $NaHCO_3$ solution. The organic layer was then extracted with 30 mL of 1N HCl. The acidic aqueous layer was then made basic (pH 9) with saturated $NaHCO_3$ solution and re-extracted with 2×25 mL of ether. The organic layer was dried over MgSO$_4$ and concentrated to an oil. A portion of this selenoxide was purified by chromatography (C-18, gradient elution using 85–98% methanol: 0.1% NH$_4$OH). Anal. Calcd for C$_{47}$H$_{69}$NO$_{11}$Se: C, 62.51; H, 7.70; N, 1.55. Found: C, 62.13; H, 1.64; N, 7.73. The remainder of the crude selenoxide (0.2 g) was heated in 10 mL of benzene for 45 min, then cooled, concentrated and chromatographed (C-18, gradient elution using 85–98% methanol: 0.1% NH$_4$OH) to give 0.07 g of 2,3-dehydro Spinosyn A as a yellow foam. This material decomposed on standing at ambient temperature. NMR (300 MHz, CDCl$_3$) d 6.85 (br s, 1H); 5.97 (br d, J=10 Hz,. 1H); 5.82 (br d, J=10 Hz, 1H); 5.65 (s, 1H); 4.82 (s, 1H); 4.65 (d, J=7Hz, 1H);4.25–4.4 (m, 2H); 4.1 (m, 1H).; 4.87 (m, 1H); 4.75 (s, 1H); 4.4 (d, J=7Hz, 1H); 4.18 (m, 1H).

Example M16

Spinosyn A, t-butyldimethylsilyl ketal

To a cooled (–40° C.) magnetically stirred solution of LDA (6.8 mmol) in 20 mL of THF was added 2 mL of HMPA and 1.0 g (6.9 mmol) of t-butyldimethylsilyl chloride. Spinosyn A (1.0 g, 1.36 mmol) in 2 mL of THF was then added over 2 min, then the solution was allowed to warm slowly to 0° C. The resulting solution was poured onto 50 mL of water and 50 mL of ether. The layers were separated, and the organic phase was washed with brine, dried and concentrated. Chromatography (reverse-phase, 85–98% MeOH/H$_2$O gradient elution) gave 0.55 g of pure Spinosyn A, t-butyldimethylsilyl ketal. $^1$H NMR (300 MHz, CDCl$_3$): d 6.78 (br s, 1H); 8.83 (m, 2H); 4.82 (s, 1H); 4.15–4.32 (m, 2H); 4.05 (d, J=6Hz, 1H); 3.83 (m, 1H); 0.9 (s, 9H); 0.2 (d, J=11 Hz, 6H). Anal. Calcd for C$_{47}$H$_{79}$NO$_{10}$Si: C, 66.71; H, 9.41; N, 1.66. Found: C, 66.54; H, 9.50; N, 1.64.

Example M17

2-Chloro Spinosyn A

A solution of the TBS ketal of Spinosyn A (0.1 g, 0.12 mmol) in 5 mL of dry THF was stirred magnetically and cooled to –78° C., and N-chlorosuccinimide (15 mg, 0.125 mmol) was added in one portion. The solution was allowed to warm slowly to ambient temperature, then partitioned between 30 mL of ether and 30 mL of brine solution. The organic layer was dried and concentrated to an oil, which was chromatographed (reverse-phase, 85–98% MeOH/H$_2$O gradient elution) to yield 40 mg of 2-(R) chloro Spinosyn A. $^1$H NMR (300 MHz, CDCl$_3$) d 4.68 (s, 1H; C2-$\underline{H}$). M.S. M+H 766.

Example M18

2-Fluoro Spinosyn A

A solution of the TBS ketal of Spinosyn A (0.05 g, 0.06 mmol) in 5 mL of THF was stirred magnetically and cooled to –78° C., and XeF$_2$ (15 mg, 0.09 mmol) was added in one portion. The solution was allowed to warm slowly to ambient temperature, then concentrated to an oil and chromatographed (reverse-phase, 85–98% MeOH/H$_2$O gradient elution) to yield 18 mg of 2-fluoro Spinosyn A. $^1$H NMR (300 Mhz, CDCl$_3$) d 5.12 (d, J=50 Hz, 1H; C2-$\underline{H}$). M.S. M+H 750.

Example M19

2-(Dimethylamino)iminomethyl Spinosyn A

To a solution of the 2-(1-methoxy-1-hydroxymethyl) Spinosyn A (0.1 g, 0.13 mmol) in 3 mL of MeOH was added 11 mg (0.18 mmol) of N,N-dimethylhydrazine. The solution was heated on a steam bath for 2 h, then cooled and concentrated. The residue was chromatographed (reverse-phase, 85–98% MeOH/H$_2$O gradient elution) to give 35 mg of the hydrazone. $^1$H NMR (300 Mhz, CDCl$_3$) d 6.65 (d, J=7 Hz, 1H; C2-C$\underline{H}$=NNMe$_2$); 4.1 (dd, J=7,4 Hz, 1H; C$_2$-C$\underline{H}$); 2.78 (s, 6H). M.S. M+H 802.8.

Example M20

2-Hydroxyiminomethyl Spinosyn A

To a solution of the 2-(1-methoxy-1-hydroxymethyl) Spinosyn A (0.06 g, 0.08 mmol) in 3 mL of MeOH was added 10 mg (0.14 mmol) of hydroxylamine hydrochloride. The solution was heated on a steam bath for 2 h, then cooled and concentrated. The residue was taken up in Et$_2$O and washed with NaHCO$_3$ solution. The organic layer was dried and concentrated to give 0.05 g of the oxime as a mixture of syn and anti isomers. $^1$H NMR (300 MHz, CDCl$_3$) d 7.55 and 6.95 (two doublets, J=6 Hz, 1H; C2-C$\underline{H}$=NOH); 4.15 and 4.72 (two dd, J=6,4.5 Hz, 1H; C2-C$\underline{H}$). Anal. Calcd for C$_{42}$H$_{66}$N$_2$O$_{11}$: C, 65.09; H, 8.58; N, 3.61. Found: C, 65.10; H, 8.86; N, 1.57.

Example M21

2-Cyano Spinosyn A

To a solution of the 2-(1-methoxy-1-hydroxymethyl) Spinosyn A (0.4 g, 0.5 mmol) in 5 mL of MeOH was added N,N-dimethylhydrazine (0.05 g, 0.8 mmol), and the solution was heated at reflux for 1 hour, then cooled and concentrated in vacuo. The residue was taken up in 1 mL of MeOH and added to a stirred, cooled (–40° C.) solution of magnesium monoperphthalate (MMPP, 85%; 0.5 g, 0.8 mmol) in 3 mL of MeOH. The solution was allowed to warm to ambient temperature and stirring was continued overnight. The solution was poured onto 10 mL of a saturated aqueous NaHCO$_3$ solution, and the product extracted in to 2×25 mL of Et$_2$O. The organic solution was dried and concentrated, then chromatographed (reverse-phase, 85–98% MeOH/H$_2$O gradient elution) to give 85 mg of 2-cyano Spinosyn A. M.S. M+H 757.5. $^1$H NMR (300 MHz, CDCl$_3$) δ 4.43 (d, J=4.7 Hz, 1H; C2-C$\underline{H}$). Anal. Calcd for C$_{42}$H$_{64}$N$_2$O$_{10}$: C, 67.81; H, 8.81; N, 1.88. Found: C, 67.68; H, 9.05; N, 1.73.

Example M22

2-Cyano-2-fluoro Spinosyn A

To 4 mL of a cooled (–40° C.) stirred dry THF solution in a 25 mL flask under N$_2$ was added butyllithium (0.1 mL of 1.6M, 0.16 mmol) and diisopropylamine (30 μl, 0.2 mmol). After 30 min, 2-cyano Spinosyn A (0.105 g, 0.14 mmol) in 0.5 mL of dry THF was added. This solution was allowed to stir an additional 0.5 h, then N-fluorobenzenesulfinimide (NFSi; 50 mg, 0.16 mmol) was added. The solution was stirred an additional 0.5 h at –40° C. and then allowed to warm slowly to 0° C. The solution was then poured into Et$_2$O and washed with brine solution. Drying and concentration furnished a light yellow oil which was chromatographed (reverse-phase, 85–98% MeOH/H$_2$O gradient elution) to give 35 mg of 2-fluoro-2-cyano Spinosyn A. M.S. M+H 775.6.

Example M23

2-Methyl Spinosyn A isomers

A 50 mL 3-necked round bottom flask was equipped with N$_2$ inlet, addition funnel and thermometer, and was charged with 15 mL of dry THF. The solution was stirred magnetically and cooled to −40° C. Butyllithium (4.5 mL of 1.6M in hexanes, 7.2 mmol) was added, followed by diisopropylamine (1.0 mL, 7.2 mmol), drop-wise over 2 min. After the addition was completed, the solution was cooled to −70° C. and HMPA (1.2 mL) was added, followed by Spinosyn A (1.0 g, 1 37 mmol) in 3 mL of dry THF. The solution was allowed to warm slowly to −40° C. over 1 h, then it was recooled to −70° C. and iodomethane (1 g, 7 mmol) in 2 mL of THF was added drop-wise, maintaining the temperature below −60° C. during the addition. The cooling bath was then removed and the solution was allowed to warm slowly to −10° C. (ca 45 min). The solution was poured into ice and water, and the organic products extracted into 2×50 mL of diethyl ether. The combined organic layer was washed with brine solution, dried over $MgSO_4$ and concentrated to a light yellow gum. Preparative reverse-phase chromatography (C18, gradient elution using 85→98% methanol:0.1% $NH_4OH$) furnished two isomeric 2-methyl Spinosyn A analogs (162.9 mg and 69.8 mg). The remainder of the material isolated was unreacted Spinosyn A. Major isomer: $^1H$ NMR (300 Mhz, $CDCl_3$) d 6.79 (br s, 1H), 1.4 (d, J=10 Hz, 3H). Anal. $C_{42}H_{67}NO_{10}$ requires C, 67.62; H, 9.05; N, 1.88. Found: C, 67.49; H, 8.50; N, 1.86. Minor isomer: $^1H$ NMR (300 Mhz, $CDCl_3$) d 6.71 (br s, 1H), 1.25 (d, 3H). Anal. Calcd for $C_{42}H_{67}NO_{10}$: C, 67.62; H, 9.05; N, 1.88. Found: C, 67.20; H, 9.31; N, 2.12.

Part N Modification of the Tricyclic Portion of the Compound in Formula I

Example N1

5-Hydroxy Spinosyn D, 7-Formyloxy Spinosyn D, 7,8-Dehydro Spinosyn D, and 7,11-Dehydro Spinosyn D Spinosyn D (7.5 g, 10 mmol) was dissolved in 20 mL of dioxane and 40 mL of formic acid (90%), and the solution was cooled to −10° C. and stirred magnetically while $SeO_2$ (2.3 g, 2.1 mmol) was added in one portion. The solution was maintained at this temperature for 4 h, then it was concentrated under vacuum, maintaining the solution temperature at or below 0° C. The reddish residue was taken up in ether (250 mL) and treated with 100 mL of a saturated $NaHCO_3$ solution. The combined layers were shaken carefully until gas evolution ceased, then filtered through Celite and the layers separated. The organic layer was washed with brine, dried and concentrated to a semisolid. Recrystallization from MeOH gave 4.5 g of a mixture of formate esters of 5- and 7-hydroxy Spinosyn D. Recrystallization from MeOH gave pure 7-formyloxy Spinosyn D, mp 184° C. M.S. M+H 790.8. The residue (ca. 2.5 g) was taken up in 30 mL of THF and treated with a solution of 0.5 g of LiOOH in 10 mL of water. This solution was allowed to stir magnetically at ambient temperature for 3 h, then partitioned between EtOAc and water. The organic layer was dried (MgSO4) and concentrated and the residue was chromatographed (reverse-phase, 80–98% $MeOH/H_2O$ gradient elution). The first major peak consisted of a mixture of 5- and 7-hydroxy Spinosyn D. Recrystallization from MeOH removed the (minor) 7-isomer and gave 1.4 g of pure 5-hydroxy Spinosyn D, mp 115° C. M.S. M+H 762.4. The second major peak was 7,8-dehydro Spinosyn D, mp 150° C. M.S. M+H 744.4. Anal. Calcd for $C_{42}H_{65}NO_{10}$: C, 67.81; H, 8.81; N, 1.88. Found: C, 67.60; H, 8.81; N, 1.88. A minor peak, eluted immediately prior to the 7,8-dehydro isomer, was isolated and identified as 7,11-dehydro Spinosyn D, mp 160° C. M.S. 744.7. Anal. Calcd for $C_{42}H_{65}NO_{10}$: C, 67.81; H, 8.81; N, 1.88. Found: C, 67.68; H, 9.05; N, 1.73.

Example N2

7,11,12,5-Bis-dehydro Spinosyn D (X543351)

Spinosyn D (3.5 g, 9 mmol) was dissolved in 10 mL of dioxane and 20 mL of formic acid (90%), and the solution was cooled to −10° C. and stirred magnetically while $SeO_2$ (2.3 g, 2. 1 mmol) was added in one portion. The solution was maintained at this temperature for 4 h, then it was allowed to warm to ambient temperature. Stirring was continued overnight, then the reddish residue was taken up in ether (250 mL) and treated with 100 mL of a saturated $NaHCO_3$ solution. The combined layers were shaken carefully until gas evolution ceased, then filtered through Celite and the layers separated. The organic layer was washed with brine, dried and concentrated. The residue was chromatographed (reverse phase, gradient elution from 85 to 98% MeOH in 0.1% aqueous $NH_4OH$). A minor fraction of 7,11,12,5-bis-dehydro Spinosyn D (30 mg) which had a $^1$max of 320 nm was collected. M.S. M+H 742.7.

Example N3

5-Keto-6,7-dehydro Spinosyn D

A mixture of 5- and 7-hydroxy Spinosyn D isomers (0.60 g, 0.79 mmol), dissolved in 5 mL of $CH_2Cl_2$, was stirred at ambient temperature and with PDC (1.6 mmol). After 1 h, the solution was partitioned between water and EtOAc, and the organic layer was separated, washed with brine, dried and concentrated. The residue was eluted, first through silica gel with $Et_2O$ to remove chromium salts, then through a reverse-phase column, (80–98% $MeOH/H_2O$ gradient elution) to furnish 60 mg of the title compound, mp 148° C. M. S. M+H 760.7.

Example N4

5-Fluoro-6,7-dehydro Spinosyn D and 7-Fluoro Spinosyn D

A mixture of 5- and 7-hydroxy isomers of Spinosyn D (1.0 g, 1.34 mmol) in 8 mL of $CH_2Cl_2$ was stirred magnetically and cooled to 0° C. under a nitrogen atmosphere. The solution was treated with DAST (0.32 g, 1.5 eq) drop-wise over 5 min. After an additional 30 min, the solution was poured onto 25 mL of aqueous bicarbonate solution and the products extracted into 30 mL of $CH_2Cl_2$. The organic layer was dried and concentrated, then chromatographed through a reverse-phase column, (80–98% $MeOH/H_2O$ gradient elution) to give 4 fractions. The first product was isolated and recrystallized from MeOH to give 0.16 g of 5-fluoro-6,7-dehydro spinosyn D, mp 165° C. M.S. M+H peak at 764.7. The second fraction eluted was 7-fluoro Spinosyn D. M. S. M+H peak at 760.8. The remaining fractions consisted primarily of unsaturated (7,8- and 7,11-dehydro) materials.

Example N5

5,6-Dihydro-6,7-dehydro Spinosyn D and 5,6-dihydro-7-11-dehydro Spinosyn D

To 0.2 g (0.27 mmol) of 7,8-dehydro Spinosyn D in 5 mL of EtOH was added 0.5 mL of cyclohexene and 50 mg (cat) of moist $Pd(OH)_2/C$. The solution was heated at reflux for 2 h, then it was cooled, filtered and concentrated to an oil. Chromatography (reverse-phase column, 80–98% MeOH/

H$_2$O gradient elution) furnished two new products. The first (40 mg) was 5,6-dihydro, 7,11-dehydro Spinosyn D, mp 166° C. NMR (300 Mhz, CDCl$_3$) δ 1.0 (d, J=7 Hz, 3H; C-6 methyl group). Anal. C$_{42}$H$_{67}$NO$_{10}$ requires C, 67.62; H, 9.05; N, 1.88. Found: C, 66.65; H, 9.07; N, 1.73. The second (60 mg) was 5,6-dihydro-6,7-dehydro Spinosyn D (mp 175° C). $^1$H NMR (300 Mhz, CDCl$_3$) δ 6.73 (br s, 1H); 4.9 (s, 1H); 4.63 (m, 1H); 4.42 (d, J=6 Hz, 1H); 4.15 (m, 1H); 1.67 (d, J=2 Hz, 3H; C-6 allylic methyl group).

Example 18

Insecticide and Miticide Utility

The compounds show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

The compounds were useful for reducing populations of insects and mites, and were used in a method of inhibiting an insect or mite population which comprises applying to a locus of the insect or mite an effective insect- or mite-inactivating amount of a compound described in the Examples above. Results reported in the following tables, wherein the following abbreviations were used:

ALH refers to aster leafhopper
BAW refers to beet armyworm
CA refers to cotton aphid
NEM refers to peanut rootknot nematode
SCRW refers to southern corn rootworm
TBW refers to tobacco budworm
TSSM refers to two spotted spider mite
GECR refers to German cockroach In conducting evaluations of insecticidal activity, each test compound was formulated as a 400 ppm solution, and this solution was then diluted with water to give lesser concentrations. The 400 ppm solution was prepared by combining 19.2 mL of 0.05% solution of Tween 20 (polyoxyethylene (20) sorbitan monolaurate) in water with a solution of 8 mg of the compound in 0.8 mL of acetone/EtOH (9/1).

Activity against aster leafhopper (*Macrosteles fascifrons*) was tested as follows. The test was run using concentrations of 400 ppm and 50 ppm. One ounce plastic cups containing a cotton wick was sprayed with 0.4 mL of formulated material using a flat-fan nozzle. The excess moisture was allowed to evaporate. Then five to ten carbon dioxide anesthetized adult leafhoppers were added to each cup. The cups were capped and held at room temperature for 24 hours. Percent mortality was then determined.

Activity against beet armyworm (*Spodoptera exiqua*) was evaluated as follows. The test is run using concentrations of 400 ppm and 50 ppm. A general purpose lepidoptera artificial diet was diluted to half strength with a 5% non nutritive agar. 8 mL of this diet material was dispensed into one ounce diet cups. One hour prior to treatment, 35 to 40 eggs were dispensed onto the diet surface. The cups were then sprayed with formulated material through a flat-fan nozzle. Treated cups were air dried prior to sealing with plastic caps. The cups were held for 6 days at room temperature. Activity was then rated based on the total number of live and dead larvae, and on the size of live larvae.

Activity against cotton aphid (*Aphis gossypii*) and two spotted spider mite (*Tetranychus urticae*) was evaluated as follows. Golden crookneck squash plants were grown to the expanded cotyledon stage (about 6 to 8 days). The plants were infested with cotton aphids and two spotted spider mites 16 to 24 hours before application of the test material by transfer of infested foliage cut from a stock colony. Immediately prior to spray application of the test material the transfer foliage is removed from the squash plants. The test is run using concentrations of 400 ppm and 50 ppm. The plants are sprayed with test solution using an atomizing sprayer at 17 psi. Both surfaces of the leaves are covered until runoff, and then allowed to dry. Activity of each compound was determined three days after treatment. Activity was rated as a percent based on the mites/aphids present in plants sprayed with solvent alone.

Activity against peanut root knot nematode (*Meloidogyne arenaria*) was evaluated as follows. Five untreated cucumber seeds are placed into the bottom of a clear one ounce cup, 20 g of clean white sand is added, and the cups were sprayed while rotating on a pedestal allowing 1.0 mL of a 400 ppm solution to be deposited on the sand. To each cup was dispensed 2.5 to 3.0 mL of deionized water containing 300 to 500 nematodes. The cups were held for 10 to 12 days in an environmental growth chamber at a temperature of 76 to 85° F. and ambient humidity of 50 to 60%. After 10 to 12 days the cups were evaluated by inverting the cup and observing nematode mortality and feeding damage to the cucumber plants.

Activity on Southern corn rootworm (*Diabrotica undecimpuctata howardi* Barber) was evaluated by adding one mL of test solution containing a predetermined concentration of test compound to a cup containing a kernel of corn in 16 g of sterile soil. This produces a soil concentration of 24 ppm. After 1.5 to 2 hours of drying, five 4th instar corn rootworm larvae were added to the individual cups. Mortality was measured at 3–4 days by emptying the cup onto a pan and inspecting the soil for live rootworms.

Activity against tobacco budworm (*Heliothis virescens*) was evaluated as follows. A general purpose lepidoptera artificial diet was diluted to half strength with a 5% non nutritive agar. 8 mL of this diet material was dispensed into each one ounce diet cup. One hour prior to treatment 18 to 20 eggs were dispensed onto the diet surface. The cups were then sprayed with formulated material through a flat-fan nozzle. The test was run using concentrations of 400 ppm and 50 ppm. Treated cups were air dried prior to sealing with plastic caps. The cups were held for 6 days at room temperature. Activity was then rated based on the total number of live and dead larvae, and on the size of live larvae.

Activity against German cockroach (*Blattella germanicus*) was evaluated as follows. 8 mL of alfalfa based green insect diet material was dispensed into a one ounce diet cup. The cups were then sprayed with formulated material through a flat-fan nozzle. The test was run using concentrations of 400 ppm and 50 ppm. Treated cups were air dried for 24 hours and infested with five late third or early fourth instar German cockroaches. The cups were capped and held for ten days in an environmental growth chamber at a temperature of 76–85° C. Activity was then rated based on the total number of live and dead insects.

Nematicide Utility

The method was practiced in accordance with standard techniques for the application of nematicides. In general, good nematicidal activity can be expected at rates of 1–10 lbs/acre. The compound can be formulated as described herein. When formulated as dispersions, nematicides are typically applied as aqueous drenches around growing plants or applied incrementally via irrigation systems. When applied as granules, nematicides may be incorporated into the soil before planting, or applied in a band on top of a seed row, or broadcast and then incorporated into the soil, or used as a side dressing to an established crop.

The following activity was found for the compounds described below:

| EXAMPLE NUMBER | INSECT | RATE | MORTALITY |
| --- | --- | --- | --- |
| A1 | TBW | 400 | 100 |
| A1 | TSSM | 400 | 100 |
| A2 | TBW | 400 | 100 |
| A3 | TBW | 400 | 100 |
| A4 | TBW | 400 | 100 |
| A5 | TBW | 400 | 100 |
| A6 | TBW | 400 | 100 |
| A7 | TBW | 400 | 100 |
| A9 | TBW | 400 | 100 |
| A10 | TBW | 400 | 100 |
| A11 | TBW | 400 | 100 |
| A12 | TBW | 400 | 100 |
| A13a | TBW | 400 | 100 |
| A13b | TBW | 400 | 100 |
| A14 | TBW | 400 | 100 |
| A15 | TBW | 400 | 100 |
| A16 | TBW | 400 | 100 |
| A17 | TBW | 400 | 100 |
| A18 | TBW | 400 | 100 |
| A18 | TSSM | 400 | 100 |
| A19 | TBW | 400 | 100 |
| A20 | TBW | 400 | 100 |
| A21 | TBW | 400 | 100 |
| A22 | TBW | 400 | 100 |
| A22 | TSSM | 400 | 100 |
| A23 | TBW | 400 | 100 |
| A23 | TSSM | 400 | 100 |
| A24 | TBW | 400 | 100 |
| A24 | TSSM | 400 | 100 |
| A25 | TBW | 400 | 100 |
| A25 | TSSM | 400 | 100 |
| A26 | TBW | 400 | 100 |
| A26 | TSSM | 400 | 100 |
| A27 | TBW | 400 | 100 |
| A28 | TBW | 400 | 100 |
| A29 | TBW | 400 | 100 |
| A29 | TSSM | 400 | 100 |
| A30 | TBW | 400 | 100 |
| A31 | TBW | 400 | 100 |
| A32 | TBW | 400 | 90 |
| A33 | TBW | 400 | 100 |
| A34 | TBW | 400 | 100 |
| A35 | TBW | 400 | 100 |
| A36 | TBW | 400 | 100 |
| A37 | TBW | 400 | 100 |
| A38 | TBW | 400 | 100 |
| A38 | TSSM | 400 | 100 |
| A39 | TBW | 400 | 100 |
| A39 | TSSM | 400 | 100 |
| A40 | TBW | 400 | 100 |
| A41 | TBW | 400 | 100 |
| A42 | TBW | 400 | 100 |
| A43 | TBW | 400 | 100 |
| A44 | TBW | 400 | 100 |
| A45a | TBW | 400 | 100 |
| A45c | TBW | 400 | 100 |
| A45c | TSSM | 400 | 100 |
| A45b | TBW | 400 | 100 |
| A46 | TBW | 80 | 100 |
| A48 | TBW | 400 | 100 |
| A49a | TBW | 400 | 80 |
| A49b | TBW | 64 | 25 |
| A50 | TBW | 400 | 100 |
| A51 | Intermed | | |
| A52 | TBW | 400 | 100 |
| A53 | TBW | 400 | 100 |
| A53 | TSSM | 400 | 100 |
| A54 | TBW | 400 | 100 |
| A54 | TSSM | 400 | 100 |
| A55 | TBW | 400 | 100 |
| A55 | TSSM | 400 | 100 |
| A56 | TBW | 400 | 100 |
| A56 | TSSM | 400 | 100 |
| A57 | TSSM | 400 | 100 |
| A58a | TBW | 400 | 100 |
| A58b | TBW | 400 | 100 |
| A59 | TBW | 400 | 100 |
| A60a | TBW | 400 | 100 |
| A60b | TBW | 400 | 100 |
| A61 | TBW | 400 | 100 |
| A62 | TBW | 400 | 100 |
| A63 | TBW | 400 | 100 |
| A63 | TSSM | 400 | 100 |
| A64a | TBW | 400 | 100 |
| A64b | TBW | 400 | 100 |
| A65 | TBW | 400 | 100 |
| A66 | TBW | 400 | 100 |
| A66 | TSSM | 400 | 100 |
| A67 | TBW | 400 | 100 |
| A67 | TSSM | 400 | 100 |
| A68 | TBW | 400 | 100 |
| A69 | TBW | 400 | 100 |
| A70 | TBW | 400 | 100 |
| A71 | TBW | 400 | 100 |
| A72 | TBW | 400 | 100 |
| A73 | TBW | 400 | 100 |
| A74 | TBW | 400 | 100 |
| A75 | TBW | 64 | 100 |
| A76 | TBW | 400 | 100 |
| A77 | TBW | 400 | 100 |
| A78a | TBW | 400 | 100 |
| A78b | TBW | 400 | 100 |
| A78c | TBW | 400 | 100 |
| A79 | TBW | 400 | 100 |
| A80a | GECR | 400 | 20 |
| A80b | TBW | 400 | 100 |
| A81 | TBW | 400 | 100 |
| A81 | TSSM | 400 | 100 |
| A85 | TBW | 400 | 100 |
| A85 | TBW | 400 | 100 |
| A87 | TBW | 400 | 100 |
| A88 | CLH | 400 | 20 |
| A89 | TBW | 400 | 100 |
| A91 | Intermed | | |
| B1 | TSSM | 400 | 90 |
| B2 | TBW | 100 | 100 |
| B3 | TSSM | 200 | 40 |
| B4 | TSSM | 100 | 50 |
| B5 | TSSM | 100 | 65 |
| B6 | TBW | 80 | 100 |
| B7 | CA | 200 | 60 |
| B8 | TBW | 400 | 100 |
| B9 | TBW | 400 | 100 |
| B10 | TBW | 400 | 100 |
| B11 | TBW | 400 | 60 |
| B12 | TSSM | 400 | 90 |
| B12 | TBW | 400 | 100 |
| B13 | TBW | 400 | 100 |
| B14 | TBW | 400 | 100 |
| B15 | TBW | 400 | 100 |
| B16 | TSSM | 400 | 100 |
| B16 | TBW | 400 | 100 |
| B17 | TBW | 400 | 100 |
| B19 | Intermed | | |

| EXAMPLE NUMBER | INSECT | RATE | MORTALITY |
| --- | --- | --- | --- |
| C1 | TBW | 80 | 100 |
| C1 | TSSM | 400 | 100 |
| C3 | TBW | 400 | 100 |
| C3 | TSSM | 400 | 100 |
| C4 | TBW | 80 | 100 |
| C5 | TBW | 400 | 100 |
| C6 | TBW | 80 | 60 |
| C7 | TBW | 80 | 100 |
| C7 | TSSM | 40 | 97 |
| C8 | TSSM | 200 | 50 |
| C9 | TBW | 400 | 100 |
| C10 | TBW | 400 | 100 |
| C11 | TBW | 400 | 100 |
| C12 | TBW | 400 | 100 |
| C12 | TSSM | 400 | 100 |
| C13a | TBW | 64 | 100 |
| C14 | TBW | 21 | 42 |
| C15 | TBW | 400 | 100 |
| C15 | TSSM | 400 | 100 |
| C16 | TBW | 64 | 64 |
| C17 | TBW | 400 | 70 |
| C18 | TBW | 400 | 100 |
| C18 | TSSM | 400 | 100 |
| C19 | TBW | 400 | 100 |
| C19 | TSSM | 400 | 100 |
| C20 | GECR | 400 | 20 |
| C21a | TBW | 400 | 100 |
| C21b | TSSM | 400 | 100 |
| C22 | TBW | 400 | 100 |
| C22 | TSSM | 400 | 100 |
| C23 | TBW | 400 | 100 |
| C23 | TSSM | 400 | 100 |
| C24 | TBW | 400 | 100 |
| C25 | TBW | 400 | 100 |
| C26 | TBW | 400 | 100 |
| C27 | TBW | 400 | 100 |
| C28 | TBW | 64 | 100 |
| C29 | TBW | 400 | 80 |
| C30 | TBW | 64 | 22 |
| C31 | TBW | 400 | 100 |
| D1 | TBW | 80 | 33 |
| D2 | TBW | 80 | 90 |
| D4 | TBW | 400 | 100 |
| D4 | TSSM | 400 | 100 |
| D5 | TBW | 64 | 95 |
| D6 | TBW | 400 | 100 |
| D7 | TBW | 64 | 58 |
| D8 | TBW | 400 | 100 |
| D9 | TBW | 400 | 100 |
| D10 | TBW | 400 | 80 |
| D11 | TBW | 400 | 100 |
| D11 | TSSM | 400 | 90 |
| D12 | TBW | 400 | 100 |
| D13 | GECR | 400 | 40 |
| D14 | TBW | 400 | 100 |
| D15 | TBW | 400 | 100 |
| D15 | TSSM | 400 | 100 |
| D16 | Intermed | | |
| D17 | BAW | 400 | 60 |
| D18 | TBW | 400 | 100 |
| D19 | TBW | 400 | 80 |
| D20 | TBW | 400 | 100 |
| D21a | GECR | 400 | 20 |
| D21b | TBW | 400 | 100 |
| E1 | ALH | 400 | 100 |
| E2 | GECR | 400 | 20 |
| E4b | TBW | 400 | 100 |
| E4b | TSSM | 400 | 60 |
| E5 | TBW | 80 | 35 |
| E6 | NEMA | 400 | 100 |
| E7 | TSSM | 200 | 100 |
| E8 | BAW | 400 | 80 |
| F1 | TBW | 400 | 100 |
| F2 | TBW | 400 | 100 |
| F3 | TBW | 400 | 100 |
| F3 | TSSM | 64 | 24 |
| F4 | TBW | 64 | 24 |
| F5a | TBW | 400 | 100 |
| F5b | TBW | 400 | 100 |
| F7 | TBW | 64 | 100 |
| F7 | TSSM | 400 | 100 |
| F8a | TBW | 400 | 100 |
| F8a | TSSM | 400 | 90 |
| F8b | TBW | 400 | 100 |
| F9a | TBW | 400 | 100 |
| F9a | TSSM | 400 | 90 |
| F9b | TBW | 400 | 100 |
| F9b | TSSM | 400 | 90 |
| F10 | Intermed | | |
| F11 | Intermed | | |
| F12a | BAW | 56 | 80 |
| F12b | TBW | 400 | 100 |
| F13a | TBW | 400 | 100 |
| F13a | TSSM | 400 | 100 |
| F13b | TBW | 400 | 100 |
| F14 | TBW | 400 | 100 |
| F15a | TBW | 400 | 100 |
| F15b | TBW | 400 | 60 |
| F16 | TBW | 400 | 100 |
| F17 | TBW | 400 | 60 |
| F18 | TBW | 400 | 100 |
| F19 | TBW | 400 | 100 |
| F20 | TBW | 400 | 100 |
| F21a | TBW | 400 | 100 |
| F22 | TBW | 400 | 100 |
| F23 | TBW | 400 | 100 |
| F24 | TBW | 400 | 100 |
| F25 | TBW | 400 | 100 |
| F26 | BAW | 400 | 100 |
| F27 | TBW | 400 | 100 |
| F28 | TBW | 400 | 100 |
| F29 | TBW | 400 | 100 |
| F29 | TSSM | 400 | 100 |
| F30 | TBW | 400 | 100 |
| F30 | TSSM | 400 | 100 |
| F31 | TBW | 400 | 100 |
| G1 | Intermed | | |
| G2 | TSSM | 200 | 20 |
| G4 | Intermed | | |
| G5 | TBW | 400 | 100 |
| G6 | Intermed | | |
| H1 | TBW | 400 | 100 |
| H1 | TSSM | 400 | 100 |
| H2 | Intermed | | |
| H3 | TBW | 400 | 100 |
| H3 | TSSM | 400 | 100 |
| H4 | TBW | 400 | 100 |
| H5 | TBW | 400 | 100 |
| H6 | TBW | 400 | 100 |
| H6 | TSSM | 400 | 100 |
| H7 | TBW | 400 | 100 |
| H8 | TBW | 400 | 100 |
| H8 | TSSM | 400 | 100 |
| I1 | TBW | 400 | 100 |
| I1 | TSSM | 400 | 100 |
| I2 | TBW | 400 | 100 |
| I2 | TSSM | 400 | 100 |
| I3 | TBW | 400 | 100 |
| I3 | TSSM | 400 | 90 |
| I4 | TBW | 400 | 100 |
| I4 | TSSM | 400 | 80 |
| I5 | TBW | 400 | 100 |
| I5 | TSSM | 400 | 100 |
| I6 | TBW | 400 | 100 |
| I6 | TSSM | 400 | 80 |
| I7 | TBW | 400 | 100 |
| I7 | TSSM | 400 | 100 |
| I8 | TBW | 400 | 100 |
| I8 | TSSM | 400 | 100 |
| I9 | TBW | 400 | 100 |
| I10 | TBW | 400 | 100 |
| I11 | Intermed | | |
| I12 | Intermed | | |
| I13 | TBW | 400 | 100 |
| I13 | TSSM | 400 | 100 |
| I14 | TBW | 400 | 100 |

| EXAMPLE NUMBER | INSECT | RATE | MORTALITY |
|---|---|---|---|
| I14 | TSSM | 400 | 100 |
| I15 | TBW | 400 | 100 |
| I16 | TBW | 400 | 100 |
| I17 | TBW | 400 | 100 |
| I18 | BAW | 400 | 80 |
| J1 | BAW | 400 | 80 |
| J2 | TBW | 400 | 40 |
| J3 | TBW | 400 | 100 |
| J4 | TBW | 400 | 100 |
| J6 | GECR | 200 | 20 |
| J7 | GECR | 200 | 20 |
| K1 | TSSM | 400 | 100 |
| K2a | CA | 400 | 50 |
| K2b | TBW | 64 | 15 |
| K5 | CPH | 400 | 100 |

Example 19 Spinosyn derivatives of Example 17
Control of *Stomoxys calcitrans* (stable fly) and *Phormia regina* (blow fly).

The test procedures were as follows.

The compound to be evaluated was dissolved in 1 part acetone/1 part ethanol to provide a stock solution of the compound at a concentration of 5,000 ppm; this solution was shaken for 15 minutes on a sonicator. Portions of the stock solution were placed in 15 ml test tubes, and portions of bovine serum were added to provide the desired dilution of the test compound. A dental wick was placed in each test tube and the serum allowed to saturate the wick.

For the blow fly test, approximately 20 blow fly larvae were placed onto the top center of the saturated dental wick, and the test tube was plugged with cotton and incubated at 27° C. and 70% humidity for 24 and 48 hours. Larval mortality counts were then made, and adjusted for any mortality in the vehicle control, to determine percent efficacy against blow fly.

For the adult stable fly test, the saturated wick was placed on a filter paper in a petri dish, and approximately 10 chilled live, hungry stable flies were placed on the center of the dish bottom. The dish was covered and allowed to incubate at 27° C. and 60% relative humidity for 48 hours. Mortality readings were made at each of 24 and 48 hours, and adjusted for any mortality in the vehicle control to determine percent efficacy against adult stable fly.

The results are reported below.

Animal Science Data for Spinosoids

| Patent Example Number | Percentage of ASF killed at 100 ppm | Percentage of ASF killed at 10 ppm | Percentage of LBF killed at 100 ppm | Percentage of LBF killed at 10 ppm |
|---|---|---|---|---|
| A2 | | | | |
| A3 | 100% | | | |
| A5 | 100% | | | |
| A6 | 100% | | | |
| A7 | 100% | | | |
| A9 | 100% | | | |
| A10 | 100% | | | |
| A11 | 100% | | | |
| A12 | 100% | | | |
| A13a | 100% | | | |
| A13b | 100% | | | |
| A14 | 100% | | | |
| A15 | 100% | | | |
| A17 | 100% | | | |
| A18 | 100% | | | |
| A19 | 100% | | | |
| A20 | 100% | | | |
| A22 | 100% | | | |
| A23 | 100% | | | |
| A26 | 100% | | | |
| A27 | 100% | | | |
| A28 | 100% | | | |
| A29 | 100% | | | |
| A30 | 100% | | | |
| A31,I17 | 100% | | | |
| A32 | 100% | | | |
| A33 | 100% | | | |
| A34 | 100% | | | |
| A36 | 100% | | | |
| A37 | 100% | | | |
| A40 | 100% | | | |
| A46 | 100% | 100% | | |
| A47 | | <50% | | |
| A48 | | 100% | | <50% |
| A49b | | <50% | | |
| A50 | 100% | | | |
| A52 | 100% | | | |
| A53 | 100% | | | |
| A54 | 100% | | | |
| A55 | 100% | | | |
| A56 | 100% | | | |
| A57 | 100% | | | |
| A58a | 100% | | | |
| A58b | 100% | | | |
| A59 | 100% | | | |
| A60a | 100% | | | |
| A60b | 100% | | | |
| A61 | 80% | | | |
| A62 | 100% | | | |
| A63 | 100% | | | |
| A64a | 100% | | | |
| A64b | 100% | | | |
| A66 | 100% | | | |
| A67 | 100% | | | |
| A68 | 100% | | | |
| A69 | 100% | | | |
| A70 | 100% | | | |
| A71 | 100% | | | |
| A72 | 100% | | | |
| A73 | <50% | | | |
| A74 | <50% | | | |
| A76 | 100% | | | |
| A77 | 100% | | | |
| A78a | 100% | | | |
| A78b | 100% | | | |
| A78c | 100% | | | |
| A79 | 100% | | | |
| A80a | 100% | | | |
| A80b | <50% | | | |
| A81 | 100% | | | |
| A86,A90 | | <50% | | |
| A87 | | 100% | | |
| A88 | | <50% | | |
| A89 | 100% | | | |
| A91 | <50% | | | |
| B1 | 90% | <50% | 100% | |
| B2 | | 60% | | <50% |
| B3 | | <50% | | <50% |
| B4 | | <50% | | <50% |
| B5 | | <50% | | <50% |
| B6 | | <50% | | 75% |
| B7 | | <50% | | <50% |
| B8 | 100% | 80% | | |
| B9 | | 80% | | 100% |

-continued

Animal Science Data for Spinosoids

| Patent Example Number | Percentage of ASF killed at 100 ppm | Percentage of ASF killed at 10 ppm | Percentage of LBF killed at 100 ppm | Percentage of LBF killed at 10 ppm |
|---|---|---|---|---|
| B10 | | <50% | | <50% |
| B11 | | <50% | | <50% |
| B12 | | <50% | | |
| B13 | | 80% | | |
| B14 | <50% | <50% | | |
| B15 | 100% | <50% | | |
| B16 | 90% | 50% | | |
| B17 | 100% | | | |
| B18 | | 90% | | |
| B19 | <50% | | | |
| C1,C13b | 100% | 80% | 100% | <50% |
| C2 | 60% | <50% | <50% | <50% |
| C3 | 100% | 100% | 100% | 100% |
| C4 | 100% | 100% | <50% | <50% |
| C5 | 100% | <50% | 100% | <50% |
| C6 | | 90% | 100% | |
| C9 | | 90% | | |
| C10 | 100% | | | |
| C11 | 100% | 90% | | |
| C16 | <50% | | | |
| C17 | 70% | | | |
| C19 | 100% | | | |
| C20 | <50% | | | |
| C21a | 100% | | | |
| C21b | 90% | | | |
| C22 | <50% | | | |
| C23 | 100% | | | |
| C24 | 100% | | | |
| C25 | 100% | | | |
| C26 | 100% | | | |
| C27 | 100% | | | |
| C28 | 60% | | | |
| C29 | 100% | | | |
| C30 | <50% | | | |
| C31 | 100% | | | |
| D1 | | <50% | | <50% |
| D2 | | 100% | | <50% |
| D3 | 100% | <50% | | |
| D4 | | 100% | | |
| D5 | 100% | | | |
| D6 | 100% | | | |
| D7 | 100% | | | |
| D8 | 100% | | | |
| D9a | <50% | | | |
| D9b | 100% | | | |
| D10 | <50% | | | |
| D12 | | 100% | | 100% |
| D13 | <50% | | | |
| D17 | 70% | | | |
| D18 | 100% | | | |
| E1 | 90% | <50% | | |
| E2,E3c | | <50% | | <50% |
| E3a | | <50% | | |
| E3b | | <50% | | |
| E4 | | | | <50% |
| E7 | 80% | <50% | | |
| E8 | | <50% | | <50% |
| F1 | | 60% | | 90% |
| F2 | | <50% | | <50% |
| F3 | | <50% | | <50% |
| F4 | | <50% | | <50% |
| F5a | | 90% | | <50% |
| F5b | | 60% | | <50% |
| F6 | | <50% | | |
| F7 | | 100% | 100% | |
| F8b | | 100% | | 100% |
| F8a | | 100% | | 90% |
| F9b | | 100% | 100% | |
| F12a | <50% | | | |
| F12b | 100% | | | |
| F13a | 100% | | | |

-continued

Animal Science Data for Spinosoids

| Patent Example Number | Percentage of ASF killed at 100 ppm | Percentage of ASF killed at 10 ppm | Percentage of LBF killed at 100 ppm | Percentage of LBF killed at 10 ppm |
|---|---|---|---|---|
| F13b | 100% | | | |
| F14 | 100% | | | |
| F16 | 100% | | | |
| F17 | 100% | | | |
| F18 | 100% | | | |
| F19 | 100% | | | |
| F22 | 100% | | | |
| F23 | 100% | | | |
| F24 | 100% | | | |
| F26 | <50% | | | |
| F27 | 100% | | | |
| F28 | 100% | | | |
| F29 | 100% | | | |
| F30 | 100% | | | |
| G1 | 100% | <50% | <50% | |
| G4 | | <50% | | |
| G5 | 100% | | | |
| G6 | <50% | | | |
| H1 | 100% | 100% | | 100% |
| H2 | | <50% | | |
| H3 | 100% | 100% | | 100% |
| H4 | 100% | 100% | | |
| H5 | 100% | 100% | | |
| H6 | | 100% | | 100% |
| H7 | 100% | 100% | 100% | 100% |
| H8 | | 100% | | |
| I1 | 100% | | | |
| I2 | 100% | | | |
| I3 | <50% | | | |
| I5 | | 100% | | |
| I6 | | 100% | | |
| I7 | | 100% | | |
| I9 | 100% | | | |
| I11 | 100% | | | |
| I14 | | 100% | | |
| I15 | | 100% | | 100% |
| I16 | | 100% | | |
| J1 | | 90% | | 100% |
| J2 | | <50% | | |
| J3 | | <50% | | |
| J4 | 100% | | | |
| J5 | | <50% | | |
| J6 | | <50% | | <50% |
| J7 | | <50% | | <50% |
| J10 | | <50% | | |
| K1 | <50% | | | |
| K2a | <50% | | | |
| K2b | <50% | | | |
| K3b | <50% | | | |
| K4 | 90% | | | |
| K5 | | <50% | | |
| K6 | <50% | | | |
| K7 | | <50% | | <50% |

What is claimed is:
1. A compound having the formula:

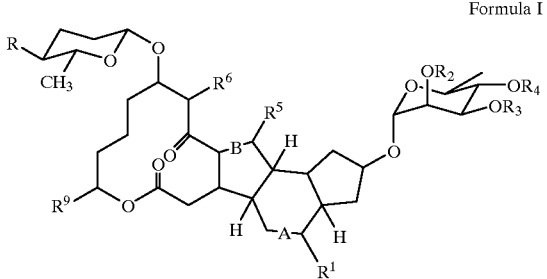

Formula I wherein:
A and B each represent a single bond, a double bond, or an epoxide linkage;
R is

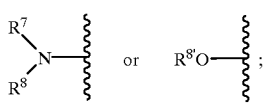

$R^1$ is hydrogen or methyl;
$R^2$, $R^3$, and $R^4$ are independently an alkyl having 1 to 4 carbon atoms, a haloalkyl having 1 to 4 carbon atoms, alkanoyl having 1 to 4 carbon atoms or a protected hydroxyl;
$R^5$ is hydrogen, alkyl having 1 to 4 carbon atoms, alkyl amino having 1 to 4 carbon atoms, or alkyl hydroxyl amino having the formula

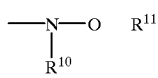

wherein $R^{10}$ and $R^{11}$ are independently H or an alkyl having 1 to 4 carbon atoms or an alkanoyl having 1 to 5 carbon atoms; $R^6$ is hydrogen or methyl;
$R^7$, $R^8$, and $R^{8'}$ are independently an alkyl having 1 to 4 carbon atoms, a haloalkyl having 1 to 4 carbon atoms, or alkanoyl having 1 to 4 carbon atoms or a protected amino; and
$R^9$ is methyl or ethyl; or an acid addition salt thereof, except that the following compounds are excluded: compounds of Formula I wherein:

A and B are both double bonds;
R is N$^{R^7R^8}$;
$R^7$ and $R^8$ are independently hydrogen or methyl;
$R^2$, $R^3$ and $R^4$ are independently hydrogen or methyl; and
$R^5$ is hydrogen.

2. The compound of claim 1 where the compound is an acid addition salt.
3. A compound comprising:

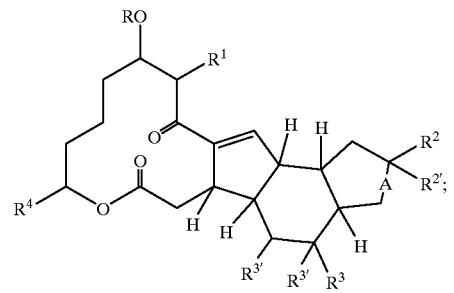

Formula II where R is

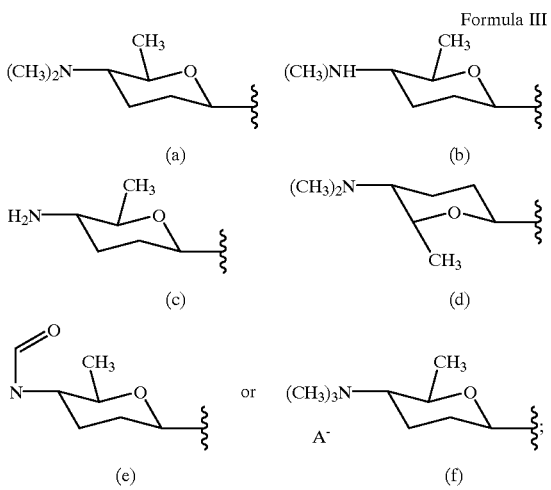

Formula III wherein $R^1$ and $R^3$ are independently hydrogen or methyl; $R^4$ is methyl or ethyl; and the following combinations are present:

| $R^2$ | | | $R^{2'}$ | R | $R^{3'}$ | 3" | A |
|---|---|---|---|---|---|---|---|
|  | | | —H | (a) | join to form a double bond | | S |

| R² | R²' | R | R³' | 3" | A |
|---|---|---|---|---|---|
| [sugar structure with H₃C—O, OCH₃, R⁵, R⁶, R⁷ ester substituents] | —H | (a) | join to form a double bond | | S |
| [sugar structure with OCH₂R¹⁰, OCH₂R¹¹, OCH₂R¹²] | —H | (a) | —H | —H | S |
| [sugar structure with R¹⁰H₂C—O, CH₂R¹¹, benzoate with R⁵, R⁶, R⁷] | —H | (a) | join to form a double bond | | S |
| [sugar structure with R¹⁰H₂C—O, CH₂R¹¹, benzoate with R⁵, R⁶, R⁷] | —H | (a) | [O bridge] | | S |
| [sugar structure with R¹⁰H₂C—O, CH₂R¹¹, ester with R⁵, R⁶] | —H | (a) | join to form a double bond | | S |

| R² | R²" | R | R³' | 3" | A |
|---|---|---|---|---|---|
| [structure: pyranose with R¹⁰H₂C—O, CH₂R¹¹, H₃C, O-P(OEt)(OEt)] | —H | (a) | join to form a double bond | | S |
| [structure: pyranose with R¹⁰H₂C—O, CH₂R¹¹, H₃C, O-P(=S)(OEt)(OEt)] | —H | (a) | join to form a double bond | | S |
| [structure: pyranose with R¹⁰H₂C—O, CH₂R¹¹, H₃C, O-C(=O)-C(=O)-O-CH₂CH₃] | —H | (a) | join to form a double bond | | S |
| [structure: pyranose with R¹⁰H₂C—O, CH₂R¹¹, H₃C, O-C(=O)-C(R⁵)(R⁶)(R⁷)] | —H | (a) | join to form a double bond | | S |
| [structure: pyranose with R¹⁰H₂C—O, CH₂R¹¹, H₃C, O-C(=O)-CH₂-R⁵] | —H | (a) | join to form a double bond | | S |

-continued
| R² | R²' | R | R³' | 3" | A |
|---|---|---|---|---|---|
| 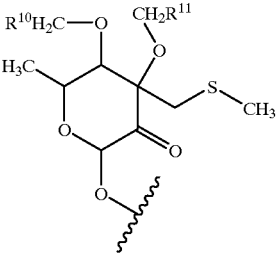 | —H | (a) | join to form a double bond | | S |
| 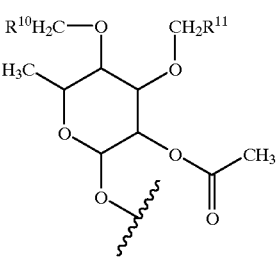 | —H | (a) | join to form a double bond | | S |
| 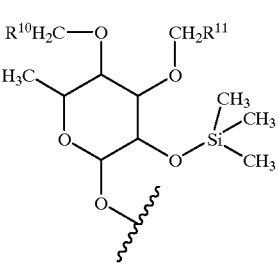 | —H | (a) | join to form a double bond | | S |
| 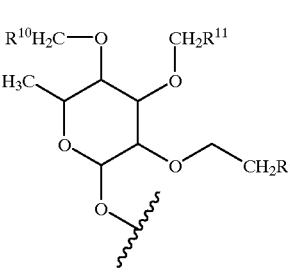 | —H | (a) | join to form a double bond | | S |
| 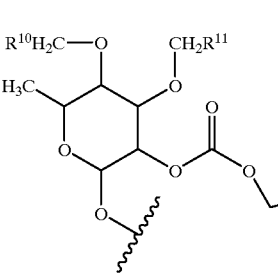 | —H | (a) | join to form a double bond | | S |

-continued

| R² | R²' | R | R³' | 3" | A |
|---|---|---|---|---|---|
| [structure: sugar with R¹⁰H₂C—O, CH₂R¹¹, H₃C, and O-SO₂-C(R⁵)(R⁶)R⁷ substituent] | —H | (a) | join to form a double bond | | S |
| [structure: sugar with R¹⁰H₂C—O, CH₂R¹¹, H₃C, and O-benzyl substituent] | —H | (a) | join to form a double bond | | S |
| [structure: sugar with R¹⁰H₂C—O, CH₂R¹¹, H₃C, and O-C(=O)CH₃ (acetyl) substituent] | —H | (a) | join to form a double bond | | S |
| [structure: sugar with CH₂R¹¹, R¹⁰H₂C—O, H₃C, O-CH₂R¹², and O-allyl (CH₂-CH=CH-) substituent] | —H | (a) | join to form a double bond | | S |
| [structure: sugar with R¹⁰H₂C—O, H₃C, CH₂R¹¹, and O-propargyl (CH₂-C≡CH) substituent] | —H | (a) | join to form a double bond | | S |

-continued

| R² | R²' | R | R³' | 3" | A |
|---|---|---|---|---|---|
| (structure: pyranose with R¹⁰H₂C—O, H₃C, O—CH₂ cyclopropyl, O—CH₂R¹¹) | —H | (a) | join to form a double bond | | S |
| (structure: pyranose with R¹⁰H₂C—O, H₃C, O—C(=S)—O—phenyl with R⁵, R⁶, R⁷, R⁸, R⁹, O—CH₂R¹¹) | —H | (a) | join to form a double bond | | S |
| (structure: pyranose with R¹⁰H₂C—O, H₃C, O—CH₂R¹¹) | —H | (a) | join to form a double bond | | S |
| (structure: pyranose with R¹⁰H₂C—O, H₃C, O—C(=O)—O—CH(CH₃)₂, O—CH₂R¹¹) | —H | (a) | join to form a double bond | | S |
| (structure: pyranose with R¹⁰H₂C—O, H₃C, O—C(=O)—CHR⁵R⁶, O—CH₂R¹¹) | —H | (a) | join to form a double bond | | S |

-continued
| R² | R²' | R | R³' | 3" | A |
|---|---|---|---|---|---|
| 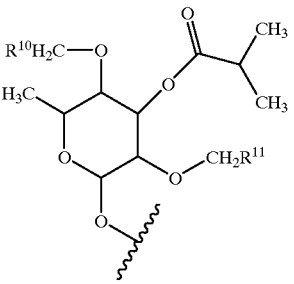 | —H | (a) | join to form a double bond | | S |
| 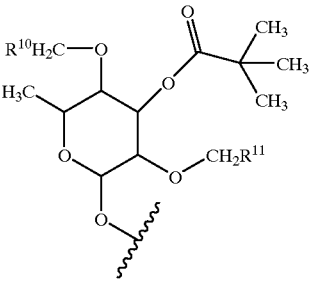 | —H | (a) | join to form a double bond | | S |
| 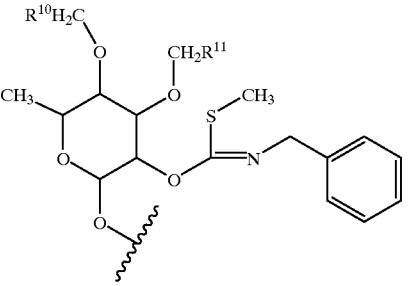 | —H | (a) | join to form a double bond | | S |
| 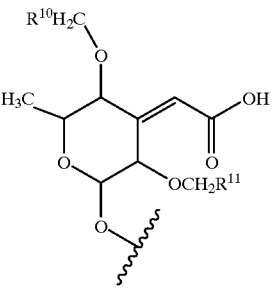 | —H | (a) | join to form a double bond | | S |
| 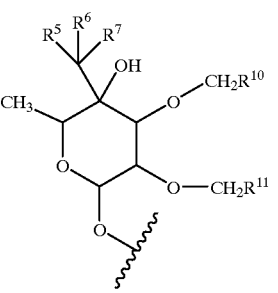 | —H | (a) | join to form a double bond | | S |

-continued

| R² | R²" | R | R³' | 3" | A |
|---|---|---|---|---|---|
| (structure) | —H | (a) | join to form a double bond | | S |
| (structure) | —H | (a) | join to form a double bond | | S |
| (structure) | —H | (a) | —H | —H | S |

-continued
| R² | R²' | R | R³' | 3" | A |
|---|---|---|---|---|---|
| 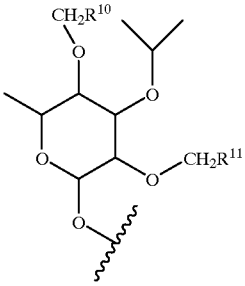 | —H | (a) | join to form a double bond | | S |
| 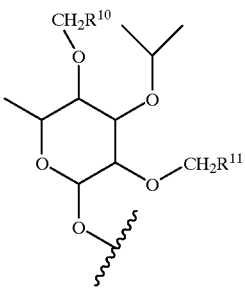 | —H | (a) | —H | —H | S |
| 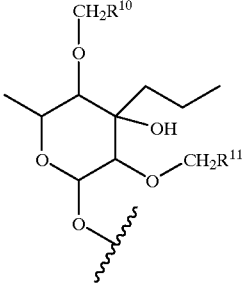 | —H | (e) | —H | —H | S |
| 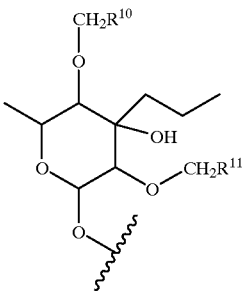 | —H | (a) | —H | —H | S |
| 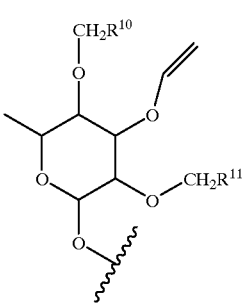 | —H | (a) | join to form a double bond | | S |

-continued

| $R^2$ | $R^{2''}$ | R | $R^{3'}$ | $3''$ | A |
|---|---|---|---|---|---|
| [structure with dimethylamino sugar, macrolactone core fused to polycyclic ring system, and disaccharide with sulfite bridge bearing $R^{10}H_2C$, $R^{11}H_2C$, $OCH_2R^{12}$ substituents] | —H | (a) | join to form a double bond | | S |
| [structure of sugar ring bearing $CH_2R^{10}$, $CH_2R^{11}$, $CH_2R^{12}$ substituents] | —H | (b) | join to form a double bond | | S |
| [structure of sugar ring bearing $CH_2R^{10}$, $CH_2R^{11}$ and imidazolylsulfonyloxy group] | —H | (a) | join to form a double bond | | S |

-continued

| R² | R²' | R | R³' | 3" | A |
|---|---|---|---|---|---|
| (structure with CH₂R¹⁰, methoxy vinyl ether) | —H | (a) | join to form a double bond | | S |
| (pyranose with CH₂R¹⁰, O-vinyl, CH₂R¹¹) | —H | (a) | —H | —H | S |
| (pyranose with CH₂R¹⁰, CH₂R¹¹, O-vinyl) | —H | (a) | join to form a double bond | | S |
| (pyranose with CH₂R¹⁰, CH₂R¹¹, phosphate dimethyl ester) | —H | (a) | join to form a double bond | | S |
| (pyranose with CH₂R¹⁰, CH₂R¹¹, phosphate dimethyl ester at different position) | —H | (a) | join to form a double bond | | S |

-continued
| R² | R²' | R | R³' | 3" | A |
|---|---|---|---|---|---|
| 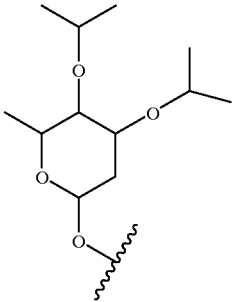 | —H | (a) | join to form a double bond | | S |
| 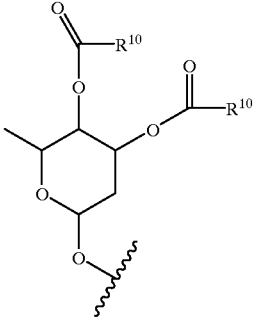 | —H | (a) | join to form a double bond | | S |
| 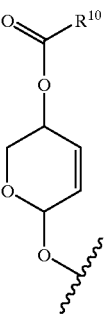 | —H | (a) | join to form a double bond | | S |
| 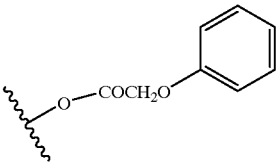 | —H | (a) | join to form a double bond | | S |
| 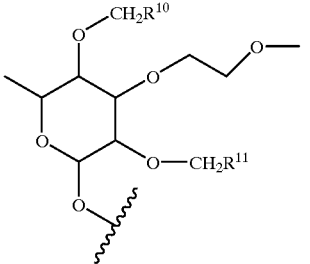 | —H | (a) | join to form a double bond | | S |

| R² | R²' | R | R³' | 3" | A |
|---|---|---|---|---|---|
| [sugar with CH₂R¹⁰, OCH₂CN, OCH₂R¹¹] | —H | (a) | join to form a double bond | | S |
| [sugar with CH₂R¹⁰, O-Si(CH₃)₃, OCH₂R¹¹] | —H | (a) | join to form a double bond | | S |
| [sugar with OCH₂R¹⁰, OCH₂COOC(CH₃)₃, OCH₂R¹¹] | —H | (a) | join to form a double bond | | S |
| [sugar with OCH₂R¹⁰, OCH₂OCH₃, OCH₂R¹¹, H₃C] | —H | (a) | —H | —H | S |
| [sugar with OCH₂R¹⁰, OCO(CH₂)₂NH₂, OCH₂R¹¹] | —H | (a) | join to form a double bond | | S |

-continued
| R² | R²' | R | R³' | 3" | A |
|---|---|---|---|---|---|
| 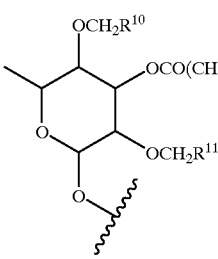 | —H | (a) | join to form a double bond | | S |
| 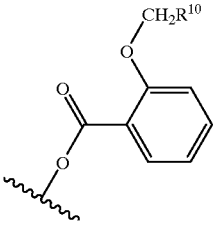 | —H | (a) | join to form a double bond | | S |
| 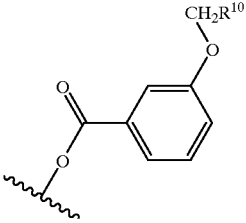 | —H | (a) | join to form a double bond | | S |
| 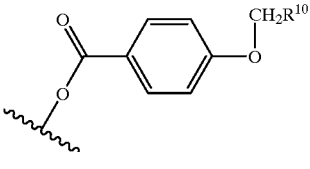 | —H | (a) | join to form a double bond | | S |
| 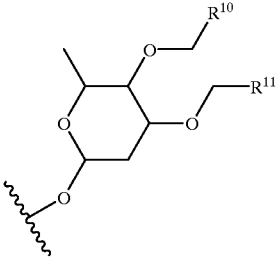 | —H | (a) | join to form a double bond | | S |

-continued

| R² | R²' | R | R³' | 3" | A |
|---|---|---|---|---|---|
| (sugar with R¹⁰, R¹¹) | —H | (a) | —H | —H | S |
| (disaccharide with OCH₃R¹⁰, OCH₂R¹¹, OCH₂R¹², OCH₂R¹³, OCH₂R¹⁴) | —H | (a) | join to form a double bond | | S |
| (sugar with NCH₃COOCH₂CCl₃) | —H | (a) | join to form a double bond | | S |
| (thiosugar with NHCH₃) | —H | (a) | join to form a double bond | | S |
| (sugar with R¹⁰CH₂OCH₂, OCH₂R¹¹, OCH₂R¹², OCH₂R¹³) | —H | (a) | join to form a double bond | | S |

-continued

| R² | R²' | R | R³' | 3" | A |
|---|---|---|---|---|---|
| sugar with OCH₂R¹⁰, OCH₂R¹¹, OCH₂C₆H₄CN₂CF₃ | —H | (a) | join to form a double bond | | S |
| sugar with OCH₂R¹⁰, OCH₂R¹¹, OCH₂R¹² | —H | (a) | —OH | —OH | S |
| sugar with OCH₂R¹⁰, CH₂CH=CH₂, OH, OCH₂R¹¹ | —H | (a) | join to form a double bond | | S |
| —OH | —CH₃ | (a) | join to form a double bond | | S |
| —H | —H | (a) | join to form a double bond | | S |
| —N(morpholine) | —H | (a) | join to form a double bond | | S |
| sugar with CH₃, OCH₂R¹⁰, OC(S)₂CH₃, OCH₂R¹¹ | —H | (a) | join to form a double bond | | S |
| sugar with CH₃, OCH₂R¹⁰, OCH₂R¹¹, OC(S)₂CH₃ | —H | (a) | join to form a double bond | | S |

-continued

| R² | R²' | R | R³' | 3" | A |
|---|---|---|---|---|---|
| sugar with CH₃, OCH₂R¹¹, OCH₂R¹² | —H | (a) | join to form a double bond | | S |
| sugar with OCH₂R¹⁰, CH₃, OCH₂R¹¹, H | —H | (b) | join to form a double bond | | S |
| sugar with OCH₂R¹⁰, CH₃, H, OCH₂R¹¹ | —H | —H | join to form a double bond | | S |
| sugar with OCH₂R¹⁰, CH₃, OCOCH₃, OCH₂R¹¹ | —H | (a) | join to form a double bond | | S |
| sugar with OCH₂R¹⁰, CH₃, OCH₂R¹¹, OCOCH₃ | —H | (a) | join to form a double bond | | S |
| sugar with OCOCH₃, CH₃, OCH₂R¹⁰, OCH₂R¹¹ | —H | (a) | join to form a double bond | | S |

-continued

| R² | R²' | R | R³' | 3" | A |
|---|---|---|---|---|---|
| [sugar with OC(S)₂CH₃, OCH₂R¹⁰, OCH₂R¹¹, CH₃] | —H | (a) | join to form a double bond | | S |
| [sugar with OCOCH₃, OCOCH₃, OH, CH₃] | —H | (a) | join to form a double bond | | S |
| [tetrahydropyranyl] | —H | (a) | join to form a double bond | | S |
| [sugar with OCH₂R¹⁰, H, OCH₂R¹¹, CH₃] | —H | (b) | join to form a double bond | | S |
| [sugar with OCH₂R¹⁰, OCH₂R¹¹, =O, CH₃] | —H | (a) | join to form a double bond | | S |
| —OCH₃ | —H | —H | join to form a double bond | | S |
| —H | —H | —H | join to form a double bond | | S |
| [complex dioxolane structure with OAc, OH groups] | —H | (a) | join to form a double bond | | S |

-continued

| R² | R²' | R | R³' | 3" | A |
|---|---|---|---|---|---|
| 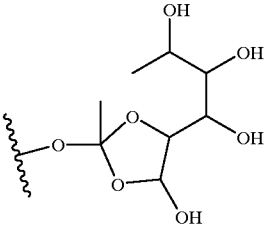 | | —H | (a) | join to form a double bond | S |
| —OCH₂OCH₂CH₂OCH₃ | | —H | (a) | join to form a double bond | S |
| —OCH₃ | | —H | (a) | join to form a double bond | S |
| —OOCCH₃ | | —H | (a) | join to form a double bond | S |
| —OOCCH₂COOCH₂CH₃ | | —H | (a) | join to form a double bond | S |
| —OCH₃ | | —H | (f) | join to form a double bond | S |
| —OCS₂CH₃ | | —H | (a) | join to form a double bond | S |
| —H | | NP | (a) | join to form a double bond | D |
| 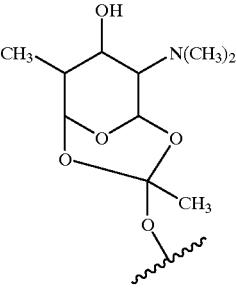 | | —H | (a) | join to form a double bond | S |
| 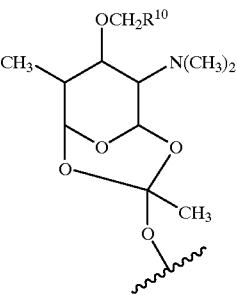 | | —H | (a) | join to form a double bond | S |
| 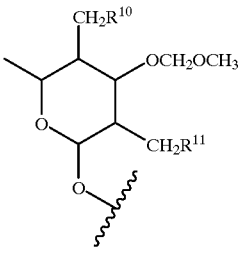 | | —H | (a) | join to form a double bond | S |

-continued

| R² | R²' | R | R³' 3" | A |
|---|---|---|---|---|
| (sugar with OCOCH₂R¹⁰, OCH₂R¹¹, OCH₂R¹²) | —H | (a) | join to form a double bond | S |
| (furanose with CH₂OCH₂R¹¹, R¹⁰H₂CO, OCH₂R¹²) | —H | (a) | join to form a double bond | S |
| (sugar with OCH₂R¹⁰, CH₂CHCH₂, OCH₂R¹¹) | —H | (a) | join to form a double bond | S |
| (sugar with OCH₂R, OC(=CH₂)CH₃, OCH₂R) | —H | (a) | join to form a double bond | S | where $R^5$, $R^6$, $R^7$, $R^8$ and $R^9$ are Cl, F, I, or Br;

$R^{10}$, $R^{11}$, $R^{12}$, R13, $R^{14}$ are independently H or an alkyl having 1 to 4 carbon atoms, or haloalkyl having 1 to 4 carbon atoms, where the halo is a halogen Br, Cl, F, or I;

$A^- = Cl^-$, $Br^-$, or $I^-$;

D=double bond;

S=single bond;

4. The compound of claim 3, where the compound is an acid addition salt.

5. A compound having the formula:

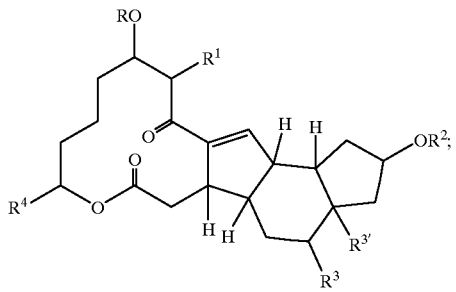

Formula IV

R is defined in the table or is Formula V as defined below:

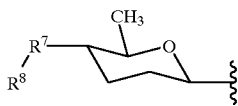
(a)

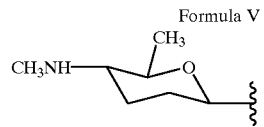
Formula V
(b)

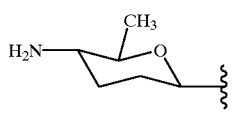
or
(c)

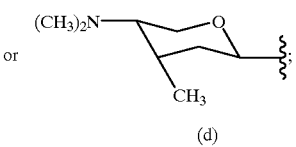
(d)

-continued $R^2$ is 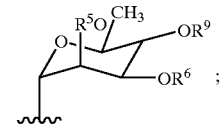 ;

Formula VI $R^1$ and $R^3$ are independently hydrogen or methyl; $R^4$ is methyl or ethyl; $R^5$, $R^6$ and $R^9$ are independently H, methyl, ethyl, propyl, butyl, or $CD^3$ and the following combinations are present:

| $R^1$ | R | $R^{3'}$ | $R^7$ | $R^8$ |
|---|---|---|---|---|
| —CH₃ | (CH₃)₂NCH₂CH₂CO— | —H | NP | NP |
| —CH₃ | CH₂=CHOC— | —H | NP | NP |
| —CH₃ | R¹⁰CH₂OC— | —H | NP | NP |
| —CH₃ | (CH₃)₂NCH₂OC— | —H | NP | NP |
| —CH₃ | (CH₃)₂N(CH₂)₃OC— | —H | NP | NP |
| —CH₃ | *N-methylpiperazinyl-CH₂-CO—* | —H | NP | NP |
| —CH₃ | *morpholinyl-CH₂-CO—* | —H | NP | NP |
| —CH₃ | *imidazolyl-CH₂-CO—* | —H | NP | NP |
| —CH₃ | *2-pyrimidinyl-piperazinyl-CH₂-CO—* | —H | NP | NP |
| —CH₃ | *4-(dimethylamino)piperidinyl-CH₂-CO—* | —H | NP | NP |

-continued
| R1 | R | R3' | R7 | R8 |
|---|---|---|---|---|
| —CH3 | 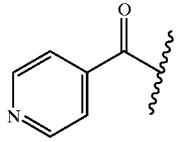 | —H | NP | NP |
| —CH3 | 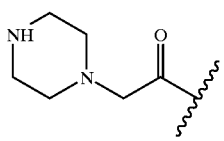 | —H | NP | NP |
| —CH3 | 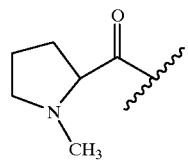 | —H | NP | NP |
| —CH3 | 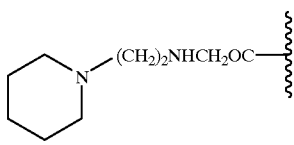 | —H | NP | NP |
| —CH3 | CH3CH2COCH2OC— | —H | NP | NP |
| —CH3 | Formula V (a) | —H | 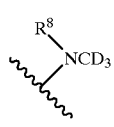 | —CH3 |
| —CH3 | Formula V (a) | —H | 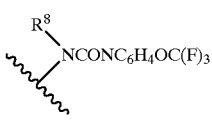 | —CH3 |
| —CH3 | Formula V (a) | —H | 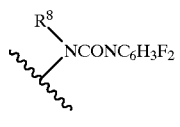 | —CH3 |
| —CH3 | Formula V (a) | —H | 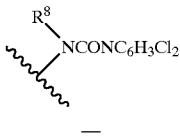 | —CH3 |
| —CH3 | Formula V (a) | —H | 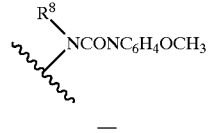 | —CH3 |

-continued
| R¹ | R | R³' | R⁷ | R⁸ |
|---|---|---|---|---|
| —CH₃ | Formula V (a) | —H | 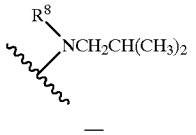 | —CH₃ |
| —CH₃ | Formula V (a) | —H | 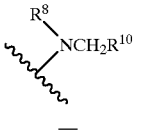 | —CH₃ |
| —CH₃ | Formula V (a) | —H | 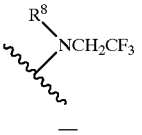 | —CH₃ |
| —CH₃ | Formula V (a) | —H | 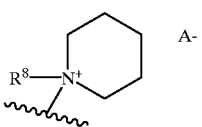 | —CH₃ |
| —CH₃ | Formula V (a) | —H | 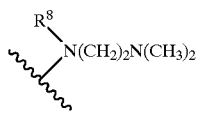 | —CH₃ |
| —CH₃ | Formula V (a) | —H | 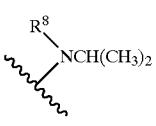 | —CH₃ |
| —CH₃ | Formula V (a) | —H | 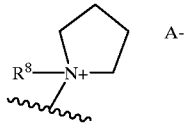 | —CH₃ |
| —CH₃ | Formula V (a) | —H | 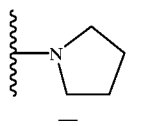 | NP |
| —CH₃ | Formula V (a) | —H | 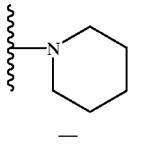 | NP |
| —CH₃ | Formula V (a) | —H | 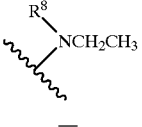 | —CH₂CH₃ |

-continued
| R¹ | R | R³' | R⁷ | R⁸ |
|---|---|---|---|---|
| —CH₃ | Formula V (a) | —H | 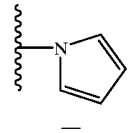 | NP |
| —CH₃ | Formula V (a) | —H | 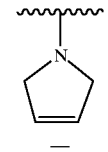 | NP |
| —CH₃ | Formula V (a) | —H | 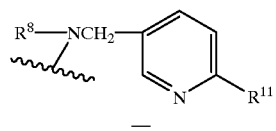 | —CH₃ |
| —CH₃ | Formula V (a) | —H | 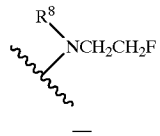 R⁸NCH₂CH₂F | —CH₃ |
| —CH₃ | Formula V (a) | —H | 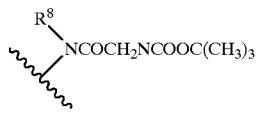 R⁸NCOCH₂NCOOC(CH₃)₃ | —CH₃ |
| —CH₃ | Formula V (a) | —H | 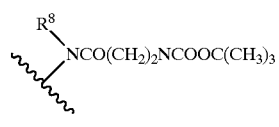 R⁸NCO(CH₂)₂NCOOC(CH₃)₃ | —CH₃ |
| —CH₃ | Formula V (a) | —H |  R⁸NCOCHCH₃NCOOCH₂C₆H₅ | —CH₃ |
| —CH₃ | Formula V (a) | —H | 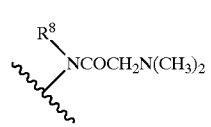 R⁸NCOCH₂N(CH₃)₂ | —CH₃ |
| —CH₃ | Formula V (a) | —H | 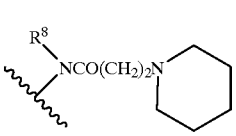 R⁸NCO(CH₂)₂N-piperidine | —CH₃ |
| —CH₃ | Formula V (a) | —H | 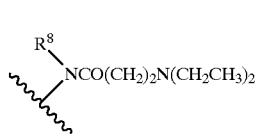 R⁸NCO(CH₂)₂N(CH₂CH₃)₂ | —CH₃ |

-continued
| R¹ | R | R³' | R⁷ | R⁸ |
|---|---|---|---|---|
| —CH₃ | Formula V (a) | —H | 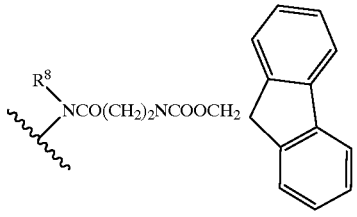 | —CH₃ |
| —CH₃ | Formula V (a) | —H | 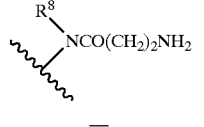 | —CH₃ |
| —CH₃ | Formula V (a) | —H | 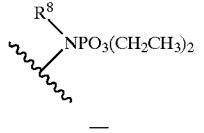 | —CH₃ |
| —CH₃ | 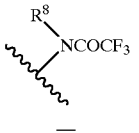 | —H | NP | NP |
| —CH₃ | —CHO | —H | NP | NP |
| —CH₃ |  | —H | NP | NP |
| —CH₃ | —COC₆H₄NO₂ | —H | NP | NP |
| —CH₃ | —COCH₂C₆H₄NO₂ | —H | NP | NP |
| —CH₃ |  | —H | NP | NP |
| —CH₃ | Formula V (a) | —H |  | —CH₃ |

-continued
| R1 | R | R3' | R7 | R8 |
|---|---|---|---|---|
| —CH₃ | 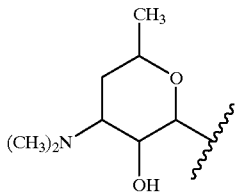 | —H | NP | NP |
| —CH₃ | Formula V (a) | —H | 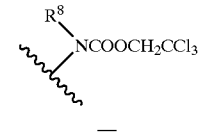 | —CH₃ |
| —CH₃ | 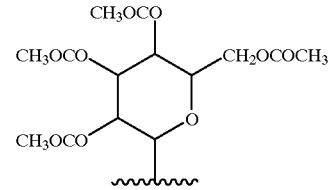 | —H | NP | NP |
| —CH₃ | Formula V (a) | —OH | 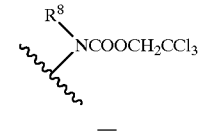 | —CH₃ |
| —CH₃ | Formula V (a) | —H | 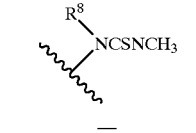 | —CH₃ |
| —CH₃ | Formula V (a) | —H | 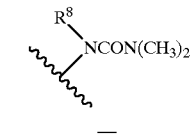 | —CH₃ |
| —CH₃ | Formula V (a) | —H | 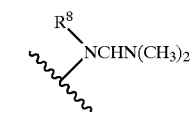 | NP |
| —CH₃ | —COCH₂C₆H₄NH₂ | —H | NP | NP |
| —CH₃ | —COCH₂C₆H₄R¹¹ | —H | NP | NP |
| —CH₃ | —COC₆H₄R¹¹ | —H | NP | NP |
| —CH₃ | —CHO | —H | NP | NP |
| —CH₃ | —COC₆H₄COC₆H₅ | —H | NP | NP |
| —CH₃ | —COCH₂C₆H₃Cl₂ | —H | NP | NP |
| —CH₃ | —COC₆H₄C₆H₅ | —H | NP | NP |
| —CH₃ | —COC₆H₄CH(CH₃)₂ | —H | NP | NP |
| —CH₃ | —COCH₂C₆H₃Cl₂ | —H | NP | NP |
| —CH₃ | —CH₂C₆H₅ | —H | NP | NP |

-continued

| R¹ | R | R³' | R⁷ | R⁸ |
|---|---|---|---|---|
| —CH₃ | Formula V (a) | —H | R⁸\NCO(CH₂)₆CH₃ | —CH₃ |
| —CH₃ | Formula V (a) | —H | R⁸\NCOCH₂Cl | —CH₃ |
| —CH₃ | Formula V (a) | —H | R⁸\N—N=O | —CH₃ |
| —CH₃ | Formula V (a) | —H | R⁸\NSO₂C₆H₅ | —CH₃ |
| —CH₃ | Formula V (a) | —H | R⁸\NCSNCH₂CH₃ | —CH₃ |
| —CH₃ | Formula V (a) | —H | NCHC₆H₅ | NP |
| —CH₃ | Formula V (a) | —H | R⁸\NCOCH₃ | —COCH₃ |
| —CH₃ | Formula V (a) | —H | R⁸\NCONCH₃ | —H |
| —CH₃ | —COC₆H₄N(CH₃)₂ | —H | NP | NP |
| —CH₃ | —COC₆H₄OCH₃ | —H | NP | NP |
| —CH₃ | —COC₆H₅ | —H | NP | NP |
| —CH₃ | —COC₆H₄CH(CH₃)₂ | —H | NP | NP |
| —CH₃ | —COCH₂C₆H₅ | —H | NP | NP |
| —CH₃ | —COCH₂C₆H₄OCH₃ | —H | NP | NP |
| —CH₃ | —COCH₂C₆H₄NO₂ | —H | NP | NP |
| —CH₃ | —CH₃ | —H | NP | NP |
| —CH₃ | —COCH₂C₆H₄CF₃ | —H | NP | NP |
| —CH₃ | —COCH₂C₆H₄OCH₃ | —H | NP | NP |

-continued

| R¹ | R | R³' | R⁷ | R⁸ |
|---|---|---|---|---|
| —CH₃ | Formula V | —H | 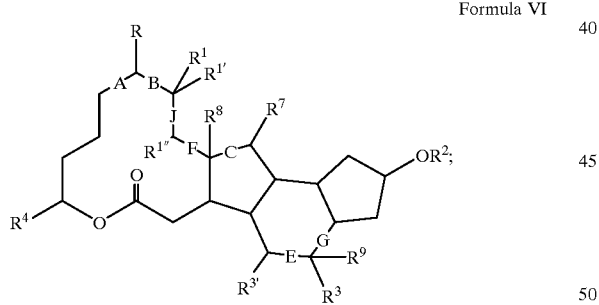 | NP |
| —CH₃ | (pyranone structure with CH₃) | —H | NP | NP |
| —CH₃ | (hydroxy tetrahydropyran structure with CH₃) | —H | NP | NP | wherein A⁼=I or Br;

NP=not present;

R¹⁰=alkyl having 1 to 4 carbon atoms or a haloalkyl having 1 to 4 carbon atoms where the halo is a halogen selected from Br, Cl, F, or I; and R¹¹=Br, Cl, F, or I.

6. The compound of claim 5 wherein the compound is an acid addition salt.

7. A compound having the formula:

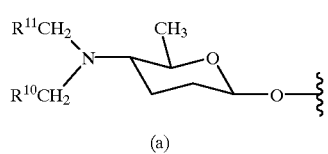

Formula VI where:

R is specified in the table below, is H or is

Formula VII

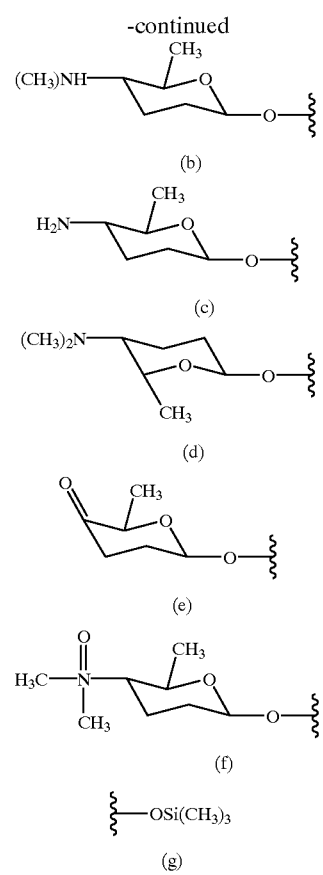

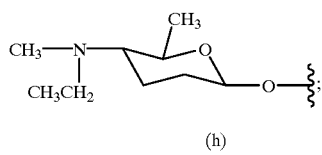
(h)

$R^2$ is specified in the table below, is H or is

Formula VIII

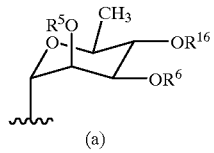
(a)

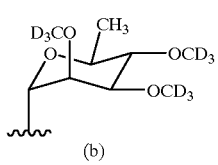
(b)

(c)

(d)

wherein $R^5$, $R^6$ and $R^{16}$ are independently methyl, ethyl, propyl or butyl; $R^1$ is H or methyl; $R^-$ is methyl or ethyl; and the following combination is present:

| R | $R^{1'}$ | $R^{1''}$ | $R^2$ |
|---|---|---|---|
| ![structure with CH2R10, acetamide, tetrahydropyran] | —H | DBO | Form VIII (a) |
| ![structure with CH2R10, isoquinolinone fused tetrahydropyran] | —H | DBO | Form VIII (a) |
| ![structure with CH2R10, allyl amine, tetrahydropyran] | —H | DBO | Form VIII (a) |
| ![structure with benzyl, N-methyl, tetrahydropyran with OMe] | —H | DBO | Form VIII (a) |

6,001,981
215                                                                                      216
-continued
| | | | |
|---|---|---|---|
| 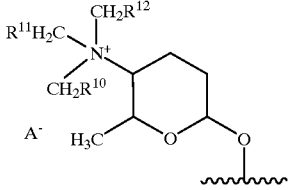 | —H | DBO | Form VIII (a) |
| 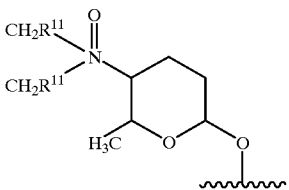 | —H | DBO | Form VIII (a) |
| 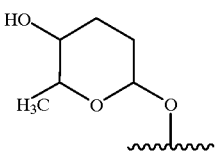 | —H | DBO | Form VIII (a) |
| 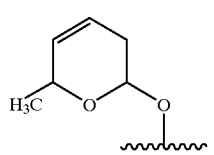 | —H | DBO | Form VIII (a) |
| 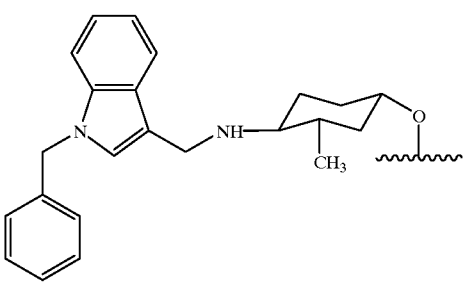 | —H | DBO | Form VIII (a) |
| 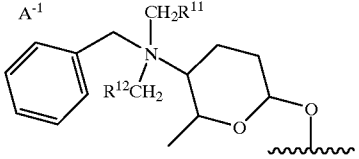 | —H | DBO | Form VIII (a) |
| 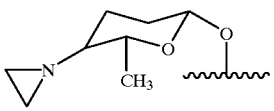 | —H | DBO | Form VIII (a) |
| 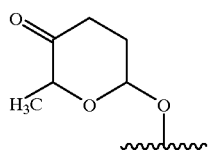 | —H | DBO | Form VIII (a) |

-continued
| | | | |
|---|---|---|---|
| 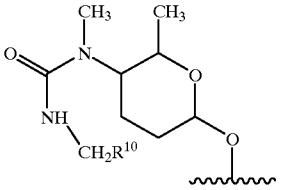 | —H | DBO | Form VIII (a) |
| 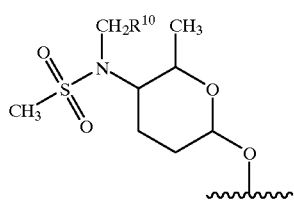 | —H | DBO | Form VIII (a) |
| 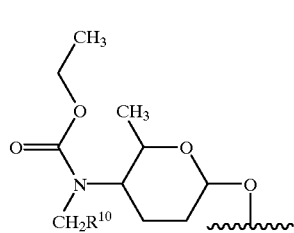 | —H | DBO | Form VIII (a) |
| 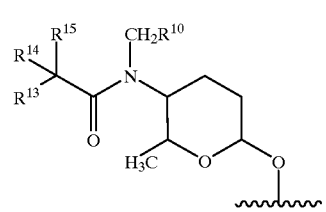 | —H | DBO | Form VIII (a) |
| 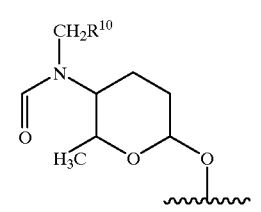 | —H | DBO | Form VIII (a) |
| 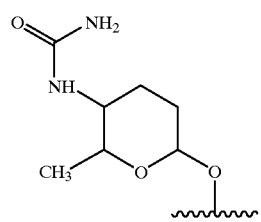 | —H | DBO | Form VIII (a) |
| 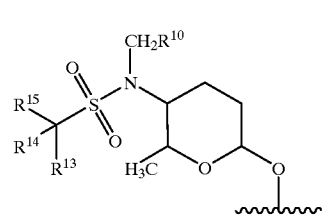 | —H | DBO | Form VIII (a) |

| | | | |
|---|---|---|---|
| 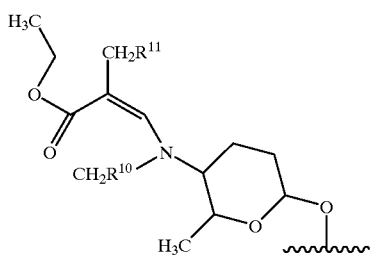 | —H | DBO | Form VIII (a) |
| 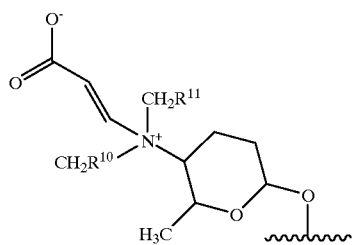 | —H | DBO | Form VIII (a) |
| 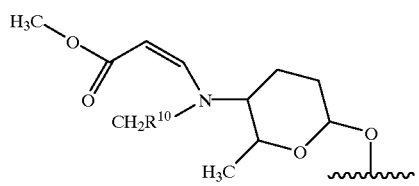 | —H | DBO | Form VIII (a) |
| 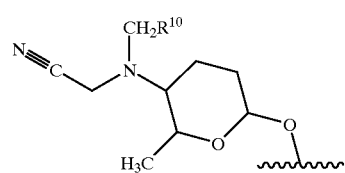 | —H | DBO | Form VIII (a) |
| 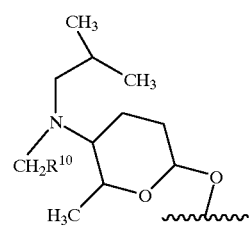 | —H | DBO | Form VIII (a) |
| 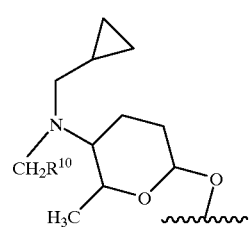 | —H | DBO | Form VIII (a) |
| 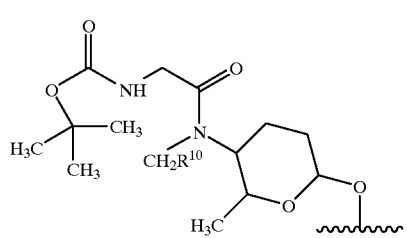 | —H | DBO | Form VIII (a) |

-continued
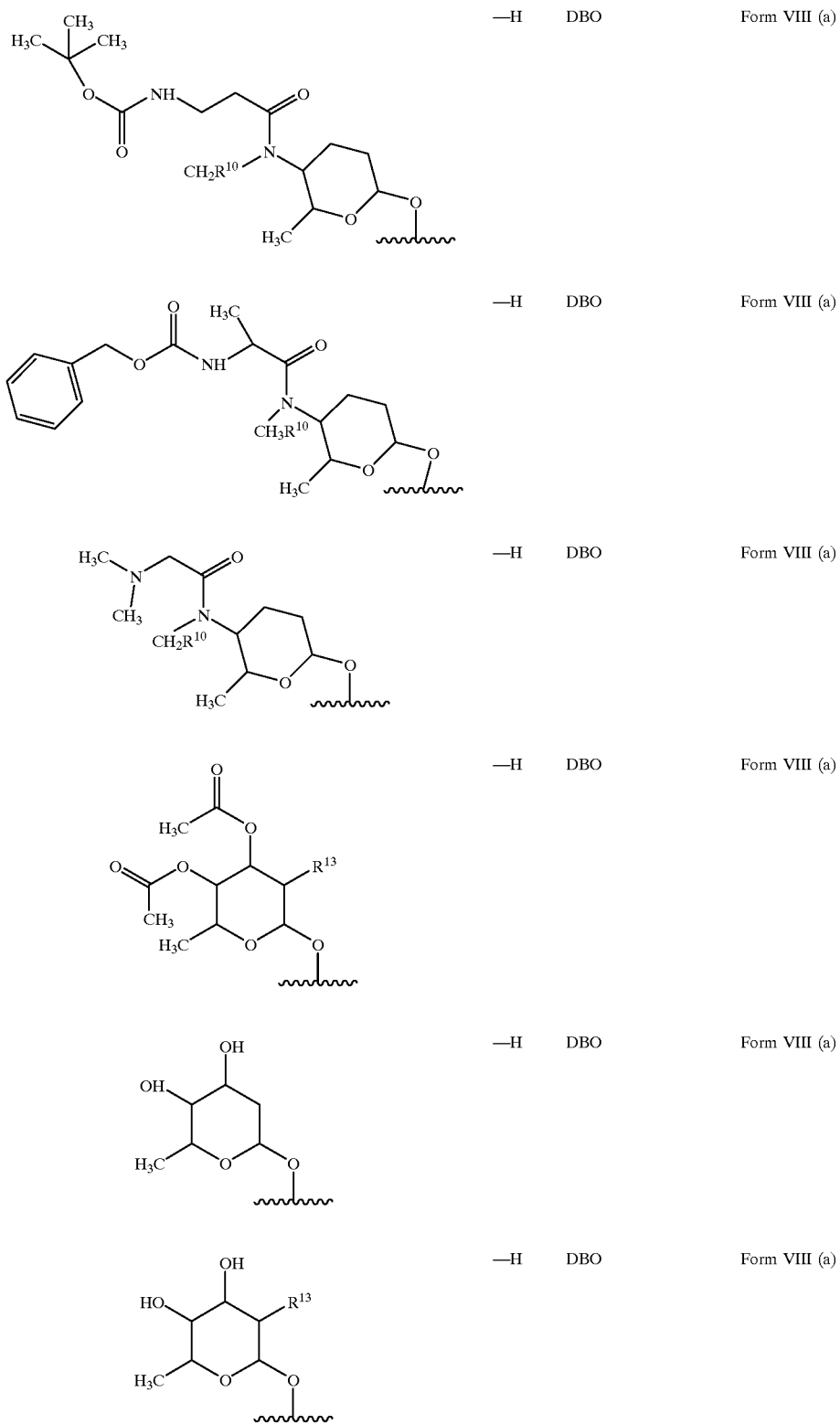
—H  DBO  Form VIII (a)
—H  DBO  Form VIII (a)
—H  DBO  Form VIII (a)
—H  DBO  Form VIII (a)
—H  DBO  Form VIII (a)
—H  DBO  Form VIII (a)

-continued

| | | | |
|---|---|---|---|
| 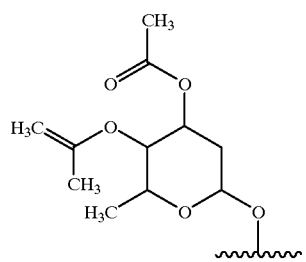 | —H | DBO | Form VIII (a) |
| —NH₂ | —H | DBO | Form VIII (a) |
| —H | NP | DBO | Form VIII (a) |
| —H | H | DBO | Form VIII (a) |
| DBO | H | DBO | Form VIII (a) |
| Form VII (a) | —H | DBO | Form VIII (a) |
| —OH | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | —OH | Form VIII (a) |
| Form VII (a) | —H | —OH | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| —OH | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (b) | —H | DBO | Form VIII (a) |
| Form VII (b) | —H | DBO | Form VIII (a) |
| Form VII (a) | —H | DBO | Form VIII (a) |
| —OH | —H | DBO | —H |
| Form VII (a) | —H | DBO | Form VIII (a) |
| —OH | —H | DBO | Form VIII (a) |
| Form VII (e) | —H | DBO | Form VIII (a) |
| Form VII (a) | —H | —OSi(CH₃)₃ | Form VIII (a) |
| Form VII (a) | —H | —OSi(CH₃)₃ | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (f) | —H | DBO | Form VIII (a) |
| (a) | —H | DBO | Form VIII (a) |
| —OH | —H | DBO | Form VIII (a) |
| —OH | —H | DBO | Form VIII (a) |
| Form VII (g) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (b) | —H | DBO | Form VIII (a) |
| Form VII (h) | —H | DBO | Form VIII (a) |
| Form VII (a) | —H | DBO | Form VIII (a) |
| —H | NP | DBO | Form VIII (a) |
| 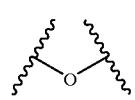 | | DBO | Form VIII (a) |
| Form VII (a) | —H | DBO | Form VIII (a) |
| Form VII (a) | —H | DBO | Form VIII (a) |
| Form VII (a) | —H | DBO | Form VIII (a) |
| Form VII (a) | NP | —H | Form VIII (a) |
| Form VII (a) | —H | Halogen | Form VIII (a) |
| Form VII (a) | —H | DBO | Form VIII (a) |

| | | | |
|---|---|---|---|
| CN | —H | DBO | Form VIII (a) |
| Form VII (a) | —H | DBO | Formula VIII (a) |
| Form VII (a) | —H | DBO | Formula VIII (a) |
| —H | NP | DBO | |
| CH₃OOCCH=CH—N (tetrahydropyran with CH₃, N-CH₃) | —H | DBO | |
| (CF₃-diazirine-phenyl-CH₂-N(CH₃)-tetrahydropyran) | —H | DBO | |
| CH₃CH₂-N(CH₃)-tetrahydropyran-O- | —H | DBO | Formula VIII (a) |
| Form VII (a) | —H | DBO | |
| Form VII (a) | —H | —OH | |
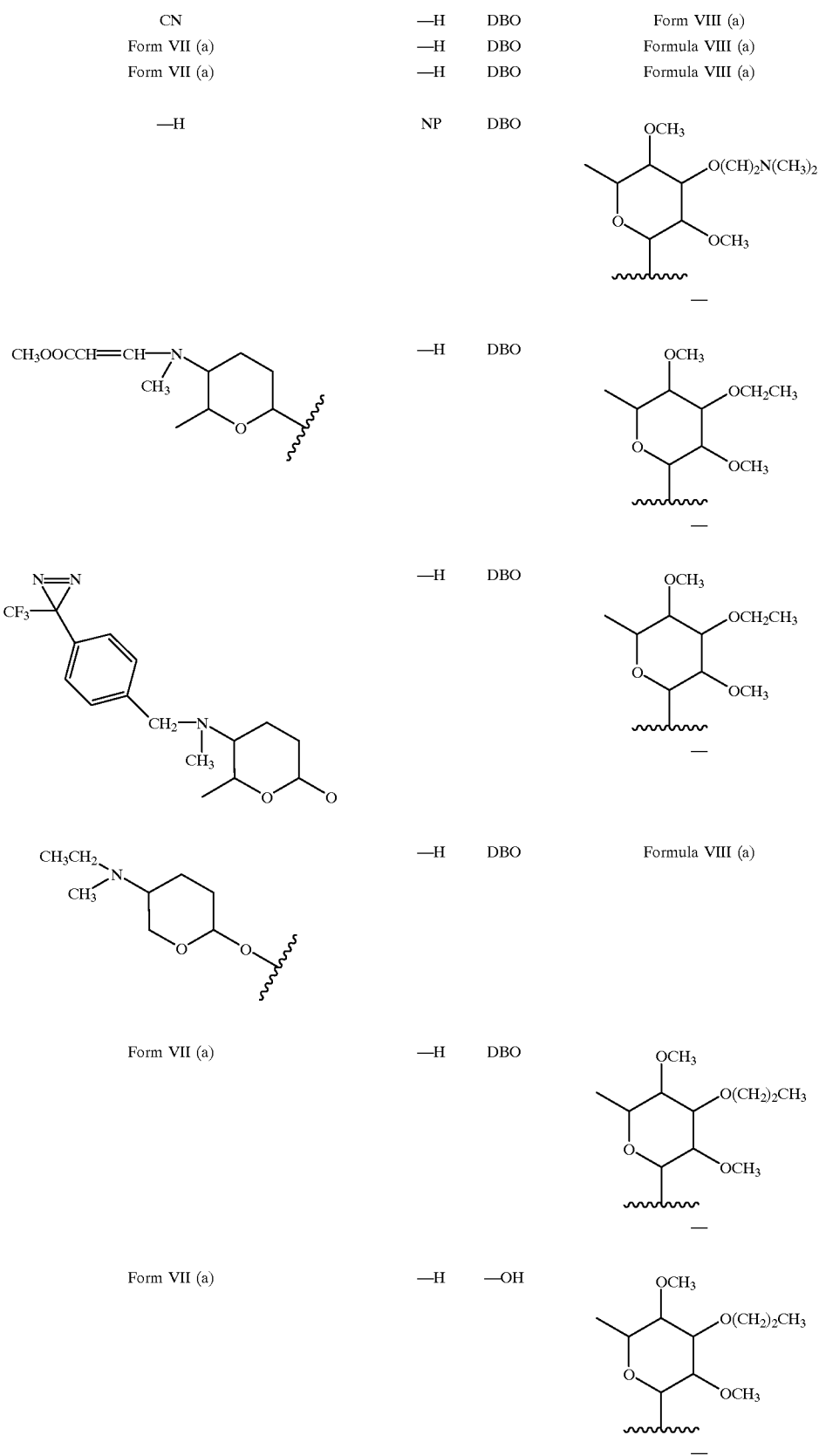

-continued

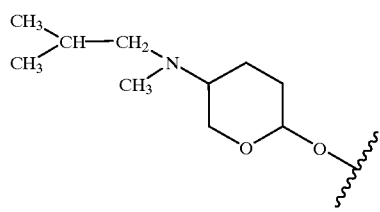 —H DBO Formula VIII (a)

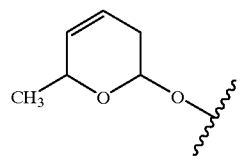 —H DBO Formula VIII (a)

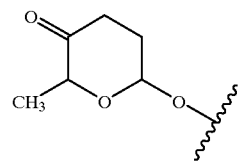 —H DBO Formula VIII (a)

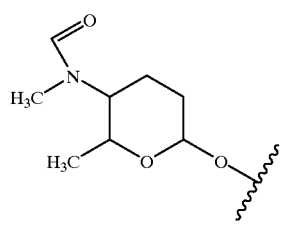 —H DBO Formula VIII (a)

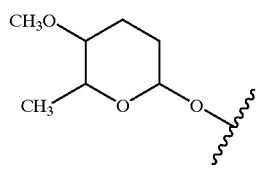 —H DBO Formula VIII (a)

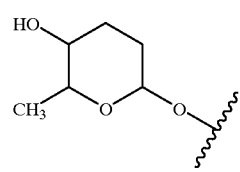 —H DBO Formula VIII (a)

| R³ | R³' | R⁹ | R⁷ | R⁸ | A | B | C | E | F | G | J |
|---|---|---|---|---|---|---|---|---|---|---|---|
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |

-continued

| | | | | | | | | | | | |
|---|---|---|---|---|---|---|---|---|---|---|---|
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | —H | NP | —H | NP | S | S | D | D | S | S | S |
| —H | H | NP | —H | NP | S | S | D | D | S | S | S |
| —H | —H | NP | —H | NP | S | S | D | D | S | S | S |
| —H | —H | NP | —H | NP | D | S | D | D | S | S | S |
| —H | —H | NP | —H | NP | S | S | D | D | S | S | S |
| —CH$_3$ | —H | NP | —N(R$^{10}$)OH | —H | S | S | S | D | S | S | S |
| —H | H | NP | CH$_2$R$^{10}$ | —H | S | S | S | D | S | S | S |
| —H | —H | NP | —CN | —H | S | S | S | D | S | S | S |
| —H | —H | NP | —H | —H | S | S | S | D | S | S | S |
| —H | —H | NP | —H | NP | S | S | D | D | S | S | S |
| —H | —H | NP | (benzylidene N-oxide group) | —H | S | S | S | D | S | S | S |
| —H | —H | NP | —H | —H | S | S | S | D | S | S | S |
| —H | —H | NP | (O-bridge group) | | S | S | S | D | S | S | S |
| —H | —H | NP | —N(R$^{10}$)OH | —H | S | S | S | D | S | S | S |
| —H | —H | NP | —N(R$^{10}$)OH | —H | S | S | S | D | S | S | S |
| —H | Halogen | NP | —H | NP | S | S | D | D | S | S | S |
| Halogen | —H | NP | —H | NP | S | S | D | D | S | S | S |
| —OSi(CH$_3$)$_3$ | —OSi(C$_3$)$_3$ | NP | —H | NP | S | S | D | D | S | S | S |
| —O(CH$_2$)$_2$OH | Halogen | — | — | NP | S | S | D | S | S | S | S |
| —OH | —OH | —H | —H | NP | S | S | D | S | S | S | S |
| (O-bridge group) | | —CH$_3$ | —H | NP | S | S | D | S | S | S | S |
| —OCOCCl$_3$ | —OCOCCl$_3$ | —H | —H | NP | S | S | D | S | S | S | S |
| Halogen | Halogen | —H | —H | NP | S | S | D | S | S | S | S |
| Halogen | —OH | —H | —H | NP | S | S | D | S | S | S | S |
| —H | —H | —H | —H | NP | S | S | D | S | S | S | S |
| —OH | —H | —H | —H | NP | S | S | D | S | S | S | S |
| —H | —OH | —H | —H | NP | S | S | D | S | S | S | S |
| —SCH$_3$ | CH$_3$COO$^-$ | —H | —H | NP | S | S | D | S | S | S | S |
| Halogen | Halogen | —H | —H | NP | S | S | D | S | S | S | S |
| —OH | —OH | —H | —H | NP | S | S | D | S | S | S | S |
| CH$_3$SO$_2$— | CH$_3$COO$^-$ | —H | —H | NP | S | S | D | S | S | S | S |
| —H | —H | —H | —H | NP | S | S | D | S | S | S | S |
| —H | —H | —H | —H | NP | S | S | D | S | S | S | S |
| Halogen | Halogen | —H | —H | NP | S | S | D | S | S | S | S |
| Halogen | Halogen | —H | —H | NP | S | S | D | S | S | S | S |
| —H | —H | NP | —CN | NP | S | S | S | D | D | S | S |
| —H | —H | NP | —CN | NP | S | S | S | D | D | S | S |

-continued

| Structure/R1 | R2 | R3 | R4 | R5 | | | | | | |
|---|---|---|---|---|---|---|---|---|---|---|
| ![carbonate -O-C(=O)-O-] | —H | —H | NP | S | S | D | S | S | S | S |
| Halogen | CH₃CO₂⁻ | —H | —H | NP | S | S | D | S | S | S | S |
| ![-O- bridge] | | —H | —H | NP | S | S | D | S | S | S | S |
| ![-O- bridge] | | —H | —H | NP | S | S | D | S | S | S | S |
| ![-O-C(=CR¹³R¹⁴)-O-] | | —H | —H | NP | S | S | D | S | S | S | S |
| ![-O- bridge] | | —H | —H | NP | S | S | D | S | S | S | S |
| Halogen | —OCH₂CH₂OH | —H | —H | NP | S | S | D | S | S | S | S |
| ![-O- bridge] | | —H | —H | NP | S | S | D | S | S | S | S |
| —H | —H | —H | —H | NP | S | S | D | S | S | S | S |
| —OSi(CH₃)₂C(CH₃)₃ | DBO | NP | —H | NP | S | S | D | S | S | D | S |
| —OCOC₆H₄R¹² | DBO | NP | —H | NP | S | S | D | S | S | D | S |
| —OH | DBO | NP | —H | NP | S | S | D | S | S | D | S |
| —H | —O(CH₂)₂OH | NP | —H | NP | S | S | D | S | S | D | S |
| —H | —H | NP | —H | —H | S | S | S | D | S | S | S |
| —H | —H | NP | —H | —H | S | S | S | D | S | S | S |
| —H | —H | NP | ![-CH₂- bridge] — | | S | S | S | D | S | S | S |
| —H | —H | NP | ![-O- bridge] — | | S | D | S | D | S | S | S |
| —H | —H | NP | ![-O- bridge] — | | S | S | S | D | S | S | S |
| —H | —H | NP | ![-O- bridge] — | | S | S | S | D | S | S | S |
| —H | —H | —H | —H | —H | S | S | S | S | S | S | S |
| —H | —H | —H | —H | —H | S | S | S | S | S | S | S |
| —H | —H | —H | —H | —H | S | S | S | S | S | S | D |

-continued

| | | | | | | | | | | | |
|---|---|---|---|---|---|---|---|---|---|---|---|
| —H | —H | —H | —H | —H | S | S | S | S | S | S | S |
| | —H | —H | NP | S | S | D | S | S | S | S | |
| —H | —H | —H | CN | —H | S | S | S | D | S | S | S |
| —H | —H | NP | —H | —H | S | S | S | D | S | S | S |
| —CH₃ | —H | NP | —H | —H | S | S | S | D | S | S | S |
| —H | —H | NP | —H | NP | S | D | D | D | S | S | S |
| —H | —H | NP | —H | NP | S | S | D | D | S | S | S |
| —H | —H | NP | —H | NP | S | S | D | D | S | S | S |
| —H | —H | —H | —H | NP | S | S | D | S | S | S | S |
| —H | —H | NP | —H | —H | S | S | S | D | S | S | S |
| —H | —H | NP | —H | NP | S | S | D | D | S | S | S |
| —H | —H | —H | —H | NP | S | S | D | S | S | S | S |
| —H | —H | —H | —H | NP | S | S | D | S | S | S | S |
| —H | —H | —H | —H | NP | S | S | D | S | S | S | S |
| —H | —H | —H | —H | NP | S | S | D | S | S | S | S |
| —H | —H | —H | —H | NP | S | S | D | S | S | S | S | wherein DBO is double bonded oxygen;

NP is not present;

$R^{10}$, $R^{11}$, and $R^{12}$ are independently hydrogen, alkyl having 1 to 4 carbon atoms or a halo alkyl having 1 to 4 carbon atoms, wherein the halogen comprising the halo alkyl is F, Cl, I, or Br;

$A^-$ is $I^-$ or $Br^-$;

$R^{13}$, $R^{14}$, and $R^{15}$ are independently F, Cl, I, or Br; and

Halogen is F, Cl, I, or Br.

8. The compound of claim 7 wherein the compound is an acid addition salt.

9. A compound of claim 7 which has been modified to give the following structure:

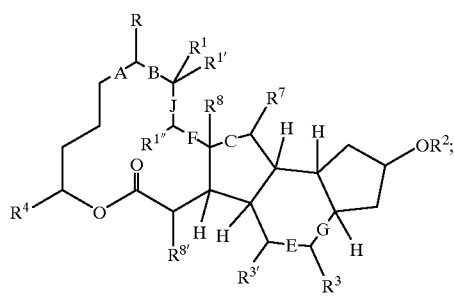

Formula IX wherein $R^2$ is

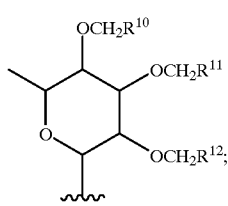

Formula X $R^1$ is not present; $R^1$ is double bonded oxygen; $R^1$ is H; $R^8$ is not present; $R^7$ is H; $R^{3'}$ is H; $R^3$ is H; R is H; $R^4$ is $CH_2CH_3$; and $R^{8'}$ is $CH_2CH_3$; A is S; B is D; C is D; E is D; F is S; G is S; and J is S.

10. The compound or claim 7 wherein the DBO oxygen in Formula I is reduced, where oxygen and $R^{1''}$ form a bond to give the following structure:

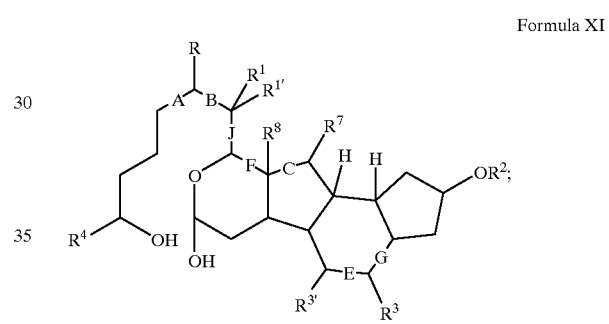

Formula XI wherein R is Formula VII(a), where Formula VII(a) $R^{10}$ and $R^{11}$ are hydrogen, alkyl having 1 to 4 carbon atoms or a halo aklyl having 1 to 4 carbon atoms, wherein the halogen comprising the halo alkyl is F, Cl, or Br; Rl is methyl or H; $R^{1'}$ is H; $R^3$ and $R^{3'}$ are methyl or H; $R^4$ is methyl or ethyl; $R^8$ is not present; $R^7$ is H; $R^2$ is Formula VIII(a), where Formula VIII(a) $R^5$ is methyl, $R^6$ is propyl, and $R^{16}$ is methyl; A is S; B is S; C is D; E is D; F is S; G is S; and J is S.

11. The compound of claim 7 wherein the double bond oxygen in Formula I is reduced, wherein the oxygen and $R^{1''}$ form a bond to give the following compound:

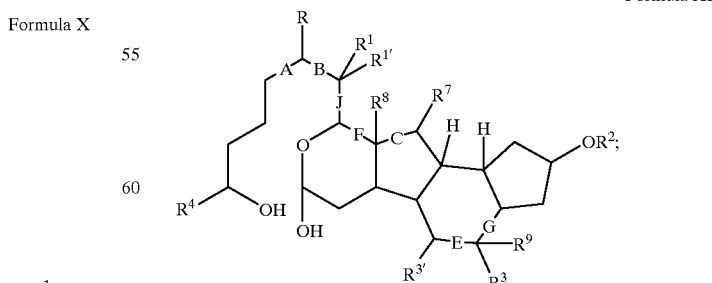

Formula XI wherein R is Formula VII(a); $R^1$ is methyl or H; $R^{1'}$ is H; $R^3$ and $R^{3'}$ are methyl or H; $R^4$ is methyl or ethyl; $R^2$ is Formula VIII(a); $R^5$, $R^6$, and R16 are methyl; $R^7$ is H; $R^8$ is H; A is S; B is S; C is S; E is S; F is S; G is S; and J is S.

12. The compound of claim 7 wherein the structure has been modified so that $R^8$ is not present and a double bond is formed to give the following compound:

Formula XII

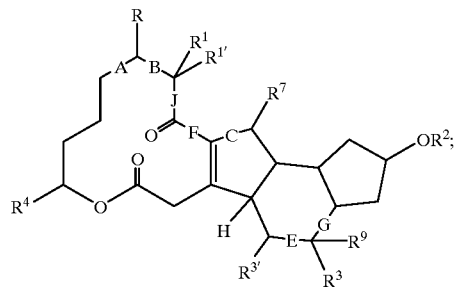

wherein R is Formula VII(a); $R^1$ is methyl or H; $R^{1'}$ is H; $R^3$ and $R^{3'}$ are methyl or H; $R^4$ is methyl or ethyl; $R^7$ is H; $R^2$ is Formula VIII(a); $R^5$, $R^6$, and $R^{16}$ are methyl; A is S; B is S; C is S; E is D; F is S; G is S; and J is S.

13. A compound having the formula:

Formula XIII

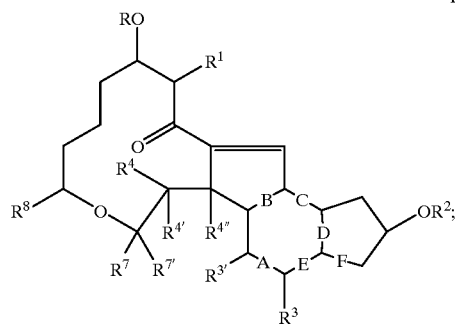

where:

R is H or selected from the group consisting of

Formula XIV

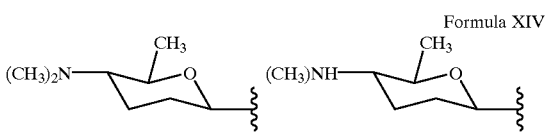

(a)                    (b)

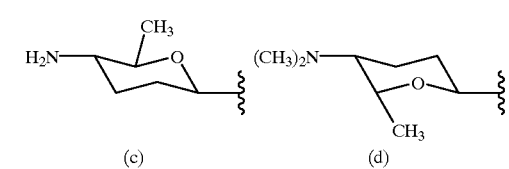

(c)                    (d)

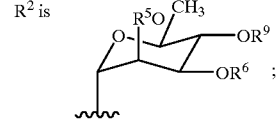  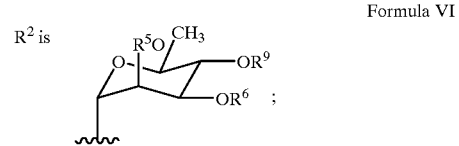

(e)

$R^2$ is

Formula VI

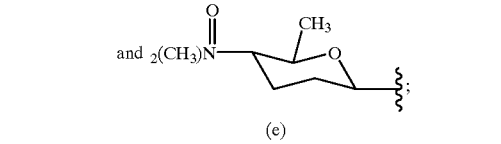

where $R^1$ is hydrogen or methyl;

$R^5$, $R^6$, and $R^9$ are hydrogen, methyl, ethyl, propyl or butyl;

$R^3$ is hydrogen or methyl;

$R^8$ is methyl or ethyl; and

R; $R^4$; $R^{4'}$; $R^{4''}$; $R^7$; $R^{7'}$; A; B; C; D; E and F are in the following combinations:

| R | $R^1$ | $R^{4'}$ | $R^{4''}$ | $R^4$ | $R^7$ | $R^{7'}$ | $R^2$ | $R^{3'}$ | A | B | C | D | E | F |
|---|---|---|---|---|---|---|---|---|---|---|---|---|---|---|
| Form XIV (a) | —CH$_3$ | —H | —H | —CH$_3$ | NP | DBO | Form VI | —H | D | S | S | S | S | S |
| Form XIV (a) | —CH$_3$ | —H | —H | —CH$_2$CH$_3$ | NP | DBO | Form VI | —H | D | S | S | S | S | S |
| Form XIV (a) | —CH$_3$ | —H | —H | —COOCH$_2$CH$_3$ | NP | DBO | Form VI | —H | D | S | S | S | S | S |
| Form XIV (a) | —CH$_3$ | —H | —H | —SCH$_3$ | NP | DBO | Form VI | —H | D | S | S | S | S | S |
| Form XIV (a) | —CH$_3$ | —H | —H | Halogen | NP | DBO | Form VI | —H | D | S | S | S | S | S |
| Form XIV (a) | —CH$_3$ | —H | —H | —COCH$_3$ | NP | DBO | Form VI | —H | D | S | S | S | S | S |
| Form XIV (a) | —CH$_3$ | —H | —H | —S—⌬ (phenyl) | NP | DBO | Form VI | —H | D | S | S | S | S | S |

-continued

| R | R¹ | R⁴' | R⁴" | R⁴ | R⁷' | R⁷ | R² | R³' | A | B | C | D | E | F |
|---|---|---|---|---|---|---|---|---|---|---|---|---|---|---|
| Form XIV (a) | —CH₃ | —H | —H | —C(=O)H | NP | DBO | Form VI | —H | D | S | S | S | S | S |
| Form XIV (a) | —CH₃ | —H | —H | —SOCH₃ | NP | DBO | Form VI | —H | D | S | S | S | S | S |
| Form XIV (a) | —CH₃ | —H | —H | —SOCH₃ | NP | DBO | Form VI | —H | D | S | S | S | S | S |
| Form XIV (a) | —CH₃ | —H | —H | —CH₃OH | NP | DBO | Form VI | —H | D | S | S | S | S | S |
| Form XIV (a) | —CH₃ | —H | —H | —CH₂N(piperidine) | NP | DBO | Form VI | —H | D | S | S | S | S | S |
| Form XIV (a) | —CH₃ | —H | —H | —COOCOCH₃ | NP | DBO | Form VI | —H | D | S | S | S | S | S |
| Form XIV (a) | —CH₃ | —H | —H | —SeC₆H₅ | NP | DBO | Form VI | —H | D | S | S | S | S | S |
| Form XIV (a) | —CH₃ | —H | join to form a double bond | | NP | DBO | Form VI | —H | D | S | S | S | S | S |
| Form XIV (a) | —CH₃ | —H | —H | —CNOH | NP | DBO | Form VI | —H | D | S | S | S | S | S |
| Form XIV (a) | —CH₃ | —H | —H | —CN | NP | DBO | Form VI | —H | D | S | S | S | S | S |
| Form XIV (a) | —CH₃ | —H | join to form a double bond | | —OSi(CH₃)₂CC(CH₃)₃ | | Form VI | —H | D | S | S | S | S | S |
| Form XIV (a) | —CH₃ | Halogen | —H | —CN | NP | DBO | Form VI | —H | D | S | S | S | S | S |
| Form XIV (a) | —CH₃ | —COHOCH₃ | —H | —H | NP | DBO | Form VI | —H | D | S | S | S | S | S |
| Form XIV (a) | —CH₃ | —SeC₆H₅ | —H | —H | NP | DBO | Form VI | —H | D | S | S | S | S | S |
| Form XIV (a) | —CH₃ | join to form a double bond | | —H | NP | DBO | Form VI | —H | D | S | S | S | S | S |
| Form XIV (a) | —CH₃ | —CNOH | —H | —H | NP | DBO | Form VI | —H | A | S | S | S | S | S |
| Form XIV (a) | —CH₃ | —C=N—N(CH₃)₂ | —H | —H | NP | DBO | Form VI | —H | D | S | S | S | S | S |
| Form XIV (a) | —CH₃ | —H | —H | —H | NP | DBO | Form VI | —H | D | S | S | S | S | D |
| Form XIV (a) | —CH₃ | —H | —H | —H | NP | DBO | Form VI | —H | D | S | S | D | S | S |
| Form XIV (a) | —CH₃ | —H | —H | —H | NP | DBO | Form VI | —H | D | D | S | D | S | S |
| Form XIV (a) | —CH₃ | —H | —H | —H | NP | DBO | Form VI | DBO | S | S | S | S | D | S |
| Form XIV (a) | —CH₃ | —H | —H | —H | NP | DBO | Form VI | Halogen | S | S | S | S | D | S |
| Form XIV (a) | —CH₃ | —H | —H | —H | NP | DBO | Form VI | —H | S | S | S | D | S | S |
| Form XIV (a) | —CH₃ | —H | —H | —H | NP | DBO | Form | —H | S | S | S | D | S | S |

-continued

| R | R¹ | R⁴' | R⁴" | R⁴ | R⁷' | R⁷ | R² | R³' | A | B | C | D | E | F |
|---|----|-----|-----|----|-----|----|----|-----|---|---|---|---|---|---|
| XIV (a) | | | | | | | VI | | | | | | | |

14. The compound of claim 13 wherein the compound is an acid addition salt.

15. A compound having the formula:

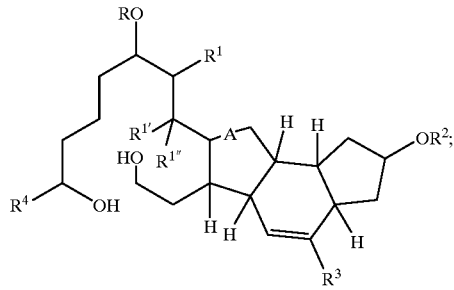

Formula XV where the compound comprises:

R is

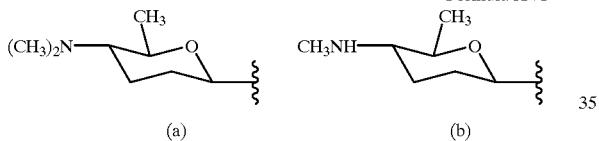

Formula XVI

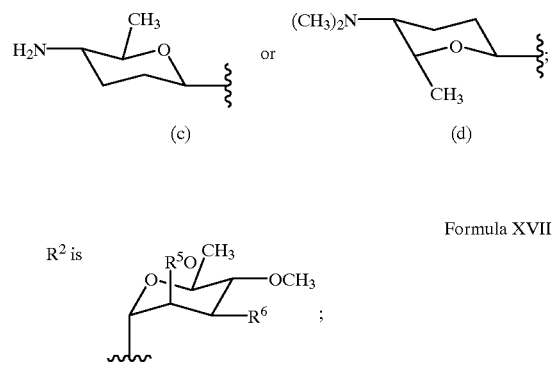

Formula XVII $R^2$ is $R^1$, $R^3$ and $R^5$ are independently hydrogen or methyl; $R^4$ is methyl or ethyl; and the following are present in combinations:

| R¹ | R¹' | R¹" | R³ | R⁴ | R⁵ | R⁶ | R | A |
|----|-----|-----|----|----|----|----|---|---|
| —CH₃ | join to form double bond —O | | —H | —CH₂CH₃ | —CH₃ | ⸺/⸺OH | (a) | S |
| —CH₃ | —OH | —H | —H | —CH₂CH₃ | —CH₃ | —OCH₃ | (a) | S |
| —CH₃ | —OH | —H | —H | —CH₂CH₃ | —CH₃ | —OCH₃ | (a) | D | wherein, A is either S=single bonded or D=double bonded; or an acid addition salt thereof.

16. The compound of claim 15 wherein the compound is an acid addition salt.

\* \* \* \* \*

UNITED STATES PATENT AND TRADEMARK OFFICE
CERTIFICATE OF CORRECTION

PATENT NO. : 6,001,981  Page 1 of 3
DATED      : December 14, 1999
INVENTOR(S): Carl Vincent DeAmicis, et al It is certified that error appears in the above-identified patent and that said Letters Patent is hereby corrected as shown below:

Col. 175, Claim 3,                    should read

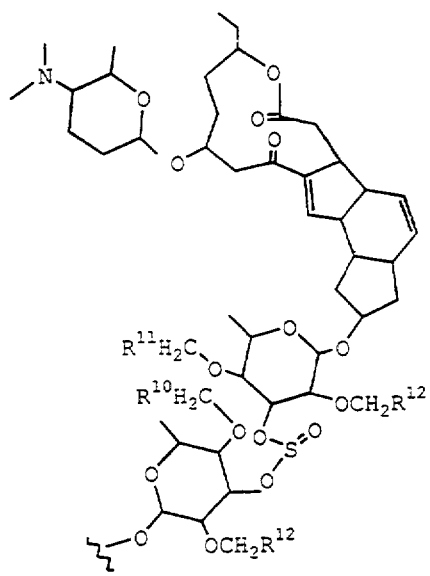 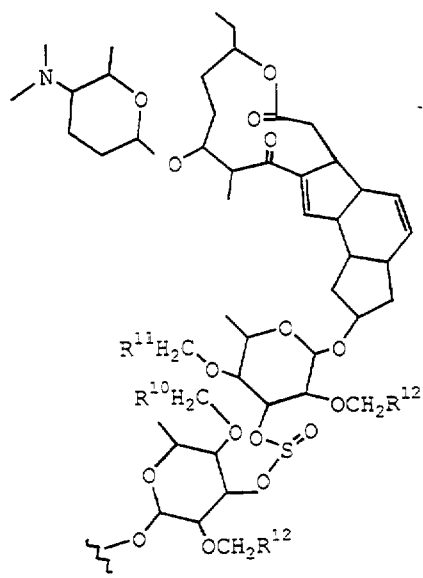

UNITED STATES PATENT AND TRADEMARK OFFICE
CERTIFICATE OF CORRECTION

PATENT NO. : 6,001,981
DATED : December 14, 1999
INVENTOR(S) : Carl Vincent DeAmicis, et al It is certified that error appears in the above-identified patent and that said Letters Patent is hereby corrected as shown below:

Col. 196, Claim 5,

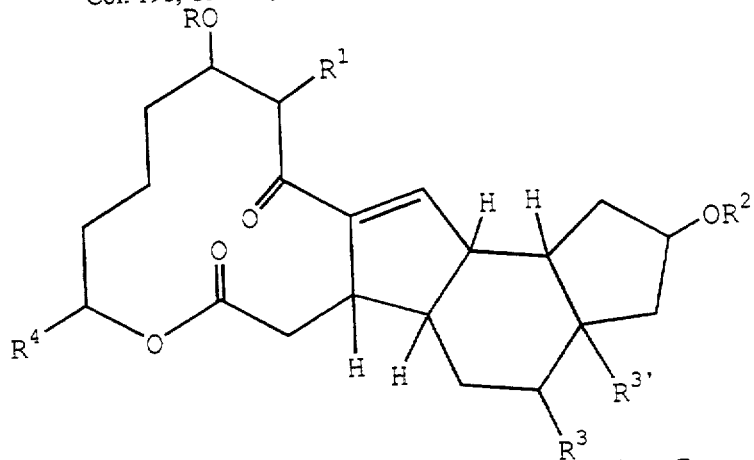

Formula IV; should read

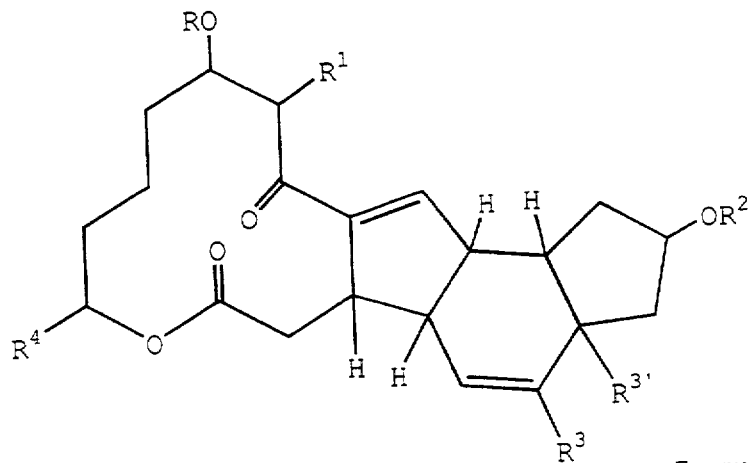

Formula IV;

UNITED STATES PATENT AND TRADEMARK OFFICE
CERTIFICATE OF CORRECTION

PATENT NO. : 6,001,981
DATED : December 14, 1999
INVENTOR(S) : Carl Vincent DeAmicis, et al It is certified that error appears in the above-identified patent and that said Letters Patent is hereby corrected as shown below:

Col. 214, Line 19, "R¯ is methyl or ethyl;" should read
-- $R^4$ is methyl or ethyl; --.

Col. 224, Line 38, "Form VIII (a)" should read
-- Form VIII(c) --.

Col. 224, Line 62, "Form VIII (a)" should read
-- Form VIII(d) --.

Col. 229, Line 32, "–$O(CH_2)_2OH$ Halogen – –" should read
-- –$O(CH_2)_2OH$ Halogen –H –H --.

Col. 230, Line 15, "NP S S D D S S S" should read
-- NP S D D D S S S --.

Col. 233, Line 64, "$R^1$ is not present; $R^1$ is double bonded oxygen;" should read
-- $R^{1'}$ is not present; $R^{1''}$ is double bonded oxygen; --.

Col. 239, Claim 13, at the end of Claim 13 insert
-- Wherein D = double bond; S = single bond; DBO = double bond oxygen; or an acid addition salt thereof --.

Signed and Sealed this

Twentieth Day of February, 2001

NICHOLAS P. GODICI

*Attest:*

*Attesting Officer*     Acting Director of the United States Patent and Trademark Office